US012460261B2

(12) United States Patent
Glezer et al.

(10) Patent No.: US 12,460,261 B2
(45) Date of Patent: *Nov. 4, 2025

(54) COMPOSITIONS AND METHODS FOR NUCLEIC ACID SEQUENCING

(71) Applicant: Singular Genomics Systems Inc., San Diego, CA (US)

(72) Inventors: Eli N. Glezer, Del Mar, CA (US); Mohammad Vatankhah Varnosfaderani, San Marcos, CA (US); Daan Witters, San Diego, CA (US); Vahid Karimkhani, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/988,274

(22) Filed: Dec. 19, 2024

(65) Prior Publication Data

US 2025/0122560 A1 Apr. 17, 2025

Related U.S. Application Data

(63) Continuation of application No. 17/542,343, filed on Dec. 3, 2021, now Pat. No. 12,227,799, which is a continuation of application No. 17/030,886, filed on Sep. 24, 2020, now Pat. No. 11,236,387, which is a continuation of application No. PCT/US2020/017060, filed on Feb. 6, 2020.

(60) Provisional application No. 62/802,062, filed on Feb. 6, 2019.

(51) Int. Cl.

| | |
|---|---|
| ***C12Q 1/6869*** | (2018.01) |
| ***C12Q 1/6844*** | (2018.01) |
| ***C12Q 1/6874*** | (2018.01) |
| ***G01N 33/53*** | (2006.01) |
| ***G01N 33/544*** | (2006.01) |

(52) U.S. Cl.

CPC ......... *C12Q 1/6869* (2013.01); *C12Q 1/6844* (2013.01); *C12Q 1/6874* (2013.01); *G01N 33/5308* (2013.01); *G01N 33/544* (2013.01); *C12Q 2533/101* (2013.01); *C12Q 2565/601* (2013.01)

(58) Field of Classification Search

CPC .. C12Q 1/6869; C12Q 1/6844; C12Q 1/6874; C12Q 2533/101; C12Q 2565/601; C12Q 2565/537; G01N 33/5308; G01N 33/544

See application file for complete search history.

(56) References Cited

U.S. PATENT DOCUMENTS 5,034,506 A 7/1991 Summerton et al.
5,235,033 A 8/1993 Summerton et al.
5,686,243 A 11/1997 Royer et al.
5,830,711 A 11/1998 Barany et al.
6,027,889 A 2/2000 Barany et al.
6,027,998 A 2/2000 Pham et al.
6,605,451 B1 8/2003 Marmaro et al.
7,057,026 B2 6/2006 Barnes et al.
7,541,444 B2 6/2009 Milton et al.
8,003,354 B2 8/2011 Shen et al.
8,039,817 B2 10/2011 Feng et al.
8,178,360 B2 5/2012 Barnes et al.
8,241,573 B2 8/2012 Banerjee et al.
8,703,461 B2 4/2014 Peris et al.
10,738,072 B1 8/2020 Graham et al.
11,236,387 B2 2/2022 Glezer et al.
11,434,525 B2 9/2022 Glezer
12,060,605 B2 8/2024 Glezer et al.
12,227,799 B2 * 2/2025 Glezer ................ C12Q 1/6874
2004/0096960 A1 5/2004 Burd et al.
2005/0013372 A1 1/2005 Srinivasan
2005/0154165 A1 7/2005 Petereit et al.
2006/0257629 A1 11/2006 Lendlein et al.
2007/0087362 A1 4/2007 Church et al.
2007/0141340 A1 6/2007 Song
2007/0196492 A1 8/2007 Ito et al.
2008/0160559 A1 7/2008 Carre et al.
2008/0242560 A1 10/2008 Gunderson et al.
2009/0253220 A1 10/2009 Banerjee
2010/0055733 A1 3/2010 Lutolf et al.
2011/0244048 A1 10/2011 Amiji et al.
2012/0270305 A1 10/2012 Reed et al.
2012/0301926 A1 11/2012 Chen et al.
2012/0309651 A1 12/2012 Pregibon et al.
2013/0012399 A1 1/2013 Myers et al.
2014/0080717 A1 3/2014 Li et al.
2014/0255333 A1 9/2014 Song et al.

(Continued)

FOREIGN PATENT DOCUMENTS

WO WO-1996/007669 A1 3/1996
WO WO-1997/031256 A2 8/1997

(Continued)

OTHER PUBLICATIONS

Feeney et al. (Apr. 1, 1982) "Chemical Modification of Proteins: An Overview", Advances in Chemistry Series, 198:3-55.
(Retrieved on Apr. 8, 2025) "Light Microscopy Core Facility", retrieved from https://microscopy.duke.edu/introduction-microscopy, 25 pages.
Abramson, R. D. et al. (Feb. 1993, e-published Aug. 26, 2004). "Nucleic acid amplification technologies," *Current Opinion in Biotechnology* 4: 41-47.
Barany, F. (Jan. 1, 1991). "Genetic Disease Detection And DNA Amplification Using Cloned Thermostable Ligase," *Proceedings of the National Academy of Sciences* 88(1): 189-193.
Barany, F. et al. (Dec. 20, 1991, e-published Jan. 28, 2003). "Cloning, overexpression and nucleotide sequence of a thermostable DNA ligase-encoding gene," *Gene* 109(1): 1-11.

(Continued)

*Primary Examiner* — Narayan K Bhat

(74) *Attorney, Agent, or Firm* — Mintz, Levin, Cohn, Ferris, Glovsky and Popeo, P.C.; Zachary L. Terranova

(57) ABSTRACT

Provided herein are methods and compositions for improved sequencing techniques using, for example, polymeric particles and/or three-dimensional structures.

20 Claims, 14 Drawing Sheets

(56) References Cited

U.S. PATENT DOCUMENTS

| | | | |
|---|---|---|---|
| 2015/0005200 | A1 | 1/2015 | Hindson et al. |
| 2016/0024555 | A1 | 1/2016 | Church et al. |
| 2017/0022553 | A1 | 1/2017 | Vijayan et al. |
| 2018/0016634 | A1 | 1/2018 | Hindson et al. |
| 2018/0119220 | A1 | 5/2018 | Grass et al. |
| 2019/0048404 | A1 | 2/2019 | Dambacher |
| 2019/0241950 | A1 | 8/2019 | Daugharthy et al. |
| 2019/0249171 | A1 | 8/2019 | Wu et al. |
| 2020/0071751 | A1 | 3/2020 | Daugharthy et al. |
| 2020/0354774 | A1 | 11/2020 | Church et al. |
| 2021/0040555 | A1 | 2/2021 | Glezer et al. |
| 2021/0139884 | A1 | 5/2021 | Kellinger et al. |
| 2021/0332349 | A1 | 10/2021 | Norberg et al. |
| 2021/0363579 | A1 | 11/2021 | Daugharthy et al. |
| 2022/0090191 | A1 | 3/2022 | Glezer et al. |
| 2022/0106588 | A1 | 4/2022 | Wu et al. |
| 2022/0154271 | A1 | 5/2022 | Glezer et al. |
| 2022/0333190 | A1 | 10/2022 | Glezer et al. |

FOREIGN PATENT DOCUMENTS

| | | | |
|---|---|---|---|
| WO | WO-1998/003673 | A1 | 1/1998 |
| WO | WO-2000/056927 | A3 | 3/2000 |
| WO | WO 2001/092579 | A2 | 12/2001 |
| WO | WO-2004/018497 | A2 | 3/2004 |
| WO | WO-2014/085603 | A1 | 6/2014 |
| WO | WO-2016/123480 | A1 | 8/2016 |
| WO | WO-2017/079406 | A1 | 5/2017 |
| WO | WO-2018/148723 | A1 | 8/2018 |
| WO | WO-2020/056044 | A1 | 3/2020 |
| WO | WO-2020/076979 | A1 | 4/2020 |
| WO | WO-2020/163630 | A1 | 8/2020 |

OTHER PUBLICATIONS

Bentley, D. R. et al. (Nov. 6, 2008). "Accurate whole human genome sequencing using reversible terminator chemistry," *Nature* 456(7218): 53-59.

Bi, W. et al. (Jul. 1, 1997). "CCR: a rapid and simple approach for mutation detection," *Nucleic Acids Research* 25: 2924-2951.

Cohen, S. M. (Feb. 8, 2012, e-published Sep. 14, 2011). "Postsynthetic Methods for the Functionalization of Metal-Organic Frameworks," *Chemical Reviews* 112(2): 970-1000.

Cook, N. (May 2003, e-published Feb. 28, 2003). "The use of NASBA for the detection of microbial pathogens in food and environmental samples," *Journal of Microbiological Methods* 53(2): 165-174.

Day, D. J. et al. (Sep. 1, 1995, e-published May 25, 2002). "Detection of steroid 21-hydroxylase alleles using gene-specific PCR and a multiplexed ligation detection reaction," *Genomics* 29: 152-162.

Dean, F. B. et al. (Apr. 16, 2002). "Comprehensive human genome amplification using multiple displacement amplification," *PNAS* 99(8): 5261-5266.

Demidov, V. (2002, e-published Jan. 9, 2014). "Rolling-circle Amplification in DNA Diagnostics: The Power of Simplicity," *Expert Review of Molecular Diagnostics* 2(6): 542-548.

Denk, W. et al. (Apr. 6, 1990). "Two-photon laser scanning fluorescence microscopy," *Science* 248(4951): 73-76.

Ehrlich, H. et al. (Jun. 21, 1991). "Recent Advances in the Polymerase Chain Reaction," *Science* 252: 1643-165.

El-Sagheer, A. H. et al. (Aug. 21, 2012, e-published Mar. 22, 2012). "Click Nucleic Acid Ligation: Applications In Biology And Nanotechnology," *Accounts of chemical research* 45(8): 1258-1267.

Fan, T. et al. (Sep. 2018, e-published Jul. 7, 2018). "Branched rolling circle amplification method for measuring serum circulating microRNA levels for early breast cancer detection," *Cancer Science* 111(1): 297-298.

Favis, R. et al. (May 2000). "Universal DNA array detection of small insertions and deletions in BRCA1 and BRCA2," *Nature Biotechnology* 18: 561-564.

Flot, J.-F. et al. (Oct. 7, 2015, e-published Apr. 29, 2015). "Contact genomics: scaffolding and phasing (meta) genomes using chromosome 3D physical signatures," *FEBS letters* 589(20): 2966-2974.

Gan, Z. et al. (May 13, 2016). "Biomimetic gyroid nanostructures exceeding their natural origins," *Sci Adv* 2(5): e:1600084.

Gustafsson, M. G. L. et al. (Jun. 15, 2008). "Three-dimensional resolution doubling in wide-field fluorescence microscopy by structured illumination," *Biophysical Journal* 94(12): 4957-4970.

Heintzmann, R. et al. (Nov. 10, 2017, e-published Dec. 13, 2017). "Super-Resolution Structured Illumination Microscopy," *Chemical Reviews* 117(23): 13890-13908.

Hsuih, T. C. et al. (Mar. 1, 1996). "Novel, ligation-dependent PCR assay for detection of hepatitis C in serum," *Journal of Clinical Microbiology* 34(3): 501-507.

International Search Report and Written Opinion mailed on Jul. 20, 2020 for PCT Application No. PCT/US2020/017060, filed Feb. 6, 2020, 23 pages.

Kato, M. et al. (Feb. 1, 1995, e-published May 1, 2002). "Polymerization of Methyl Methacrylate with the Carbon Tetrachloride/Dichlorotris (triphenylphosphine)ruthenium(II)/Methylaluminum Bis(2,6-di-tert-butylphenoxide) Initiating System: Possibility of Living Radical Polymerization," *Macromolecules* 28(5): 1721-1723.

Lage, J. M. et al. (Feb. 1, 2003). "Whole genome analysis of genetic alterations in small DNA samples using hyperbranched strand displacement amplification and array-CGH," *Genome research* 13(2): 294-307.

Landegren, U. et al. (Aug. 26, 1988). "A ligase-mediated gene detection technique," *Science* 4869: 1077-80.

Larsson, C. et al. (Apr. 11, 2010). "In situ detection and genotyping of individual mRNA molecules," *Nature America* 7: 395-397.

Lizardi, P. et al. (Jul. 1998). "Mutation detection and single-molecule counting using isothermal rolling-circle amplification," *Nature Genetics* 19: 225-232.

Mag, M. et al. (Nov. 24, 1992, e-published Mar. 5, 2001). "Synthesis and Selective Cleavage of an Oligodeoxynucleotide Containing a Bridged Non-Chiral Internucleotide 3'-Phosphoramidate Linkage," *Tetrahedron Letters* 33(48): 7319-22.

Manuguerra, I. et al. (Apr. 17, 2018). "Gene assembly via one-pot chemical ligation of DNA promoted by DNA nanostructure," *Chemical Communications* 54(36): 4529-4532.

Moad, G. et al. (Jun. 14, 2005). "Living Radical Polymerization by the RAFT Process," *Australian Journal of Chemistry* 58(6): 379-410.

Nalawade, A. C. et al. (Nov. 26, 2015). "Inverse high internal phase emulsion polymerization (i-HIPE) of GMMA, HEMA and GDMA for the preparation of superporous hydrogels as a tissue engineering scaffold," *Journal of Materials Chemistry B* 4(3): 450-460.

Nilsson, M. et al. (Sep. 30, 1994). "Padlock Probes: Circularizing Oligonucleotides for Localized DNA Detection," *Science* 265: 2085-2088.

Odeh, F. et al. (Dec. 18, 2019). "Aptamers chemistry: Chemical modifications and conjugation strategies," *Molecules* 25(1): 3.

Otsu, T. et al. (Feb. 16, 1982). "Role of initiator-transfer agent-terminator (iniferter) in radical polymerizations: Polymer design by organic disulfides as iniferters," *Macromolecular Rapid Communications* 3: 127-132.

Partial Search Report mailed Oct. 6, 2022 for EP Application No. 20752608.8, filed Feb. 6, 2020, 19 pages.

Polstra, A. M. et al. (Sep. 4, 2002). "Development of real-time NASBA assays with molecular beacon detection to quantify mRNA coding for HHV-8 lytic and latent genes," *BMC Infectious Diseases* 2(1): 1-10.

Rabenau, H. F. et al. (Apr. 2000). "Low correlation of serology with detection of Chlamydia trachomatis by ligase chain reaction and antigen EIA," *Infection* 28: 97-102.

Sapoznik, E. et al. (Nov. 12, 2020). "A versatile oblique plane microscope for large-scale and high-resolution imaging of subcellular dynamics," *eLife* 9: e57681.

Schweitzer, B. et al. (Feb. 1, 2001, e-published Feb. 5, 2001). "Combining nucleic acid amplification and detection," *Current Opinion in Biotechnology* 12(1): 21-27.

Southworth, M. W. et al. (May 28, 1996). "Cloning of thermostable DNA polymerases from hyperthermophilic marine Archaea with

(56) References Cited

OTHER PUBLICATIONS emphasis on *Thermococcus* sp. 9 degrees N-7 and mutations affecting 3'-5' exonuclease activity," *Proceedings of the National Academy of Sciences* 93(11): 5281-5285.

Veregin, R. P. N. et al. (Sep. 1, 1993, e-published May 1, 2002). "Free radical polymerizations for narrow polydispersity resins: electron spin resonance studies of the kinetics and mechanism," *Macromolecules* 26(20): 5316-5320.

Walker, G. T. et al. (Apr. 11, 1992). "Strand Displacement Amplification—An Isothermal, In Vitro DNA Amplification Technique," *Nucleic Acids Research* 20(7): 1691-1696.

Walker, J. W. et al. (Oct. 1, 1988, e-published May 1, 2002). "Photolabile 1-(2-Nitrophenyl)ethyl Phosphate Esters of Adenine Nucleotide Analogues. Synthesis and Mechanism of Photolysis," *Journal of the American Chemical Society* 110(21): 7170-7177.

Wang, J. et al. (May 1, 1995, e-published May 1, 2002). "Controlled/"living" radical polymerization. atom transfer radical polymerization in the presence of transition-metal complexes," *Macromolecules* 117(20): 5614-5615.

Wikipedia (Dec. 23, 2018). "Illumina Dye Sequencing,"located at https://en.wikipedia.org/wiki/Illumina_dye_sequencing, 6 pages, last accessed Jul. 15, 2022.

Yeole, N. (May 25, 2010). "Thiocarbonylthio Compounds," *Synlett* 10: 1572-1573.

York, A. G. et al. (Oct. 6, 2013). "Instant super-resolution imaging in live cells and embryos via analog image processing," *Nature Methods* 10: 1122-1126.

Zhou, H. C. et al. (Jan. 26, 2012, e-published Feb. 8, 2012). "Introduction to Metal-Organic Frameworks," *Chemical Reviews* 112(2): 673-674.

Zirvi, M. et al. (Dec. 1, 1999). "Ligase-based detection of mononucleotide sequences," *Nucleic Acids Research* 27(24): e40-e47.

* cited by examiner

Illustration of a 10 lane flow cell looking down in the z direction

COMPOSITIONS AND METHODS FOR NUCLEIC ACID SEQUENCING

CROSS-REFERENCE TO RELATED APPLICATIONS

This application claims the benefit of U.S. application Ser. No. 17/542,343 filed Dec. 3, 2021, which is a continuation of U.S. application Ser. No. 17/030,886, filed Sep. 24, 2020, now issued as U.S. Pat. No. 11,236,387, which is a continuation of International Application No. PCT/US2020/017060, filed Feb. 6, 2020, which claims the priority benefit of U.S. Provisional Application No. 62/802,062, filed Feb. 6, 2019, each of which is incorporated herein by reference in their entirety and for all purposes.

BACKGROUND

Sequencing-by-synthesis (SBS) is often performed by imaging clusters of amplicons having multiple identical copies of a starting molecule, rather than single-molecule analysis. As sequencing capacity has grown, it has pushed the limits of the density of cluster spacing that can be imaged. The maximum resolving power of imaging systems is limited by factors such as diffraction. Achieving high resolution typically involves using microscope objectives with a high numerical aperture (NA), which can limit the practical size of the field of view (FOV), and hence the total information content in each image.

Various methods of super-resolution imaging that have been developed enable optical imaging at resolution beyond diffraction limits. However, these approaches are not well suited to the high imaging rates typically utilized for DNA sequencing.

SUMMARY

In view of the foregoing, there is a need for improved methods of nucleic acid sequencing. The present disclosure addresses this need, and provides additional benefits as well.

In an aspect, provided herein are compositions including a plurality of cores surrounded by a shell polymer. In embodiments, each core of the plurality of cores is surrounded by a shell polymer, and the core is formed by polymerized units of core monomers forming a core polymer. In embodiments, one or more core polynucleotide primer(s) is attached to the core polymer within the core and a target nucleic acid is hybridized to the core primer. In embodiments, at least two different primers are attached to the core polymer within the core (e.g., a forward and a reverse primer). In embodiments, the shell polymer is formed by polymerized units of shell monomers, and the shell polymer is not attached to a polynucleotide primer.

In an aspect, provided herein are methods of amplifying a target polynucleotide, the methods including contacting a composition including a plurality of cores with a sample comprising a target polynucleotide, and amplifying the target polynucleotide to produce an amplicon. In embodiments, each core of the plurality of cores is surrounded by a shell polymer, and the core is formed by polymerized units of core monomers forming a core polymer. In embodiments, one or more core polynucleotide primer(s) is attached to the core polymer within the core. In embodiments, at least two different primers are attached to the core polymer within the core (e.g., a forward and a reverse primer). In embodiments, the shell polymer is formed by polymerized units of shell monomers, and the shell polymer is not attached to a polynucleotide primer. In embodiments, amplifying the target includes extension of the core primer hybridized to the target polynucleotide within the core.

In an aspect, provided herein are methods of sequencing target polynucleotides, the method including contacting a polymer scaffold with a sample that includes target polynucleotides, amplifying the target polynucleotides to produce discrete amplicon clusters, and sequencing the amplicon clusters. In embodiments, the polymer scaffold includes a polymer covalently attached to polynucleotide primers. In embodiments, amplifying the target includes extension of primers along the target polynucleotides within the polymer scaffold. In embodiments, each amplicon cluster originates from amplification of a single target polynucleotide, and the amplicon clusters are arranged in multiple two-dimensional planes. In embodiments, sequencing comprises detecting sequences of signals within the polymer scaffold through each of the plurality of two-dimensional planes.

BRIEF DESCRIPTION OF THE DRAWINGS

FIG. 1A depicts hexagonal closest packed (HCP) and FIG. 1B depicts cubic closest packed (CCP) type 3D structures.

FIG. 2A shows spherical particles with a core/shell structure arranged in a two-dimensional (2D) array. FIG. 2B shows spherical particles with a core/shell structure in a 3D arrangement. FIG. 2C shows an example of a 2D array in which shell polymers have expanded to fill space between particles shown in FIG. 2A. Similar expansion may be permitted in 3D arrangements as well.

FIG. 3A illustrates DNA clusters (shown as spheres) at random positions in a three-dimensional matrix (e.g., as in a polymer scaffold). FIG. 3B shows a microscopic image of an example scaffold, and a schematic showing attachments between a surface, a polymer, and polynucleotides.

FIG. 13A depicts a silica support particle (Si-support) coated in a core copolymer (core) containing active groups (e.g., DMA-GMA azide copolymer). Without an inert shell protecting the Si-support-core particle, they are capable of fusing together. FIG. 13B shows a silica support particle (Si-support) coated in a core copolymer (core) containing active groups (e.g., DMA-GMA azide copolymer), further surrounded in an inert copolymer (e.g., PEG). The Si-support-core-shell particles (represented by the dark circles) are not physically able to contact due to the presence of the inert shell. FIG. 13C shows an array of a plurality of Si-supported core-shell particles, wherein the average diameter of the silica support is 530 nm, the average diameter of the core (e.g., DMA-GMA azide) is 710 nm, and the average diameter of the shell is 955 nm.

FIG. 14A shows a polymer scaffold of particles (e.g., core-shell or core-shell-shell particles) arranged in an array. Not shown are the internal cores, which contain oligonucleotides, nor the multiple fluorescent events upon nucleotide incorporation within the particles. Using, e.g., confocal microscopy or multi-photon microscopy, two-dimensional planes of images are collected by scanning along one axis (e.g., the z direction). Note, multiple two-dimensional planes may be acquired for the same particles in the xy plane (e.g., Scan-1 and Scan-2) whereby detection events may be occurring on different z-planes within those particles, or two-dimensional planes may be acquired for the different particles in the xy plane (e.g., Scan-1 and Scan-3). These images, shown in FIG. 14B, may then be further processed to determine the fluorescent event, and thus the sequence of the target polynucleotide.

DETAILED DESCRIPTION

Figure 1A:
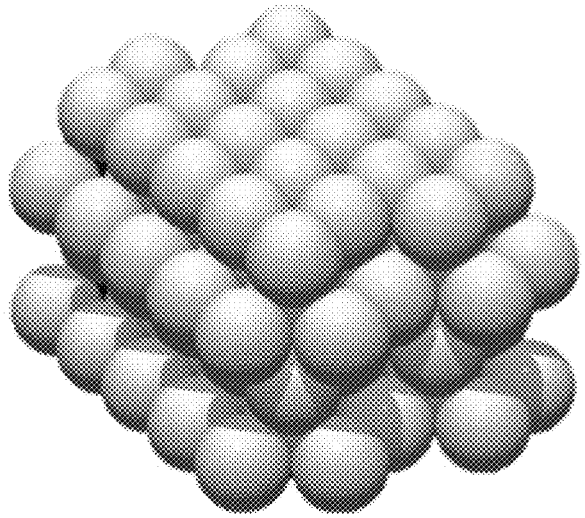
FIGS. 1A-B illustrates examples of closest packed three-dimensional (3D) structures.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms “a”, “an”, and “the” include the plural reference unless the context clearly indicates otherwise.

Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term “about” means a range of values including the specified value, which a person of ordinary skill in the art would consider reasonably similar to the specified value. In embodiments, the term “about” means within a standard deviation using measurements generally acceptable in the art. In embodiments, about means a range extending to +/−10% of the specified value. In embodiments, about means the specified value.

Throughout this specification, unless the context requires otherwise, the words “comprise”, “comprises” and “comprising” will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In the description, relative terms such as "before," "after," "above," "below," "up," "down," "top" and "bottom" as well as derivative thereof (e.g., "horizontally," "downwardly," "upwardly," etc.) should be construed to refer to the orientation as then described or as shown in the drawing or figure under discussion. These relative terms are for convenience of description and do not require that the system be constructed or operated in a particular orientation.

The terms "attached," "bind," and "bound" as used herein are used in accordance with their plain and ordinary meanings and refer to an association between atoms or molecules. The association can be direct or indirect. For example, attached molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. Another example of complementary sequences are a template sequence and an amplicon sequence polymerized by a polymerase along the template sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, one or both sequences in a pair of complementary sequences form portions of longer polynucleotides, which may or may not include additional regions of complementarity.

As used herein, the term "hybridize" or "specifically hybridize" refers to a process where two complementary nucleic acid strands anneal to each other under appropriately stringent conditions. Hybridizations are typically and preferably conducted with oligonucleotides. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not.

As used herein, the term "stringent condition" refers to condition(s) under which a polynucleotide probe or primer will hybridize preferentially to its target sequence, and to a lesser extent to, or not at all to, other sequences. A "stringent hybridization" and "stringent hybridization wash conditions" in the context of nucleic acid hybridization are sequence dependent, and are different under different environmental parameters.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "polynucleotide template" refers to any polynucleotide molecule that may be bound by a polymerase and utilized as a template for nucleic acid synthesis. As used herein, the term "polynucleotide primer" refers to any polynucleotide molecule that may hybridize to a polynucleotide template, be bound by a polymerase, and be extended in a template-directed process for nucleic acid synthesis, such as in a PCR or sequencing reaction. Polynucleotide primers attached to a core polymer within a core are referred to as "core polynucleotide primers." A primer can be of any length depending on the particular technique it will be used for. For example, PCR primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

As used herein, the term "analogue", in reference to a chemical compound, refers to a compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as primers attached to a polymer. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both.

As used herein, the term "core" refers to a polymer within which polynucleotide primers are attached, and that is surrounded by a "shell polymer" to which no polynucleotide primers are attached. The presence of the polynucleotide primer within the core permits a nucleic acid amplification reaction to take place, while the shell polymer provides a physical barrier between amplification reactions in adjacent cores. The cores are "surrounded" by the shell polymer in the sense that the shell polymer completely covers each core, and no core is in direct contact with any other core. The shell layer may enclose (e.g., surround, encapsulate, envelope) a core. In embodiments, each core surrounded by the shell polymer forms a discrete particle, the outer surface of which is defined by the shell polymer. In embodiments, the shells of discrete core-shell particles suspended in a container (e.g., a well, tube, or flow cell) expands, to fill any space between adjacent particles. In such cases, the boundaries of individual particles may no longer be readily discernable, but each core remains separated from each other by the shell polymer surrounding each, which can be readily observed by, e.g., detecting products of a nucleic acid amplification reaction. The core polymer may itself surround a solid support particle, such as a glass, ceramic, metal, silica, magnetic, or paramagnetic particle (e.g., a 500 nm silica nanoparticle). Solid support particles may be composed of any appropriate material. In embodiments, the support particle is an amorphous solid. In embodiments, the support particle is a crystalline solid. For example, solid support particles may include appropriate metals and metal oxides thereof (a metal particle core), carbon (an organic particle core) silica and oxides thereof (a silica particle core) or boron and oxides thereof (a boron particle core). For example, the core/shell layers may be formed around a supporting bead (alternatively referred to as a support particle), for example, a silica, magnetic, or paramagnetic bead. The term "support particle" as used herein may refer to any particle or substance having a diameter in the micrometer range, such as a "microparticle," which typically has a diameter of approximately 1 m and higher, or a "nanoparticle," which typically has a diameter of 1 nm to 1 μm. The core, optionally including a solid silica support particle, may be referred to herein as a nanoparticle core wherein the longest diameter is less than 1000 nanometers. Lengths and sizes of particles and their surrounding cores as described herein may be measured using Transmission Electron Microscopy (TEM). The term "silica" is used according to its plain and ordinary meaning and refers to a composition (e.g. a solid composition such as a particle) containing oxides of silicon such as Si atoms (e.g., in a tetrahedral coordination) with 4 oxygen atoms surrounding a central Si atom. A silica support particle may refer to a particle including a matrix of silicon-oxygen bonds.

As used herein, the term "polymer" refers to macromolecules having one or more structurally unique repeating units. The repeating units are referred to as "monomers," which are polymerized for for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

Figure 1B:
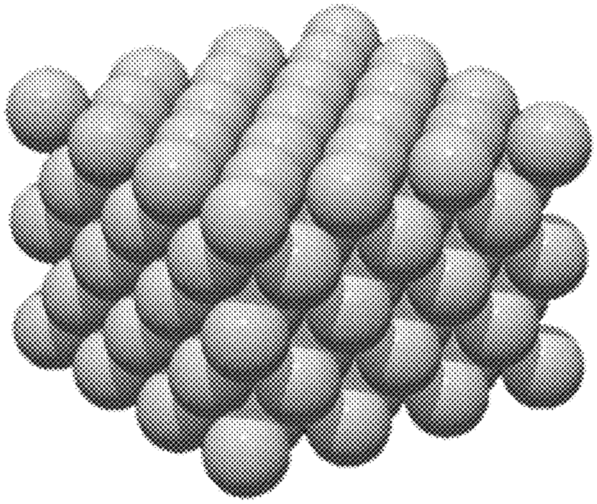

As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. Example are illustrated in FIGS. 1A-B, in which spheres are uniformly arranged, packed as closely together as their dimensions permit, and yet leave internal gaps. The fraction of the space actually occupied by the particles as compared to the entire bulk volume is referred to as the "space-filled fraction."

In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. In particular embodiments, a channel can be located in a flow cell, for example, being embedded within the flow cell. A channel in a flow cell can include one or more windows that are transparent to light in a particular region of the wavelength spectrum. In embodiments, the channel contains one or more polymers of the disclosure. In embodiments, the channel is filled by the one or more polymers, and flow through the channel (e.g., as in a sample fluid) is directed through the polymer in the channel.

As used herein, the term “substrate” refers to a solid support material. The substrate can be non-porous or porous. The substrate can be rigid or flexible. A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term “alkyl,” by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term “alkylene,” by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A “lower alkyl” or “lower alkylene” is a shorter chain alkyl or alkylene group, generally having eight or fewer carbon atoms. The term “alkenylene,” by itself or as part of another substituent, means, unless otherwise stated, a divalent radical derived from an alkene.

The term “heteroalkyl,” by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term “heteroalkenyl,” by itself or in combination with another term, means, unless otherwise stated, a heteroalkyl including at least one double bond. A heteroalkenyl may optionally include more than one double bond and/or one or more triple bonds in additional to the one or more double bonds. The term “heteroalkynyl,” by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term “heteroalkylene,” by itself or as part of another substituent, means, unless otherwise stated, a divalent radical derived from heteroalkyl, as exemplified, but not limited by, $—CH_2—CH_2—S—CH_2—CH_2—$ and $—CH_2—$ S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzooxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

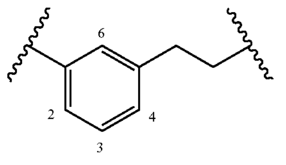

or

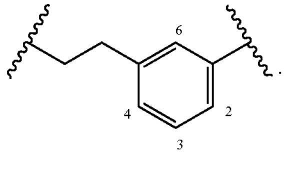

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'C(O)NR"R'", —NR"C$(O)_2$R', —NR—C(NR'R"R'")=NR"", —NR—C(NR'R")=NR'", —S(O)R', —$S(O)_2$R', —$S(O)_2$NR'R", —$NRSO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', halogen, —SiR'R"R", —OC(O)R', —C(O)R', —$CO_2$R', —CONR'R", —OC(O)NR'R", —NR"C(O)R', —NR'C(O)NR"R'", —NR"C$(O)_2$R', —NR—C(NR'R"R'")=NR"", —NR—C(NR'R")=NR'", —S(O)R', —$S(O)_2$R', —$S(O)_2$NR'R", —$NRSO_2$R', —NR'NR"R", —ONR'R", —NR'C(O)NR"NR'"R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'$, $-O-$, $-NR-$, $-S-$, $-S(O)-$, $-S(O)_2-$, $-S(O)_2NR'$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X' is $-O-$, $-NR'$, $-S-$, $-S(O)-$, $-S(O)_2-$, or $-S(O)_2NR'$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_5$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_5$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $R^{L5}$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L\text{-}4.1}$, $R^{L5.1}$ . . . $R^{L100.1}$) may be further substituted with one or more second substituent groups (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$ respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$, $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L.2}$, $R^{L5.2}$ . . . $R^{L100.2}$) may be further substituted with one or more third substituent groups (e.g., $R^{1.3}$, $R^{2.3}$, $R^{3.3}$, $R^{43}$, $R^{5.3}$ . . . $R^{13}$. $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited

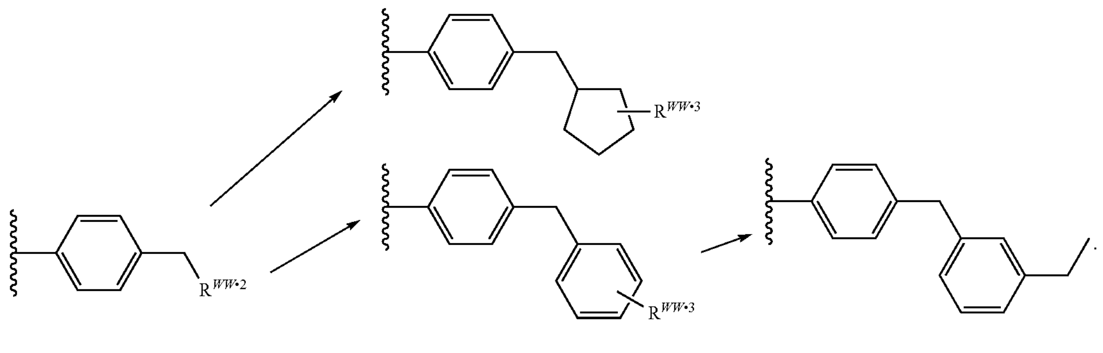

-continued

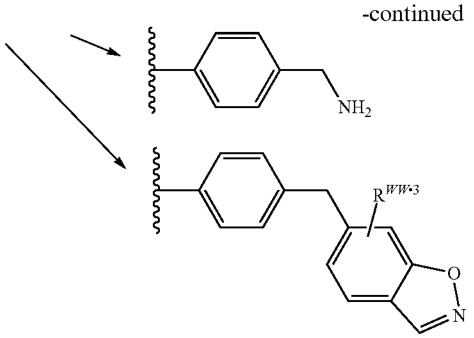

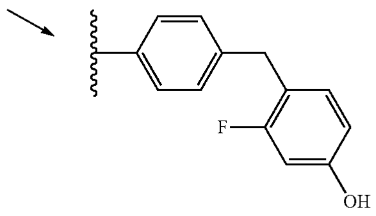

$R^{WW.1}$ is independently oxo, halogen, $-CX^{WW.13}$, $-CHX^{WW.12}$, $-CH_2X^{WW.1}$, $-OCX^{WW.13}$, $-OCH_2X^{WW.1}$, $-OCHX^{WW.12}$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, $-CX^{WW.3}_3$, $-CHX^{WW.3}_2$, $-CH_2X^{WW.3}$, $-OCX^{WW.3}_3$, $-OCH_2X^{WW.3}$, $-OCHX^{WW.3}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW}$—, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{LWW.2}$ substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$. $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{L1}$0.2-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $—CX^{LWW.1}_3$, $—CHX^{LWW.1}_2$, $—CH_2X^{LWW.1}$, $—OCX^{LWW.1}_3$$—OCH_2X^{LWW.1}$, $—OCHX^{LWW.1}_2$—CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$_substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, $—CX^{LWW.3}_3$, $—CHX^{LWW.3}_2$, $—CH_2X^{LWW.3}$, $—OCX^{LWW.3}_3$, $—OCH_2X^{LWW.3}$, $OCHX^{LWW.3}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, $—CX^{WW}_3$, $—CHX^{WW}_2$, $—CH_2X^{WW}$, $—OCX^{WW}_3$, $—OCH_2X^{WW}$, $—OCHX^{WW}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, $—SO_2NH—$, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$ substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$ substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{1.3}$ substituents are present, each $R^{1.3}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{1.3}$ and optionally differently.

Descriptions of compounds (e.g., polymers) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds.; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "non-reactive moiety" is used in accordance with its plain ordinary meaning and refers to a moiety that does not react with a nucleophile or an electrophile (e.g., under reaction conditions wherein other moieties in the same molecule may react with a nucleophile or electrophile, under click chemistry reaction conditions such as those conditions wherein an azide may react with dibenzocyclooctyne (DBCO) or an epoxide). In embodiments, the non-reactive moiety is attached to a polymer. In embodiments, the non-reactive moiety is hydrophilic. In embodiments, the non-reactive moiety increases the water solubility of a polymer that includes the non-reactive moiety. In embodiments, the non-reactive moiety is not a bioconjugate reactive moiety. In embodiments, the non-reactive moiety is an unsubstituted alkyl. In embodiments, the non-reactive moiety is hydrogen.

The term "nucleophile" as used herein refers to a chemical group that is capable of donating electron density. All molecules or ions with a free pair of electrons or at least one pi bond can act as nucleophiles.

The term "electrophile" as used herein refers to a chemical group that is capable of accepting electron density. An"electrophilic substituent", "electrophilic chemical moiety", or "electrophic moiety" refers to an electron-poor chemical group, substitutent, or moiety (monovalent chemical group), which may react with an electron-donating group, such as a nucleophile, by accepting an electron pair or electron density to form a bond.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Compositions

In an aspect, provided herein are compositions useful in nucleic acid sequencing, including for producing three-dimensional structures in which a sequencing reaction may occur and which can be imaged through multiple two-dimensional planes. In embodiments, the three-dimensional structures comprise a polymer matrix forming a 3D scaffold, and are suitable for generation of monoclonal DNA clusters. In embodiments, the 3D scaffold has a controlled spacing, a periodic structure, and/or separation between sequencing micro-volumes (e.g., clusters of amplicons). In embodiments, the 3D structure does not cause excessive light scattering, and allows for high-resolution imaging. The polymer(s) may have an index of refraction close to water. The 3D structure may allow for efficient movement of small molecules, including nucleotides, through the structure while also allowing for large molecules (enzymes, DNA templates) to be introduced into it. The optical system used to image the 3D volume may be capable of optically resolving or "sectioning" the volume, and imaging through multiple layers in the volume without unwanted interference from other layers. In embodiments, the 3D structures are formed by a collection of cores, with each core being surrounded by a polymer shell.

In an aspect, provided herein are compositions including a plurality of cores surrounded by a shell polymer. In embodiments, each core of the plurality of cores is surrounded by a shell polymer, and the core is formed by polymerized units of core monomers forming a core polymer. In embodiments, one or more core polynucleotide primer(s) is attached to the core polymer within the core and a target nucleic acid is hybridized to the core primer. In embodiments, at least two different primers are attached to the core polymer within the core (e.g., a forward and a reverse primer). In embodiments, the shell polymer is formed by polymerized units of shell monomers, and the shell polymer is not attached to a polynucleotide primer.

In embodiments, the plurality of cores are arranged in a two-dimensional array. In general, arrangement in a two-dimensional array involves the formation of a single layer of cores, and does not include multiple layers of cores. In general, signals in a given field of view within a two-dimensional array can be imaged at a single depth of focus. In embodiments, arranging cores in a two-dimensional array includes distributing particles on a surface (e.g., a surface of a well) such that substantially all particles (e.g., at least 90%, 95%, 99%, or 100%) are in contact with the surface, and each particle includes a core surrounded by a shell polymer (also referred to herein as "core-shell particles"). The maximum number of particles capable of forming a two-dimensional array without the formation of additional layers will depend on the size of the particles and the dimensions of the surface to which they are applied, as can be calculated by one skilled in the art. Two-dimensional arrays may be uniform (e.g., particles packed closely together with substantially no gaps, or having gaps of uniform size and in uniform intervals), or non-uniform (e.g., particles having an unordered arrangement of particles, such that some particles are closer together than others). For example, to produce a non-uniform arrangement of particles on a flat surface, particles may be applied to a surface at a concentration such that particles only occupy about 80% of the surface area, and are allowed to come to rest at random positions. In embodiments, a two-dimensional array is stabilized by cross-linking particles to a surface and/or to one another. In embodiments comprising core-shell particles, polymers may expand within the array to fill available space.

Figure 14A:
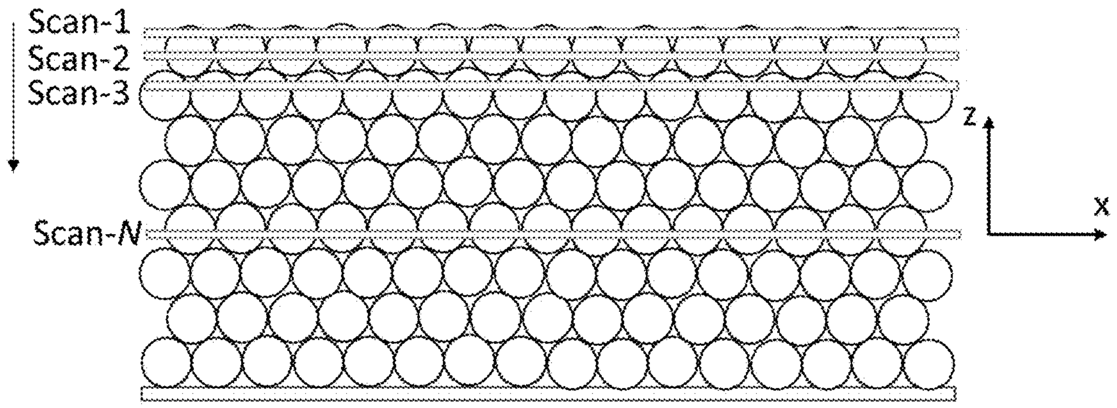
FIGS. 14A-14B depict multi-dimensional detection for polymer scaffolds described herein.
Figure 14B:
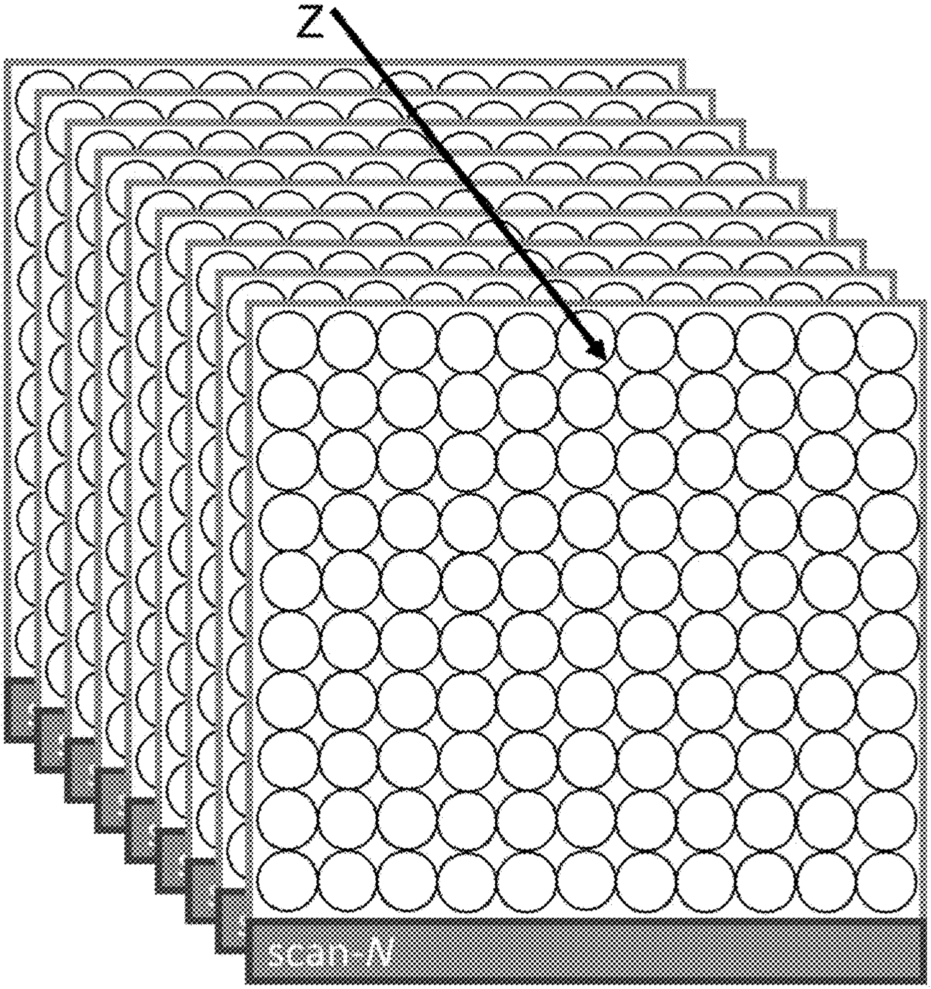
Figure 15:
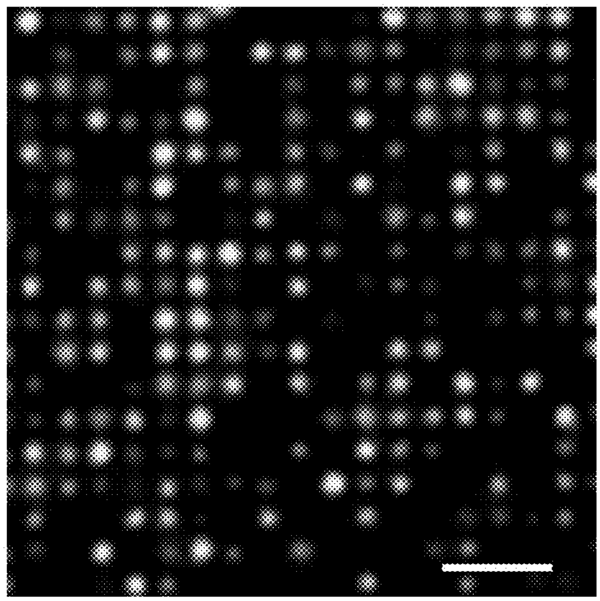
FIG. 15 shows a 2D image of a single nucleotide extension of a primer hybridized to a target polynucleotide template. The particles are an average 500 nm silica core particle surrounded with a GMA-DMA polymer, which are immobilized on a surface with 3 um spacing between the particles. The target polynucleotides are conjugated on the polymer and fluorophore-labeled nucleotides are enzymatically incorporated for sequencing application. The resulting image is captured during excitation of the fluorophore. Scale bar=10 um.

In embodiments, the plurality of cores are arranged in multiple two-dimensional planes (see, e.g., FIGS. 14A-14B). In this context, "multiple two-dimensional planes" refers to a general arrangement in which cores form a three-dimensional matrix, as opposed to a single layer in a two-dimensional array. By occupying multiple two-dimensional planes, the three-dimensional matrix may be considered as a plurality of layers, each of which can be separately imaged by focusing at different depths through the three-dimensional matrix, e.g., along an axis. The term "layer" is not to be construed as requiring any uniform arrangement through or boundaries within the matrix.

In embodiments, the plurality of cores are uniformly arranged. In some embodiments, the plurality of cores are not uniformly arranged. In general, an arrangement is considered "uniform" when the spacing between cores is defined and substantially the same from one core to the next. For example, in the case of closely-pack core-shell particles in which each core and shell has about the same dimensions, each core is separated from an adjacent core by a space defined by the thickness of two shells. In general, an arrangement lacking a substantially regular spacing between cores is considered non-uniform. For example, core-shell particles may be collected in a volume at a concentration that allows for irregular gaps (e.g., bubble-like spaces of a suspending fluid) surrounded by particles that form the matrix. In embodiments, a three-dimensional matrix of cores is stabilized by cross-linking core-shell particles to a surface and/or to one another.

In embodiments, the plurality of cores surrounded by the shell polymer form a plurality of discrete particles. In embodiments, the plurality of discrete particles exhibit a filled space fraction of about or at least about 40%, 50%, 60%, 70%, or more. In embodiments, the plurality of discrete particles exhibit a filled-space fraction of at least 70%. In embodiments, the plurality of discrete particles exhibit a filled-space fraction of about 74%.

In embodiments, the plurality of cores are contained in a channel of a substrate. In embodiments, the channel has a width of about 3 to about 5 millimeters. In embodiments, the width is at least or at most, 1, 2, 3, 4, 5, 6, 7, 8, 9, or 10 millimeters or a number or a range between any two of these values. In embodiments, the width is about 1 to about 10, about 2 to about 9, about 3 to about 8, about 4 to about 7, or about 5 to about 6 millimeters or a number or a range between any two of these values. In embodiments, the channel has a length of about 5 to about 10 centimeters. In embodiments, the length is at least or at most, 1, 2, 3, 4, 5, 6, 7, 8, 9, 10, 11, 12, 13, 14, 15, 16, 17, 18, 19, or 20 centimeters or a number or a range between any two of these values. In embodiments, the length is about 1 to about 20, about 2 to about 19, about 3 to about 18, about 4 to about 17, about 5 to about 16, about 6 to about 15, about 7 to about 14, about 8 to about 13, about 9 to about 12, about 10 to about 11 centimeters or a number or a range between any two of these values. In embodiments, the channel has a depth of about 50 to about 300 microns. In embodiments, the channel has a depth of about 50 to about 200 microns. In embodiments, the depth is at least or at most 10, 30, 50, 70, 90, 110, 130, 150, 170, 190, 210, 230, 250, 270, 290, or 300 microns or a number or a range between any two of these values. In embodiments, the channel has a depth of about 10 to about 300, about 50 to about 200, about 100 to about 150 microns or a number or a range between any two of these values. In embodiments, the channel has a width of about 3-5 mm, a length of about 5-10 cm, and a depth of about 50-200 μm.

In embodiments, the composition fills the channel. In embodiments, the composition fills the channel, and contacting the composition with a sample and/or reagents for conducting a reaction (e.g., an amplification reaction and/or a sequencing reaction) includes flowing the sample and/or reagents through the composition (e.g., through a matrix of core-shell particles). In some embodiments, the composition forms a layer within the channel over which a fluid containing a sample and/or reagents for conducting a reaction can flow. In embodiments, the composition forms a layer that is about or less than about 95%, 90%, 85%, 80%, 70%, 60%, 50%, or less of the volume of the channel, as defined by the channel dimensions.

In embodiments, the composition further includes a solvent. In embodiments, the presence of the solvent expands the volume of the composition by up to 10%, up to 20%, up to 30%, up to 40%, up to 50%, up to 60%, up to 70%, up to 80%, up to 100%, up to 150%, up to 200%, or more relative to the absence of the solvent. In embodiments, the solvent expands the volume of the composition by 10-200%, 30-150%, or 50-100%, relative to the absence of the solvent. In embodiments, the presence of the solvent expands the volume of the composition by up to 90% relative to the absence of the solvent. In embodiments, the solvent is water.

In embodiments, polymers of the present disclosure (e.g., core polymers, shell polymers, and matrices of core-shell particles) swell with a solvent in which they are suspended, and the refractive index of the suspension is about the same as the solvent. In embodiments, the plurality of cores, the shell polymer, or both include water. In embodiments, the plurality of cores and the shell polymer both include water. In embodiments, the core polymer, the shell polymer, or both have a refractive index of about 1.2-1.6, 1.25-1.5, or 1.3-1.4 when hydrated. In embodiments, the core polymer, the shell polymer, or both have a refractive index of about 1.3 when hydrated.

The core polymer may be polymerized from a mixture of functionalized and non-functionalized monomers, such that at least some functionalized monomers that provide attachment points for primers are spaced from one another by one or more monomers lacking such attachment points. The frequency of monomer units attached to primers within a core polymer can be adjusted by changing the concentration of the corresponding functionalized monomer in the mixture of monomers. In embodiments, monomer units of the core polymer that are attached to a polynucleotide primer are separated by, on average, about or at least about 1, 2, 3, 4, 5, 10, 15, 20, 25, 30, 40, 50, or more monomer units that are not attached to a primer. In embodiments, some of the core monomers are the same as some of the shell monomers. In embodiments, primer-attached monomers are separated by, on average, about 1-50, 2-40, 3-30, 4-25, or 5-20 monomers not attached to primers. The mixture can comprise monomers with different functional groups.

The manner in which a polynucleotide primer is attached to the core polymer will depend on the type of functional group used to form the attachment. A variety of suitable functional groups are available, examples of which are provided herein. In embodiments, shell polymers, while not attached to a polynucleotide primer, may nonetheless comprise one or more functional groups. Functional groups in the shell polymer may be used for a purpose other than attaching to a primer, such as for crosslinking between multiple shells and/or a surface to fix relative positions of cores. The core polymer may be polymerized from a mixture of functionalized and non-functionalized monomers, and/or a mixture of monomers with different functional groups. In embodiments, functional groups are selected that specifically react with their intended target (e.g., a paired functional group attached to a desired target, such as a primer), while also exhibiting anti-fouling characteristics that prevent, or have a reduced propensity for, non-specific binding of enzymes, dye-labeled nucleotides, and nucleic acids.

Core polymers and shell polymers can comprise any of a variety of polymers. In embodiments, the plurality of cores, the shell polymer, or both are a hydrogel. In embodiments, each of the plurality of cores is a hydrogel. In embodiments, the shell polymer is a hydrogel. In embodiments, the plurality of cores and the shell polymer are a hydrogel. Examples of hydrogels include, but are not limited to agarose- and acrylamide-based gels, such as polyacrylamide, poly-N-isopropylacrylamide, poly N-isopropylpoly-acrylamide, 2-hydroxyethyl acrylate and methacrylate, zwitterionic monomers, polyethylene glycol acrylate and methacrylate. In embodiments, an aqueous solution of one or more types of monomers is dispersed in a droplet, and then polymerized, e.g., to form a gel. Another example of a hydrogel includes alginic acid that can be gelled by the addition of calcium ions. As a further example, gelation initiators (e.g., ammonium persulfate and TEMED for acrylamide, or $Ca^{2+}$ for alginate) can be added to a droplet, for example, by co-flow with the aqueous phase, by co-flow through the oil phase, or by coalescence of two different drops. In embodiments, the monomers include acrylate and/or methacrylate monomers. In embodiments, monomers include hydrophilic and/or hydrophobic monomers. In embodiments, the core polymer, the shell polymer, or both comprise a polymer of one or more of acrylate, methacrylate, polyolefins, styrene, polycarbonates, polyurethanes, polysiloxanes, polyalkyloxides, polynorbornene, or polysaccharides. In embodiments, the core polymer, the shell polymer, or both comprise a polymer of one or more of GMA (glycidyl methacrylate), HEMA (Hydroxyethylmethacrylate), HEA (Hydroxyethylacrylate), or HPMA(hydroxypropylmethacrylate). In further embodiments, polymer particles are collectively polymerized from monomers in a solution. The type and concentration of monomers, and the duration of the polymerization reaction may be selected to produce particles of polymers having a desired average size. In embodiments, polymerization from core monomers is terminated and the resulting cores are contacted with a different solution including the shell monomers to polymerize shells surrounding cores.

In embodiments, each core has a core diameter, the shell polymer surrounding each core has a thickness defining an outer shell diameter, and the core and shell diameters are designed to have particular dimensions. In embodiments, the core diameter may be about 5% to about 95%, about 10% to about 90%, about 20% to about 80%, about 30% to about 70%, or about 40% to about 60% of the outer shell diameter, or a number or a range between any two of these values. In embodiments, the core diameter about or at most about 10%, 20%, 30%, 40%, 50%, 60%, 70%, 80%, 90%, 95%, or 99% of the shell diameter or a number or a range between any two of these values. In embodiments, the core diameter is about 20% to about 80% of the outer shell diameter, or about 50% of the shell diameter.

In embodiments, the core diameter is about 50-2000 nanometers, 500-1500 nanometers, about 1000 nanometers, or a number or a range between any two of these values. In embodiments, the core diameter is at least, about, or at most 100, 200, 300, 400, 500, 600, 700, 800, 900, 1000, 1100, 1200, 1300, 1400, 1500, 1600, 1700, 1800, 1900, 2000 nanometers or a number or a range between any two of these values. In embodiments, the shell diameter is about 0.1-10 microns, 0.25-5 microns, 0.5-2 microns, 1 micron, or a number or a range between any two of these values. In embodiments, the shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm or a number or a range between any two of these values. In embodiments, the core diameter is about 200-1200 nanometers, and/or the shell diameter is about 0.25-5 μm (microns).

In embodiments, the core polynucleotide primer is covalently attached to the core polymer. In embodiments, the 5' end of the polynucleotide contains a functional group that is tethered to the core. Non-limiting examples of covalent attachment include amine-modified polynucleotides reacting with epoxy or isothiocyanate groups on the core, succinylated polynucleotides reacting with aminophenyl or aminopropyl functional groups on the core, dibenzocyclooctyne-modified polynucleotides reacting with azide functional groups on the core (or vice versa), trans-cyclooctyne-modified polynucleotides reacting with tetrazine or methyl tetrazine groups on the core (or vice versa), disulfide modified polynucleotides reacting with mercapto-functional groups on the core, amine-functionalized polynucleotides reacting with carboxylic acid groups on the core via 1-ethyl-3-(3-dimethylaminopropyl)-carbodiimide hydrochloride (EDC) chemistry, thiol-modified polynucleotides attaching to a core via a disulphide bond or maleimide linkage, alkyne-modified polynucleotides attaching to a core via copper-catalyzed click reactions to azide functional groups on the core, and acrydite-modified polynucleotides polymerizing with free acrylic acid monomers on the core to form polyacrylamide or reacting with thiol groups on the core. In embodiments, the core polynucleotide primer is attached to the core polymer through electrostatic binding. For example, the negatively charged phosphate backbone of the primer may be bound electrostatically to positively charged monomers in the core.

In embodiments, each core includes multiple copies of one or more core polynucleotide primer(s). In embodiments, the one or more core polynucleotide primers include at least two different primers attached to the core polymer within the core (e.g., a forward and a reverse primer), each of which may be present in multiple copies. In embodiments, about or at most at most about 50%, 40%, 30%, 25%, 20%, 15%, 10%, 5%, or less of the core monomers in the core polymer of each core are attached to a copy of the core polynucleotide primer. In embodiments, about 1-25%, about 2-20%, about 3-15%, about 4-14%, or about 5-12% of the core monomers in the core polymer of each core are attached to a copy of the core polynucleotide primer, or a number or a range between any two of these values. In embodiments, about 5-10% of the core monomers in the core polymer of each core are attached to a copy of the core polynucleotide primer.

In embodiments, the core polymer and shell polymer are permeable to a polymerase for amplifying the target polynucleotide. In embodiments, the shell polymer has a higher permeability than the core polymer. In embodiments, the core polymer and shell polymer have the same permeability. In embodiments, the shell polymer is permeable to a polymerase for amplifying the target polynucleotide, such that the interface of the core is in contact with the polymerase. In embodiments, the core polymer and shell polymer are permeable to a sequencing reaction mixture. The term "sequencing reaction mixture" refers to an aqueous mixture that contains the reagents necessary to allow addition of a nucleotide to a polynucleotide strand by a polymerase (e.g., addition of a dNTP or dNTP analogue to a DNA strand by a DNA polymerase). Exemplary mixtures include buffers (e.g., saline-sodium citrate (SSC), tris(hydroxymethyl)aminomethane or "Tris"), salts (e.g., KCl or $(NH_4)_2SO_4$)), nucleotides, polymerases, cleaving agent (e.g., tri-n-butylphosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the shell polymer is permeable to a sequencing reaction mixture for amplifying the target polynucleotide, such that the interface of the core is in contact with the sequencing reaction mixture.

In embodiments, each core contains one or more reagents for amplifying the target polynucleotide (e.g., a sequencing reaction mixture). Examples of reagents include but are not limited to polymerase, buffer, and nucleotides. In embodiments, the nucleotides are reversibly terminated nucleotides carrying fluorescent dyes, such that the identity of a nucleotide added in a sequencing reaction can be identified based on the fluorescent dye with which it is associated.

In embodiments, each core further includes a detectable label that indicates the identity of a nucleotide in the target polynucleotide. In embodiments, the detectable label is a fluorescent label.

In embodiments, each core further includes a silica, magnetic, or paramagnetic material, such as in the form of a bead. For example, the core/shell layers may be formed around a supporting bead, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place.

Methods

In an aspect, provided herein are methods of amplifying a target polynucleotide. The methods include contacting a composition including a plurality of cores with a sample that includes a target polynucleotide and amplifying the target polynucleotide to produce an amplicon. In embodiments, amplifying the target includes extension of a core primer hybridized to the target polynucleotide within the core. In embodiments, each core of the plurality of cores is surrounded by a shell polymer, and the core is formed by polymerized units of core monomers forming a core polymer. In embodiments, a core polynucleotide primer is attached to the core polymer within the core and a target nucleic acid is hybridized to the core primer. In embodiments, at least two different primers are attached to the core polymer within the core (e.g., a forward and a reverse primer), which may facilitate generating multiple amplification products from a target polynucleotide. In embodiments, the shell polymer is formed by polymerized units of shell monomers, and the shell polymer is not attached to a polynucleotide primer.

In embodiments, the method further includes sequencing the amplicon. Sequencing includes, for example, detecting a sequence of signals within the core. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein.

In embodiments of the methods provided herein, the plurality of cores are arranged in a two-dimensional array. In embodiments, the cores are arranged in the two-dimensional array after an amplifying step. Examples of two-dimensional arrays are described herein, such as with respect to the various compositions described herein.

In embodiments of the methods provided herein, the plurality of cores are arranged in multiple two-dimensional planes. Examples of two-dimensional arrays are described herein, such as with respect to the various compositions described herein.

In embodiments of the methods provided herein, the plurality of cores are uniformly arranged. In embodiments, the plurality of cores are not uniformly arranged.

In embodiments of the methods provided herein, the plurality of cores surrounded by the shell polymer form a plurality of discrete particles. In embodiments, the plurality of discrete particles exhibit a filled space fraction of about or at least about 40%, 50%, 60%, 70%, or more. In embodiments, the plurality of discrete particles exhibit a filled-space fraction of at least 70%. In embodiments, the plurality of discrete particles exhibit a filled-space fraction of about 74%.

In embodiments of the methods provided herein, arrangement of the cores may take place before the step of contacting a composition including a plurality of cores with a sample that includes a target polynucleotide. In embodiments of the methods provided herein, arrangement of the cores may take place after the step of contacting a composition including a plurality of cores with a sample that includes a target polynucleotide but before the step of amplifying the target polynucleotide to produce an amplicon. In embodiments of the methods provided herein, arrangement of the cores may take place after the step of amplifying the target polynucleotide to produce an amplicon.

In embodiments of the methods provided herein, the plurality of shells are cross-linked to each other and/or to a surface of a container that contains a plurality of cores. In embodiments, the plurality of shells are cross-linked to each other. In some embodiments, the plurality of shells are cross-linked to a surface of a container that contains a plurality of cores. In general, cross-linking involves joining two or more molecules, such as by a covalent bond, non-covalent interactions, or interactions with one or more intermediate molecules. Examples of crosslinking reagents (or crosslinkers) include molecules that contain two or more reactive ends capable of chemically attaching to specific functional groups. Non-limiting examples of functional groups are described herein, such as with respect to the various compositions of the present disclosure.

In embodiments of the methods provided herein, the plurality of cores are contained in a channel of a substrate. In embodiments, the channel has a width of about 3 to about 5 millimeters. In embodiments, the width is at least or at most, 1, 2, 3, 4, 5, 6, 7, 8, 9, or 10 millimeters or a number or a range between any two of these values. In embodiments, the width is about 1 to about 10, about 2 to about 9, about 3 to about 8, about 4 to about 7, or about 5 to about 6 millimeters or a number or a range between any two of these values. In embodiments, the channel has a length of about 5 to about 10 centimeters. In embodiments, the length is at least or at most, 1, 2, 3, 4, 5, 6, 7, 8, 9, 10, 11, 12, 13, 14, 15, 16, 17, 18, 19, or 20 centimeters or a number or a range between any two of these values. In embodiments, the length is about 1 to about 20, about 2 to about 19, about 3 to about 18, about 4 to about 17, about 5 to about 16, about 6 to about 15, about 7 to about 14, about 8 to about 13, about 9 to about 12, about 10 to about 11 centimeters or a number or a range between any two of these values. In embodiments, the channel has a depth of about 50 to about 300 microns. In embodiments, the channel has a depth of about 50 to about 200 microns. In embodiments, the depth is at least or at most 10, 30, 50, 70, 90, 110, 130, 150, 170, 190, 210, 230, 250, 270, 290, or 300 microns or a number or a range between any two of these values. In embodiments, the channel has a depth of about 10 to about 300, about 50 to about 200, about 100 to about 150 microns or a number or a range between any two of these values. In embodiments, the channel has a width of about 3-5 mm, a length of about 5-10 cm, and a depth of about 50-200 μm.

In embodiments, the composition fills the channel. In embodiments, the composition fills the channel, and contacting the composition with a sample and/or reagents for conducting a reaction (e.g., an amplification reaction and/or a sequencing reaction) includes flowing the sample and/or reagents through the composition (e.g., through a matrix of core-shell particles). In some embodiments, the composition forms a layer within the channel over which a fluid containing a sample and/or reagents for conducting a reaction can flow. In embodiments, the composition forms a layer that is about or less than about 95%, 90%, 85%, 80%, 70%, 60%, 50%, or less of the volume of the channel, as defined by the channel dimensions.

In embodiments, the composition further includes a solvent. In embodiments, the presence of the solvent expands the volume of the composition by up to 10%, up to 20%, up to 30%, up to 40%, up to 50%, up to 60%, up to 70%, up to 80%, up to 100%, up to 150%, up to 200%, or more relative to the absence of the solvent. In embodiments, the solvent expands the volume of the composition by 10-200%, 30-150%, or 50-100%, relative to the absence of the solvent. In embodiments, the presence of the solvent expands the volume of the composition by up to 90% relative to the absence of the solvent. In embodiments, the solvent is water.

In embodiments, polymers of the present disclosure (e.g., core polymers, shell polymers, and matrices of core-shell particles) swell with a solvent in which they are suspended, and the refractive index of the suspension is about the same as the solvent. In embodiments, the plurality of cores, the shell polymer, or both include water. In embodiments, the plurality of cores and the shell polymer both include water. In embodiments, the core polymer, the shell polymer, or both have a refractive index of about 1.2-1.6, 1.25-1.5, or 1.3-1.4 when hydrated. In embodiments, the core polymer, the shell polymer, or both have a refractive index of about 1.3 when hydrated.

In embodiments of the methods provided herein, the core polymer may be polymerized from a mixture of functionalized and non-functionalized monomers, such that at least some functionalized monomers that provide attachment points for primers are spaced from one another by one or more monomers lacking such attachment points. Non-limiting examples of monomers and mixtures thereof for the formation of polymers (e.g., core polymers and shell polymers) and for attachment to polynucleotide primers are provided herein, such as with regard to the various compositions of the present disclosure. In embodiments, some of the core monomers are the same as some of the shell monomers. In embodiments, shell polymers, while not attached to a polynucleotide primer, may nonetheless comprise one or more functional groups. Functional groups in the shell polymer may be used for a purpose other than attaching to a primer, such as for crosslinking between multiple shells and/or a surface to fix relative positions of cores. The core polymer may be polymerized from a mixture of functionalized and non-functionalized monomers, and/or a mixture of monomers with different functional groups.

Core polymers and shell polymers can comprise any of a variety of polymers, such as a polymer described herein with respect to any of the various compositions of the present disclosure. In embodiments of the methods provided herein, the plurality of cores, the shell polymer, or both are a hydrogel. In embodiments, each of the plurality of cores is a hydrogel. In embodiments, the shell polymer is a hydrogel. In embodiments, the plurality of cores and the shell polymer are hydrogel. Non-limiting examples of hydrogels are described above, such as with regard to the various compositions of the present disclosure.

In embodiments of the methods provided herein, each core has a core diameter, the shell polymer surrounding each core has a thickness defining an outer shell diameter, and the core and shell diameters are designed to have particular dimensions. In embodiments, the core diameter may be about 5% to about 95%, about 10% to about 90%, about 20% to about 80%, about 30% to about 70%, or about 40% to about 60% of the outer shell diameter, or a number or a range between any two of these values. In embodiments, the core diameter about or at most about 10%, 20%, 30%, 40%, 50%, 60%, 70%, 80%, 90%, 95%, or 99% of the shell diameter or a number or a range between any two of these values. In embodiments, the core diameter is about 20% to about 80% of the outer shell diameter, or about 50% of the shell diameter.

In embodiments of the methods provided herein, the core diameter is about 50-2000 nanometers, 500-1500 nanometers, about 1000 nanometers, or a number or a range between any two of these values. In embodiments, the core diameter is at least, about, or at most 100, 200, 300, 400, 500, 600, 700, 800, 900, 1000, 1100, 1200, 1300, 1400, 1500, 1600, 1700, 1800, 1900, 2000 nanometers or a number or a range between any two of these values. In embodiments, the shell diameter is about 0.1-10 microns, 0.25-5 microns, 0.5-2 microns, 1 micron, or a number or a range between any two of these values. In embodiments, the shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the core diameter is about 200-1200 nanometers, and/or the shell diameter is about 0.25-5 μm (microns).

In embodiments, the polynucleotide primer is covalently or non-covalently attached to the core polymer. The attachment can be any suitable attachment, examples of which are described herein, such as with respect to the various compositions of the present disclosure. In embodiments of the methods provided herein, each core includes multiple copies of the core polynucleotide primer. In embodiments, about or at most at most about 50%, 40%, 30%, 25%, 20%, 15%, 10%, 5%, or less of the core monomers in the core polymer of each core are attached to a copy of the core polynucleotide primer. In embodiments, about 1-25%, about 2-20%, about 3-15%, about 4-14%, or about 5-12% of the core monomers in the core polymer of each core are attached to a copy of the core polynucleotide primer, or a number or a range between any two of these values. In embodiments, about 5-10% of the core monomers in the core polymer of each core are attached to a copy of the core polynucleotide primer.

In embodiments, amplifying (and optionally sequencing) comprises contacting compositions of the present disclosure with a polymerase. In embodiments of the methods provided herein, the core polymer and shell polymer are permeable to a polymerase for amplifying the target polynucleotide. In embodiments, the shell polymer has a higher permeability than the core polymer. In embodiments, the core polymer and shell polymer have the same permeability. In embodiments, amplifying (and optionally sequencing) comprises contacting compositions of the present disclosure with a sequencing reaction mixture.

In embodiments of the methods provided herein, the contacting step is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymer matrix (e.g., a matrix of core-shell particles) prior to subsequent steps (e.g. amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions comprises a temperature that is about or at least about 5, 10, 15, 20, or more degrees above the average Tm of primers in the reaction.

In embodiments of the methods provided herein, the amplifying step further includes contacting the plurality of cores with one or more reagents for amplifying the target polynucleotide. Examples of reagents include but are not limited to polymerase, buffer, and nucleotides (e.g., a sequencing reaction mixture). In embodiments, the nucleotides are reversibly-terminated nucleotides carrying fluorescent dyes.

In embodiments of the methods provided herein, the sample includes a plurality of target polynucleotides at a concentration selected such that a majority of the cores in which the amplification occurs includes amplicons of only one original target polynucleotide. In embodiments, about or at least about 60%, 70%, 80%, 90%, 95%, or more of the cores in which amplification occurs contains amplicons of only one original target polynucleotide.

In embodiments, the methods further include a step of separating cores that include amplicons from cores that do not include amplicons. For example, cores that do not include amplicon, also referred to as "blank" cores, can be separated from cores with amplicon by charge-based separation. Since DNA carries a negative charge, the cores that contain amplified products will be significantly charged compared to the "blank" cores. The cores containing amplicons can be separated from the "blank" particles by an electric field. By choosing a relatively low seeding ratio, e.g. <20%, or <10%, or <5%, the probability of having more than 1 template per particle (multiple seeding) can be greatly reduced. The large fraction of unseeded "blank" particles can then be removed by charge-based separation, resulting in nearly pure population of single-seeded particles for monoclonal amplification. In embodiments, the methods comprise amplifying a target polynucleotide in solution, separating cores containing amplicons from "blank" cores, and depositing the cores containing amplicons in a container (e.g., a flow cell) for sequencing.

In embodiments, the methods further include repeating the contacting and amplifying steps using the separated cores that do not include an amplicon. In embodiments, the contacting is repeated with an aliquot of the same sample as in the original contacting, and cores from the repeated steps are pooled (e.g., in a container, such as a flow cell) prior to sequencing. In embodiments, repeating the contacting and amplifying steps does not involve separating cores that do not include an amplicon from those that do.

In embodiments of the methods provided herein, the sequencing step includes extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'—OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. No. 8,178,360.

In embodiments of the methods provided herein, the detecting step includes imaging through each of the multiple two-dimensional planes at a resolution sufficient to distinguish one imaged plane from an adjacent imaged plane. In embodiments of the methods provided herein, the detecting step includes imaging through each of the multiple two-dimensional planes at a resolution sufficient to distinguish one particle from an adjacent particle. In embodiments of the methods provided herein, the detecting step includes imaging through each of the multiple two-dimensional planes at a resolution sufficient to distinguish one particle from another vertically adjacent particle. In embodiments, overlap of a signal of a core in one layer appearing in adjacent layer, is computationally resolved, for example, by imaging software. In embodiments of the methods provided herein, the imaging is accomplished by confocal microscopy, multi-photon microscopy, or light sheet fluorescence microscopy (LSFM). In embodiments, the imaging is accomplished by confocal microscopy. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. In embodiments, the imaging is accomplished by LSFM.

In embodiments of the methods provided herein, the amplifying step includes amplifying a target polynucleotide in two or more cores in the plurality of discrete particles, and the sequencing step includes sequencing an amplicon in two or more cores in the plurality of discrete particles. In embodiments, a plurality of different target polynucleotides are amplified and sequenced in a single collection of a plurality of cores. It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification comprises an isothermal amplification reaction. In embodiments, amplification comprises bridge amplification. In general, bridge amplification uses repeated steps of annealing of primers to templates, primer extension, and separation of extended primers from templates. Because primers are attached within the core polymer, the extension products released upon separation from an initial template is also attached within the core. The 3' end of an amplification product is then permitted to anneal to a nearby reverse primer that is also attached within the core, forming a "bridge" structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Adding a primer binding site to target nucleic acids can be accomplished by any suitable method, examples of which include the use of random primers having common 5' sequences and ligating adapter nucleotides that include the primer binding site.

In embodiments of the methods provided herein, each core further includes a silica, magnetic, or paramagnetic material, such as in the form of a bead or particle. For example, the core/shell layers may be formed around and encapsulating a supporting bead, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place. In embodiments, each core includes a silica particle. In embodiments, the core surrounds the silica particle.

In an aspect, provided herein are methods of sequencing target polynucleotides, the methods including contacting a polymer scaffold with a sample that includes target polynucleotides, amplifying the target polynucleotides to produce discrete amplicon clusters, and sequencing the amplicon clusters. In embodiments, the polymer scaffold includes a polymer covalently attached to polynucleotide primers. In embodiments, amplifying the target includes extension of primers along the target polynucleotides within the polymer scaffold. In embodiments, each amplicon cluster originates from amplification of a single target polynucleotide, and the amplicon clusters are arranged in multiple two-dimensional planes. In embodiments, sequencing comprises detecting sequences of signals within the polymer scaffold through each of the plurality of two-dimensional planes.

In embodiments of the methods provided herein, the target polynucleotides are at a concentration in the sample selected to produce amplicon clusters having a desired density. For example, the concentration of target polynucleotides is selected based on a calculation of (a) the average size of a cluster of amplicons that will result from amplification under selected conditions (e.g. a selected duration and number of extension steps), and (b) a desired separation between adjacent amplicon clusters in the scaffold.

In embodiments of the methods provided herein, the amplicon clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. The mean or median separation may be measured center-to-center (i.e., the center of one amplicon cluster to the center of a second amplicon cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values.

In embodiments of the methods provided herein, the contacting step is performed under non-hybridizing conditions. Examples of non-hybridizing conditions are described above, and include but are not limited to low salt, high temperature, or presence of additives such as formamide.

In embodiments of the methods provided herein, the scaffold polymer includes water. In embodiments, the scaffold polymer has a refractive index of about 1.2-1.6, 1.25-1.5, or 1.3-1.4 when hydrated. In embodiments, the scaffold polymer has a refractive index of about 1.3 when hydrated.

The scaffold polymer may include any of a variety of suitable polymers, and may be formed by the polymerization of any of a variety of suitable monomers or mixtures thereof. Examples of monomers (including functionalized monomers), mixtures of monomers (including mixtures of functionalized and non-functionalized monomers for spaced primer attachment), and polymers suitable for forming the polymer scaffold include, without limitation, any of the monomers, mixtures of monomers, and polymers described herein, such as with regard to the various compositions described herein. In embodiments of the methods provided herein, the scaffold polymer is a hydrogel, non-limiting examples of which are described above. In embodiments, the polymer scaffold is formed as in the plurality of cores described in connection with various core-shell compositions described herein, but lacks a shell polymer forming discrete cores. In embodiments, rather than utilizing a shell polymer to create a space between cores, spacing between amplicon clusters in a scaffold polymer is controlled by factors such as the concentration of target polynucleotides in a sample applied to the scaffold polymer, and the size of the amplicon clusters produced under selected amplification conditions. By selecting conditions in which amplicon clusters have a desired spacing, clusters within the scaffold can be resolved during sequencing.

In embodiments of the methods provided herein, the amplifying step further includes contacting the polymer scaffold with one or more reagents for amplifying the target polynucleotides. Examples of reagents include but are not limited to polymerase, buffer, and nucleotides.

In embodiments of the methods provided herein, the sequencing step includes extending a sequencing primer to incorporate a detectable label that indicates the identity of a nucleotide in the target polynucleotide, detecting the detectable label, and repeating the extending and detecting of steps. In embodiments, the sequencing step may be accomplished by a sequencing-by-synthesis (SBS) process, non-limiting examples of which are described above.

In embodiments of the methods provided herein, detecting includes imaging through each of the multiple two-dimensional planes at a resolution sufficient to distinguish one imaged plane from an adjacent imaged plane. In embodiments, overlap of a signal of an amplicon cluster in one layer appearing in an adjacent layer is computationally resolved, for example, by imaging software. In embodiments of the methods provided herein, the imaging is accomplished by confocal microscopy, multi-photon microscopy, or light sheet fluorescence microscopy (LSFM). In embodiments, the imaging is accomplished by confocal microscopy. In embodiments, the imaging is accomplished by multi-photon microscopy. In embodiments, the imaging is accomplished by LSFM.

In embodiments of the methods provided herein, the polymer scaffold is formed by a process that includes forming an emulsion of oil droplets in a hydrophilic continuous phase, polymerizing a plurality of monomers to form the polymer scaffold, and removing the oil to form a plurality of interconnected pores in the polymer scaffold. In embodiments, the hydrophilic continuous phase includes a plurality of monomers, non-limiting examples of which are described above.

In embodiments of the method provided herein, the polymer scaffold is formed by a process that includes: reacting a plurality of monomers in a water/alcohol solution and maintaining the reaction temperature to less than 60° C.; increasing the reaction temperature to greater than or equal to 60° C.; mixing a plurality of crosslinkers (e.g., Bis-AAM) into the water/alcohol solution; and polymerizing the plurality of monomers and the plurality of crosslinkers to form the polymer scaffold. In embodiments, the plurality of monomers include two types of monomers, including monomers with functional groups that react with polynucleotide primers, and monomers that do not contain functional groups.

In embodiments, the polymer scaffold is in the form of a gyroid structure. An example gyroid structure is illustrated in FIG. 3C. Additional examples of gyroid structures are described in Gan et al., Sci Adv. 2016 May; 2(5): e1600084, which is incorporated herein by reference.

In embodiments of the methods provided herein, the polymer scaffold is formed by a process that includes functionalizing the polymer scaffold with a plurality of first reactive groups, and contacting the functionalized polymer scaffold with polynucleotide primers including a second reactive group. The first reactive group and second reactive group react to form a covalent bond. Examples of such covalent bond reactions include, but are not limited to, amine-modified polynucleotides reacting with epoxy or isothiocyanate groups on the polymer scaffold, succinylated polynucleotides reacting with aminophenyl or aminopropyl functional groups on the polymer scaffold, dibenzocyclooctyne-modified polynucleotides reacting with azide functional groups on the polymer scaffold (or vice versa), trans-cyclooctyne-modified polynucleotides reacting with tetrazine or methyl tetrazine groups on the polymer scaffold (or vice versa), disulfide modified polynucleotides reacting with mercapto-functional groups on the polymer scaffold, amine-functionalized polynucleotides reacting with carboxylic acid groups on the polymer scaffold via 1-ethyl-3-(3-dimethylaminopropyl)-carbodiimide hydrochloride (EDC) chemistry, thiol-modified polynucleotides attaching to a polymer scaffold via a disulphide bond or maleimide linkage, alkyne-modified polynucleotides attaching to the polymer scaffold via copper-catalyzed click reactions to azide functional groups on the polymer scaffold, and acrydite-modified polynucleotides polymerizing with free acrylic acid monomers on the core to form polyacrylamide or reacting with thiol groups on the polymer scaffold.

I. Compounds

In an aspect is provided a polymer including a subunit having the formula:

(Ia)

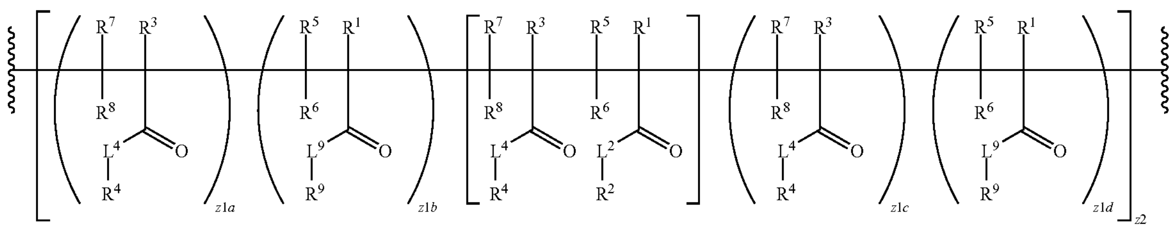

or (Ib)

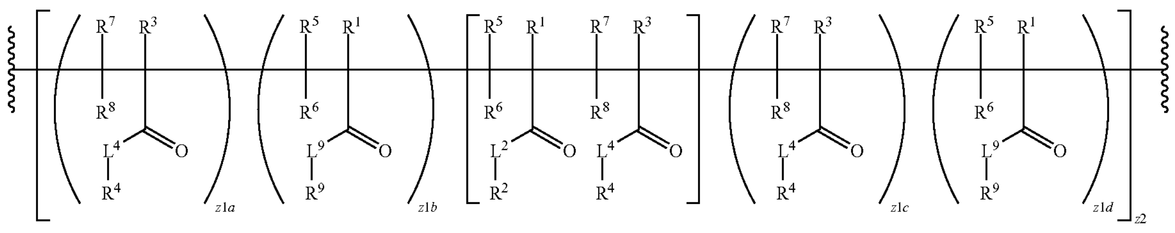

.

$R^1$, $R^3$, $R^5$, $R^6$, $R^7$, and $R^8$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^2$ is independently $-L^{2A}$-$L^{2B}$-$L^{2C}$-$L^{2D}$-$L^{2E}$-.

$L^{2A}$, $L^{2B}$, $L^{2C}$, $L^{2D}$, and $L^{2E}$ are independently a bond, $-S(O)_2-$, $-S(O)-$, $-S(O)_2NH-$, $-NH-$, $-O-$, $-S-$, $-SS-$, $-C(O)-$, $-C(O)NH-$, $-C(O)CH_2-$, $-NHC(O)-$, $-NHC(O)NH-$, $-C(O)O-$, $-OC(O)-$, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^2$ is independently an oligonucleotide moiety.

The symbols z1a, z1b, z1c, and z1d are each independently an integer from 0 to 5000.

$L^4$ is independently -$L^{4A}$, -$L^{4B}$-$L^{4C}$-$L^{4D}$-$L^{4E}$-.

$L^{4A}$ $L^{4B}$ $L^{4C}$, $L^{4D}$, and $L^{4E}$ are independently a bond, —$S(O)_2$—, —S(O)—, —$S(O)_2$NH—, —NH—, —O—, —S—, —C(O)—, —C(O)NH—, —C(O)$CH_2$—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_4NR^{4A}R^{4B}$, $NHC(O)NR^{4A}R^{4B}$, $N(O)_{m4}$, —$NR^{4A}R^{4B}$, —$C(O)R^{4C}$, —C(O)—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$OC(O)R^{4C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$. $C_3$-$C_6$. $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); wherein $R^4$ is a first non-reactive moiety.

$R^{4A}$, $R^{4B}$, $R^{4C}$, and $R^{4D}$ are independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{4A}$ and $R^{4B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

$L^9$ is independently -$L^{9A}$-$L^{9B}$-$L^{9C}$-$L^{9D}$-$L^{9E}$-.

$L^{9A}$, $L^{9B}$, $L^{9C}$, $L^{9D}$, and $L^{9E}$ are independently a bond, —$S(O)_2$—, —S(O)—, —$S(O)_2$NH—, —NH—, —O—, —S—, —SS—, —C(O)—, —C(O)NH—, —C(O)$CH_2$—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^9$ is independently an oligonucleotide or a second non-reactive moiety.

The symbol z2 is independently an integer from 1 to 5000.

X and $X^4$ are independently —F, —Cl, —Br, or —I.

The symbol n4 is independently an integer from 0 to 4.

The symbols m4 and v4 are each independently an integer from 1 to 2.

In embodiments, the polymer is covalently bonded to a solid surface through a covalent linker. In embodiments, the polymer is covalently bonded to a solid surface through a covalent linker at more than one position of the solid surface. In embodiments, the polymer is covalently bonded to a solid surface through more than one covalent linker at more than one position of the solid surface. In embodiments, the solid surface is the surface of a core. In embodiments, the solid surface is the surface of a core, wherein the core includes a silica particle.

In embodiments, the polymer includes a subunit having the formula:

(II)

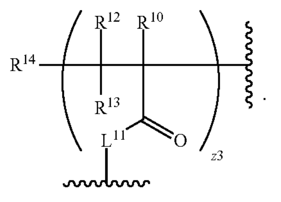

$R^{10}$, $R^{12}$, $R^{13}$, and $R^{14}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^{11}$ is bonded to the solid surface. In embodiments, $L^{11}$ is covalently bonded to the solid surface.

$L^{11}$ is independently $-L^{11A}$, $-L^{11B}$, $-L^{11C}$-$L^{11D}$, $-L^{11E}$-.

$L^{11A}$, $L^{11B}$, $L^{11C}$, $L^{11D}$, and $L^{11E}$ are independently a bond, $—S(O)_2—$, —S(O)—, $—S(O)_2NH—$, —NH—, —O—, —S—, —SS—, —C(O)—, —C(O)NH—, $—C(O)CH_2—$, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

The symbol z3 is independently an integer from 1 to 5000.

In embodiments, the polymer is covalently bonded to the solid surface by a linker $L^{12}$, wherein $L^{12}$ is $-L^{12A}$-$L^{12B}$-$L^{12C}$-$L^{12D}$-$L^{12E}$-.

$L^{12A}$ $L^{12B}$, $L^{12C}$, $L^{12D}$, and $L^{12E}$ are independently a bond, $—S(O)_2—$, —S(O)—, $—S(O)_2NH—$, —NH—, —O—, —S—, —C(O)—, —C(O)NH—, —C(O) $CH_2—$, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, the polymer does not include $L^{12}$ when the polymer includes a subunit of formula (II).

In embodiments, the polymer includes a subunit having the formula:

(III)

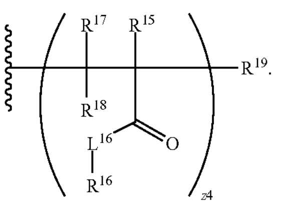

$R^{15}$, $R^{17}$, $R^{18}$, and $R^{19}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^{16}$ is independently $-L^{16A}$-$L^{16B}$-$L^{16C}$-$L^{16D}$-$L^{16E}$-.

$L^{16A}$ $L^{16B}$ $L^{16C}$, $L^{16D}$, and $L^{16E}$ are independently a bond, $—S(O)_2—$, —S(O)—, $—S(O)_2NH—$, —NH—, —O—, —S—, —C(O)—, —C(O)NH—, —C(O) $CH_2—$, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^{16}$ is independently hydrogen, halogen, $—CX^{16}_3$, $—CHX^{16}_2$, $—CH_2X^{16}$, $—OCX^{16}_3$, $—OCH_2X^{16}$, $—OCHX^{16}_2$, —CN, $—SO_{n16}R^{16D}$, $SO_{v16}NR^{16A}R^{16B}$, $NHC(O)NR^{16A}R^{16B}$, $N(O)_{m16}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OC(O)R^{16C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); wherein $R^{16}$ is a third non-reactive moiety.

$R^{16A}$, $R^{16B}$, $R^{16C}$, and $R^{16D}$ are independently hydrogen, $—CX_3$, —CN, —COOH, $—CONH_2$, $—CHX_2$, $—CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{16A}$ and $R^{16B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

The symbol z4 is independently an integer from 1 to 5000.

X and $X^{16}$ are independently —F, —Cl, —Br, or —I.

The symbol n16 is independently an integer from 0 to 4.

The symbols v16 and m16 are each independently 1 to 2.

In embodiments, $R^1$ is independently —CN. In embodiments, $R^1$ is independently substituted or unsubstituted alkyl. In embodiments, $R^1$ is independently substituted or unsubstituted $C_1$-$C_4$ alkyl. In embodiments, $R^1$ is independently unsubstituted $C_1$-$C_4$ alkyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted tert-butyl. In embodiments, $R^1$ is independently substituted or unsubstituted heteroalkyl. In embodiments, $R^1$ is independently substituted or unsubstituted 2 to 6 membered heteroalkyl.

In embodiments, each $R^1$ is the same.

In embodiments, $L^2$ is independently a substituted or unsubstituted heteroalkylene.

In embodiments, $L^{2A}$ is independently a bond.

In embodiments, $L^{2B}$ and $L^{2D}$ are independently substituted or unsubstituted heteroalkylene; $L^{2C}$ is independently a substituted or unsubstituted heteroarylene; and $L^{2E}$ is independently a bond.

In embodiments, $L^{2B}$ and $L^{2E}$ are independently substituted or unsubstituted heteroalkylene; $L^{2C}$ is independently a substituted or unsubstituted heteroarylene; and $L^{2D}$ is independently a substituted or unsubstituted arylene.

In embodiments, $L^{2A}$ is independently a substituted or unsubstituted heteroalkylene. In embodiments, $L^{2A}$ is independently

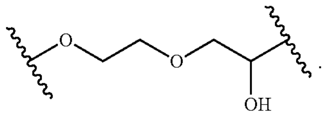 [SMILES: *OCCOCC(*)O]

In embodiments, $L^{2A}$ is independently

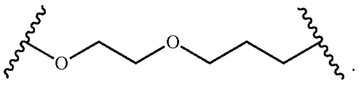 [SMILES: *CCCOCCO*]

In embodiments, $L^{2A}$ is independently

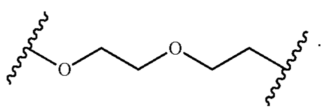 [SMILES: *CCOCCO*]

In embodiments, $L^{2A}$ is independently

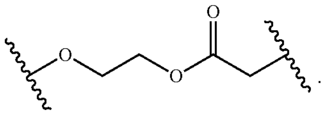 [SMILES: *CC(=O)OCCO*]

In embodiments, $L^{2A}$ is independently

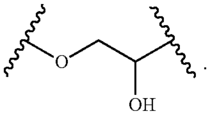 [SMILES: *OCC(*)O]

In embodiments, $L^{2A}$ is independently

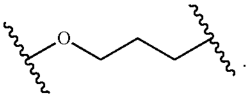 [SMILES: *CCCO*]

In embodiments, $L^{2A}$ is independently

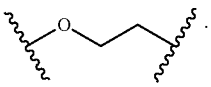 [SMILES: *CCO*]

In embodiments $L^{2A}$ is independently

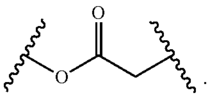 [SMILES: *CC(=O)O*]

In embodiments, $L^{2A}$ is independently

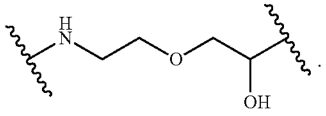 [SMILES: *NCCOCC(*)O]

In embodiments, $L^{2A}$ is independently

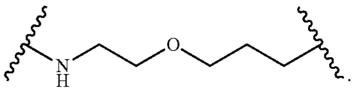 [SMILES: *CCCOCCN*]

In embodiments, $L^{2A}$ is independently

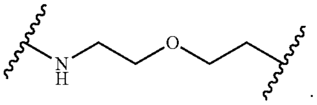 [SMILES: *CCOCCN*]

In embodiments, $L^{2A}$ is independently

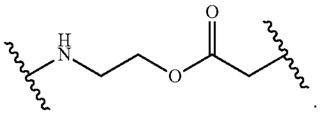 [SMILES: *CC(=O)OCCN*]

In embodiments, $L^{2A}$ is independently

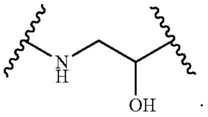 [SMILES: *NCC(*)O]

In embodiments, $L^{2A}$ is independently

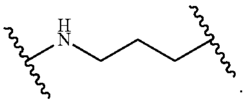

In embodiments, $L^{2A}$ is independently

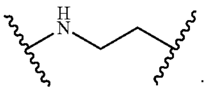 [SMILES: *CCN*]

In embodiments, $L^{2A}$ is independently

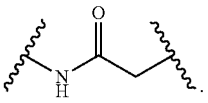 [SMILES: *CC(=O)N*]

In embodiments, $L^{2B}$ is independently a substituted heteroarylene. In embodiments, $L^{2B}$ is independently

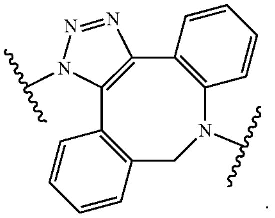 [SMILES: *N1Cc2ccccc2-c2c(nnn2*)-c2ccccc21]

In embodiments, $L^{2B}$ is independently

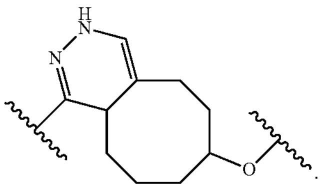 [SMILES: *OC1CCCC2C(=CNN=C2*)CC1]

In embodiments, $L^{2B}$ is independently

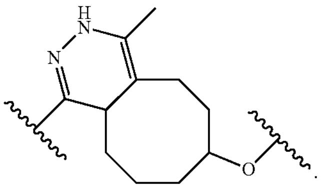 [SMILES: *OC1CCCC2C(*)=NNC(C)=C2CC1]

In embodiments, $L^{2B}$ is independently

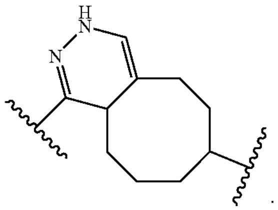 [SMILES: *C1=NNC=C2CCC(*)CCCC21]

In embodiments, $L^{2B}$ is independently

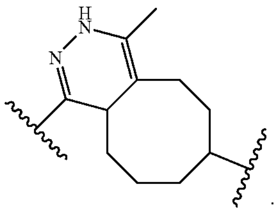 [SMILES: *C1=NNC(C)=C2CCC(*)CCCC12]

In embodiments, $L^{2B}$ is independently

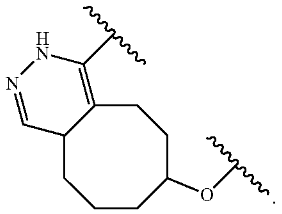 [SMILES: *OC1CCCC2C=NNC(*)=C2CC1]

In embodiments, $L^{2B}$ is independently

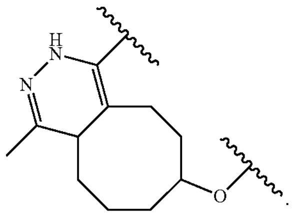 [SMILES: *OC1CCCC2C(C)=NNC(*)=C2CC1]

In embodiments, $L^{2B}$ is independently

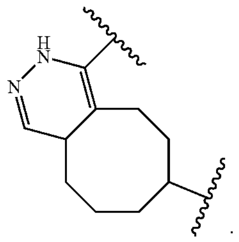 [SMILES: *C1=C2CCC(*)CCCC2C=NN1]

In embodiments, $L^{2B}$ is independently

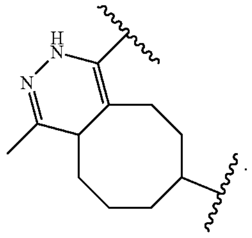 [SMILES: *C1=C2CCC(*)CCCC2C(C)=NN1]

In embodiments, $L^{2C}$ is independently a substituted or unsubstituted heteroalkylene. In embodiments, $L^{2C}$ is independently

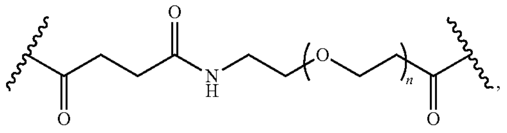

wherein n is independently an integer from 4 to 12. In embodiments, $L^{2C}$ is independently

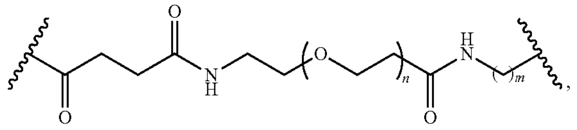

wherein n is independently an integer from 4 to 12 and m is independently an integer from 4 to 12. In embodiments, $L^{2C}$ is independently

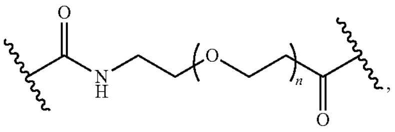

wherein n is independently an integer from 4 to 12. In embodiments, $L^{2C}$ is independently

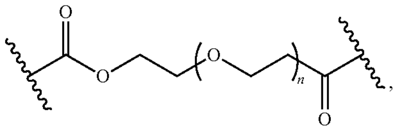

wherein n is independently an integer from 4 to 12. In embodiments, $L^{2C}$ is independently

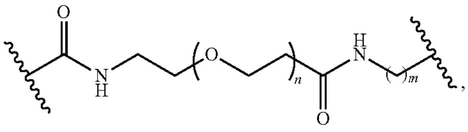

wherein n is independently an integer from 4 to 12 and m is independently an integer from 4 to 12. In embodiments, $L^{2C}$ is independently

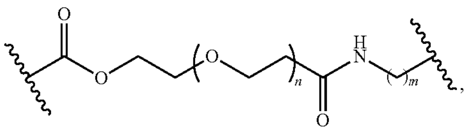

wherein n is independently an integer from 4 to 12 and m is independently an integer from 4 to 12.

In embodiments, $L^{2D}$ is independently a substituted or unsubstituted heteroalkylene. In embodiments, $L^{2D}$ is independently

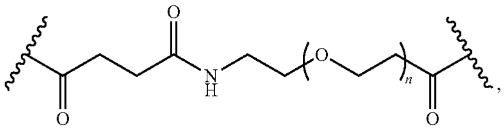

wherein n is independently an integer from 4 to 12. In embodiments, $L^{2D}$ is independently

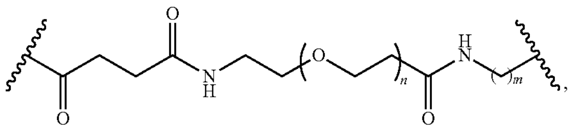

wherein n is independently an integer from 4 to 12 and m is independently an integer from 4 to 12. In embodiments, $L^{2D}$ is independently

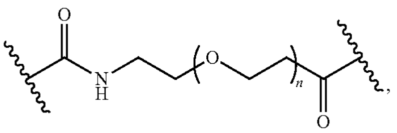

wherein n is independently an integer from 4 to 12. In embodiments, $L^{2D}$ is independently

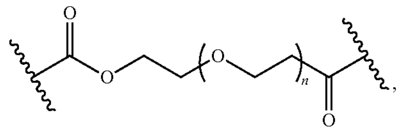

wherein n is independently an integer from 4 to 12. In embodiments, $L^{2D}$ is independently

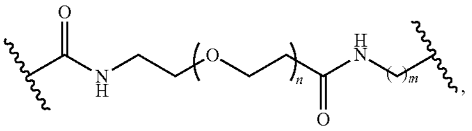

wherein n is independently an integer from 4 to 12 and m is independently an integer from 4 to 12. In embodiments, $L^{2D}$ is independently

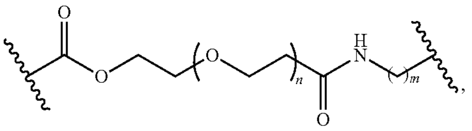

wherein n is independently an integer from 4 to 12 and m is independently an integer from 4 to 12.

In embodiments, $-L^{2C}-L^{2D}-L^{2E}-$ is independently a substituted or unsubstituted heteroalkylene. In embodiments, $-L^{2C}-L^{2D}-L^{2E}-$ is independently

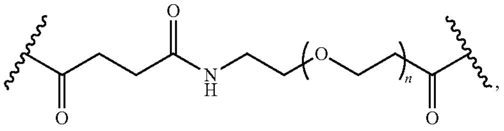

wherein n is independently an integer from 4 to 12. In embodiments, $-L^{2C}-L^{2D}-L^{2E}-$ is independently

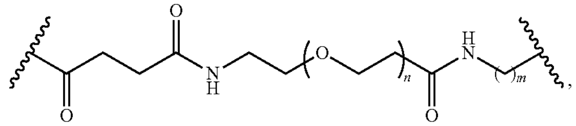

wherein n is independently an integer from 4 to 12 and m is independently an integer from 4 to 12. In embodiments, $-L^{2C}-L^{2D}-L^{2E}-$ is independently

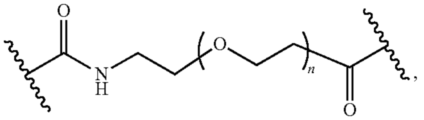

wherein n is independently an integer from 4 to 12. In embodiments, $-L^{2C}-L^{2D}-L^{2E}-$ is independently

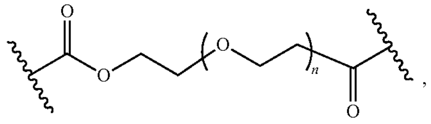

wherein n is independently an integer from 4 to 12. In embodiments, $-L^{2C}-L^{2D}-L^{2E}-$ is independently

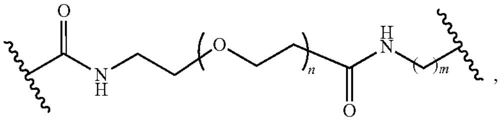

wherein n is independently an integer from 4 to 12 and m is independently an integer from 4 to 12. In embodiments, $-L^{2C}-L^{2D}-L^{2E}-$ is independently

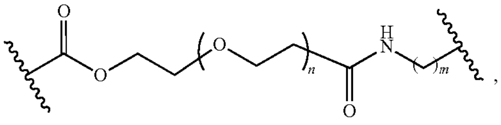

wherein n is independently an integer from 4 to 12 and m is independently an integer from 4 to 12.

In embodiments, $L^2$ is independently

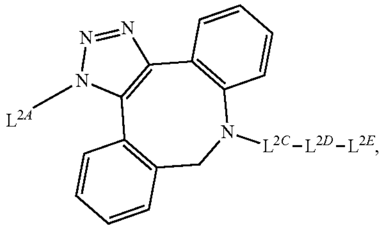

wherein $L^{2A}$, $L^{2C}$, $L^{2D}$, and $L^{2E}$ are as described herein, including in embodiments. In embodiments, $L^2$ is independently

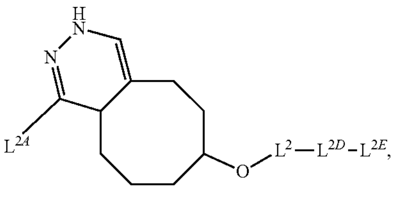

wherein $L^{2A}$, $L^{2C}$, $L^{2D}$, and $L^{2E}$ are as described herein, including in embodiments. In embodiments, $L^2$ is independently

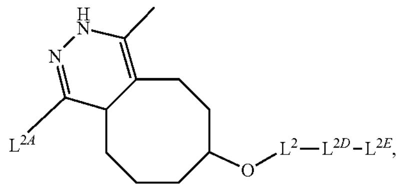

wherein $L^{2A}$ $L^{2C}$ $L^2$D, and $L^{2E}$ are as described herein, including in embodiments. In embodiments, $L^2$ is independently

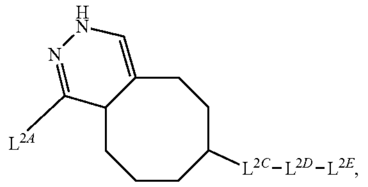

wherein $L^{2A}$ $L^{2C}$ $L^2$D, and $L^{2E}$ are as described herein, including in embodiments. In embodiments, $L^2$ is independently

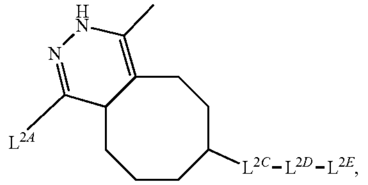

wherein $L^{2A}$, $L^{2C}$, $L^2$D, and $L^{2E}$ are as described herein, including in embodiments. In embodiments, $L^2$ is independently

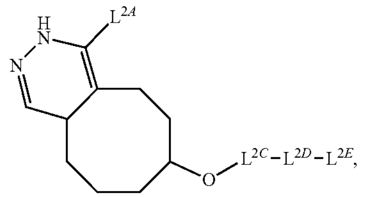

wherein $L^{2A}$, $L^{2C}$, $L^{2D}$, and $L^{2E}$ are as described herein, including in embodiments. In embodiments, $L^2$ is independently

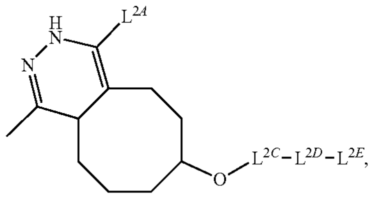

wherein $L^{2A}$, $L^{2C}$, $L^{2D}$, and $L^{2E}$ are as described herein, including in embodiments. In embodiments, $L^2$ is independently

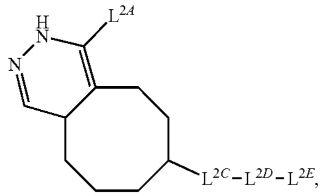

wherein $L^{2A}$, $L^{2C}$, $L^2$D, and $L^{2E}$ are as described herein, including in embodiments. In embodiments, $L^2$ is independently

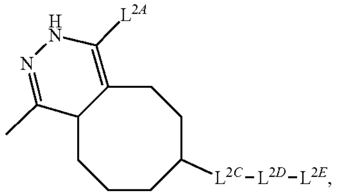

wherein $L^{2A}$, $L^{2C}$, $L^{2D}$, and $L^{2E}$ are as described herein, including in embodiments.

In embodiments, $-L^{2A}-L^{2B}-L^{2C}-$ is independently

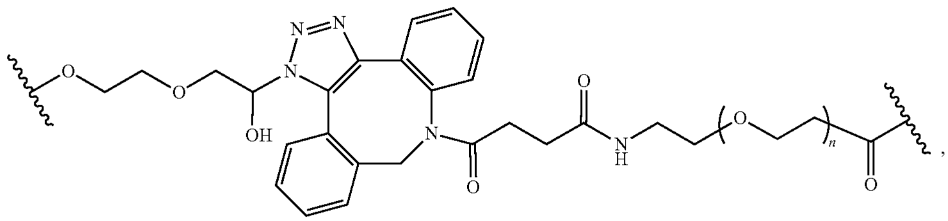

wherein n is independently an integer from 4 to 12. In embodiments, -$L^{2A}$-$L^{2B}$-$L^{2C}$- is independently

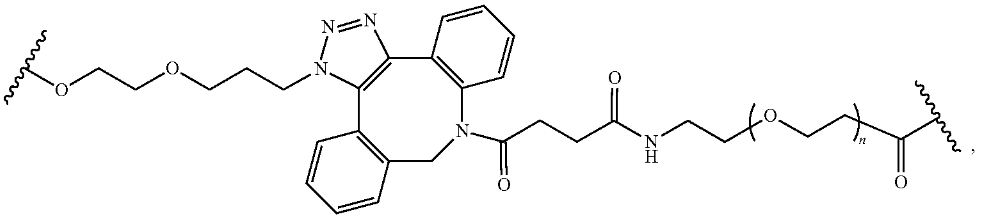

wherein n is independently an integer from 4 to 12. In embodiments, -$L^{2A}$-$L^{2B}$-$L^{2C}$- is independently

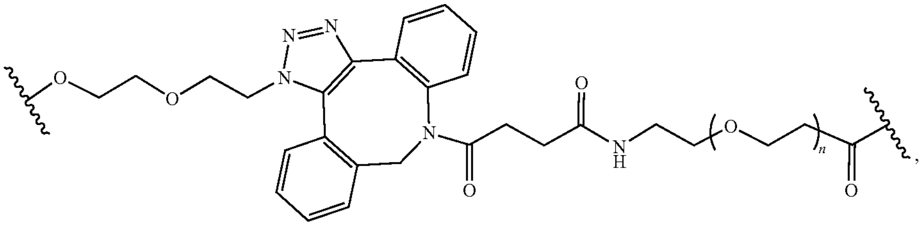

wherein n is independently an integer from 4 to 12. In embodiments, -$L^{2A}$-$L^{2B}$-$L^{2C}$- is independently

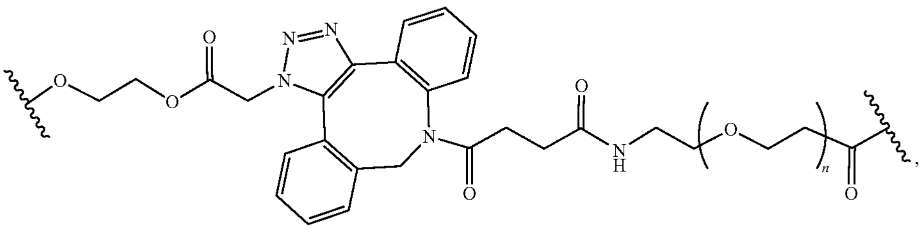

wherein n is independently an integer from 4 to 12. In embodiments, -$L^{2A}$-$L^{2B}$-$L^{2C}$- is independently

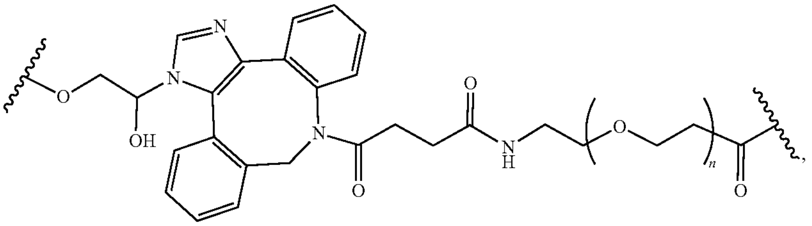

wherein n is independently an integer from 4 to 12. In embodiments, -$L^{2A}$-$L^{2B}$-$L^{2C}$- is independently

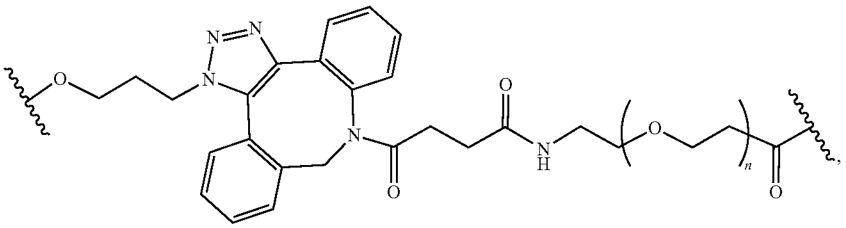

wherein n is independently an integer from 4 to 12. In embodiments, $-L^{2A}-L^{2B}-L^{2C}-$ is independently

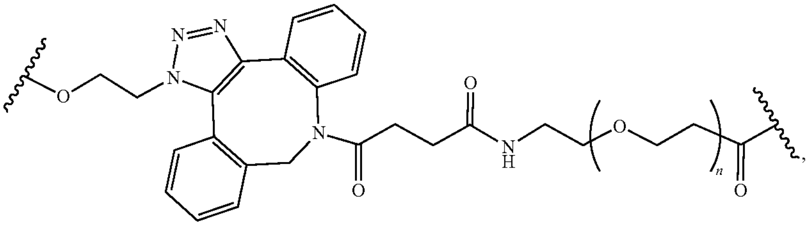

wherein n is independently an integer from 4 to 12. In embodiments, $-L^{2A}-L^{2B}-L^{2C}-$ is independently

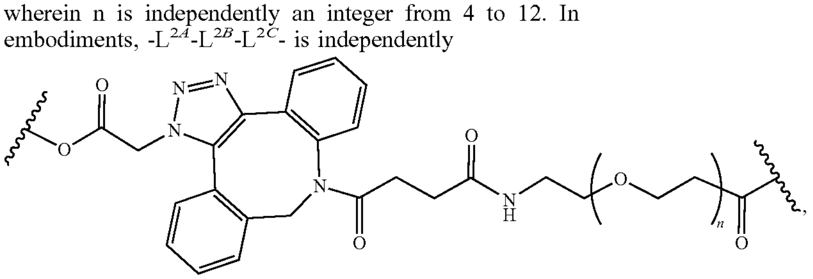

wherein n is independently an integer from 4 to 12. In embodiments, $-L^{2A}-L^{2B}-L^{2C}-$ is independently

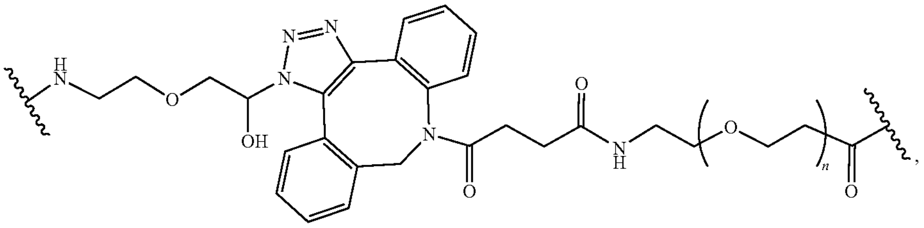

wherein n is independently an integer from 4 to 12. In embodiments, $-L^{2A}-L^{2B}-L^{2C}-$ is independently

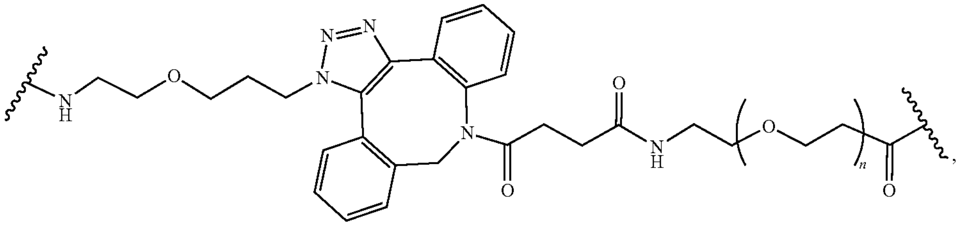

wherein n is independently an integer from 4 to 12. In embodiments, $-L^{2A}-L^{2B}-L^{2C}-$ is independently

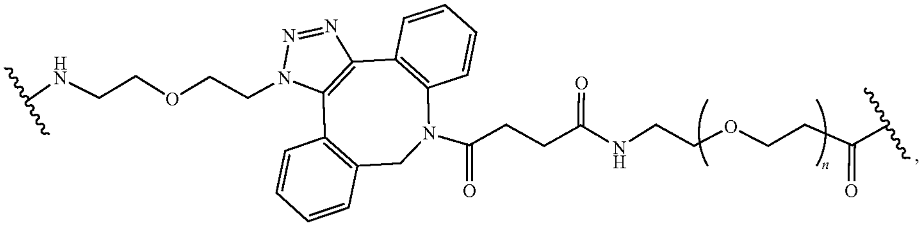

wherein n is independently an integer from 4 to 12. In embodiments, $-L^{2A}-L^{2B}-L^{2C}-$ is independently

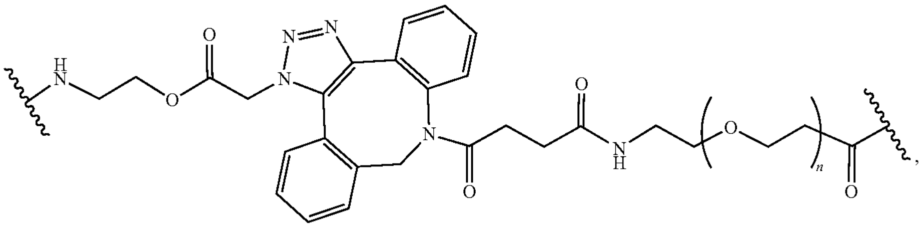

wherein n is independently an integer from 4 to 12. In embodiments, $-L^{2A}-L^{2B}-L^{2C}-$ is independently

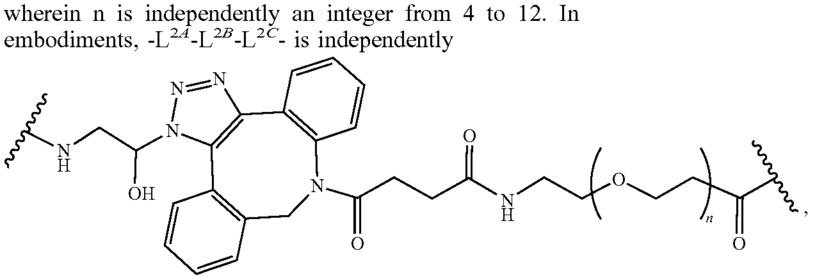

wherein n is independently an integer from 4 to 12. In embodiments, $-L^{2A}-L^{2B}-L^{2C}-$ is independently

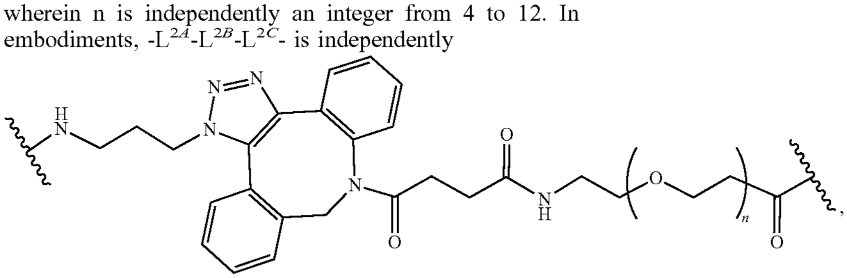

wherein n is independently an integer from 4 to 12. In embodiments, $-L^{2A}-L^{2B}-L^{2C}-$ is independently

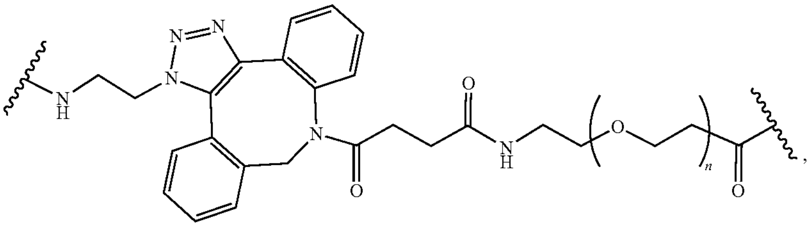

wherein n is independently an integer from 4 to 12. In embodiments, $-L^{2A}-L^{2B}-L^{2C}-$ is independently

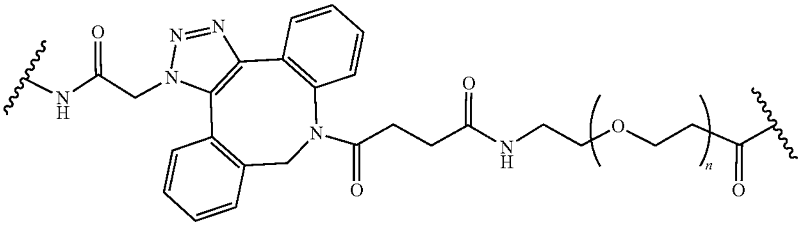, wherein n is independently an integer from 4 to 12.

In embodiments, $L^{2D}$ is independently —S—S— and $L^{2E}$ is independently an unsubstituted $C_4$-$C_8$ alkylene. In embodiments, $L^{2D}$ is independently

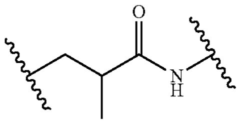 [SMILES: *CC(C)C(=O)N*]

and $L^{2E}$ is independently an unsubstituted $C_4$-$C_8$ alkylene.

In embodiments, $L^2$ is independently a substituted or unsubstituted heteroalkylene.

In embodiments, $L^2$ is independently

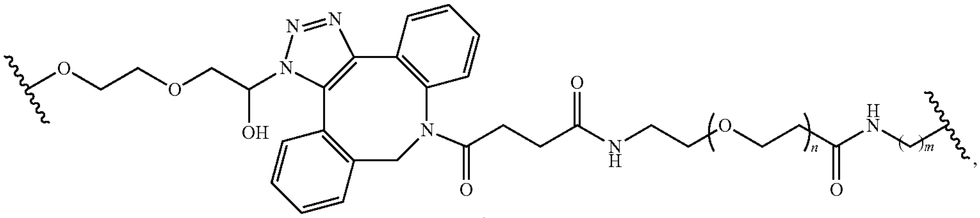,

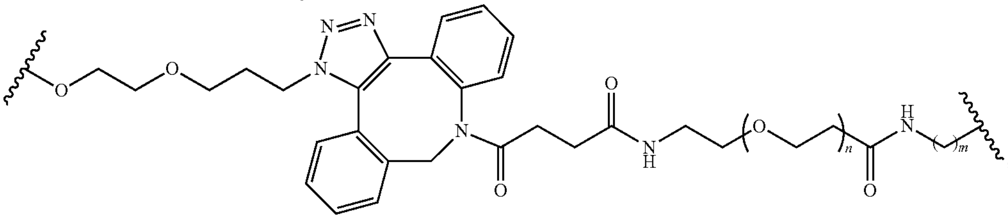,

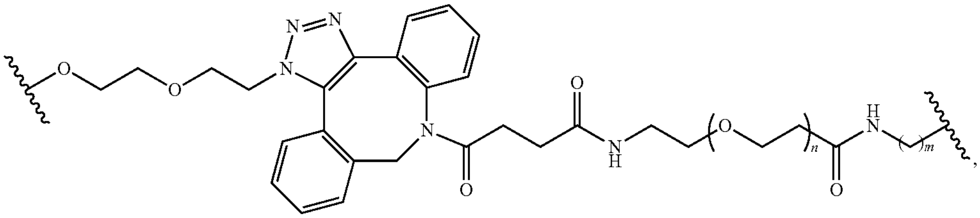, or

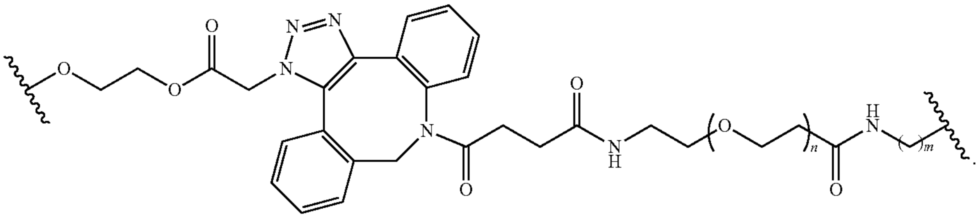.

The symbol n is independently an integer from 4 to 12, and the symbol m is an integer from 4 to 12.

In embodiments, $L^2$ is independently

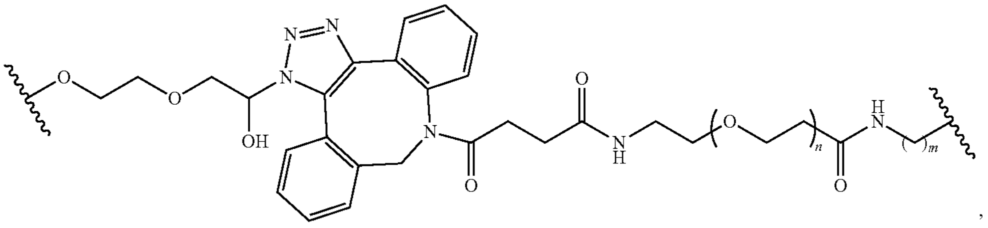

wherein n is independently an integer from 4 to 12, and m is an integer from 4 to 12.

In embodiments, $L^2$ is independently

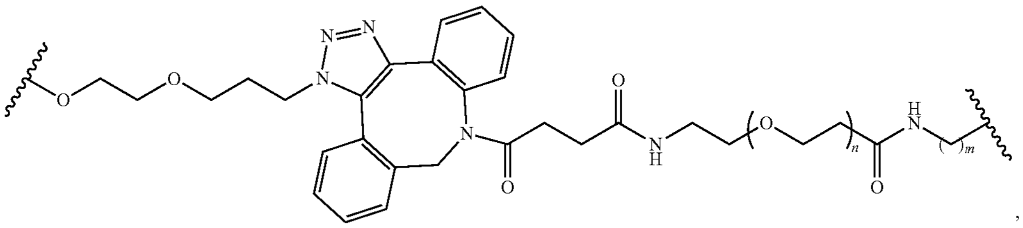

wherein n is independently an integer from 4 to 12, and m is an integer from 4 to 12.

In embodiments, $L^2$ is independently

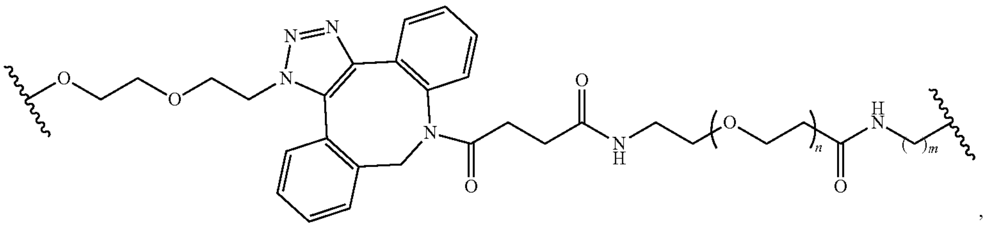

wherein n is independently an integer from 4 to 12, and m is an integer from 4 to 12.

In embodiments, $L^2$ is independently

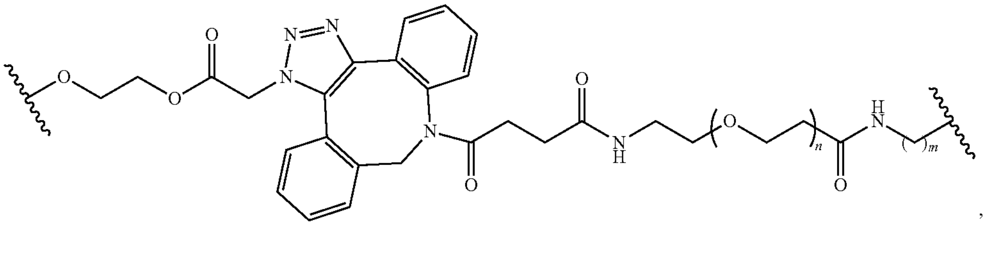

wherein n is independently an integer from 4 to 12, and m is an integer from 4 to 12.

In embodiments, $L^2$ is independently
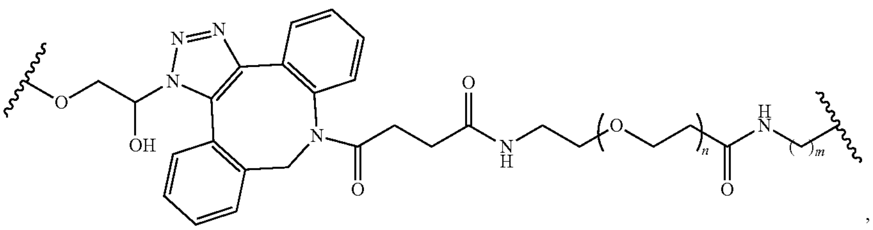
,
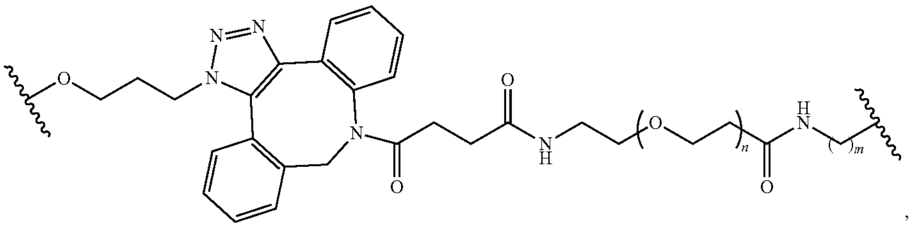
,
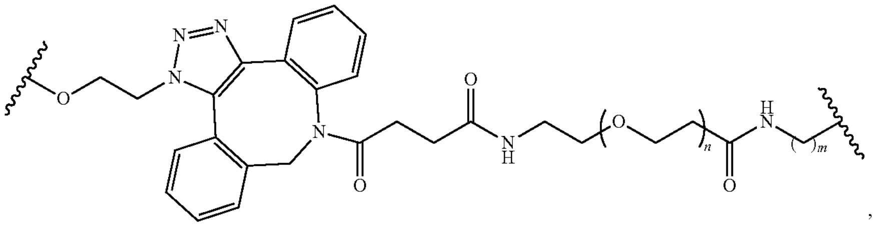
, or
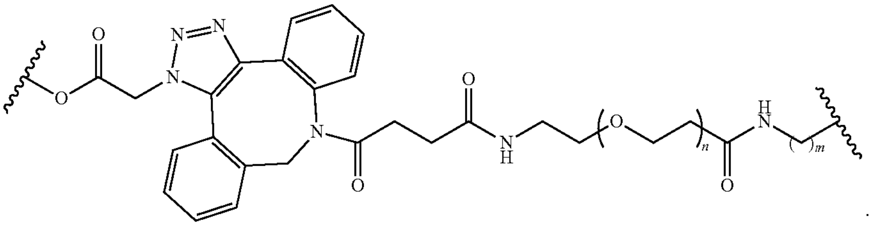
.
The symbol n is independently an integer from 4 to 12, and the symbol m is independently an integer from 4 to 12.
In embodiments, $L^2$ is independently
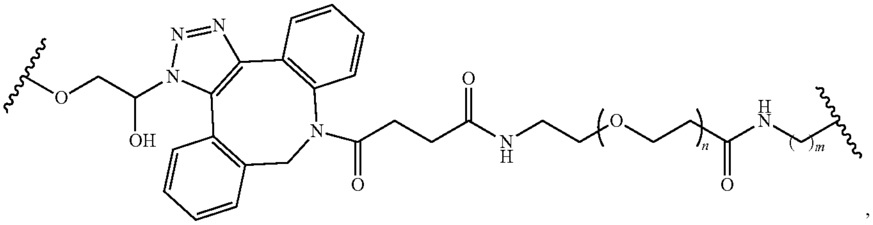
,
wherein n is independently an integer from 4 to 12, and m is independently an integer from 4 to 12.

In embodiments, $L^2$ is independently

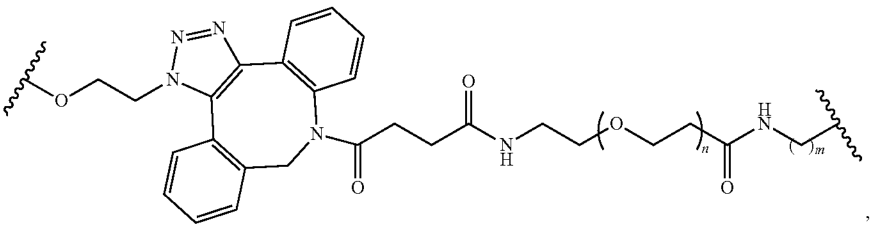

, wherein n is independently an integer from 4 to 12, and m is independently an integer from 4 to 12.

In embodiments, $L^2$ is independently

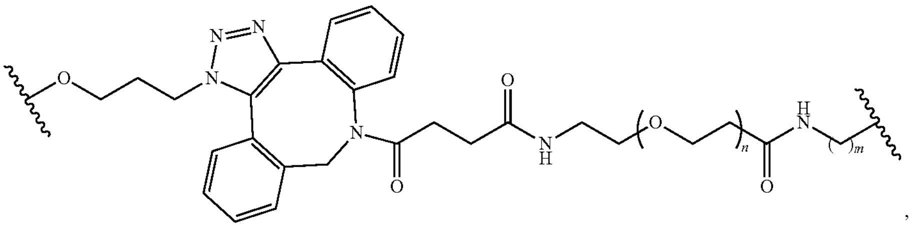

, wherein n is independently an integer from 4 to 12, and m is independently an integer from 4 to 12.

In embodiments, $L^2$ is independently

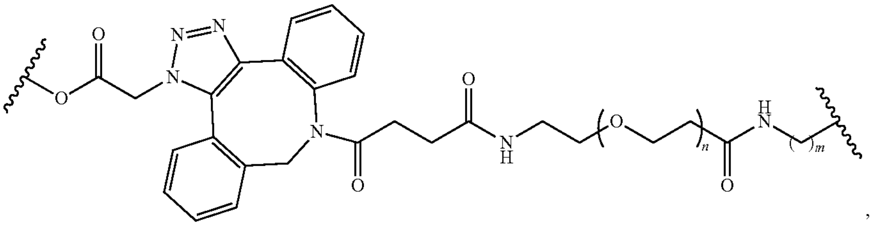

, wherein n is independently an integer from 4 to 12, and m is independently an integer from 4 to 12.

In embodiments, $L^2$ is independently

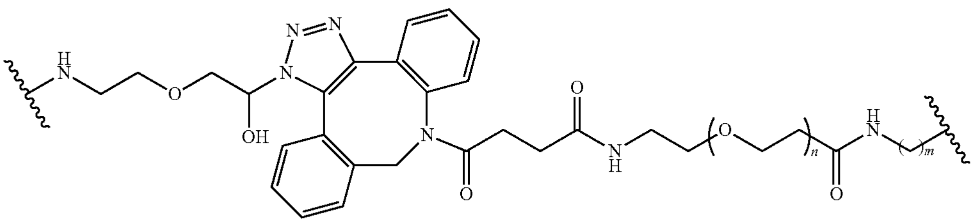

,

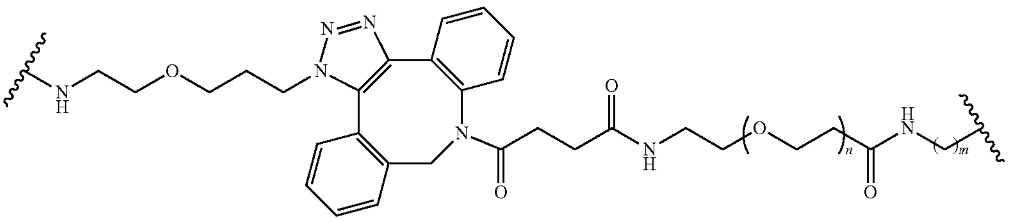

,

-continued

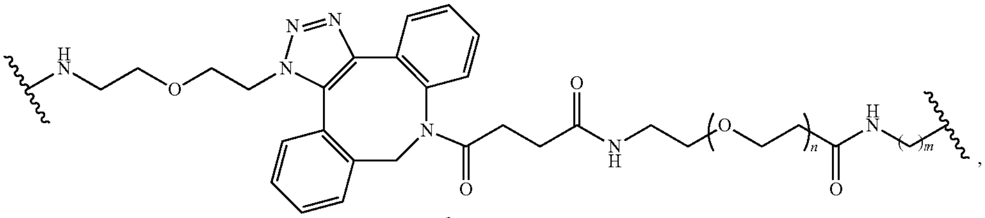

, or

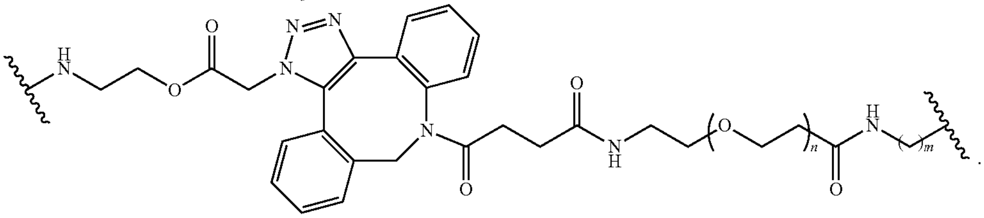

.

The symbol n is independently an integer from 4 to 12, and the symbol m is independently an integer from 4 to 12.

In embodiments, $L^2$ is independently

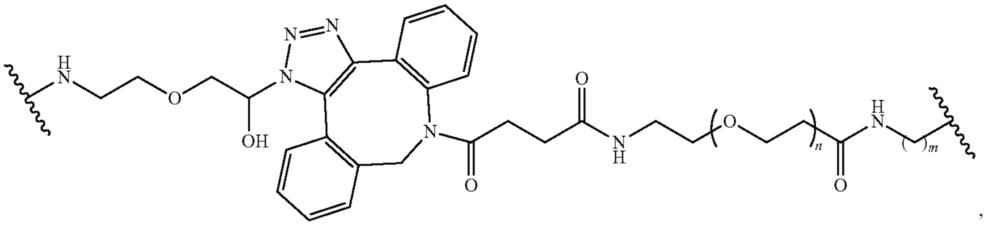

, wherein n is independently an integer from 4 to 12, and m is independently an integer from 4 to 12.

In embodiments, $L^2$ is independently

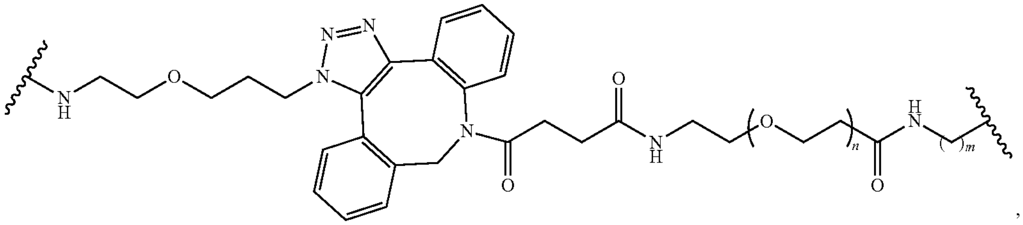

, wherein n is independently an integer from 4 to 12, and m is independently an integer from 4 to 12.

In embodiments, $L^2$ is independently

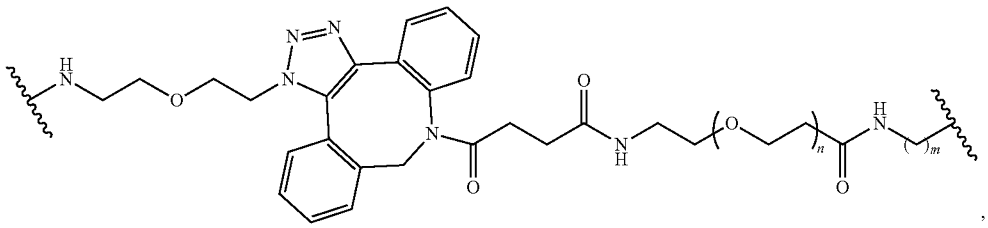

, wherein n is independently an integer from 4 to 12, and m is independently an integer from 4 to 12.

In embodiments, $L^2$ is independently
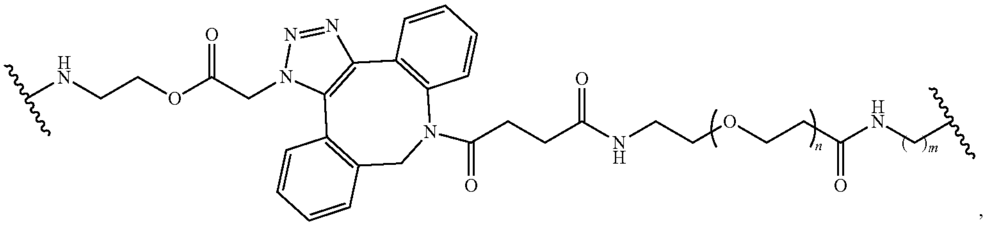
,
wherein n is independently an integer from 4 to 12, and m is independently an integer from 4 to 12.
In embodiments, $L^2$ is independently
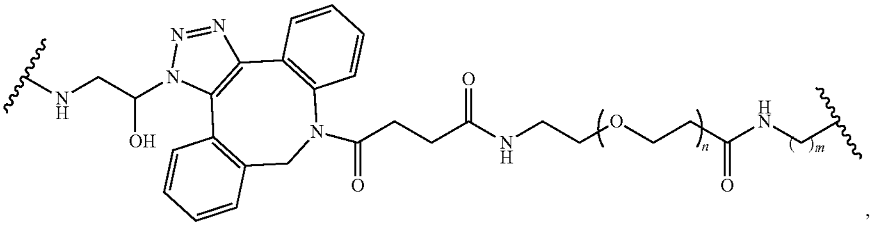
,
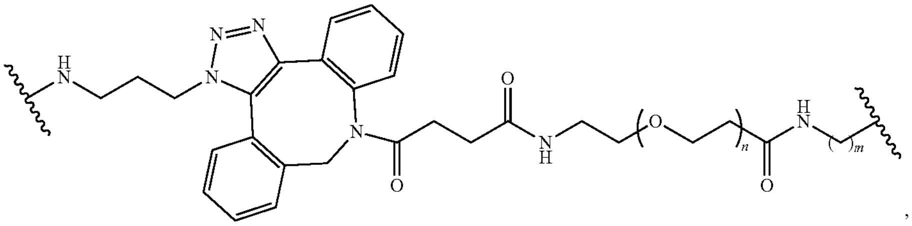
,
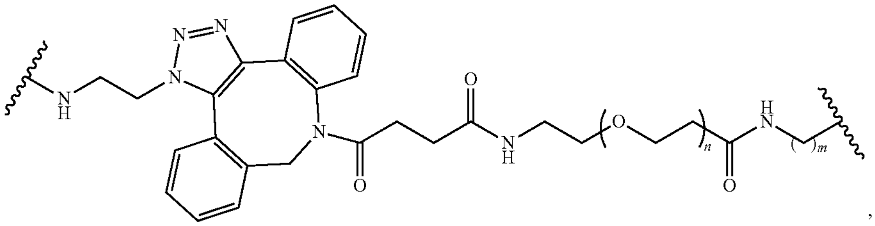
, or
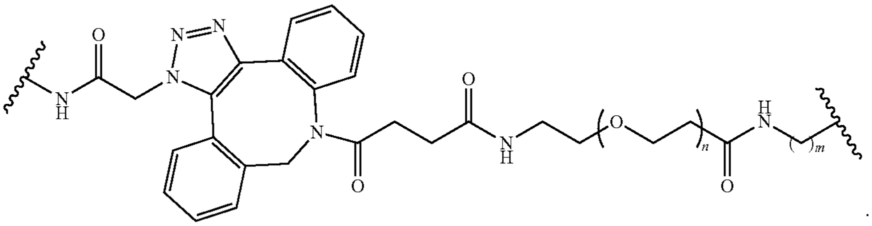
.
The symbol n is independently an integer from 4 to 12, and the symbol m is independently an integer from 4 to 12.

In embodiments, $L^2$ is independently

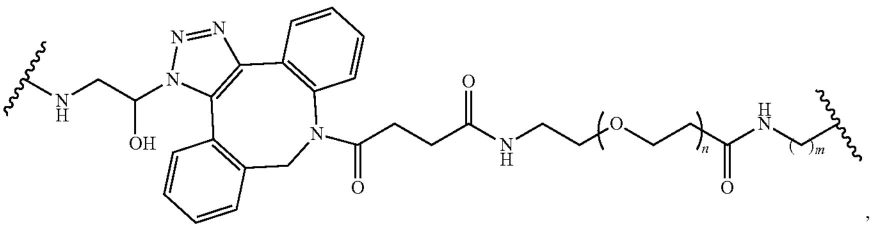

, wherein n is independently an integer from 4 to 12, and m is independently an integer from 4 to 12.

In embodiments, $L^2$ is independently

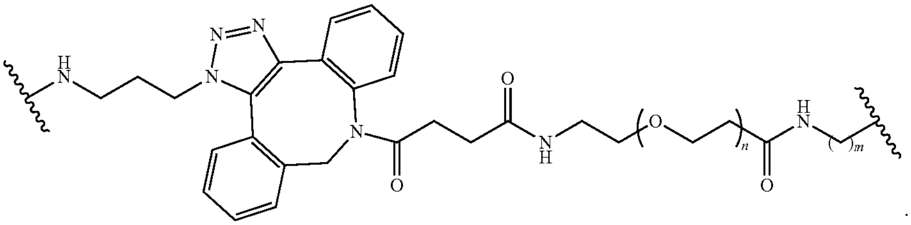

.

wherein n is independently an integer from 4 to 12, and m is independently an integer from 4 to 12.

In embodiments, $L^2$ is independently

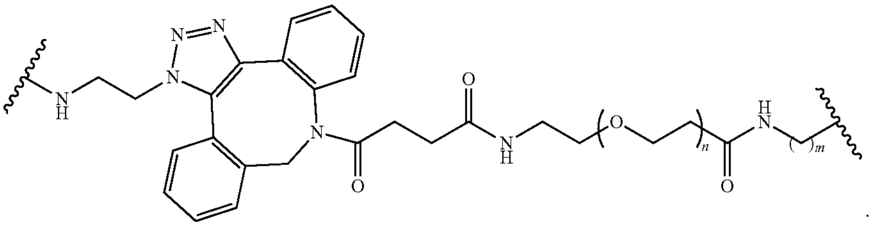

.

wherein n is independently an integer from 4 to 12, and m is independently an integer from 4 to 12.

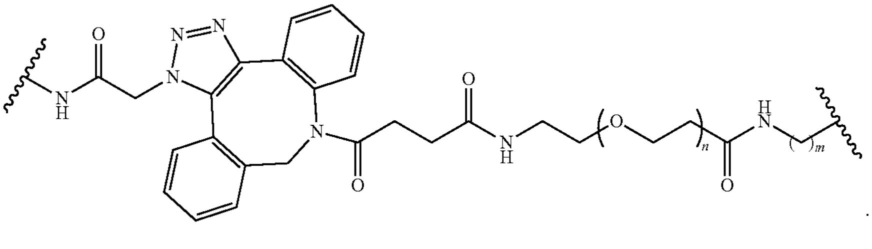

.

In embodiments, each $L^2$ is the same.

In embodiments, $R^3$ is independently —CN. In embodiments, $R^3$ is independently substituted or unsubstituted alkyl. In embodiments, $R^3$ is independently substituted or unsubstituted $C_1$-$C_4$ alkyl. In embodiments, $R^3$ is independently unsubstituted $C_1$-$C_4$ alkyl. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted n-propyl. In embodiments, $R^3$ is independently unsubstituted isopropyl. In embodiments, $R^3$ is independently unsubstituted butyl. In embodiments, $R^3$ is independently unsubstituted n-butyl. In embodiments, $R^3$ is independently unsubstituted tert-butyl. In embodiments, $R^3$ is independently substituted or unsubstituted heteroalkyl.

In embodiments, $R^3$ is independently substituted or unsubstituted 2 to 6 membered heteroalkyl.

In embodiments, each $R^3$ is the same.

In embodiments, $L^4$ is independently substituted or unsubstituted heteroalkylene.

In embodiments, $L^{4B}$ and $L^{4D}$ are independently substituted or unsubstituted heteroalkylene; $L^{4C}$ is independently a substituted or unsubstituted heteroarylene; and $L^{4E}$ is independently a bond.

In embodiments, $L^{4B}$ and $L^{4E}$ are independently substituted or unsubstituted heteroalkylene; $L^{4C}$ is independently a substituted or unsubstituted heteroarylene; and $L^{4D}$ is independently a substituted or unsubstituted arylene.

In embodiments, $L^{4A}$ is independently a bond.

In embodiments, each $L^4$ is the same.

In embodiments, $R^4$ is independently a non-reactive moiety selected from hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently a non-reactive moiety selected from hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently hydrogen, $-OCH_2CH_2-(OCH_2CH_2)_p-OCH_3$ or $-N(CH_3)_2$; and p is an integer from 0 to 10.

In embodiments, each $R^4$ is the same.

In embodiments, $-L^4-R^4$ is independently $-OCH_2CH_2-(OCH_2CH_2)_p-OCH_3$ or $-N(CH_3)_2$; and p is an integer from 4 to 10.

In embodiments, $R^5$ and $R^6$ are independently hydrogen.

In embodiments, $R^5$ is independently hydrogen. In embodiments, $R^5$ is independently substituted or unsubstituted $C_1$-$C_4$ alkyl. In embodiments, $R^5$ is independently unsubstituted $C_1$-$C_4$ alkyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently unsubstituted n-propyl. In embodiments, $R^5$ is independently unsubstituted isopropyl. In embodiments, $R^5$ is independently unsubstituted butyl. In embodiments, $R^5$ is independently unsubstituted n-butyl. In embodiments, $R^5$ is independently unsubstituted tert-butyl.

In embodiments, each $R^5$ is the same.

In embodiments, $R^6$ is independently hydrogen. In embodiments, $R^6$ is independently substituted or unsubstituted $C_1$-$C_4$ alkyl. In embodiments, $R^6$ is independently unsubstituted $C_1$-$C_4$ alkyl. In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently unsubstituted n-propyl. In embodiments, $R^6$ is independently unsubstituted isopropyl. In embodiments, $R^6$ is independently unsubstituted butyl. In embodiments, $R^6$ is independently unsubstituted n-butyl. In embodiments, $R^6$ is independently unsubstituted tert-butyl.

In embodiments, each $R^6$ is the same.

In embodiments, $R^7$ and $R^8$ are independently hydrogen.

In embodiments, $R^7$ is independently hydrogen. In embodiments, $R^7$ is independently substituted or unsubstituted $C_1$-$C_4$ alkyl. In embodiments, $R^7$ is independently unsubstituted $C_1$-$C_4$ alkyl. In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently unsubstituted n-propyl. In embodiments, $R^7$ is independently unsubstituted isopropyl. In embodiments, $R^7$ is independently unsubstituted butyl. In embodiments, $R^7$ is independently unsubstituted n-butyl. In embodiments, $R^7$ is independently unsubstituted tert-butyl.

In embodiments, each $R^7$ is the same.

In embodiments, $R^8$ is independently hydrogen. In embodiments, $R^8$ is independently substituted or unsubstituted $C_1$-$C_4$ alkyl. In embodiments, $R^8$ is independently unsubstituted $C_1$-$C_4$ alkyl. In embodiments, $R^8$ is independently unsubstituted methyl. In embodiments, $R^8$ is independently unsubstituted ethyl. In embodiments, $R^8$ is independently unsubstituted propyl. In embodiments, $R^8$ is independently unsubstituted n-propyl. In embodiments, $R^8$ is independently unsubstituted isopropyl. In embodiments, $R^8$ is independently unsubstituted butyl. In embodiments, $R^8$ is independently unsubstituted n-butyl. In embodiments, $R^8$ is independently unsubstituted tert-butyl.

In embodiments, each $R^8$ is the same.

In embodiments, $L^{9A}$ is independently a bond.

In embodiments, $L^{9B}$ and $L^{9D}$ are independently substituted or unsubstituted heteroalkylene; $L^{9C}$ is independently a substituted or unsubstituted heteroarylene; and $L^{9E}$ is independently a bond.

In embodiments, $L^{9B}$ and $L^{9E}$ are independently substituted or unsubstituted heteroalkylene; $L^{9C}$ is independently a substituted or unsubstituted heteroarylene; and $L^{9D}$ is independently a substituted or unsubstituted arylene.

In embodiments, $L^{9A}$ is independently a substituted or unsubstituted heteroalkylene. In embodiments, $L^{9A}$ is independently

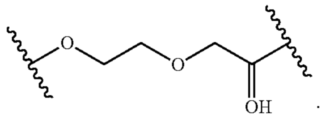 [SMILES: *OCCOCC(*)=O]

In embodiments, $L^{9A}$ is independently

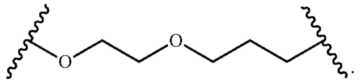 [SMILES: *CCCOCCO*]

In embodiments, $L^{9A}$ is independently

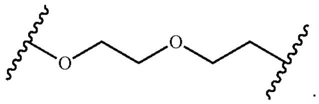 [SMILES: *CCOCCO*]

In embodiments, $L^{9A}$ is independently

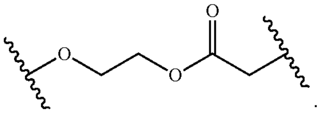 [SMILES: *CC(=O)OCCO*]

In embodiments, $L^{9A}$ is independently

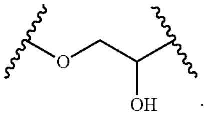 [SMILES: *OCC(*)O]

In embodiments, $L^{9A}$ is independently

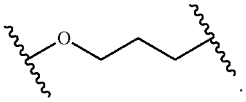 [SMILES: *CCCO*]

In embodiments, $L^{9A}$ is independently

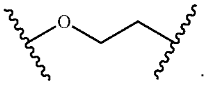

In embodiments, $L^{9A}$ is independently

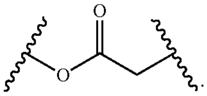 [SMILES: *CC(=O)O*]

In embodiments, $L^{9A}$ is independently

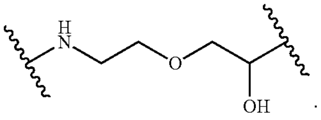 [SMILES: *NCCOCC(*)O]

In embodiments, $L^{9A}$ is independently

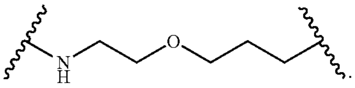 [SMILES: *CCCOCCN*]

In embodiments, $L^{9A}$ is independently

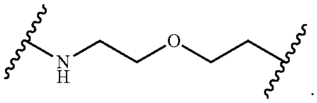 [SMILES: *CCOCCN*]

In embodiments, $L^{9A}$ is independently

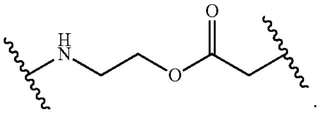 [SMILES: *CC(=O)OCCN*]

In embodiments, $L^{9A}$ is independently

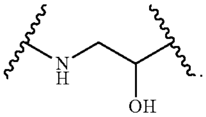 [SMILES: *NCC(*)O]

In embodiments, $L^{9A}$ is independently

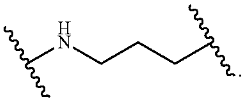 [SMILES: *CCCN*]

In embodiments, $L^{9A}$ is independently

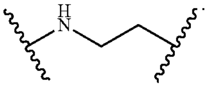 [SMILES: *CCN*]

In embodiments, $L^{9A}$ is independently

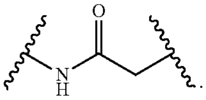 [SMILES: *CC(=O)N*]

In embodiments, $L^{9B}$ is independently a substituted or unsubstituted heteroarylene. In embodiments, $L^{9B}$ is independently

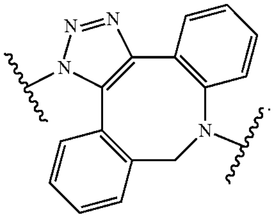 [SMILES: *N1Cc2ccccc2-c2c(nnn2*)-c2ccccc21]

In embodiments, $L^{9B}$ is independently

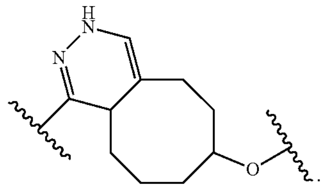 [SMILES: *OC1CCCC2C(=CNN=C2*)CC1]

In embodiments, $L^{9B}$ is independently

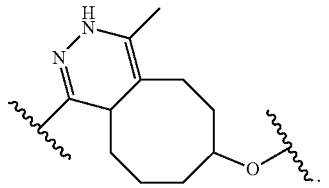 [SMILES: *OC1CCCC2C(*)=NNC(C)=C2CC1]

In embodiments, $L^{9B}$ is independently

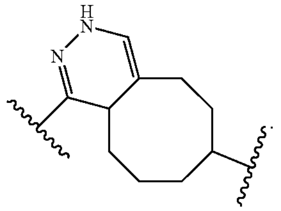 [SMILES: *C1=NNC=C2CCC(*)CCCC21]

In embodiments, $L^{9B}$ is independently

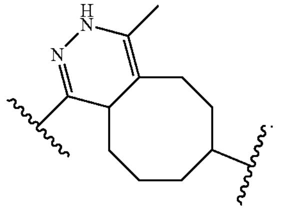 [SMILES: *C1=NNC(C)=C2CCC(*)CCCC12]

In embodiments, $L^{9B}$ is independently

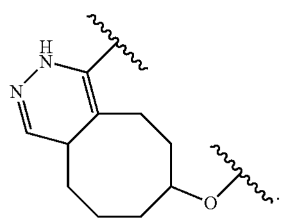 [SMILES: *OC1CCCC2C=NNC(*)=C2CC1]

In embodiments, $L^{9B}$ is independently

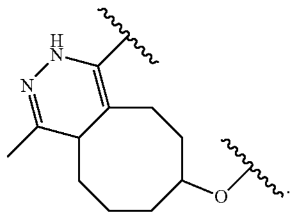 [SMILES: *OC1CCCC2C(C)=NNC(*)=C2CC1]

In embodiments, $L^{9B}$ is independently

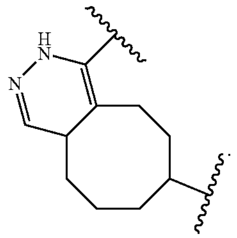 [SMILES: *C1=C2CCC(*)CCCC2C=NN1]

In embodiments, $L^{9B}$ is independently

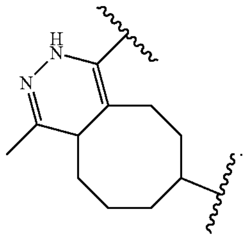 [SMILES: *C1=C2CCC(*)CCCC2C(C)=NN1]

In embodiments, $L^{9C}$ is independently a substituted or unsubstituted heteroalkylene. In embodiments, $L^{9C}$ is independently

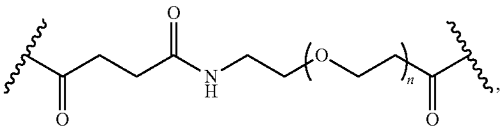

wherein n is independently an integer from 4 to 12. In embodiments, $L^{9C}$ is independently

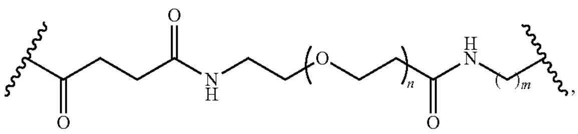

wherein n is independently an integer from 4 to 12 and m is independently an integer from 4 to 12. In embodiments, $L^{9C}$ is independently

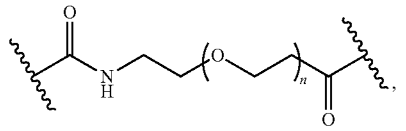, wherein n is independently an integer from 4 to 12. In embodiments, $L^{9C}$ is independently

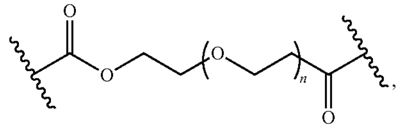, wherein n is independently an integer from 4 to 12. In embodiments, $L^{9C}$ is independently

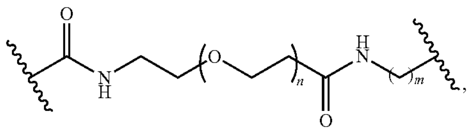, wherein n is independently an integer from 4 to 12 and m is independently an integer from 4 to 12. In embodiments, $L^{9C}$ is independently

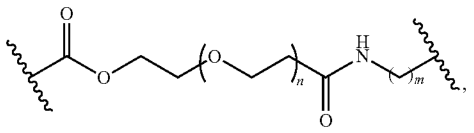, wherein n is independently an integer from 4 to 12 and m is independently an integer from 4 to 12.

In embodiments, $L^{9D}$ is independently a substituted or unsubstituted heteroalkylene. In embodiments, $L^{9D}$ is independently

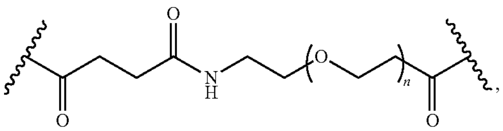, wherein n is independently an integer from 4 to 12. In embodiments, $L^{9D}$ is independently

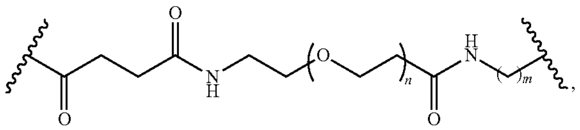, wherein n is independently an integer from 4 to 12 and m is independently an integer from 4 to 12. In embodiments, $L^{9D}$ is independently

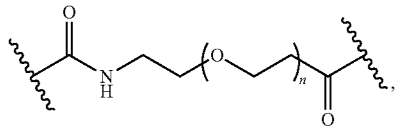, wherein n is independently an integer from 4 to 12. In embodiments, $L^{9D}$ is independently

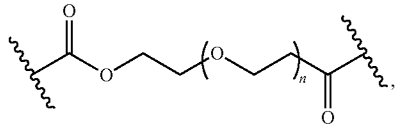, wherein n is independently an integer from 4 to 12. In embodiments, $L^{9D}$ is independently

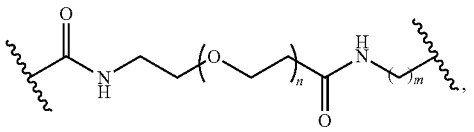, wherein n is independently an integer from 4 to 12 and m is independently an integer from 4 to 12. In embodiments, $L^{9D}$ is independently

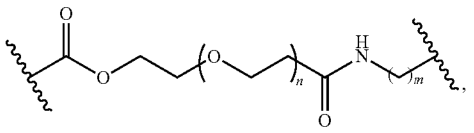, wherein n is independently an integer from 4 to 12 and m is independently an integer from 4 to 12.

In embodiments, $-L^{9C}-L^{9D}-L^{9E}-$ is independently a substituted or unsubstituted heteroalkylene. In embodiments, $-L^{9C}-L^{9D}-L^{9E}-$ is independently

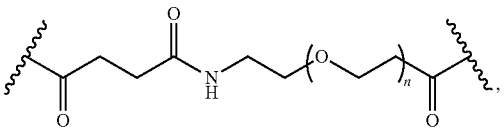, wherein n is independently an integer from 4 to 12. In embodiments, $-L^{9C}-L^{9D}-L^{9E}-$ is independently

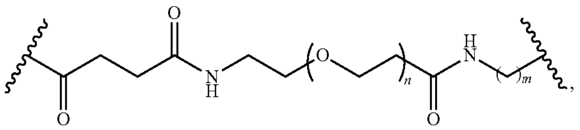, wherein n is independently an integer from 4 to 12 and m is independently an integer from 4 to 12. In embodiments, $-L^{9C}-L^{9D}-L^{9E}-$ is independently

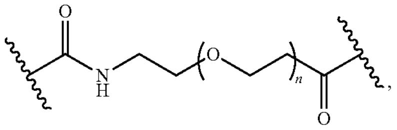

wherein n is independently an integer from 4 to 12. In embodiments, $-L^{9C}-L^{9D}-L^{9E}-$ is independently

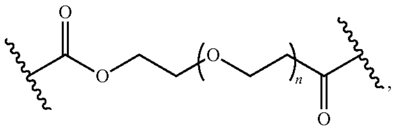

wherein n is independently an integer from 4 to 12. In embodiments, $-L^{9C}-L^{9D}-L^{9E}-$ is independently

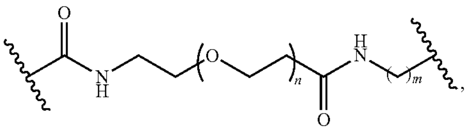

wherein n is independently an integer from 4 to 12 and m is independently an integer from 4 to 12. In embodiments, $-L^{9C}-L^{9D}-L^{9E}-$ is independently

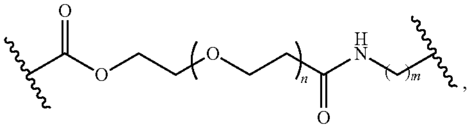

wherein n is independently an integer from 4 to 12 and m is independently an integer from 4 to 12.

In embodiments, $L^9$ is independently

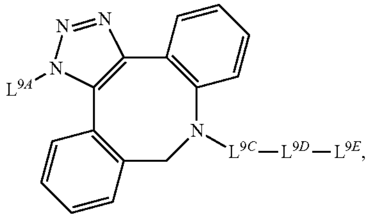

wherein $L^{9A}$, $L^{9C}$, $L^{9D}$, and $L^{9E}$ are as described herein, including in embodiments. In embodiments, $L^9$ is independently

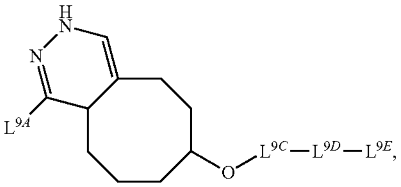

wherein $L^{9A}$, $L^{9C}$, $L^{9D}$, and $L^{9E}$ are as described herein, including in embodiments. In embodiments, $L^9$ is independently

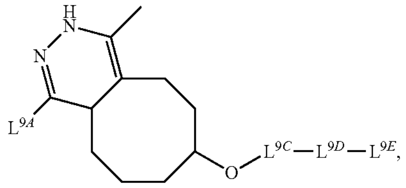

wherein $L^{9A}$, $L^{9C}$, $L^{9D}$, and $L^{9E}$ are as described herein, including in embodiments. In embodiments, $L^9$ is independently

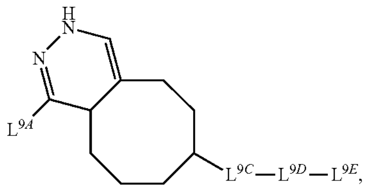

wherein $L^{9A}$ $L^{9C}$, $L^{9D}$, and $L^{9E}$ are as described herein, including in embodiments. In embodiments, $L^9$ is independently

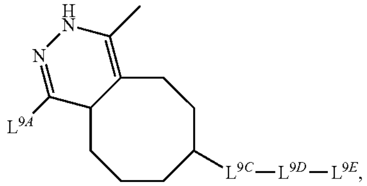

wherein $L^{9A}$, $L^{9C}$, $L^{9D}$, and $L^{9E}$ are as described herein, including in embodiments. In embodiments, $L^9$ is independently

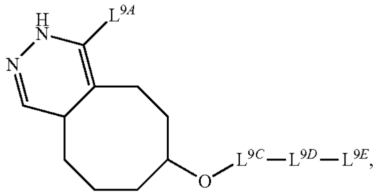

wherein $L^{9A}$, $L^{9C}$, $L^{9D}$, and $L^{9E}$ are as described herein, including in embodiments. In embodiments, $L^9$ is independently

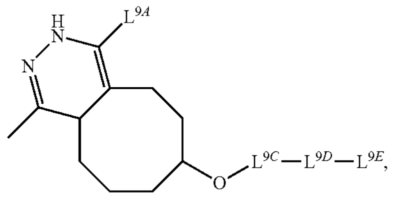

wherein $L^{9A}$, $L^{9C}$, $L^{9D}$, and $L^{9E}$ are as described herein, including in embodiments. In embodiments, $L^9$ is independently

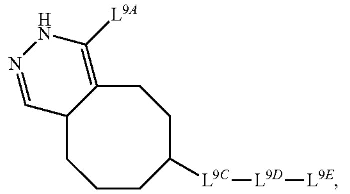

wherein $L^{9A}$, $L^{9C}$, $L^{9D}$, and $L^{9E}$ are as described herein, including in embodiments. In embodiments, $L^9$ is independently

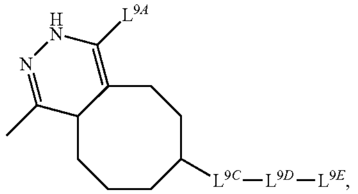

wherein $L^{9A}$, $L^{9C}$, $L^{9D}$, and $L^{9E}$ are as described herein, including in embodiments.

In embodiments, $-L^{9A}-L^{9B}-L^{9C}-$ is independently

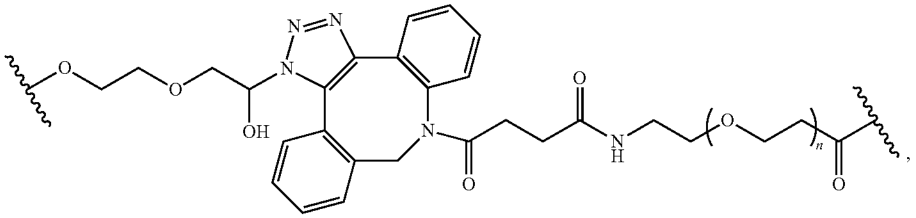

wherein n is independently an integer from 4 to 12. In embodiments, $-L^{9A}-L^{9B}-L^{9C}-$ is independently

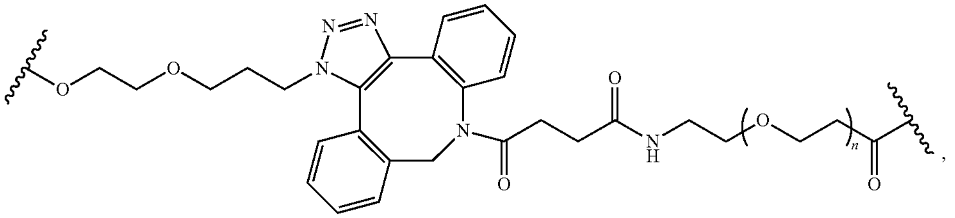

wherein n is independently an integer from 4 to 12. In embodiments, $-L^{9A}-L^{9B}-L^{9C}-$ is independently

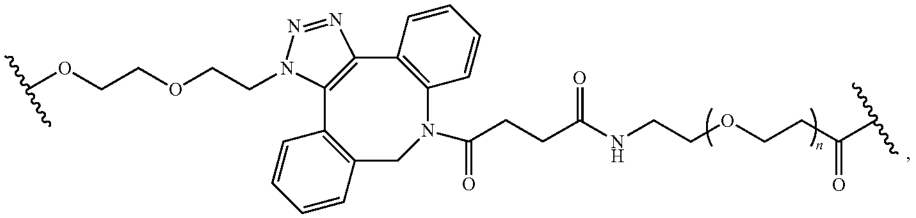

wherein n is independently an integer from 4 to 12. In embodiments, -$L^{9A}$-$L^{9B}$-$L^{9C}$- is independently

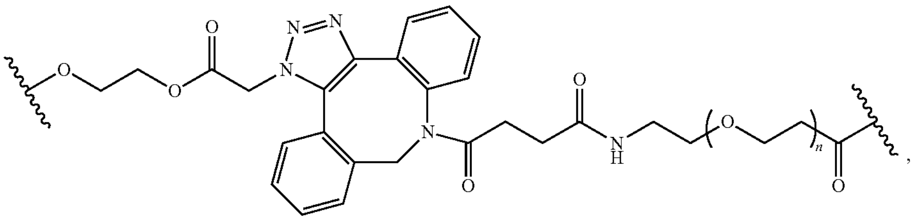

wherein n is independently an integer from 4 to 12. In embodiments, -$L^{9A}$-$L^{9B}$-$L^{9}$C— is independently

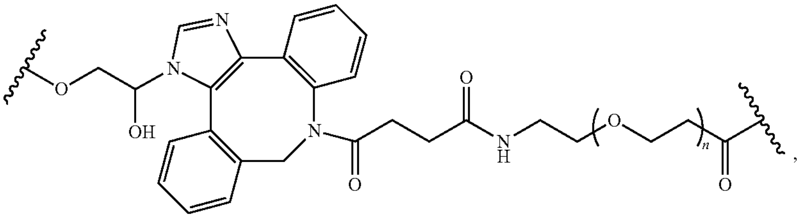

wherein n is independently an integer from 4 to 12. In embodiments, -$L^{9A}$-$L^{9B}$-$L^{9C}$- is independently

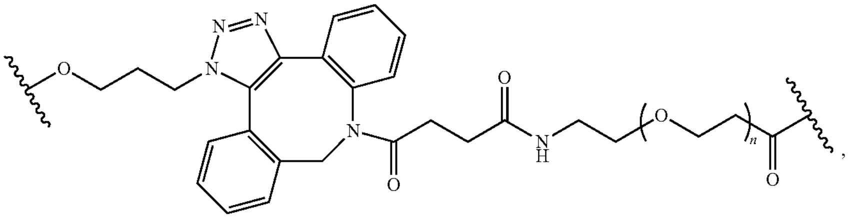

wherein n is independently an integer from 4 to 12. In embodiments, -$L^{9A}$-$L^{9B}$-$L^{9C}$- is independently

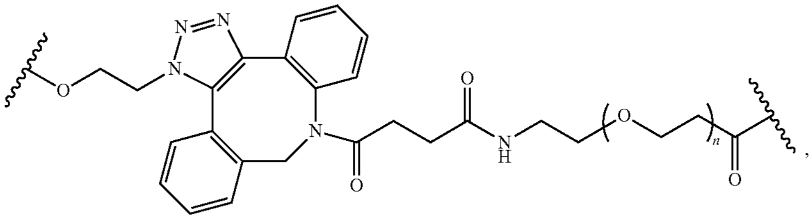

wherein n is independently an integer from 4 to 12. In embodiments, -$L^{9A}$-$L^{9B}$-$L^{9C}$- is independently

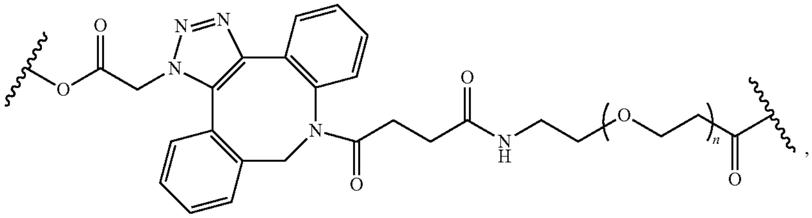

wherein n is independently an integer from 4 to 12. In embodiments. $-L^{9A}-L^{9B}-L^{9C}-$ is independently

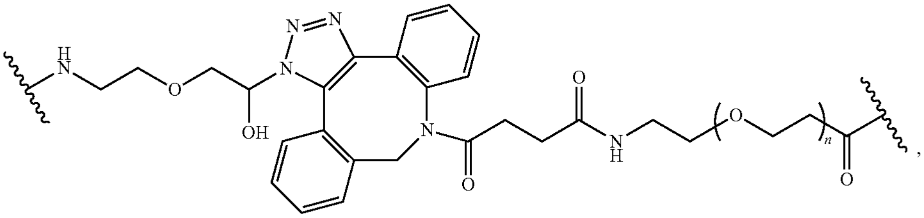

wherein n is independently an integer from 4 to 12. In embodiments, $-L^{9A}-L^{9B}-L^{9C}-$ is independently

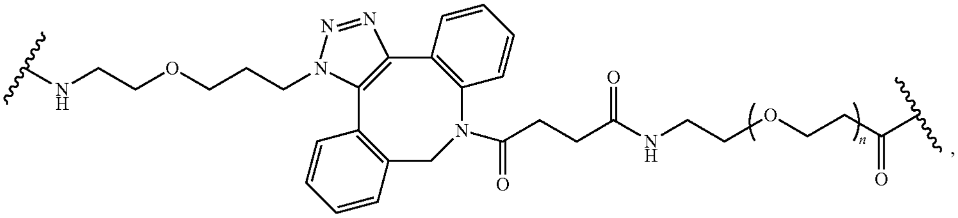

wherein n is independently an integer from 4 to 12. In embodiments, $-L^{9A}-L^{9B}-L^{9C}-$ is independently

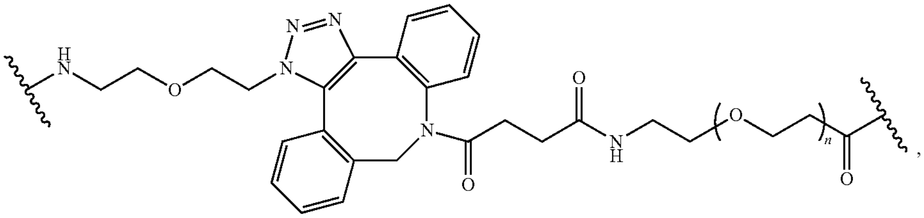

wherein n is independently an integer from 4 to 12. In embodiments, $-L^{9A}-L^{9B}-L^{9}$C— is independently

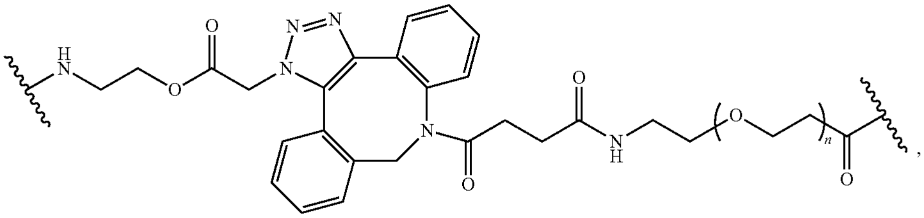

wherein n is independently an integer from 4 to 12. In embodiments, $-L^{9A}-L^{9B}-L^{9C}-$ is independently

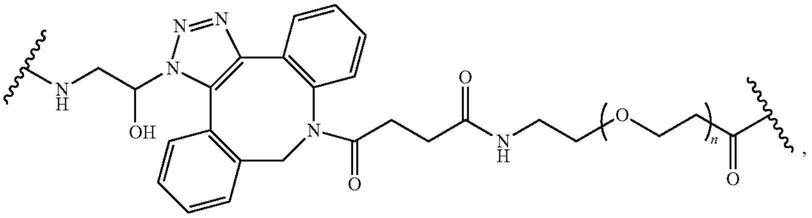

wherein n is independently an integer from 4 to 12. In embodiments, $-L^{9A}-L^{9B}-L^{9C}-$ is independently

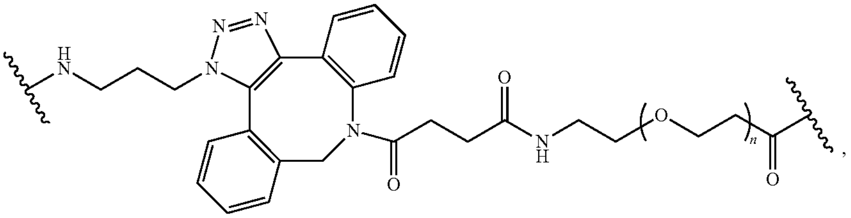

wherein n is independently an integer from 4 to 12. In embodiments, $-L^{9A}-L^{9B}-L^{9C}-$ is independently

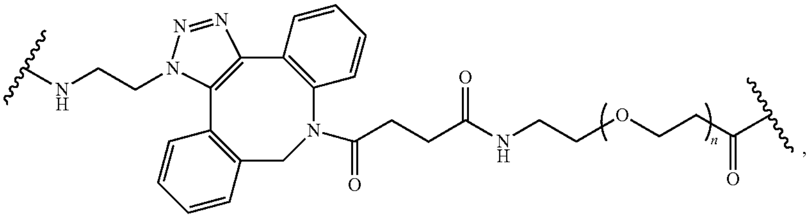

wherein n is independently an integer from 4 to 12. In embodiments, $-L^{9A}-L^{9B}-L^{9C}-$ is independently

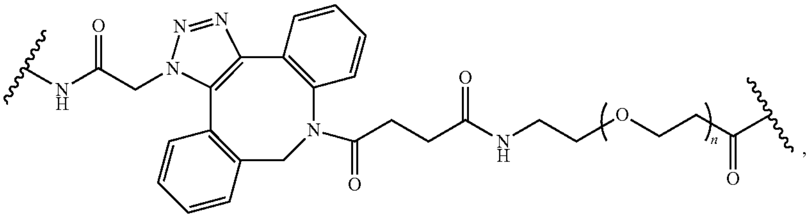

wherein n is independently an integer from 4 to 12.

In embodiments, $L^{9D}$ is independently —S—S— and $L^{9E}$ is independently an unsubstituted $C_4$-$C_8$ alkylene. In embodiments, $L^{9D}$ is independently

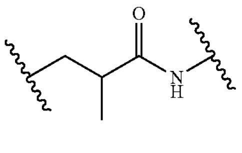 [SMILES: *CC(C)C(=O)N*]

and $L^{9E}$ is independently an unsubstituted $C_4$-$C_8$ alkylene.

In embodiments, $L^9$ is independently
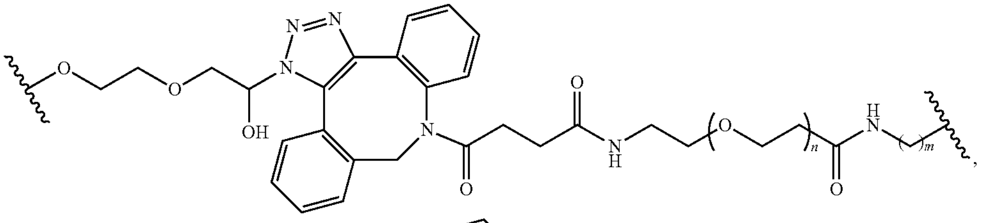
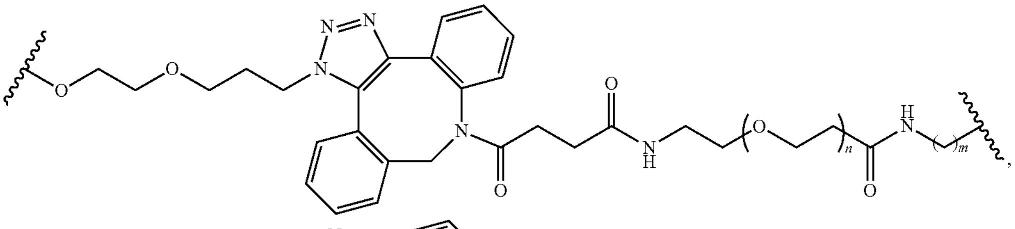
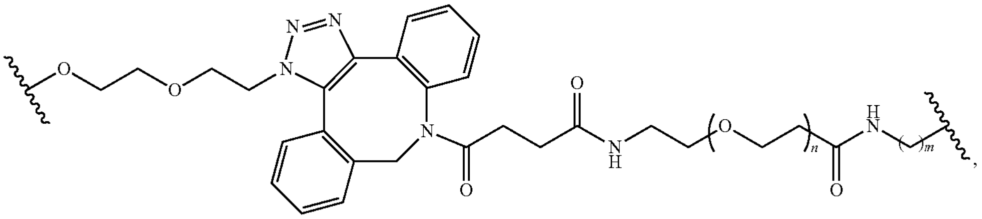
or
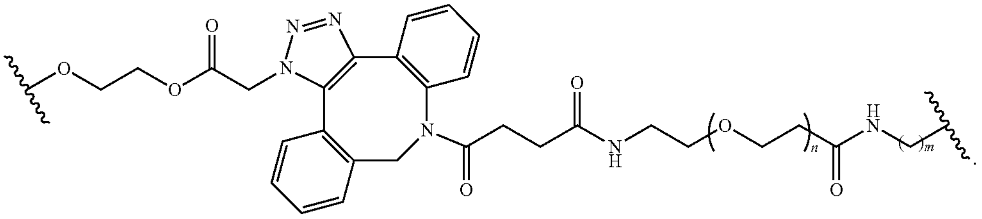
The symbol n is independently an integer from 4 to 12, and the symbol m is independently an integer from 4 to 12.
In embodiments, $L^9$ is independently
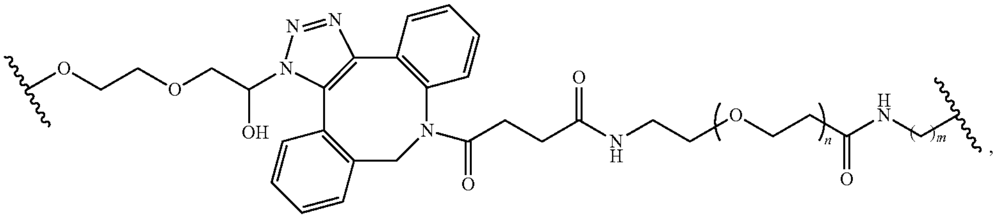
wherein n is independently an integer from 4 to 12, and m is independently an integer from 4 to 12.
In embodiments, $L^9$ is independently
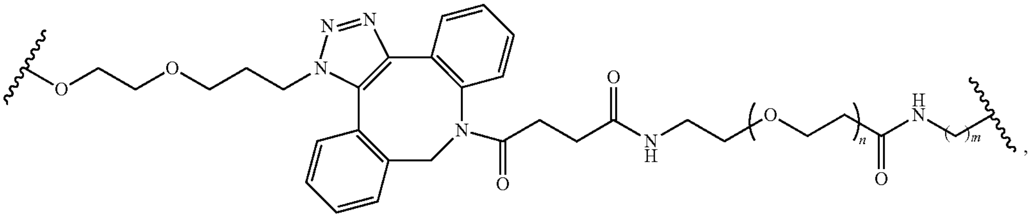

wherein n is independently an integer from 4 to 12, and m is independently an integer from 4 to 12.

In embodiments, $L^9$ is independently

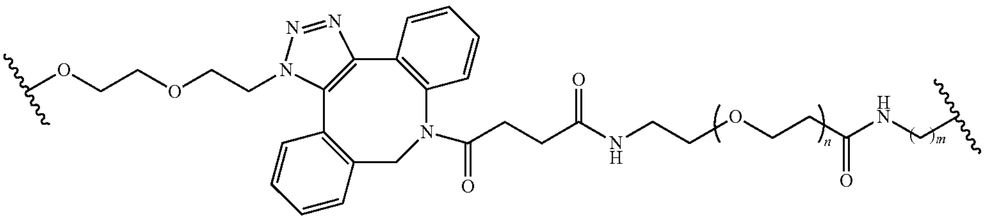, wherein n is independently an integer from 4 to 12, and m is independently an integer from 4 to 12.

In embodiments, $L^9$ is independently

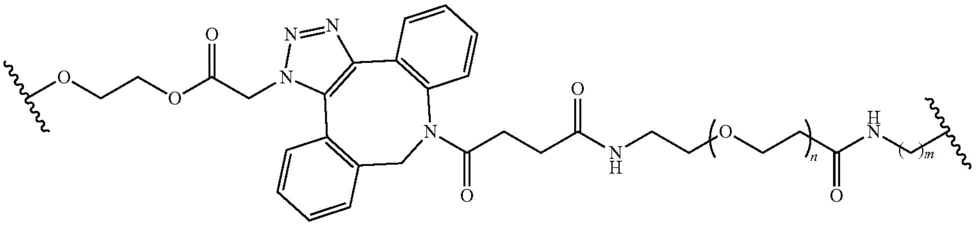, wherein n is independently an integer from 4 to 12, and m is independently an integer from 4 to 12.

In embodiments, $L^9$ is independently

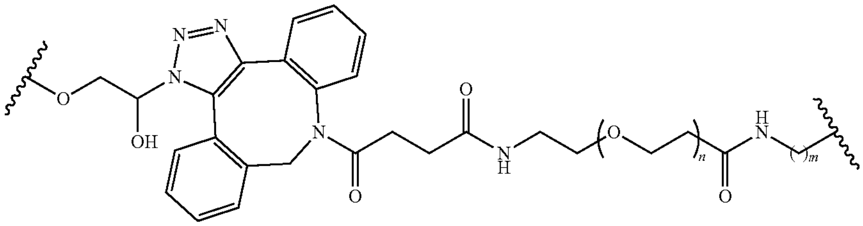,

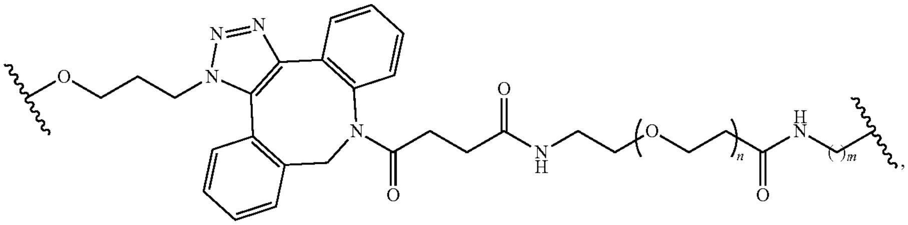,

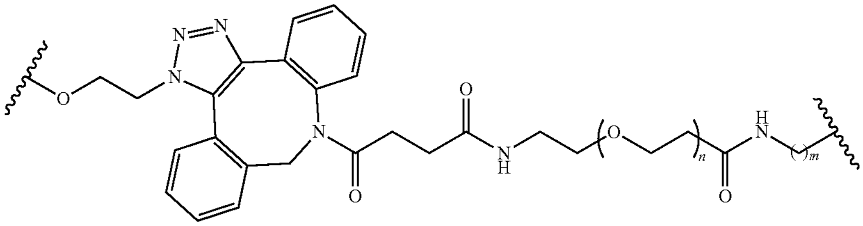, or

-continued

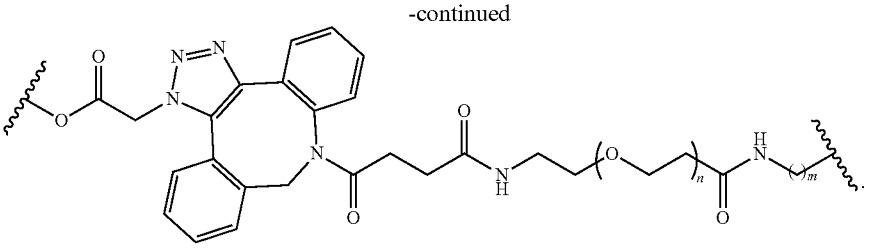

The symbol n is independently an integer from 4 to 12, and the symbol m is independently an integer from 4 to 12.

In embodiments, $L^9$ is independently

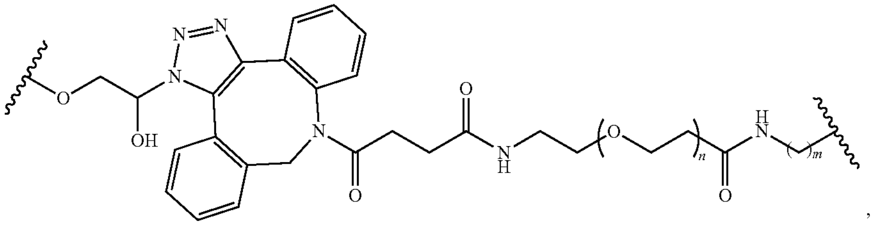

wherein n is independently an integer from 4 to 12, and m is independently an integer from 4 to 12.

In embodiments, $L^9$ is independently

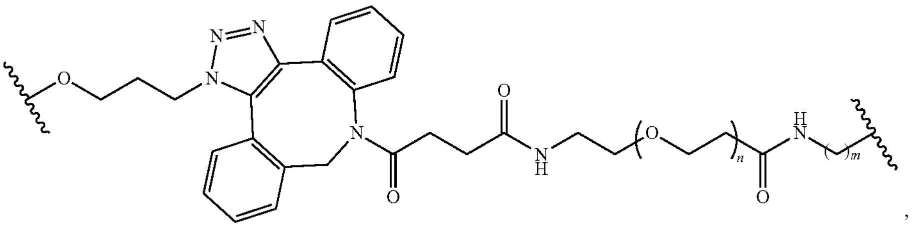

wherein n is independently an integer from 4 to 12, and m is independently an integer from 4 to 12.

In embodiments, $L^9$ is independently

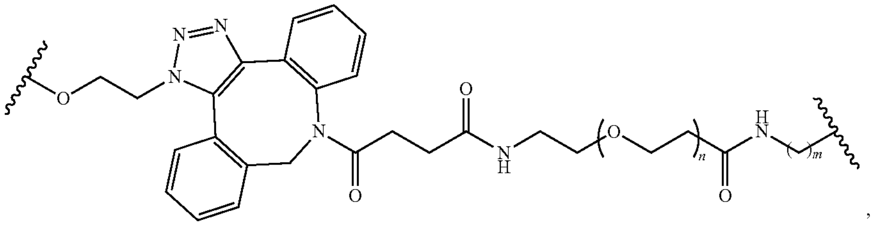

wherein n is independently an integer from 4 to 12, and m is independently an integer from 4 to 12.

In embodiments, $L^9$ is independently
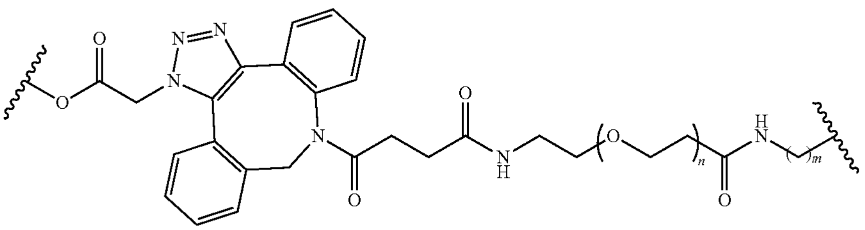
,
wherein n is independently an integer from 4 to 12, and m is independently an integer from 4 to 12.
In embodiments, $L^9$ is independently
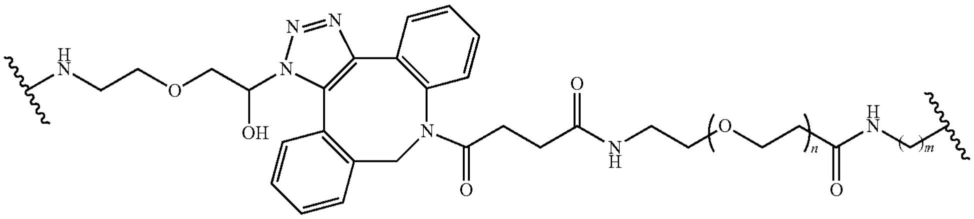
,
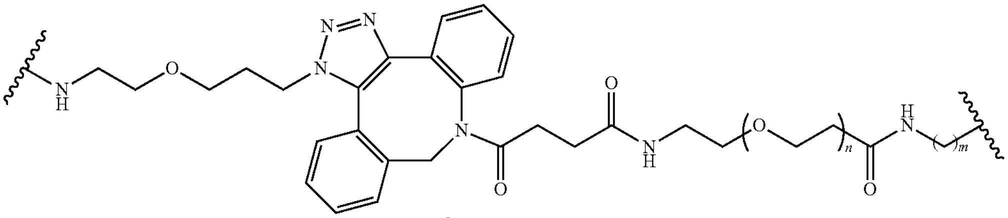
,
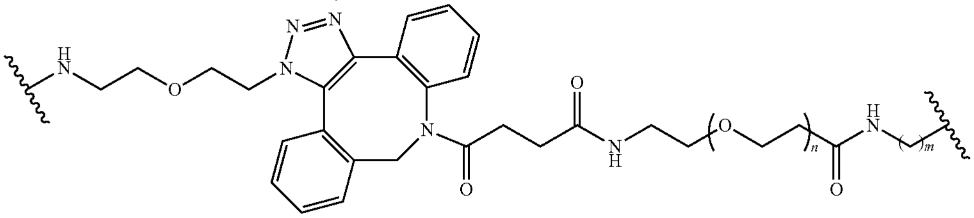
, or
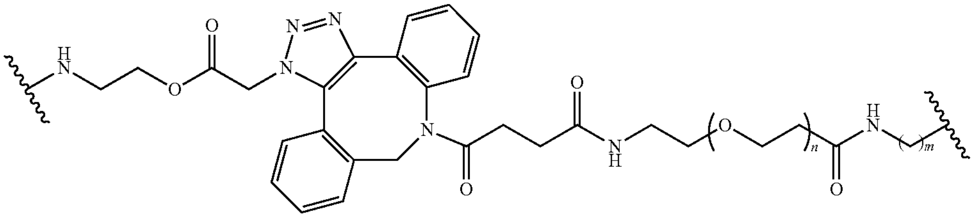
.
The symbol n is independently an integer from 4 to 12, and the symbol m is independently an integer from 4 to 12.
In embodiments, $L^9$ is independently
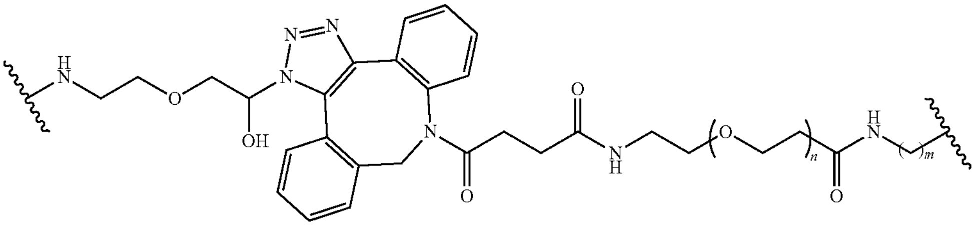
, wherein n is independently an integer from 4 to 12, and m is independently an integer from 4 to 12.

In embodiments, $L^9$ is independently

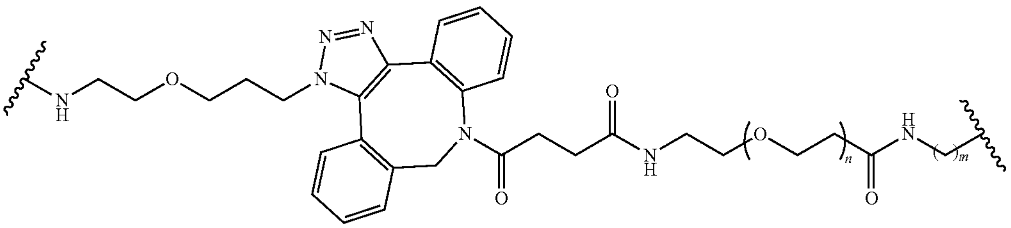

, wherein n is independently an integer from 4 to 12, and m is independently an integer from 4 to 12.

In embodiments, $L^9$ is independently

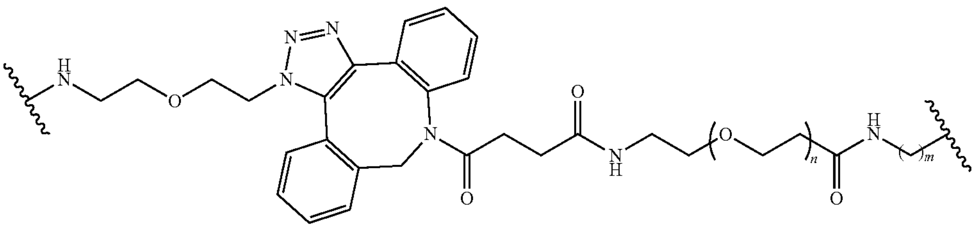

, wherein n is independently an integer from 4 to 12, and m is independently an integer from 4 to 12.

In embodiments, $L^9$ is independently

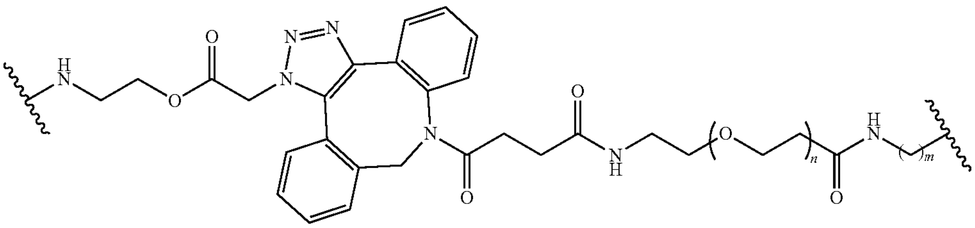

, wherein n is independently an integer from 4 to 12, and m is independently an integer from 4 to 12.

In embodiments, $L^9$ is independently

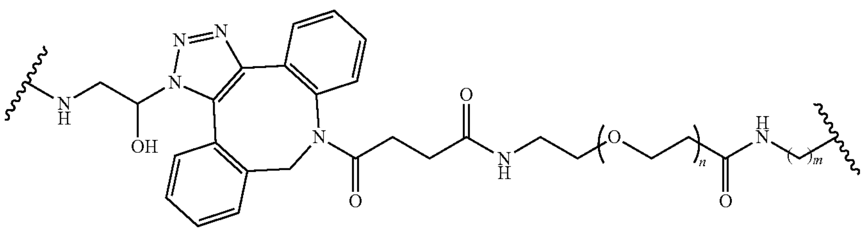

,

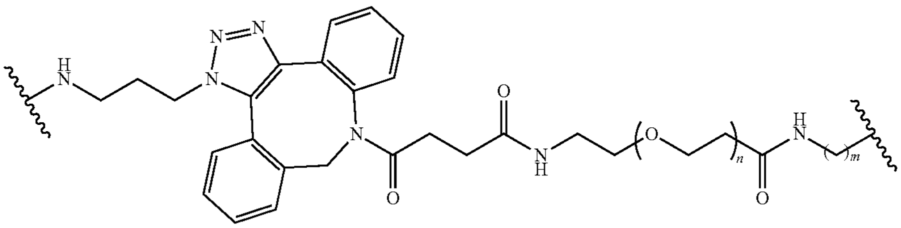

,

-continued

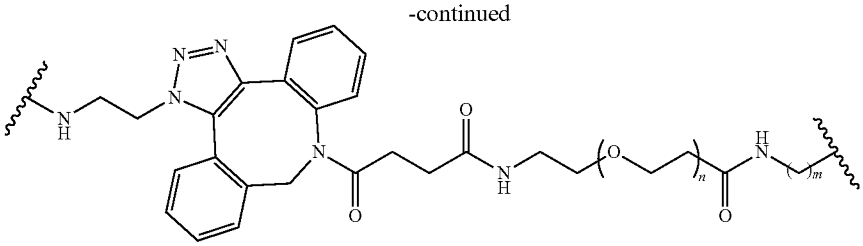

, or

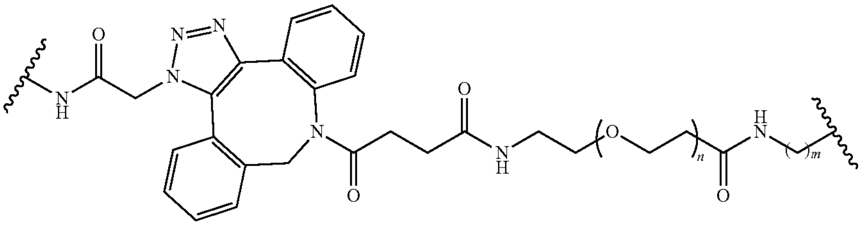

.

The symbol n is independently an integer from 4 to 12, and the symbol m is independently an integer from 4 to 12.

In embodiments, $L^9$ is independently

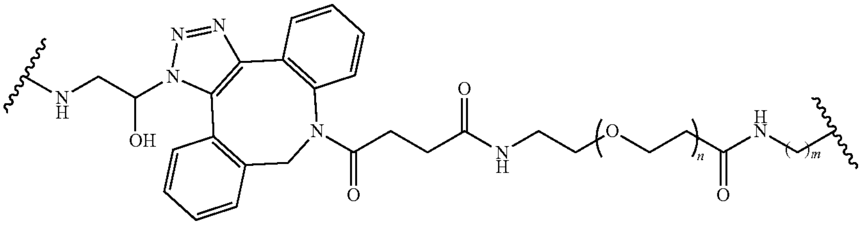

, wherein n is independently an integer from 4 to 12, and m is independently an integer from 4 to 12.

In embodiments, $L^9$ is independently

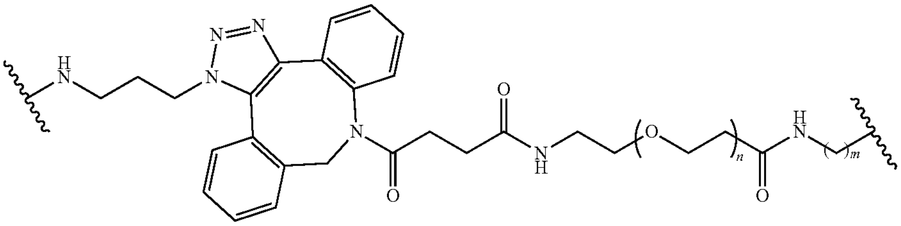

, wherein n is independently an integer from 4 to 12, and m is independently an integer from 4 to 12.

In embodiments, $L^9$ is independently

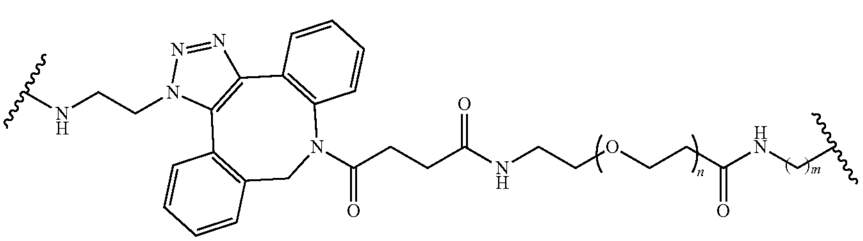

, wherein n is independently an integer from 4 to 12, and m is independently an integer from 4 to 12.

In embodiments, $L^9$ is independently

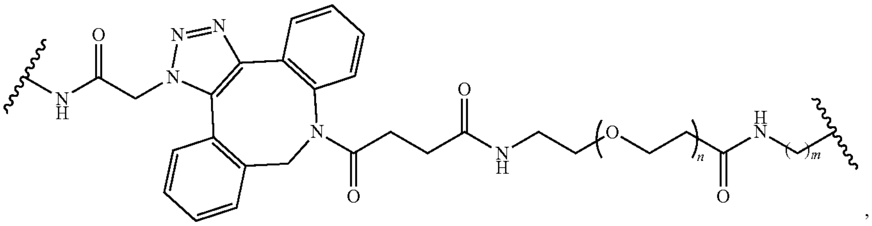

wherein n is independently an integer from 4 to 12, and m is independently an integer from 4 to 12.

In embodiments, each $L^9$ is the same.

In embodiments, $R^9$ is independently 1) an oligonucleotide moiety; or 2) a second non-reactive moiety selected from hydrogen, halogen, $—CX^9_3$, $—CHX^9_2$, $—CH_2X^9$, $—OCX^{93}$, $—OCH_2X^9$, $—OCHX^9_2$, —CN, $—SO_{n9}R^{9D}$, $SO_{v9}NR^{9A}R^{9B}$, $NHC(O)NR^{9A}R^{9B}$, $N(O)_{m9}$, $—NR^{9A}R^{9B}$, $—C(O)R^{9C}$, $—C(O)—OR^{9C}$, $—C(O)NR^{9A}R^{9B}$, $—OR^9D$, $—NR^{9A}SO_2R^{9D}$, $—NR^{9A}C(O)R^{9C}$, $—NR^{9A}C(O)OR^{9C}$, $—NR^{9A}OR^{9C}$, $—OC(O)R^{9C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$. $C_3$-$C_6$. $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{9A}$, $R^{9B}$, $R^{9C}$, and $R^{9D}$ are independently hydrogen, $—CX_3$, —CN, —COOH, $—CONH_2$, $—CHX_2$, $—CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{9A}$ and $R^{9B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

X and $X^9$ are independently —F, —Cl, —Br, or —I.

The symbol n9 is independently an integer from 0 to 4

The symbols m9 and v9 are each independently an integer from 1 to 2.

In embodiments, $R^9$ is independently an oligonucleotide moiety.

In embodiments, when $R^2$ and $R^9$ are each independently an oligonucleotide moiety, the $R^2$ and $R^9$ oligonucleotide moieties are the same. In embodiments, when $R^2$ and $R^9$ are each independently an oligonucleotide moiety, the $R^2$ and $R^9$ oligonucleotide moieties are different.

In embodiments, when $R^4$ is a first non-reactive moiety and $R^9$ is a second non-reactive moiety, $R^4$ and $R^9$ are different. In embodiments, when $R^4$ is a first non-reactive moiety and $R^9$ is a second non-reactive moiety, $R^4$ and $R^9$ are the same.

In embodiments, $R^9$ is independently a non-reactive moiety selected from halogen, $—CX^9_3$, $—CHX^9_2$, $—CH_2X^9$, $—OCX^{93}$, $—OCH_2X^9$, $—OCHX^9_2$, —CN, $—SO_{n9}R^{9D}$, $—SO_{v9}NR^{9A}R^{9B}$, $NHC(O)NR^{9A}R^{9B}$, $N(O)_{m9}$, $—NR^{9A}R^{9B}$, $C(O)R^{9C}$, $—C(O)—OR^{9C}$, $—C(O)NR^{9A}R^{9B}$, $—OR^9D$, $—NR^{9A}SO_2R^{9D}$, $—NR^{9A}C(O)R^{9C}$, $—NR^{9A}C(O)OR^{9C}$, $—NR^{9A}OR^{9C}$, $—OC(O)R^{9C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^9$ is independently a non-reactive moiety selected from halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^9$ is independently hydrogen, $—OCH_2CH_2—(OCH_2CH_2)_p—OCH_3$ or $—N(CH_3)_2$; and p is independently an integer from 0 to 10.

In embodiments, each $R^9$ is the same.

In embodiments, $-L^9-R^9$ is independently $—OCH_2CH_2—(OCH_2CH_2)_p—OCH_3$ or $—N(CH_3)_2$; and p is independently an integer from 4 to 10.

In embodiments, $R^{10}$ is independently —CN. In embodiments, $R^{10}$ is independently substituted or unsubstituted alkyl. In embodiments, $R^{10}$ is independently substituted or unsubstituted $C_1$-$C_4$ alkyl. In embodiments, $R^{10}$ is independently unsubstituted $C_1$-$C_4$ alkyl. In embodiments, $R^{10}$ is independently unsubstituted methyl. In embodiments, $R^{10}$ is independently unsubstituted ethyl. In embodiments, $R^{10}$ is independently unsubstituted propyl. In embodiments, $R^{10}$ is independently unsubstituted n-propyl. In embodiments, $R^{10}$ is independently unsubstituted isopropyl. In embodiments, $R^{10}$ is independently unsubstituted butyl. In embodiments, $R^{10}$ is independently unsubstituted n-butyl. In embodiments, $R^{10}$ is independently unsubstituted tert-butyl. In embodiments, $R^{10}$ is independently substituted or unsubstituted heteroalkyl. In embodiments, $R^{10}$ is independently substituted or unsubstituted 2 to 6 membered heteroalkyl.

In embodiments, each $R^{10}$ is the same.

In embodiments, $L^{11}$ is independently a substituted or unsubstituted heteroalkylene.

In embodiments, LA is independently a bond.

In embodiments, $L^{11B}$ and $L^{11D}$ are independently substituted or unsubstituted heteroalkylene; $L^{11C}$ is independently a substituted or unsubstituted heteroarylene; and $L^{11E}$ is independently a bond.

In embodiments, $L^{11B}$ and $L^{11E}$ are independently substituted or unsubstituted heteroalkylene; $L^{11C}$ is independently a substituted or unsubstituted heteroarylene; and $L^{11D}$ is independently a substituted or unsubstituted arylene.

In embodiments, $L^{11A}$ is independently a substituted or unsubstituted heteroalkylene. In embodiments, $L^{11A}$ is independently

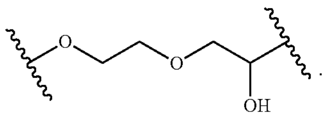 [SMILES: *OCCOCC(*)O]

In embodiments, $L^{11A}$ is independently

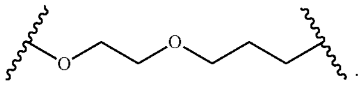 [SMILES: *CCCOCCO*]

In embodiments, $L^{11A}$ is independently

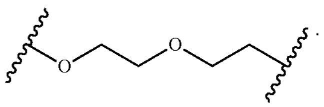 [SMILES: *CCOCCO*]

In embodiments, $L^{11A}$ is independently

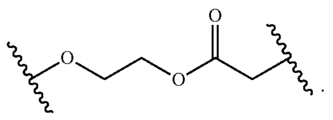 [SMILES: *CC(=O)OCCO*]

In embodiments, $L^{11A}$ is independently

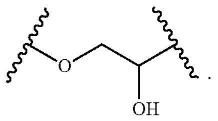 [SMILES: *OCC(*)O]

In embodiments, $L^{11A}$ is independently

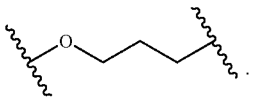 [SMILES: *CCCO*]

In embodiments, $L^{11A}$ is independently

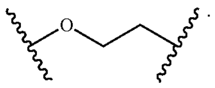 [SMILES: *CCO*]

In embodiments, $L^{11A}$ is independently

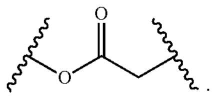 [SMILES: *CC(=O)O*]

In embodiments, $L^{11A}$ is independently

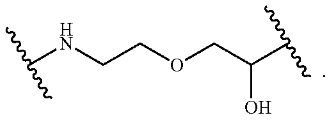 [SMILES: *NCCOCC(*)O]

In embodiments, $L^{11A}$ is independently

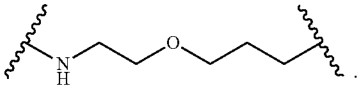 [SMILES: *CCCOCCN*]

In embodiments, $L^{11A}$ is independently

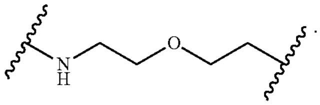 [SMILES: *CCOCCN*]

In embodiments, $L^{11A}$ is independently

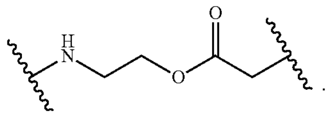 [SMILES: *CC(=O)OCCN*]

In embodiments, $L^{11A}$ is independently

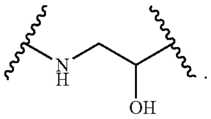 [SMILES: *NCC(*)O]

In embodiments, $L^{11A}$ is independently

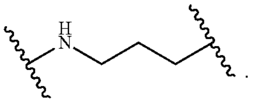 [SMILES: *CCCN*]

In embodiments, $L^{11A}$ is independently

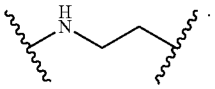 [SMILES: *CCN*]

In embodiments, $L^{11A}$ is independently

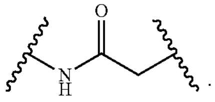 [SMILES: *CC(=O)N*]

In embodiments, $L^{11B}$ is independently a substituted or unsubstituted heteroarylene. In embodiments, $L^{11B}$ is independently

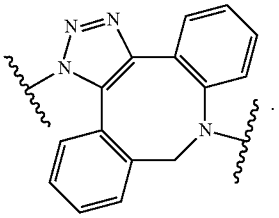 [SMILES: *N1Cc2ccccc2-c2c(nnn2*)-c2ccccc21]

In embodiments, $L^{11B}$ is independently

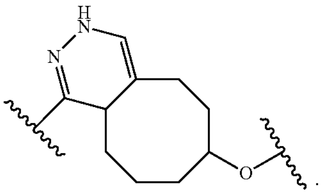 [SMILES: *OC1CCCC2C(=CNN=C2*)CC1]

In embodiments, $L^{11B}$ is independently

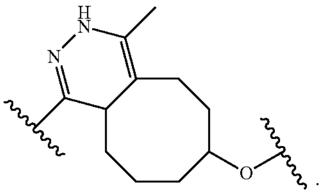 [SMILES: *OC1CCCC2C(*)=NNC(C)=C2CC1]

In embodiments, $L^{11B}$ is independently

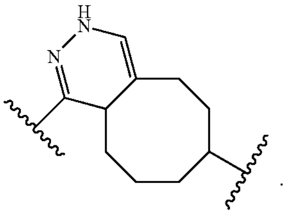 [SMILES: *C1=NNC=C2CCC(*)CCCC21]

In embodiments, $L^{11B}$ is independently

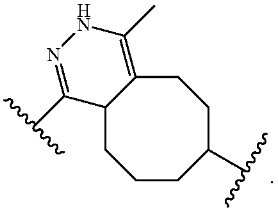 [SMILES: *C1=NNC(C)=C2CCC(*)CCCC12]

In embodiments, $L^{11B}$ is independently

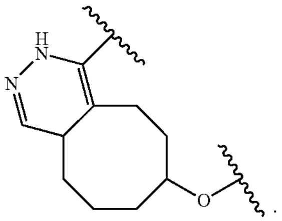 [SMILES: *OC1CCCC2C=NNC(*)=C2CC1]

In embodiments, $L^{11B}$ is independently

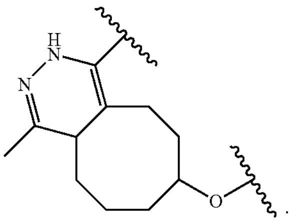 [SMILES: *OC1CCCC2C(C)=NNC(*)=C2CC1]

In embodiments, $L^{11B}$ is independently

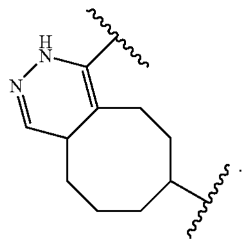 [SMILES: *C1=C2CCC(*)CCCC2C=NN1]
.

In embodiments, $L^{11B}$ is independently

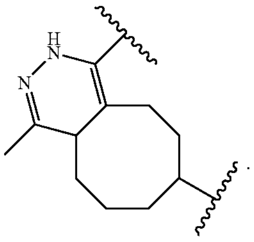 [SMILES: *C1=C2CCC(*)CCCC2C(C)=NN1]
.

In embodiments, $L^{11C}$ is independently a substituted or unsubstituted heteroalkylene. In embodiments, $L^{11C}$ is independently

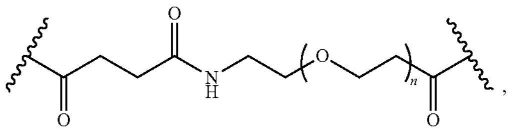
, wherein n is independently an integer from 4 to 12. In embodiments, $L^{11C}$ is independently

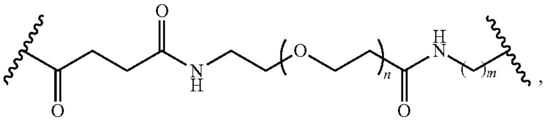
, wherein n is independently an integer from 4 to 12 and m is independently an integer from 4 to 12. In embodiments, $L^{11C}$ is independently

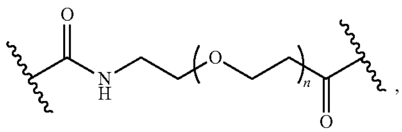
, wherein n is independently an integer from 4 to 12. In embodiments, $L^{11C}$ is independently

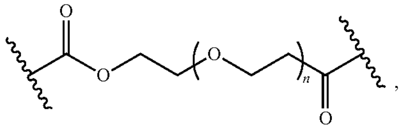
, wherein n is independently an integer from 4 to 12. In embodiments, $L^{11C}$ is independently

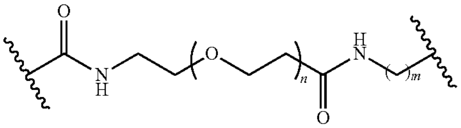
, wherein n is independently an integer from 4 to 12 and m is independently an integer from 4 to 12. In embodiments, $L^{11C}$ is independently

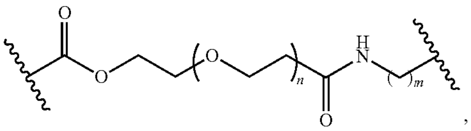
, wherein n is independently an integer from 4 to 12 and m is independently an integer from 4 to 12.

In embodiments, $L^{11D}$ is independently a substituted or unsubstituted heteroalkylene. In embodiments, $L^{11D}$ is independently

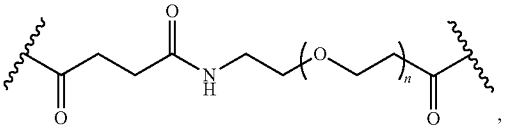
, wherein n is independently an integer from 4 to 12. In embodiments, $L^{11}$ is independently

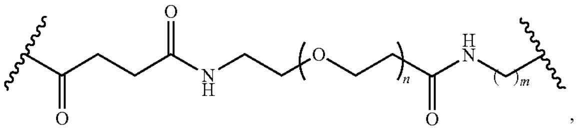
, wherein n is independently an integer from 4 to 12 and m is independently an integer from 4 to 12. In embodiments, $L^{111}$ is independently

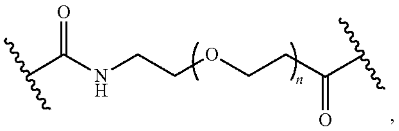
, wherein n is independently an integer from 4 to 12. In embodiments, $L^{11D}$ is independently

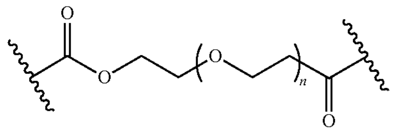
, wherein n is independently an integer from 4 to 12. In embodiments, $L^{11D}$ is independently

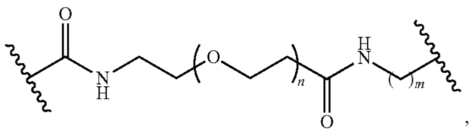
, wherein n is independently an integer from 4 to 12 and m is independently an integer from 4 to 12. In embodiments, $L^{1}$ is independently

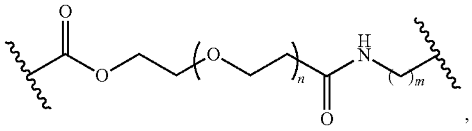
, wherein n is independently an integer from 4 to 12 and m is independently an integer from 4 to 12.

In embodiments, $-L^{11C}-L^{11D}-L^{11E}-$ is independently a substituted or unsubstituted heteroalkylene. In embodiments, $-L^{11C}-L^{11D}-L^{11E}$ is independently

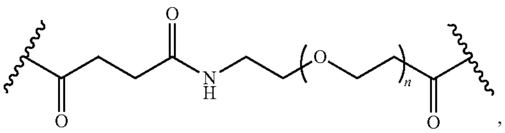
, wherein n is independently an integer from 4 to 12. In embodiments, $-L^{11C}-L^{11D}$, $-L^{11E}-$ is independently

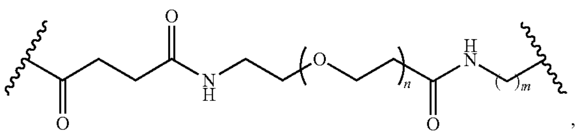
, wherein n is independently an integer from 4 to 12 and m is independently an integer from 4 to 12. In embodiments, $-L^{11C}-L^{11D}$, $-L^{11E}-$ is independently

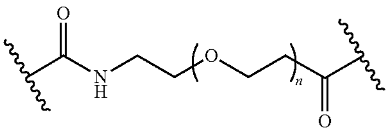
, wherein n is independently an integer from 4 to 12. In embodiments, $-L^{11C}-L^{11D}-L^{11E}-$ is independently

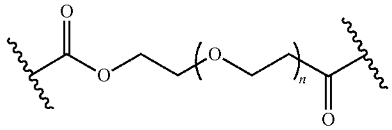
, wherein n is independently an integer from 4 to 12. In embodiments, $-L^{11C}-L^{11D}-L^{11E}-$ is independently

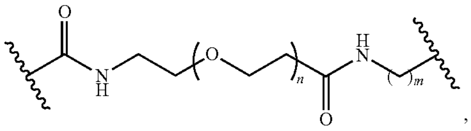
, wherein n is independently an integer from 4 to 12 and m is independently an integer from 4 to 12. In embodiments, $-L^{11C}-L^{11D}$, $-L^{11E}-$ is independently

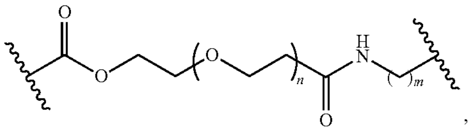
, wherein n is independently an integer from 4 to 12 and m is independently an integer from 4 to 12.

In embodiments, $L^{11}$ is independently

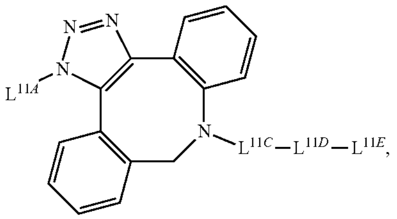

wherein $L^{11A}$ $L^{11C}$, $L^{11D}$, and $L^{11E}$ are as described herein, including in embodiments. In embodiments, $L^{11}$ is independently

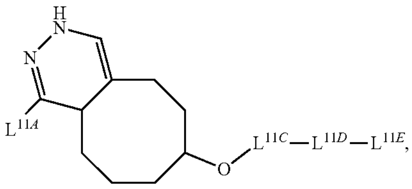

wherein $L^{11A}$ $L^{11C}$, $L^{11D}$, and $L^{11E}$ are as described herein, including in embodiments. In embodiments, $L^{11}$ is independently

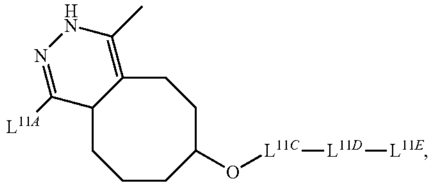

wherein $L^{11A}$ $L^{11C}$, $L^{11D}$, and $L^{11E}$ are as described herein, including in embodiments. In embodiments, $L^{11}$ is independently

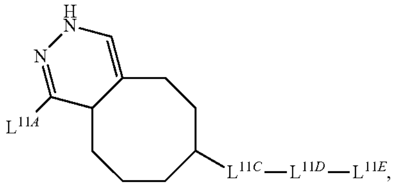

wherein $L^{11A}$, $L^{11C}$, $L^{11D}$, and $L^{11E}$ are as described herein, including in embodiments. In embodiments, $L^{11}$ is independently

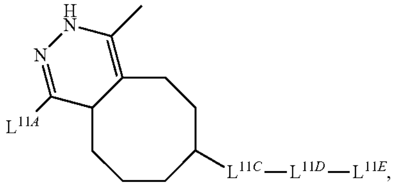

wherein $L^{11A}$, $L^{11C}$, $L^{11D}$, and $L^{11E}$ are as described herein, including in embodiments. In embodiments, $L^{11}$ is independently

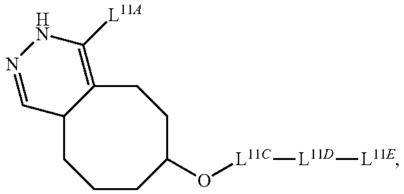

wherein $L^{11A}$ $L^{11C}$, $L^{11D}$, and $L^{11E}$ are as described herein, including in embodiments. In embodiments, $L^{11}$ is independently

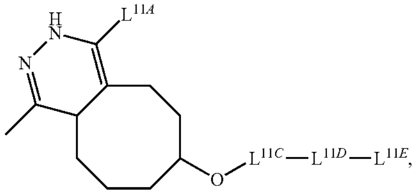

wherein $L^{11A}$ $L^{11C}$, $L^{11D}$, and $L^{11E}$ are as described herein, including in embodiments. In embodiments, $L^{11}$ is independently

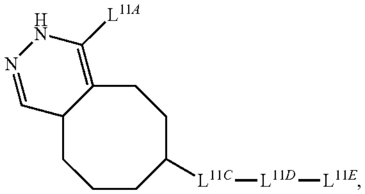

wherein $L^{11A}$ $L^{11C}$, $L^{11D}$, and $L^{11E}$ are as described herein, including in embodiments. In embodiments, $L^{11}$ is independently

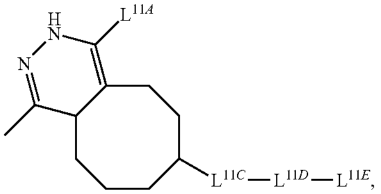

wherein $L^{11A}$ $L^{11C}$, $L^{11D}$, and $L^{11E}$ are as described herein, including in embodiments.

In embodiments, -$L^{11A}$-$L^{11B}$, -$L^{11C}$- is independently

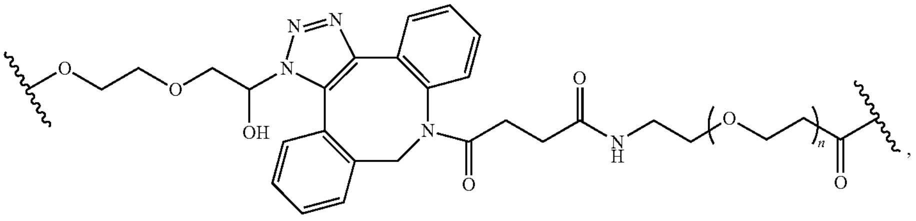

wherein n is independently an integer from 4 to 12. In embodiments, $-L^{11A}-L^{11B}$, $-L^{11C}-$ is independently

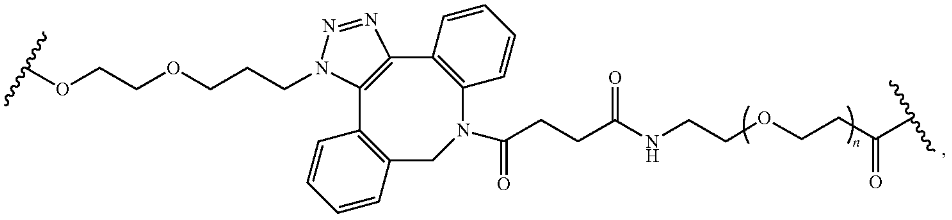

wherein n is independently an integer from 4 to 12. In embodiments, $-L^{11A}-L^{11B}$, $-L^{11C}-$ is independently

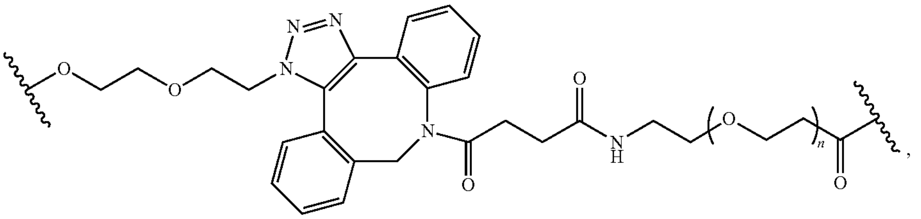

wherein n is independently an integer from 4 to 12. In embodiments, $-L^{11A}-L^{11B}$, $-L^{11C}-$ is independently

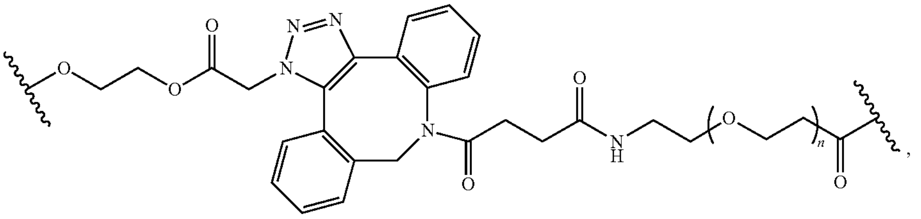

wherein n is independently an integer from 4 to 12. In embodiments, $-L^{11A}-L^{11B}$, $-L^{11C}-$ is independently

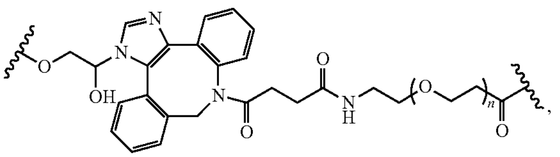

wherein n is independently an integer from 4 to 12. In embodiments, $-L^{11A}-L^{11B}-L^{11C}-$ is independently

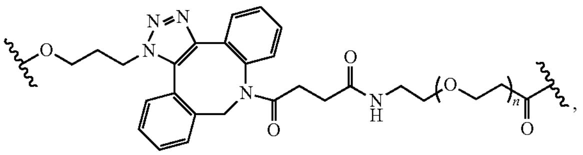

wherein n is independently an integer from 4 to 12. In embodiments, $-L^{11A}-L^{11B}$, $-L^{11C}-$ is independently

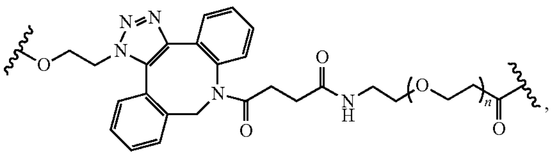

wherein n is independently an integer from 4 to 12. In embodiments, $-L^{11A}-L^{11B}-L^{11C}-$ is independently

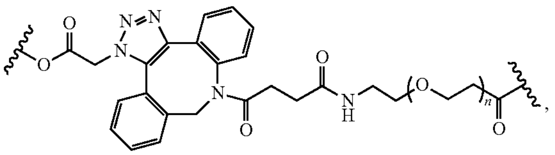

wherein n is independently an integer from 4 to 12. In embodiments, $-L^{11A}-L^{11B}-L^{11C}-$ is independently

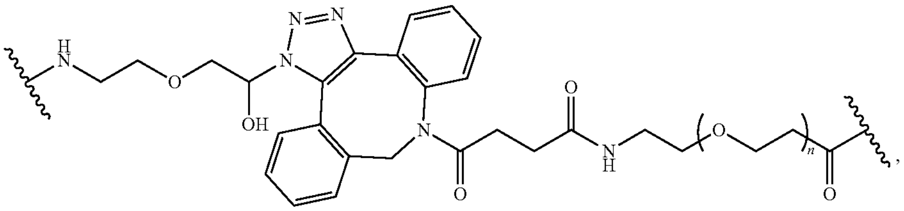

wherein n is independently an integer from 4 to 12. In embodiments, $-L^{11A}-L^{11B}$, $-L^{11C}-$ is independently

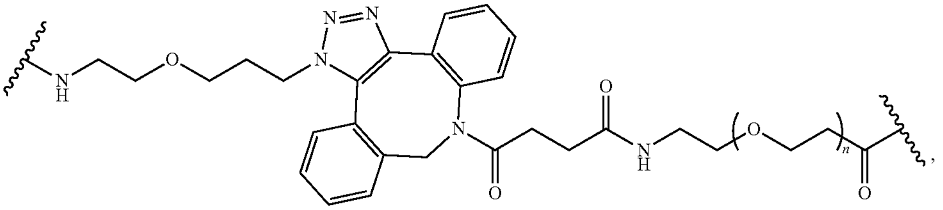

wherein n is independently an integer from 4 to 12. In embodiments, $-L^{11A}-L^{11B}$, $-L^{11C}-$ is independently

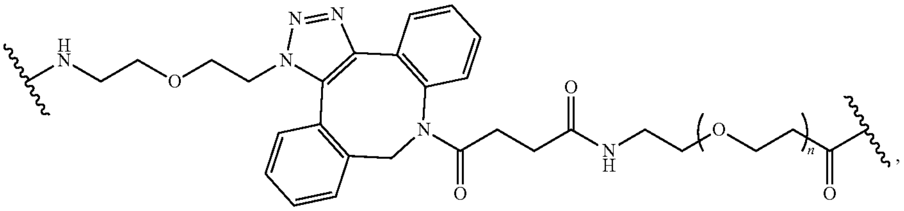

wherein n is independently an integer from 4 to 12. In embodiments, $-L^{11A}-L^{11B}-L^{11C}-$ is independently

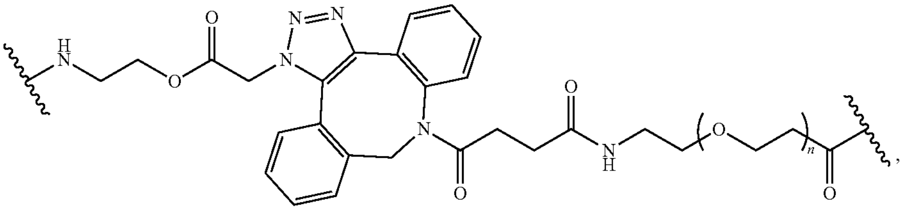

wherein n is independently an integer from 4 to 12. In embodiments, $-L^{11A}-L^{11B}-L^{11C}-$ is independently

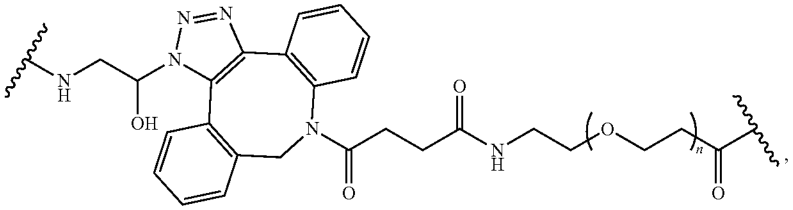

wherein n is independently an integer from 4 to 12. In embodiments, $-L^{11A}-L^{11B}$, $-L^{11C}-$ is independently

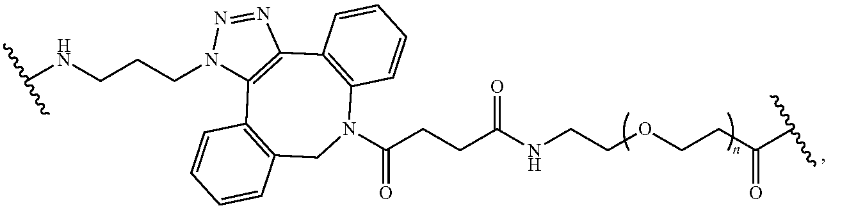

wherein n is independently an integer from 4 to 12. In embodiments, $-L^{11A}-L^{11B}$, $-L^{11C}-$ is independently

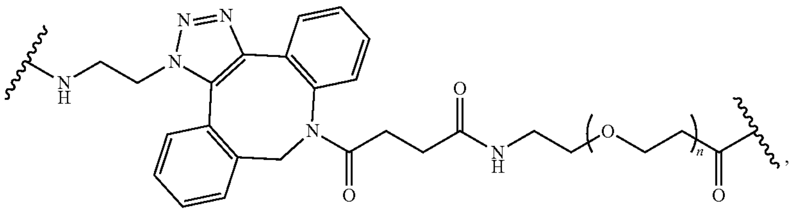

wherein n is independently an integer from 4 to 12. In embodiments, $-L^{11A}-L^{11B}$, $-L^{11C}-$ is independently

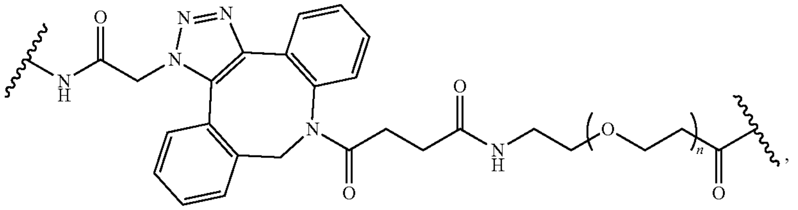

wherein n is independently an integer from 4 to 12.

In embodiments, $L^{11D}$ is independently —S—S— and $L^{11E}$ is independently an S unsubstituted $C_4$-$C_8$ alkylene. In embodiments, $L^{11D}$

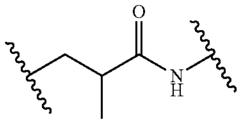 [SMILES: *CC(C)C(=O)N*]

and $L^{11E}$ is independently an unsubstituted $C_4$-$C_8$ alkylene.

In embodiments, $L^{11}$ is independently

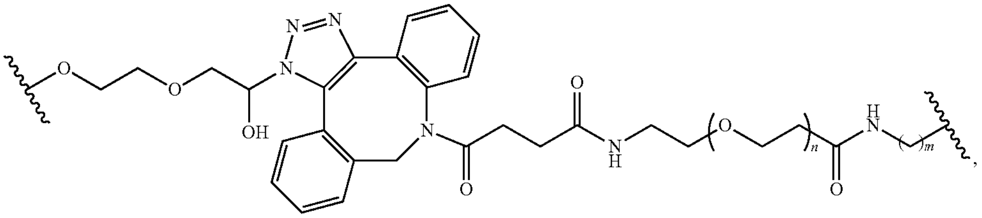

-continued

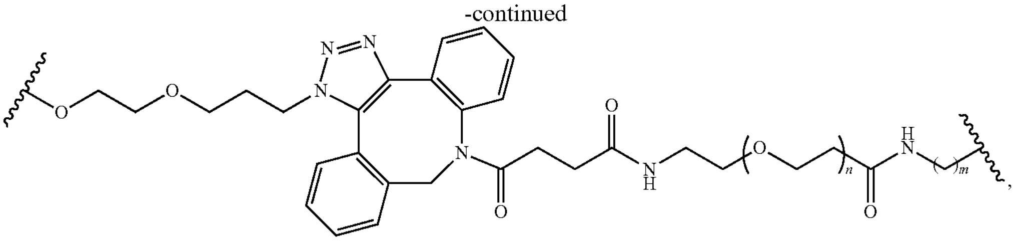

,

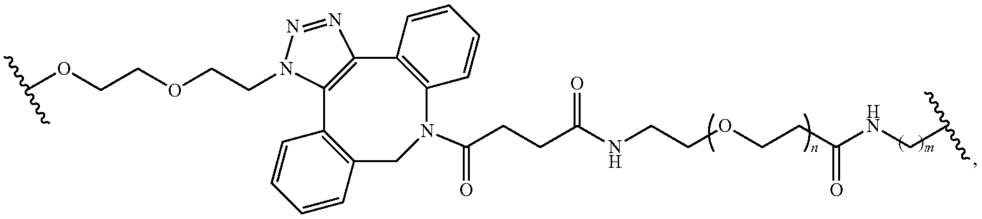

, or

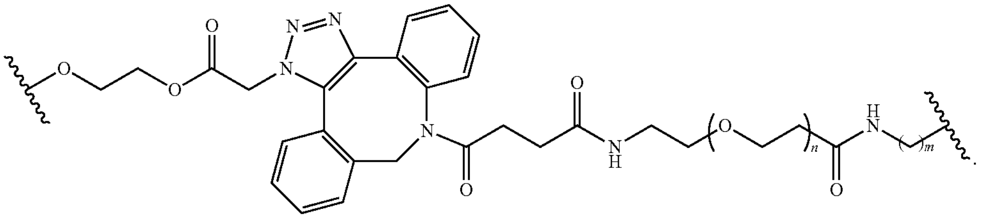

.

The symbol n is independently an integer from 4 to 12, and the symbol m is independently an integer from 4 to 12.

In embodiments, $L^{11}$ is independently

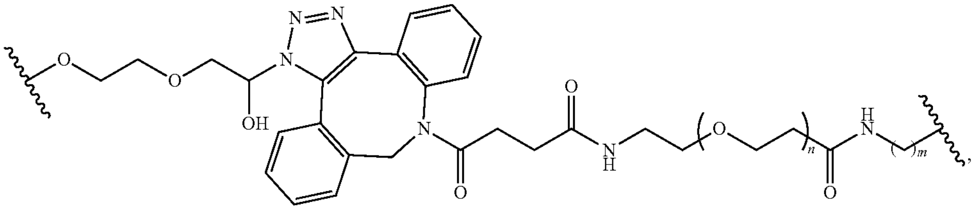

, wherein n is independently an integer from 4 to 12, and m is independently an integer from 4 to 12.

In embodiments, $L^{11}$ is independently

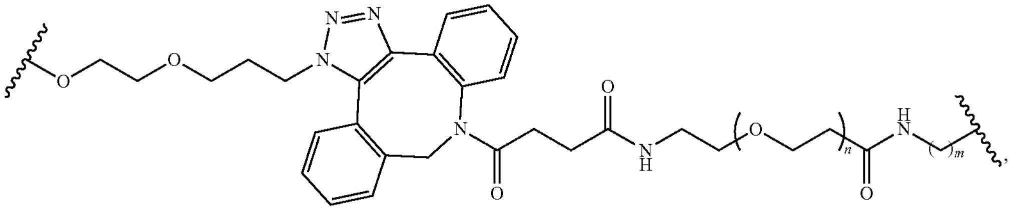

, wherein n is independently an integer from 4 to 12, and m is independently an integer from 4 to 12.

In embodiments, $L^{11}$ is independently
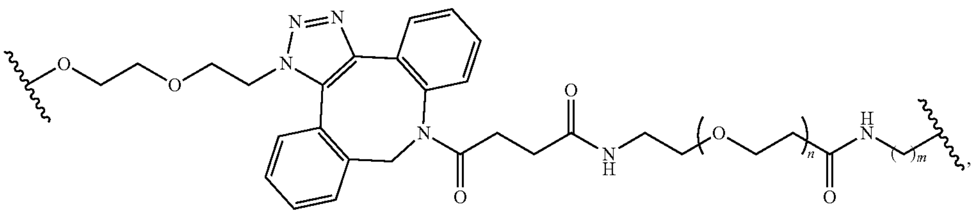
wherein n is independently an integer from 4 to 12, and m is independently an integer from 4 to 12.
In embodiments, $L^{11}$ is independently
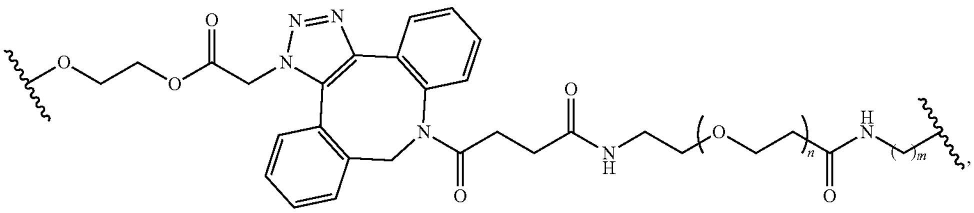
wherein n is independently an integer from 4 to 12, and m is independently an integer from 4 to 12.
In embodiments, $L^{11}$ is independently
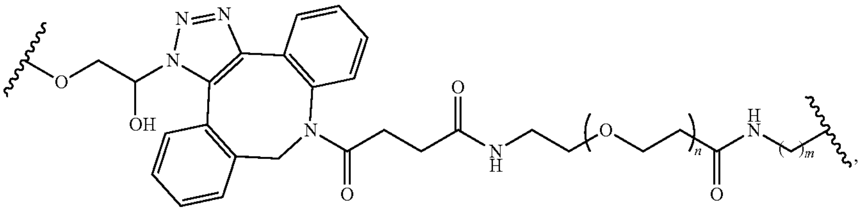
,
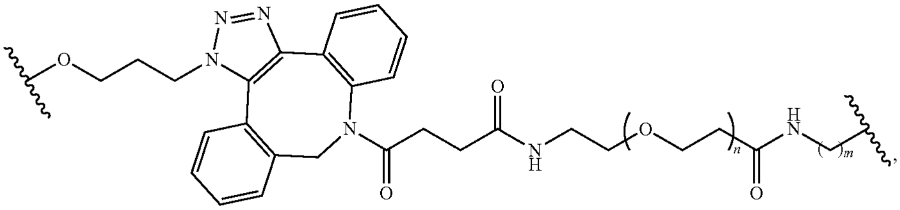
,
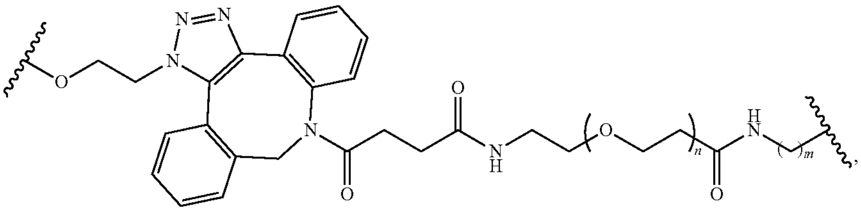
, or
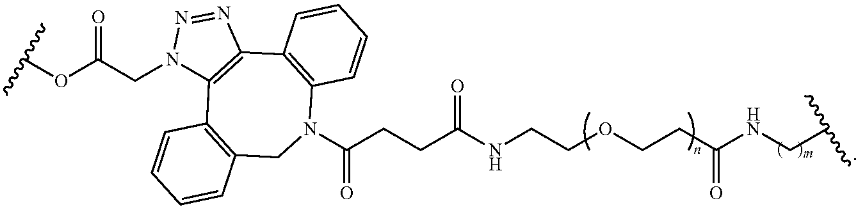
.

The symbol n is independently an integer from 4 to 12, and the symbol m is independently an integer from 4 to 12.

In embodiments, $L^{11}$ is independently

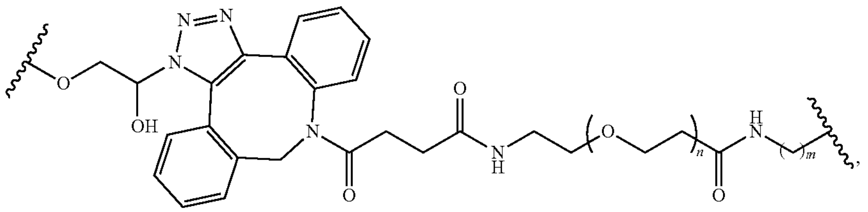

wherein n is independently an integer from 4 to 12, and m is independently an integer from 4 to 12.

In embodiments, $L^{11}$ is independently

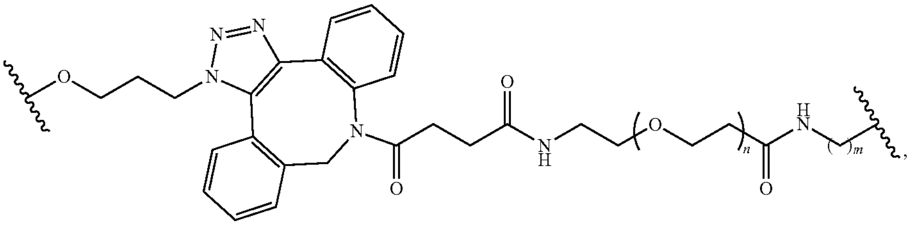

wherein n is independently an integer from 4 to 12, and m is independently an integer from 4 to 12.

In embodiments, $L^{11}$ is independently

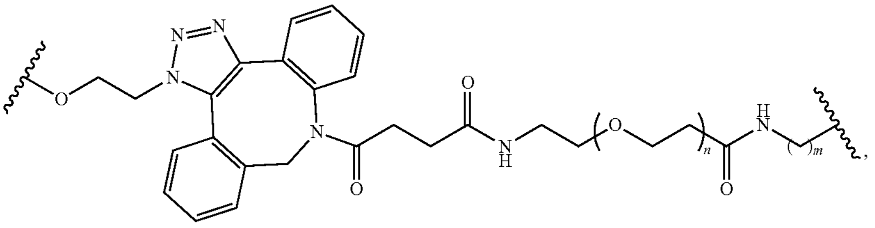

wherein n is independently an integer from 4 to 12, and m is independently an integer from 4 to 12.

In embodiments, $L^{11}$ is independently

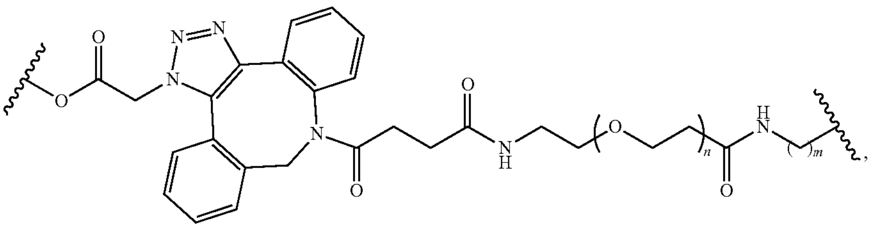

wherein n is independently an integer from 4 to 12, and m is independently an integer from 4 to 12.

In embodiments, $L^{11}$ is independently
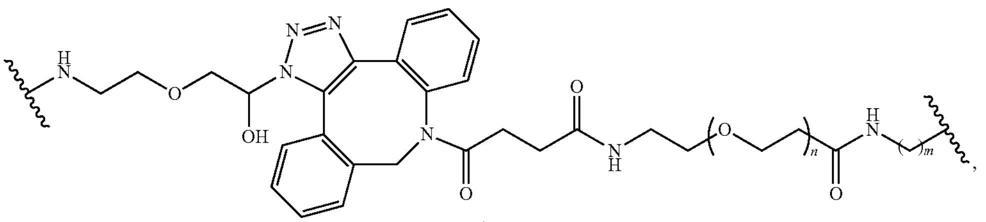
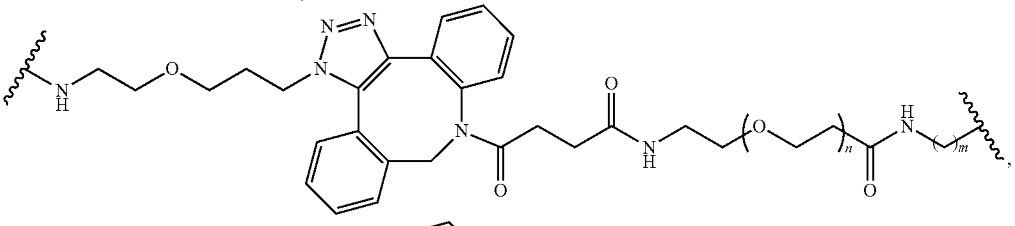
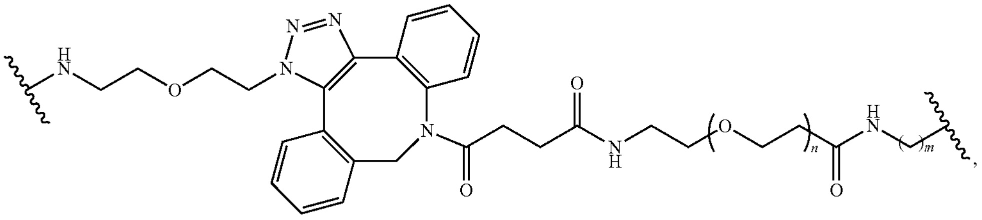
or
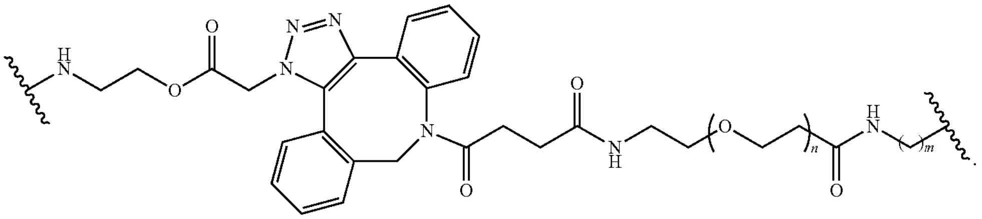
The symbol n is independently an integer from 4 to 12, and the symbol m is independently an integer from 4 to 12.
In embodiments, $L^{11}$ is independently
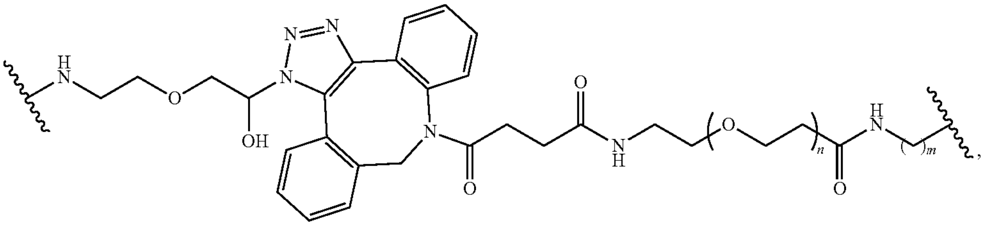
wherein n is independently an integer from 4 to 12, and m is independently an integer from 4 to 12.
In embodiments, $L^{11}$ is independently
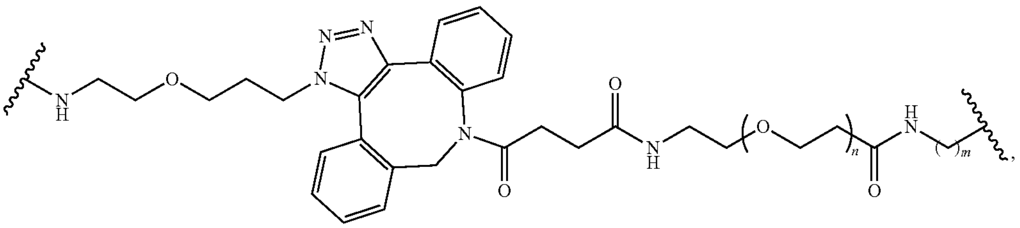

wherein n is independently an integer from 4 to 12, and m is independently an integer from 4 to 12.

In embodiments, $L^{11}$ is independently

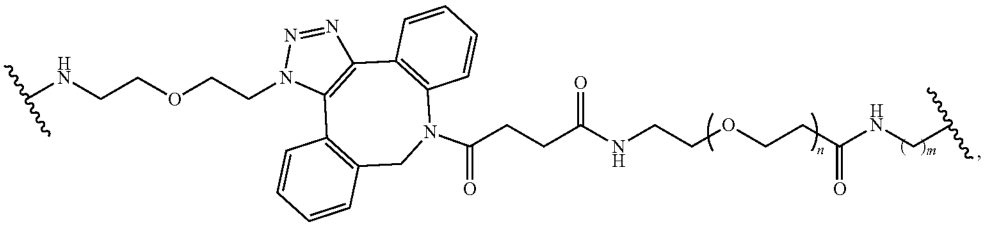

wherein n is independently an integer from 4 to 12, and m is independently an integer from 4 to 12.

In embodiments, $L^{11}$ is independently

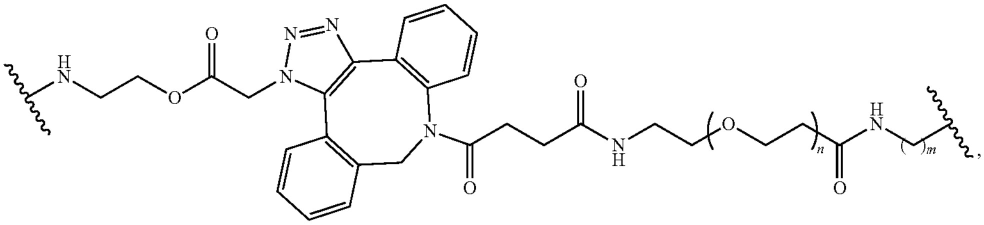

wherein n is independently an integer from 4 to 12, and m is independently an integer from 4 to 12.

In embodiments, $L^{11}$ is independently

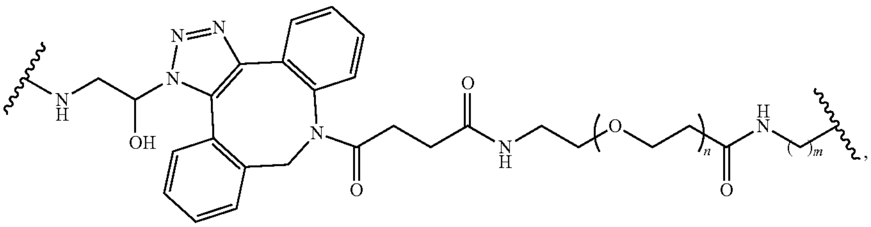

,

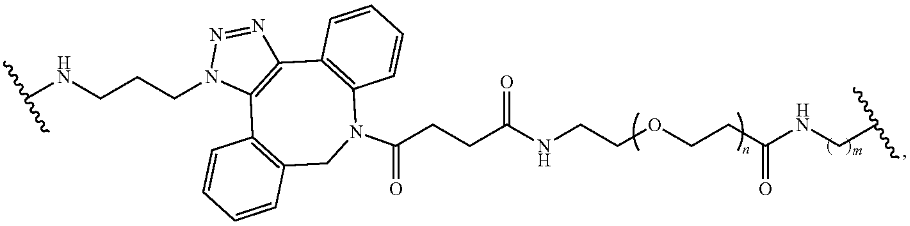

,

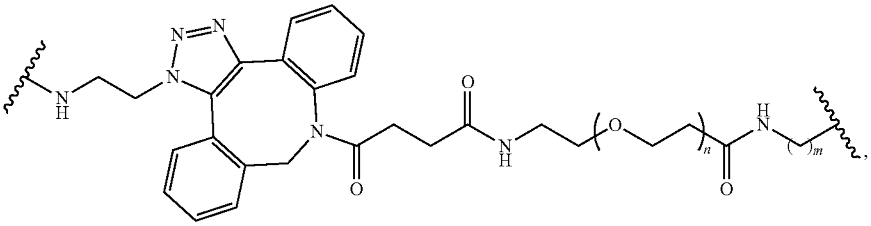

, or

-continued

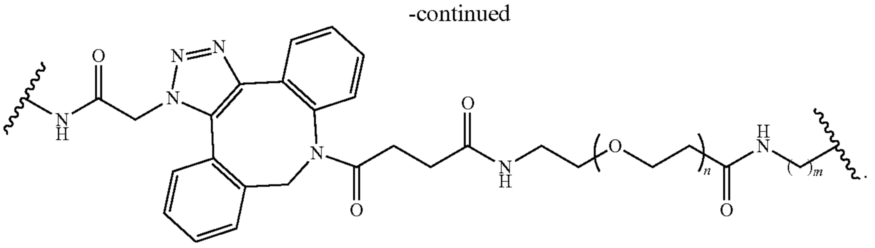

The symbol n is independently an integer from 4 to 12, and the symbol m is independently an integer from 4 to 12.

In embodiments, $L^{11}$ is independently

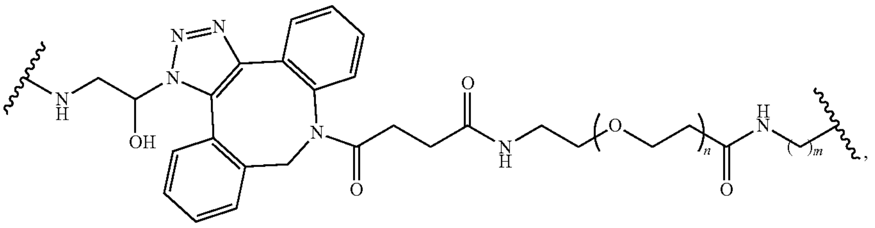

wherein n is independently an integer from 4 to 12, and m is independently an integer from 4 to 12.

In embodiments, $L^{11}$ is independently

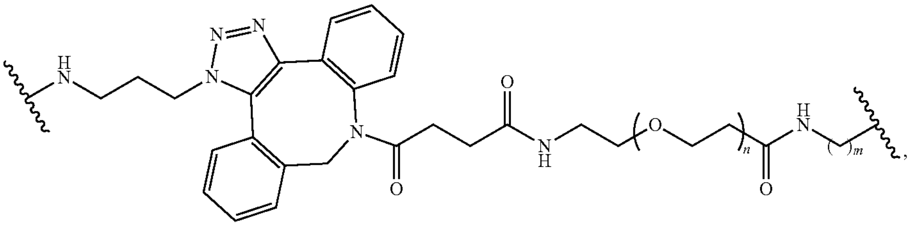

wherein n is independently an integer from 4 to 12, and m is independently an integer from 4 to 12.

In embodiments, $L^{11}$ is independently

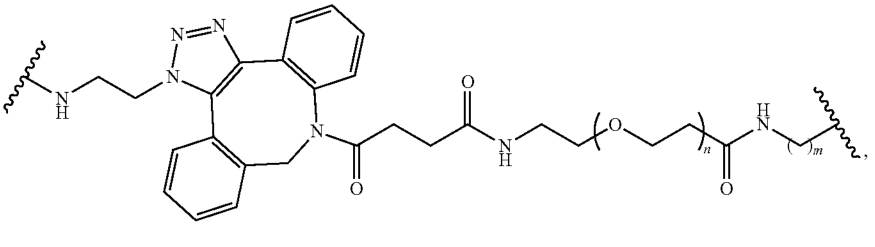

wherein n is independently an integer from 4 to 12, and m is independently an integer from 4 to 12.

In embodiments, $L^{11}$ is independently

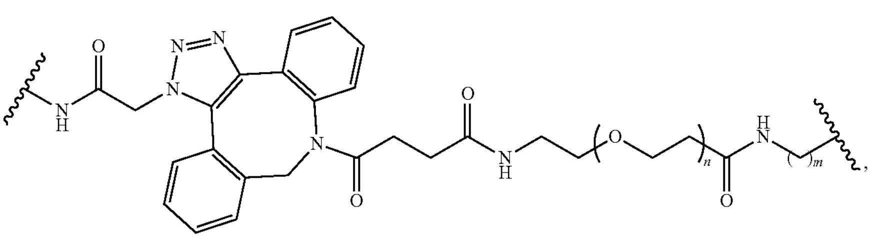

wherein n is independently an integer from 4 to 12, and m is independently an integer from 4 to 12.

In embodiments, $L^{11}$ is independently

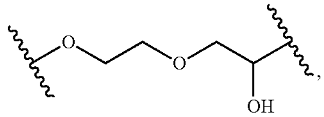

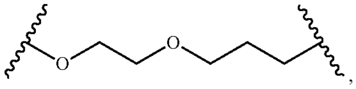

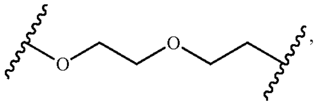

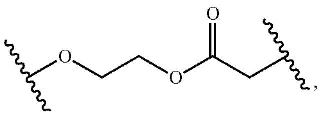, 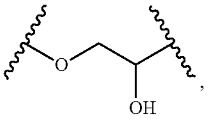

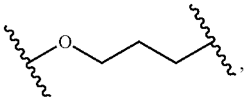, 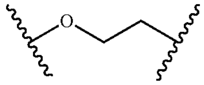, or

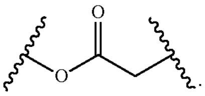

In embodiments, $L^{11}$ is independently

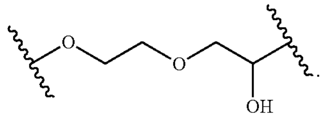 [SMILES: *OCCOCC(*)O]

In embodiments, $L^{11}$ is independently

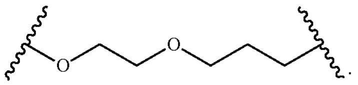 [SMILES: *CCCOCCO*]

In embodiments, $L^{11}$ is independently

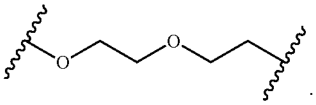 [SMILES: *CCOCCO*]

In embodiments, $L^{11}$ is independently

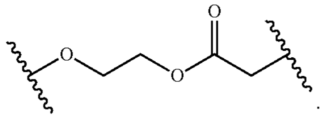 [SMILES: *CC(=O)OCCO*]

In embodiments, $L^{11}$ is independently

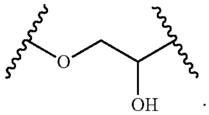 [SMILES: *OCC(*)O]

In embodiments, $L^{11}$ is independently

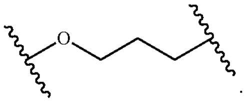 [SMILES: *CCCO*]

In embodiments, $L^{11}$ is independently

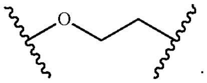 [SMILES: *CCO*]

In embodiments, $L^{11}$ is independently

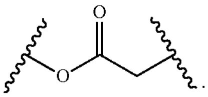 [SMILES: *CC(=O)O*]

In embodiments, each $L^{11}$ is the same.

In embodiments, $L^2$ is independently a substituted or unsubstituted heteroalkylene.

In embodiments, $L^{12B}$ and $L^{12D}$ are independently substituted or unsubstituted heteroalkylene; $L^{12C}$ is independently a substituted or unsubstituted heteroarylene; and $L^{12E}$ is independently a bond.

In embodiments, $L^{12B}$ and $L^{12E}$ are independently substituted or unsubstituted heteroalkylene; $L^{12C}$ is independently a substituted or unsubstituted heteroarylene; and $L^{12D}$ is independently a substituted or unsubstituted arylene.

In embodiments, $L^{12A}$ is independently a bond.

In embodiments, $L^{12}$ is independently

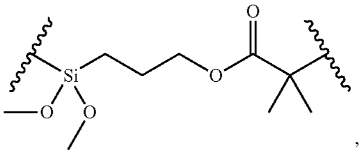 [SMILES: *C(C)(C)C(=O)OCCC[Si](*)(OC)OC]

,

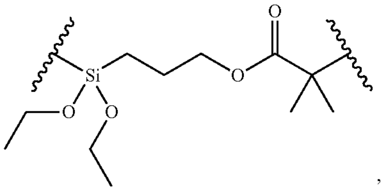 [SMILES: *C(C)(C)C(=O)OCCC[Si](*)(OCC)OCC]

,

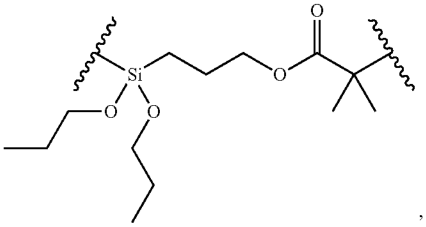 [SMILES: *C(C)(C)C(=O)OCCC[Si](*)(OCCC)OCCC]

,

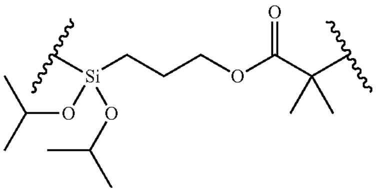

, or

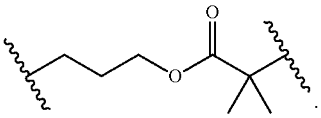 [SMILES: *CCCOC(=O)C(*)(C)C]

.

In embodiments, $L^{12}$ is independently

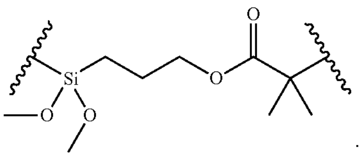

.

In embodiments, $L^{12}$ is independently

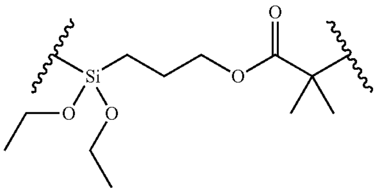

.

In embodiments, $L^{12}$ is independently

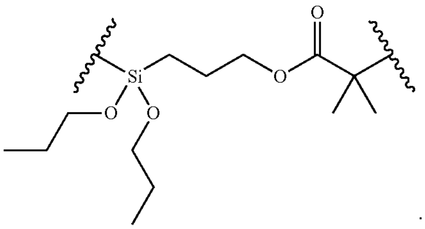

.

In embodiments, $L^{12}$ is independently

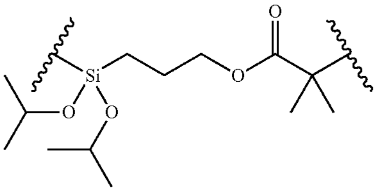

.

In embodiments, $L^{12}$ is independently

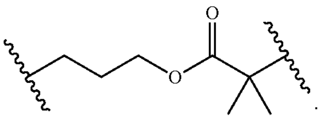

.

In embodiments, $L^{12}$ is independently

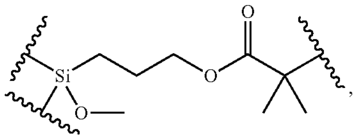

,

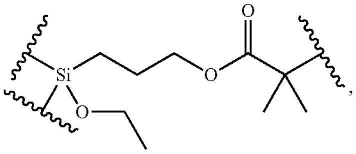

,

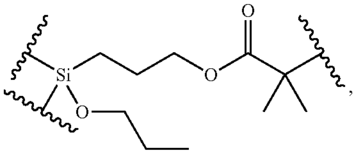

,

-continued

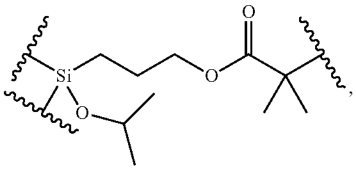

, or

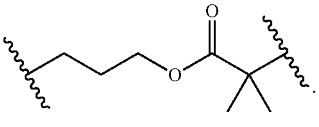

In embodiments, $L^{12}$ is independently

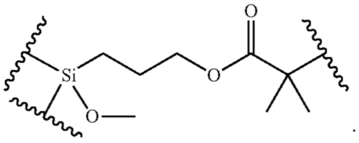 [SMILES: *C(C)(C)C(=O)OCCC[Si](*)(*)OC]

In embodiments, $L^{12}$ is independently

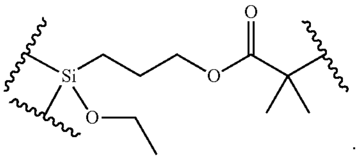 [SMILES: *C(C)(C)C(=O)OCCC[Si](*)(*)OCC]

In embodiments, $L^{12}$ is independently

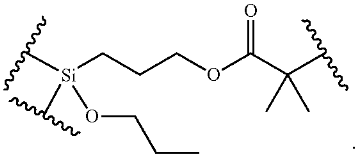 [SMILES: *C(C)(C)C(=O)OCCC[Si](*)(*)OCCC]

In embodiments, $L^{12}$ is independently

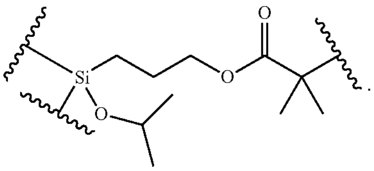 [SMILES: *C(C)(C)C(=O)OCCC[Si](*)(*)OC(C)C]

In embodiments $L^{12}$ is independently

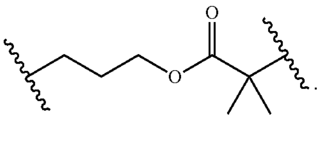

In embodiments, $L^{12}$ is independently

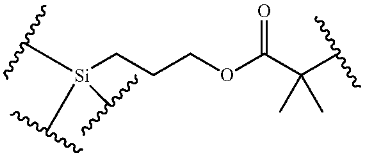

or

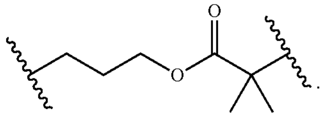 [SMILES: *CCCOC(=O)C(*)(C)C]

In embodiments, $L^{12}$ is independently

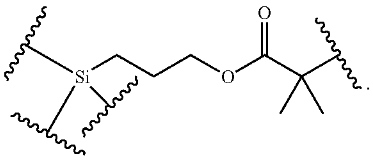 [SMILES: *C(C)(C)C(=O)OCCC[Si](*)(*)*]

In embodiments, $L^{12}$ is independently

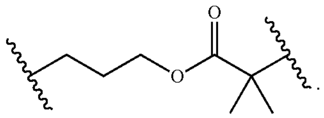 [SMILES: *CCCOC(=O)C(*)(C)C]

In embodiments, each $L^{12}$ is the same.

In embodiments, $R^{12}$ and $R^{13}$ are independently hydrogen.

In embodiments, $R^{12}$ is independently hydrogen. In embodiments, $R^{12}$ is independently substituted or unsubstituted $C_1$-$C_4$ alkyl. In embodiments, $R^{12}$ is independently unsubstituted $C_1$-$C_4$ alkyl. In embodiments, $R^{12}$ is independently unsubstituted methyl. In embodiments, $R^{12}$ is independently unsubstituted ethyl. In embodiments, $R^{12}$ is independently unsubstituted propyl. In embodiments, $R^{12}$ is independently unsubstituted n-propyl. In embodiments, $R^{12}$ is independently unsubstituted isopropyl. In embodiments, $R^{12}$ is independently unsubstituted butyl. In embodiments, $R^{12}$ is independently unsubstituted n-butyl. In embodiments, $R^{12}$ is independently unsubstituted tert-butyl.

In embodiments, each $R^{12}$ is the same.

In embodiments, $R^{13}$ is independently hydrogen. In embodiments, $R^{13}$ is independently substituted or unsubstituted $C_1$-$C_4$ alkyl. In embodiments, $R^{13}$ is independently unsubstituted $C_1$-$C_4$ alkyl. In embodiments, $R^{13}$ is independently unsubstituted methyl. In embodiments, $R^{13}$ is independently unsubstituted ethyl. In embodiments, $R^{13}$ is independently unsubstituted propyl. In embodiments, $R^{13}$ is independently unsubstituted n-propyl. In embodiments, $R^{13}$ is independently unsubstituted isopropyl. In embodiments, $R^{13}$ is independently unsubstituted butyl. In embodiments, $R^{13}$ is independently unsubstituted n-butyl. In embodiments, $R^{13}$ is independently unsubstituted tert-butyl.

In embodiments, each $R^{13}$ is the same.

In embodiments, $R^{14}$ is independently halogen. In embodiments, $R^{14}$ is independently —Br. In embodiments, $R^{14}$ is independently —OH. In embodiments, $R^{14}$ is independently substituted or unsubstituted alkyl. In embodiments, $R^{14}$ is independently substituted or unsubstituted $C_1$-$C_4$ alkyl. In embodiments, $R^{14}$ is independently unsubstituted $C_1$-$C_4$ alkyl. In embodiments, $R^{14}$ is independently unsubstituted methyl. In embodiments, $R^{14}$ is independently unsubstituted ethyl. In embodiments, $R^{14}$ is independently unsubstituted propyl. In embodiments, $R^{14}$ is independently unsubstituted n-propyl. In embodiments, $R^{14}$ is independently unsubstituted isopropyl. In embodiments, $R^{14}$ is independently unsubstituted butyl. In embodiments, $R^{14}$ is independently unsubstituted n-butyl. In embodiments, $R^{14}$ is independently unsubstituted tert-butyl. In embodiments, $R^{14}$ is independently substituted or unsubstituted heteroalkyl. In embodiments, $R^{14}$ is independently substituted or unsubstituted 2 to 6 membered heteroalkyl. In embodiments, $R^{14}$ is independently substituted or unsubstituted $C_1$-$C_4$ alkyl. In embodiments, $R^{14}$ is independently —O-(unsubstituted $C_1$-$C_4$ alkyl). In embodiments, $R^{14}$ is independently unsubstituted methoxy. In embodiments, $R^{14}$ is independently unsubstituted ethoxy. In embodiments, $R^{14}$ is independently unsubstituted propoxy. In embodiments, $R^{14}$ is independently unsubstituted n-propoxy. In embodiments, $R^{14}$ is independently unsubstituted isopropoxy. In embodiments, $R^{14}$ is independently unsubstituted butoxy. In embodiments, $R^{14}$ is independently unsubstituted n-butoxy. In embodiments, $R^{14}$ is independently unsubstituted tert-butoxy. In embodiments, $R^{14}$ is independently —$C(CH_3)_2CN$. In embodiments, $R^{14}$ is independently —$CH_2CN$. In embodiments, $R^{14}$ is independently —$CH_2Ph$. In embodiments, $R^{14}$ is independently

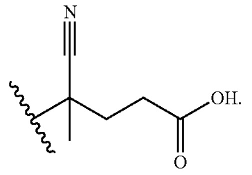 [SMILES: *C(C)(C#N)CCC(=O)O]

In embodiments, $R^{14}$ is independently

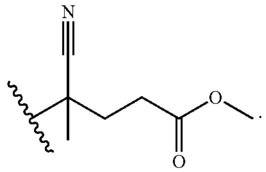 [SMILES: *C(C)(C#N)CCC(=O)OC]

In embodiments, $R^{14}$ is independently

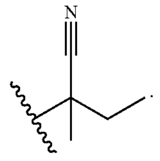 [SMILES: *C(C)(C#N)CC]

independently

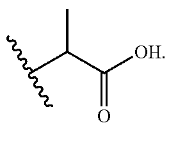

In embodiments, $R^{14}$ is independently

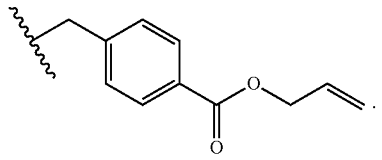 [SMILES: *Cc1ccc(C(=O)OCC=C)cc1]

In embodiments, $R^{14}$ is independently

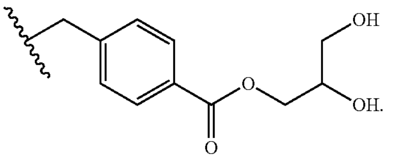 [SMILES: *Cc1ccc(C(=O)OCC(O)CO)cc1]

In embodiments, $R^{14}$ is independently

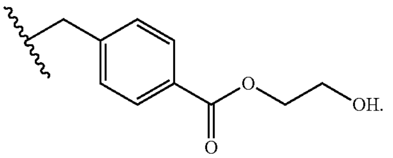 [SMILES: *Cc1ccc(C(=O)OCCO)cc1]

In embodiments, $R^{14}$ is independently

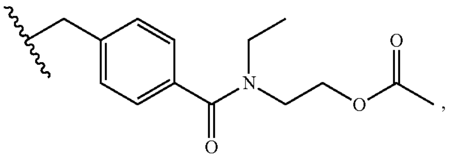 [SMILES: *Cc1ccc(C(=O)N(CC)CCOC(C)=O)cc1]

In embodiments, $R^{14}$ is independently

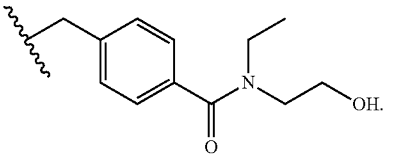 [SMILES: *Cc1ccc(C(=O)N(CC)CCO)cc1]

In embodiments, each $R^{14}$ is the same.

In embodiments, $R^{15}$ is independently —CN. In embodiments, $R^{15}$ is independently substituted or unsubstituted alkyl. In embodiments, $R^{15}$ is independently substituted or unsubstituted $C_1$-$C_4$ alkyl. In embodiments, $R^{15}$ is independently unsubstituted $C_1$-$C_4$ alkyl. In embodiments, $R^{15}$ is independently unsubstituted methyl. In embodiments, $R^{15}$ is independently unsubstituted ethyl. In embodiments, $R^{15}$ is independently unsubstituted propyl. In embodiments, $R^{15}$ is independently unsubstituted n-propyl. In embodiments, $R^{15}$ is independently unsubstituted isopropyl. In embodiments, $R^{15}$ is independently unsubstituted butyl. In embodiments, $R^{15}$ is independently unsubstituted n-butyl. In embodiments, $R^{15}$ is independently unsubstituted tert-butyl. In embodiments, $R^{15}$ is independently substituted or unsubstituted heteroalkyl. In embodiments, $R^{15}$ is independently substituted or unsubstituted 2 to 6 membered heteroalkyl.

In embodiments, each $R^{15}$ is the same.

In embodiments, $L^{16}$ is independently substituted or unsubstituted heteroalkylene.

In embodiments, $L^{16B}$ and $L^{16D}$ are independently substituted or unsubstituted heteroalkylene; $L^{16C}$ is independently a substituted or unsubstituted heteroarylene; and $L^{16E}$ is independently a bond.

In embodiments, $L^{16B}$ and $L^{16E}$ are independently substituted or unsubstituted heteroalkylene; $L^{16C}$ is independently a substituted or unsubstituted heteroarylene; and $L^{16D}$ is independently a substituted or unsubstituted arylene.

In embodiments, $L^{16A}$ is independently a bond.

In embodiments, each $L^{16}$ is the same.

In embodiments, $R^{16}$ is independently a non-reactive moiety selected from hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC(O)NHNH$_2$, —NHC(O)NH$_2$, $-NHSO_2H$, —NHC(O)H, —NHC(O)OH, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{16}$ is independently a non-reactive moiety selected from hydrogen, substituted or unsubstituted alkyl (e.g., $C_1$-$C_5$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{16}$ is independently hydrogen, $-OCH_2CH_2-(OCH_2CH_2)_p-OCH_3$ or $-N(CH_3)_2$; and p is an integer from 0 to 10. In embodiments, p is an integer from 1 to 10.

In embodiments, each $R^{16}$ is the same.

In embodiments, when $R^4$ is a first non-reactive moiety, $R^9$ is a second non-reactive moiety, and $R^{16}$ is a third non-reactive moiety, $R^4$, $R^9$, and $R^{16}$ are different. In embodiments, when $R^4$ is a first non-reactive moiety, $R^9$ is a second non-reactive moiety, and $R^{16}$ is a third non-reactive moiety, $R^4$, $R^9$, and $R^{16}$ are the same.

In embodiments, when $R^4$ is a non-reactive moiety and $R^{16}$ is a non-reactive moiety, $R^4$ and $R^{16}$ are different. In embodiments, when $R^4$ is a non-reactive moiety and $R^{16}$ is a non-reactive moiety, $R^4$ and $R^{16}$ are the same.

In embodiments, $-L^{16}-R^{16}$ is independently $-OCH_2CH_2-(OCH_2CH_2)_p-OCH_3$ or $-N(CH_3)_2$; and p is an integer from 4 to 10.

In embodiments, $R^{17}$ and $R^{18}$ are independently hydrogen.

In embodiments, $R^{17}$ is independently hydrogen. In embodiments, $R^{17}$ is independently substituted or unsubstituted $C_1$-$C_4$ alkyl. In embodiments, $R^{17}$ is independently unsubstituted $C_1$-$C_4$ alkyl. In embodiments, $R^{17}$ is independently unsubstituted methyl. In embodiments, $R^{17}$ is independently unsubstituted ethyl. In embodiments, $R^{17}$ is independently unsubstituted propyl. In embodiments, $R^{17}$ is independently unsubstituted n-propyl. In embodiments, $R^{17}$ is independently unsubstituted isopropyl. In embodiments, $R^{17}$ is independently unsubstituted butyl. In embodiments, $R^{17}$ is independently unsubstituted n-butyl. In embodiments, $R^{17}$ is independently unsubstituted tert-butyl.

In embodiments, each $R^{17}$ is the same.

In embodiments, $R^{18}$ is independently hydrogen. In embodiments, $R^{18}$ is independently substituted or unsubstituted $C_1$-$C_4$ alkyl. In embodiments, $R^{18}$ is independently unsubstituted $C_1$-$C_4$ alkyl. In embodiments, $R^{18}$ is independently unsubstituted methyl. In embodiments, $R^{18}$ is independently unsubstituted ethyl. In embodiments, $R^{18}$ is independently unsubstituted propyl. In embodiments, $R^{18}$ is independently unsubstituted n-propyl. In embodiments, $R^{18}$ is independently unsubstituted isopropyl. In embodiments, $R^{18}$ is independently unsubstituted butyl. In embodiments, $R^{18}$ is independently unsubstituted n-butyl. In embodiments, $R^{WW}$ is independently unsubstituted tert-butyl.

In embodiments, each $R^{18}$ is the same.

In embodiments, $R^{19}$ is independently halogen. In embodiments, $R^{19}$ is independently -Br. In embodiments, $R^{19}$ is independently —OH. In embodiments, $R^{19}$ is independently substituted or unsubstituted alkyl. In embodiments, $R^{19}$ is independently substituted or unsubstituted $C_1$-$C_4$ alkyl. In embodiments, $R^{19}$ is independently unsubstituted $C_1$-$C_4$ alkyl. In embodiments, $R^{19}$ is independently unsubstituted methyl. In embodiments, $R^{19}$ is independently unsubstituted ethyl. In embodiments, $R^{19}$ is independently unsubstituted propyl. In embodiments, $R^{19}$ is independently unsubstituted n-propyl. In embodiments, $R^{19}$ is independently unsubstituted isopropyl. In embodiments, $R^{19}$ is independently unsubstituted butyl. In embodiments, $R^{19}$ is independently unsubstituted n-butyl. In embodiments, $R^{19}$ is independently unsubstituted tert-butyl. In embodiments, $R^{19}$ is independently substituted or unsubstituted heteroalkyl. In embodiments, $R^{19}$ is independently substituted or unsubstituted 2 to 6 membered heteroalkyl. In embodiments, $R^{19}$ is independently substituted or unsubstituted $C_1$-$C_4$ alkyl. In embodiments, $R^{19}$ is independently —O-(unsubstituted $C_1$-$C_4$ alkyl). In embodiments, $R^{19}$ is independently unsubstituted methoxy. In embodiments, $R^{19}$ is independently unsubstituted ethoxy. In embodiments, $R^{19}$ is independently unsubstituted propoxy. In embodiments, $R^{19}$ is independently unsubstituted n-propoxy. In embodiments, $R^{19}$ is independently unsubstituted isopropoxy. In embodiments, $R^{19}$ is independently unsubstituted butoxy. In embodiments, $R^{19}$ is independently unsubstituted n-butoxy. In embodiments, $R^{19}$ is independently unsubstituted tert-butoxy. In embodiments, $R^{19}$ is independently $-C(CH_3)_2CN$. In embodiments, $R^{19}$ is independently $-CH_2CN$. In embodiments, $R^{19}$ is independently $-CH_2Ph$. In embodiments, $R^{19}$ is independently

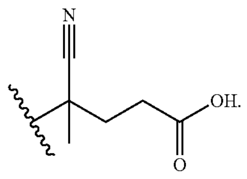 [SMILES: *C(C)(C#N)CCC(=O)O]

In embodiments, $R^{19}$ is independently

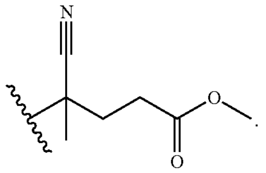 [SMILES: *C(C)(C#N)CCC(=O)OC]

In embodiments, $R^{19}$ is independently

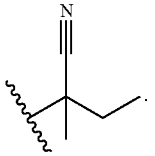 [SMILES: *C(C)(C#N)CC]

In embodiments, $R^{19}$ is independently

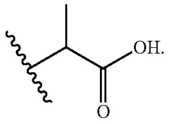 [SMILES: *C(C)C(=O)O]

In embodiments, $R^{19}$ is independently

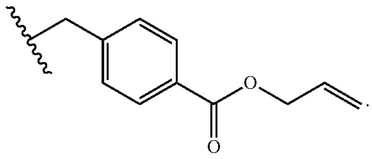 [SMILES: *Cc1ccc(C(=O)OCC=C)cc1]

In embodiments, $R^{19}$ is independently

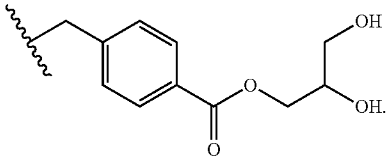 [SMILES: *Cc1ccc(C(=O)OCC(O)CO)cc1]

In embodiments, $R^{19}$ is independently

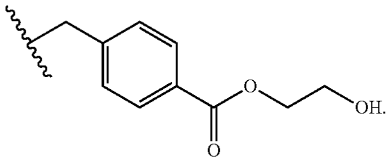 [SMILES: *Cc1ccc(C(=O)OCCO)cc1]

In embodiments, $R^{19}$ is independently

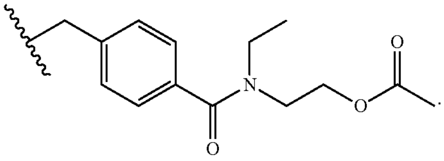 [SMILES: *Cc1ccc(C(=O)N(CC)CCOC(C)=O)cc1]

In embodiments, $R^{19}$ is independently

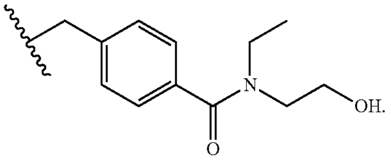 [SMILES: *Cc1ccc(C(=O)N(CC)CCO)cc1]

In embodiments, each $R^{19}$ is the same.

In embodiments, z1a is independently an integer from 0 to 10. In embodiments, z1a is independently an integer from 0 to 20. In embodiments, z1a is independently an integer from 0 to 30. In embodiments, z1a is independently an integer from 0 to 40. In embodiments, z1a is independently an integer from 0 to 50. In embodiments, z1a is independently an integer from 0 to 60. In embodiments, z1a is independently an integer from 0 to 70. In embodiments, z1a is independently an integer from 0 to 80. In embodiments, z1a is independently an integer from 0 to 90. In embodiments, z1a is independently an integer from 0 to 100. In embodiments, z1a is independently an integer from 0 to 150. In embodiments, z1a is independently an integer from 0 to 200. In embodiments, z1a is independently an integer from 0 to 250. In embodiments, z1a is independently an integer from 0 to 300. In embodiments, z1a is independently an integer from 0 to 350. In embodiments, z1a is independently an integer from 0 to 400. In embodiments, z1a is independently an integer from 0 to 450. In embodiments, z1a is independently an integer from 0 to 500. In embodiments, z1a is independently an integer from 0 to 550. In embodiments, z1a is independently an integer from 0 to 600. In embodiments, z1a is independently an integer from 0 to 650. In embodiments, z1a is independently an integer from 0 to 700. In embodiments, z1a is independently an integer from 0 to 750. In embodiments, z1a is independently an integer from 0 to 800. In embodiments, z1a is independently an integer from 0 to 850. In embodiments, z1a is independently an integer from 0 to 900. In embodiments, z1a is independently an integer from 0 to 950. In embodiments, z1a is independently an integer from 0 to 1000. In embodiments, z1a is independently an integer from 0 to 1500. In embodiments, z1a is independently an integer from 0 to 2000. In embodiments, z1a is independently an integer from 0 to 2500. In embodiments, z1a is independently an integer from 0 to 3000. In embodiments, z1a is independently an integer from 0 to 3500. In embodiments, z1a is independently an integer from 0 to 4000. In embodiments, z1a is independently an integer from 0 to 4500. In embodiments, z1a is independently an integer from 0 to 5000.

In embodiments, z1a is independently an integer from 1 to 10. In embodiments, z1a is independently an integer from 1 to 20. In embodiments, z1a is independently an integer from 1 to 30. In embodiments, z1a is independently an integer from 1 to 40. In embodiments, z1a is independently an integer from 1 to 50. In embodiments, z1a is independently an integer from 1 to 60. In embodiments, z1a is independently an integer from 1 to 70. In embodiments, z1a is independently an integer from 1 to 80. In embodiments, z1a is independently an integer from 1 to 90. In embodiments, z1a is independently an integer from 1 to 100. In embodiments, z1a is independently an integer from 1 to 150. In embodiments, z1a is independently an integer from 1 to 200. In embodiments, z1a is independently an integer from 1 to 250. In embodiments, z1a is independently an integer from 1 to 300. In embodiments, z1a is independently an integer from 1 to 350. In embodiments, z1a is independently an integer from 1 to 400. In embodiments, z1a is independently an integer from 1 to 450. In embodiments, z1a is independently an integer from 1 to 500. In embodiments, z1a is independently an integer from 1 to 550. In embodiments, z1a is independently an integer from 1 to 600. In embodiments, z1a is independently an integer from 1 to 650. In embodiments, z1a is independently an integer from 1 to 700. In embodiments, z1a is independently an integer from 1 to 750. In embodiments, z1a is independently an integer from 1 to 800. In embodiments, z1a is independently an integer from 1 to 850. In embodiments, z1a is independently an integer from 1 to 900. In embodiments, z1a is independently an integer from 1 to 950. In embodiments, z1a is independently an integer from 1 to 1000. In embodiments, z1a is independently an integer from 1 to 1500. In embodiments, z1a is independently an integer from 1 to 2000. In embodiments, z1a is independently an integer from 1 to 2500. In embodiments, z1a is independently an integer from 1 to 3000. In embodiments, z1a is independently an integer from 1 to 3500. In embodiments, z1a is independently an integer from 1 to 4000. In embodiments, z1a is independently an integer from 1 to 4500. In embodiments, z1a is independently an integer from 1 to 5000.

In embodiments, z1b is independently an integer from 0 to 10. In embodiments, z1b is independently an integer from 0 to 20. In embodiments, z1b is independently an integer from 0 to 30. In embodiments, z1b is independently an integer from 0 to 40. In embodiments, z1b is independently an integer from 0 to 50. In embodiments, z1b is independently an integer from 0 to 60. In embodiments, z1b is independently an integer from 0 to 70. In embodiments, z1b is independently an integer from 0 to 80. In embodiments, z1b is independently an integer from 0 to 90. In embodiments, z1b is independently an integer from 0 to 100. In embodiments, z1b is independently an integer from 0 to 150. In embodiments, z1b is independently an integer from 0 to 200. In embodiments, z1b is independently an integer from 0 to 250. In embodiments, z1b is independently an integer from 0 to 300. In embodiments, z1b is independently an integer from 0 to 350. In embodiments, z1b is independently an integer from 0 to 400. In embodiments, z1b is independently an integer from 0 to 450. In embodiments, z1b is independently an integer from 0 to 500. In embodiments, z1b is independently an integer from 0 to 550. In embodiments, z1b is independently an integer from 0 to 600. In embodiments, z1b is independently an integer from 0 to 650. In embodiments, z1b is independently an integer from 0 to 700. In embodiments, z1b is independently an integer from 0 to 750. In embodiments, z1b is independently an integer from 0 to 800. In embodiments, z1b is independently an integer from 0 to 850. In embodiments, z1b is independently an integer from 0 to 900. In embodiments, z1b is independently an integer from 0 to 950. In embodiments, z1b is independently an integer from 0 to 1000. In embodiments, z1b is independently an integer from 0 to 1500. In embodiments, z1b is independently an integer from 0 to 2000. In embodiments, z1b is independently an integer from 0 to 2500. In embodiments, z1b is independently an integer from 0 to 3000. In embodiments, z1b is independently an integer from 0 to 3500. In embodiments, z1b is independently an integer from 0 to 4000. In embodiments, z1b is independently an integer from 0 to 4500. In embodiments, z1b is independently an integer from 0 to 5000.

In embodiments, z1b is independently an integer from 1 to 10. In embodiments, z1b is independently an integer from 1 to 20. In embodiments, z1b is independently an integer from 1 to 30. In embodiments, z1b is independently an integer from 1 to 40. In embodiments, z1b is independently an integer from 1 to 50. In embodiments, z1b is independently an integer from 1 to 60. In embodiments, z1b is independently an integer from 1 to 70. In embodiments, z1b is independently an integer from 1 to 80. In embodiments, z1b is independently an integer from 1 to 90. In embodiments, z1b is independently an integer from 1 to 100. In embodiments, z1b is independently an integer from 1 to 150. In embodiments, z1b is independently an integer from 1 to 200. In embodiments, z1b is independently an integer from 1 to 250. In embodiments, z1b is independently an integer from 1 to 300. In embodiments, z1b is independently an integer from 1 to 350. In embodiments, z1b is independently an integer from 1 to 400. In embodiments, z1b is independently an integer from 1 to 450. In embodiments, z1b is independently an integer from 1 to 500. In embodiments, z1b is independently an integer from 1 to 550. In embodiments, z1b is independently an integer from 1 to 600. In embodiments, z1b is independently an integer from 1 to 650. In embodiments, z1b is independently an integer from 1 to 700. In embodiments, z1b is independently an integer from 1 to 750. In embodiments, z1b is independently an integer from 1 to 800. In embodiments, z1b is independently an integer from 1 to 850. In embodiments, z1b is independently an integer from 1 to 900. In embodiments, z1b is independently an integer from 1 to 950. In embodiments, z1b is independently an integer from 1 to 1000. In embodiments, z1b is independently an integer from 1 to 1500. In embodiments, z1b is independently an integer from 1 to 2000. In embodiments, z1b is independently an integer from 1 to 2500. In embodiments, z1b is independently an integer from 1 to 3000. In embodiments, z1b is independently an integer from 1 to 3500. In embodiments, z1b is independently an integer from 1 to 4000. In embodiments, z1b is independently an integer from 1 to 4500. In embodiments, z1b is independently an integer from 1 to 5000.

In embodiments, z1c is independently an integer from 0 to 10. In embodiments, z1c is independently an integer from 0 to 20. In embodiments, z1c is independently an integer from 0 to 30. In embodiments, z1c is independently an integer from 0 to 40. In embodiments, z1c is independently an integer from 0 to 50. In embodiments, z1c is independently an integer from 0 to 60. In embodiments, z1c is independently an integer from 0 to 70. In embodiments, z1c is independently an integer from 0 to 80. In embodiments, z1c is independently an integer from 0 to 90. In embodiments, z1c is independently an integer from 0 to 100. In embodiments, z1c is independently an integer from 0 to 150. In embodiments, z1c is independently an integer from 0 to 200. In embodiments, z1c is independently an integer from 0 to 250. In embodiments, z1c is independently an integer from 0 to 300. In embodiments, z1c is independently an integer from 0 to 350. In embodiments, z1c is independently an integer from 0 to 400. In embodiments, z1c is independently an integer from 0 to 450. In embodiments, z1c is independently an integer from 0 to 500. In embodiments, z1c is independently an integer from 0 to 550. In embodiments, z1c is independently an integer from 0 to 600. In embodiments, z1c is independently an integer from 0 to 650. In embodiments, z1c is independently an integer from 0 to 700. In embodiments, z1c is independently an integer from 0 to 750. In embodiments, z1c is independently an integer from 0 to 800. In embodiments, z1c is independently an integer from 0 to 850. In embodiments, z1c is independently an integer from 0 to 900. In embodiments, z1c is independently an integer from 0 to 950. In embodiments, z1c is independently an integer from 0 to 1000. In embodiments, z1c is independently an integer from 0 to 1500. In embodiments, z1c is independently an integer from 0 to 2000. In embodiments, z1c is independently an integer from 0 to 2500. In embodiments, z1c is independently an integer from 0 to 3000. In embodiments, z1c is independently an integer from 0 to 3500. In embodiments, z1c is independently an integer from 0 to 4000. In embodiments, z1c is independently an integer from 0 to 4500. In embodiments, z1c is independently an integer from 0 to 5000.

In embodiments, z1c is independently an integer from 1 to 10. In embodiments, z1c is independently an integer from 1 to 20. In embodiments, z1c is independently an integer from 1 to 30. In embodiments, z1c is independently an integer from 1 to 40. In embodiments, z1c is independently an integer from 1 to 50. In embodiments, z1c is independently an integer from 1 to 60. In embodiments, z1c is independently an integer from 1 to 70. In embodiments, z1c is independently an integer from 1 to 80. In embodiments, z1c is independently an integer from 1 to 90. In embodiments, z1c is independently an integer from 1 to 100. In embodiments, z1c is independently an integer from 1 to 150. In embodiments, z1c is independently an integer from 1 to 200. In embodiments, z1c is independently an integer from 1 to 250. In embodiments, z1c is independently an integer from 1 to 300. In embodiments, z1c is independently an integer from 1 to 350. In embodiments, z1c is independently an integer from 1 to 400. In embodiments, z1c is independently an integer from 1 to 450. In embodiments, z1c is independently an integer from 1 to 500. In embodiments, z1c is independently an integer from 1 to 550. In embodiments, z1c is independently an integer from 1 to 600. In embodiments, z1c is independently an integer from 1 to 650. In embodiments, z1c is independently an integer from 1 to 700. In embodiments, z1c is independently an integer from 1 to 750. In embodiments, z1c is independently an integer from 1 to 800. In embodiments, z1c is independently an integer from 1 to 850. In embodiments, z1c is independently an integer from 1 to 900. In embodiments, z1c is independently an integer from 1 to 950. In embodiments, z1c is independently an integer from 1 to 1000. In embodiments, z1c is independently an integer from 1 to 1500. In embodiments, z1c is independently an integer from 1 to 2000. In embodiments, z1c is independently an integer from 1 to 2500. In embodiments, z1c is independently an integer from 1 to 3000. In embodiments, z1c is independently an integer from 1 to 3500. In embodiments, z1c is independently an integer from 1 to 4000. In embodiments, z1c is independently an integer from 1 to 4500. In embodiments, z1c is independently an integer from 1 to 5000.

In embodiments, z1d is independently an integer from 0 to 10. In embodiments, z1d is independently an integer from 0 to 20. In embodiments, z1d is independently an integer from 0 to 30. In embodiments, z1d is independently an integer from 0 to 40. In embodiments, z1d is independently an integer from 0 to 50. In embodiments, z1d is independently an integer from 0 to 60. In embodiments, z1d is independently an integer from 0 to 70. In embodiments, z1d is independently an integer from 0 to 80. In embodiments, z1d is independently an integer from 0 to 90. In embodiments, z1d is independently an integer from 0 to 100. In embodiments, z1d is independently an integer from 0 to 150. In embodiments, z1d is independently an integer from 0 to 200. In embodiments, z1d is independently an integer from 0 to 250. In embodiments, z1d is independently an integer from 0 to 300. In embodiments, z1d is independently an integer from 0 to 350. In embodiments, z1d is independently an integer from 0 to 400. In embodiments, z1d is independently an integer from 0 to 450. In embodiments, z1d is independently an integer from 0 to 500. In embodiments, z1d is independently an integer from 0 to 550. In embodiments, z1d is independently an integer from 0 to 600. In embodiments, z1d is independently an integer from 0 to 650. In embodiments, z1d is independently an integer from 0 to 700. In embodiments, z1d is independently an integer from 0 to 750. In embodiments, z1d is independently an integer from 0 to 800. In embodiments, z1d is independently an integer from 0 to 850. In embodiments, z1d is independently an integer from 0 to 900. In embodiments, z1d is independently an integer from 0 to 950. In embodiments, z1d is independently an integer from 0 to 1000. In embodiments, z1d is independently an integer from 0 to 1500. In embodiments, z1d is independently an integer from 0 to 2000. In embodiments, z1d is independently an integer from 0 to 2500. In embodiments, z1d is independently an integer from 0 to 3000. In embodiments, z1d is independently an integer from 0 to 3500. In embodiments, z1d is independently an integer from 0 to 4000. In embodiments, z1d is independently an integer from 0 to 4500. In embodiments, z1d is independently an integer from 0 to 5000.

In embodiments, z1d is independently an integer from 1 to 10. In embodiments, z1d is independently an integer from 1 to 20. In embodiments, z1d is independently an integer from 1 to 30. In embodiments, z1d is independently an integer from 1 to 40. In embodiments, z1d is independently an integer from 1 to 50. In embodiments, z1d is independently an integer from 1 to 60. In embodiments, z1d is independently an integer from 1 to 70. In embodiments, z1d is independently an integer from 1 to 80. In embodiments, z1d is independently an integer from 1 to 90. In embodiments, z1d is independently an integer from 1 to 100. In embodiments, z1d is independently an integer from 1 to 150. In embodiments, z1d is independently an integer from 1 to 200. In embodiments, z1d is independently an integer from 1 to 250. In embodiments, z1d is independently an integer from 1 to 300. In embodiments, z1d is independently an integer from 1 to 350. In embodiments, z1d is independently an integer from 1 to 400. In embodiments, z1d is independently an integer from 1 to 450. In embodiments, z1d is independently an integer from 1 to 500. In embodiments, z1d is independently an integer from 1 to 550. In embodiments, z1d is independently an integer from 1 to 600. In embodiments, z1d is independently an integer from 1 to 650. In embodiments, z1d is independently an integer from 1 to 700. In embodiments, z1d is independently an integer from 1 to 750. In embodiments, z1d is independently an integer from 1 to 800. In embodiments, z1d is independently an integer from 1 to 850. In embodiments, z1d is independently an integer from 1 to 900. In embodiments, z1d is independently an integer from 1 to 950. In embodiments, z1d is independently an integer from 1 to 1000. In embodiments, z1d is independently an integer from 1 to 1500. In embodiments, z1d is independently an integer from 1 to 2000. In embodiments, z1d is independently an integer from 1 to 2500. In embodiments, z1d is independently an integer from 1 to 3000. In embodiments, z1d is independently an integer from 1 to 3500. In embodiments, z1d is independently an integer from 1 to 4000. In embodiments, z1d is independently an integer from 1 to 4500. In embodiments, z1d is independently an integer from 1 to 5000.

In embodiments, z2 is independently an integer from 0 to 10. In embodiments, z2 is independently an integer from 0 to 20. In embodiments, z2 is independently an integer from 0 to 30. In embodiments, z2 is independently an integer from 0 to 40. In embodiments, z2 is independently an integer from 0 to 50. In embodiments, z2 is independently an integer from 0 to 60. In embodiments, z2 is independently an integer from 0 to 70. In embodiments, z2 is independently an integer from 0 to 80. In embodiments, z2 is independently an integer from 0 to 90. In embodiments, z2 is independently an integer from 0 to 100. In embodiments, z2 is independently an integer from 0 to 150. In embodiments, z2 is independently an integer from 0 to 200. In embodiments, z2 is independently an integer from 0 to 250. In embodiments, z2 is independently an integer from 0 to 300. In embodiments, z2 is independently an integer from 0 to 350. In embodiments, z2 is independently an integer from 0 to 400. In embodiments, z2 is independently an integer from 0 to 450. In embodiments, z2 is independently an integer from 0 to 500. In embodiments, z2 is independently an integer from 0 to 550. In embodiments, z2 is independently an integer from 0 to 600. In embodiments, z2 is independently an integer from 0 to 650. In embodiments, z2 is independently an integer from 0 to 700. In embodiments, z2 is independently an integer from 0 to 750. In embodiments, z2 is independently an integer from 0 to 800. In embodiments, z2 is independently an integer from 0 to 850. In embodiments, z2 is independently an integer from 0 to 900. In embodiments, z2 is independently an integer from 0 to 950. In embodiments, z2 is independently an integer from 0 to 1000. In embodiments, z2 is independently an integer from 0 to 1500. In embodiments, z2 is independently an integer from 0 to 2000. In embodiments, z2 is independently an integer from 0 to 2500. In embodiments, z2 is independently an integer from 0 to 3000. In embodiments, z2 is independently an integer from 0 to 3500. In embodiments, z2 is independently an integer from 0 to 4000. In embodiments, z2 is independently an integer from 0 to 4500. In embodiments, z2 is independently an integer from 0 to 5000.

In embodiments, z2 is independently an integer from 1 to 10. In embodiments, z2 is independently an integer from 1 to 20. In embodiments, z2 is independently an integer from 1 to 30. In embodiments, z2 is independently an integer from 1 to 40. In embodiments, z2 is independently an integer from 1 to 50. In embodiments, z2 is independently an integer from 1 to 60. In embodiments, z2 is independently an integer from 1 to 70. In embodiments, z2 is independently an integer from 1 to 80. In embodiments, z2 is independently an integer from 1 to 90. In embodiments, z2 is independently an integer from 1 to 100. In embodiments, z2 is independently an integer from 1 to 150. In embodiments, z2 is independently an integer from 1 to 200. In embodiments, z2 is independently an integer from 1 to 250. In embodiments, z2 is independently an integer from 1 to 300. In embodiments, z2 is independently an integer from 1 to 350. In embodiments, z2 is independently an integer from 1 to 400. In embodiments, z2 is independently an integer from 1 to 450. In embodiments, z2 is independently an integer from 1 to 500. In embodiments, z2 is independently an integer from 1 to 550. In embodiments, z2 is independently an integer from 1 to 600. In embodiments, z2 is independently an integer from 1 to 650. In embodiments, z2 is independently an integer from 1 to 700. In embodiments, z2 is independently an integer from 1 to 750. In embodiments, z2 is independently an integer from 1 to 800. In embodiments, z2 is independently an integer from 1 to 850. In embodiments, z2 is independently an integer from 1 to 900. In embodiments, z2 is independently an integer from 1 to 950. In embodiments, z2 is independently an integer from 1 to 1000. In embodiments, z2 is independently an integer from 1 to 1500. In embodiments, z2 is independently an integer from 1 to 2000. In embodiments, z2 is independently an integer from 1 to 2500. In embodiments, z2 is independently an integer from 1 to 3000. In embodiments, z2 is independently an integer from 1 to 3500. In embodiments, z2 is independently an integer from 1 to 4000. In embodiments, z2 is independently an integer from 1 to 4500. In embodiments, z2 is independently an integer from 1 to 5000.

In embodiments, z3 is independently an integer from 0 to 10. In embodiments, z3 is independently an integer from 0 to 20. In embodiments, z3 is independently an integer from 0 to 30. In embodiments, z3 is independently an integer from 0 to 40. In embodiments, z3 is independently an integer from 0 to 50. In embodiments, z3 is independently an integer from 0 to 60. In embodiments, z3 is independently an integer from 0 to 70. In embodiments, z3 is independently an integer from 0 to 80. In embodiments, z3 is independently an integer from 0 to 90. In embodiments, z3 is independently an integer from 0 to 100. In embodiments, z3 is independently an integer from 0 to 150. In embodiments, z3 is independently an integer from 0 to 200. In embodiments, z3 is independently an integer from 0 to 250. In embodiments, z3 is independently an integer from 0 to 300. In embodiments, z3 is independently an integer from 0 to 350. In embodiments, z3 is independently an integer from 0 to 400. In embodiments, z3 is independently an integer from 0 to 450. In embodiments, z3 is independently an integer from 0 to 500. In embodiments, z3 is independently an integer from 0 to 550. In embodiments, z3 is independently an integer from 0 to 600. In embodiments, z3 is independently an integer from 0 to 650. In embodiments, z3 is independently an integer from 0 to 700. In embodiments, z3 is independently an integer from 0 to 750. In embodiments, z3 is independently an integer from 0 to 800. In embodiments, z3 is independently an integer from 0 to 850. In embodiments, z3 is independently an integer from 0 to 900. In embodiments, z3 is independently an integer from 0 to 950. In embodiments, z3 is independently an integer from 0 to 1000. In embodiments, z3 is independently an integer from 0 to 1500. In embodiments, z3 is independently an integer from 0 to 2000. In embodiments, z3 is independently an integer from 0 to 2500. In embodiments, z3 is independently an integer from 0 to 3000. In embodiments, z3 is independently an integer from 0 to 3500. In embodiments, z3 is independently an integer from 0 to 4000. In embodiments, z3 is independently an integer from 0 to 4500. In embodiments, z3 is independently an integer from 0 to 5000.

In embodiments, z3 is independently an integer from 1 to 10. In embodiments, z3 is independently an integer from 1 to 20. In embodiments, z3 is independently an integer from 1 to 30. In embodiments, z3 is independently an integer from 1 to 40. In embodiments, z3 is independently an integer from 1 to 50. In embodiments, z3 is independently an integer from 1 to 60. In embodiments, z3 is independently an integer from 1 to 70. In embodiments, z3 is independently an integer from 1 to 80. In embodiments, z3 is independently an integer from 1 to 90. In embodiments, z3 is independently an integer from 1 to 100. In embodiments, z3 is independently an integer from 1 to 150. In embodiments, z3 is independently an integer from 1 to 200. In embodiments, z3 is independently an integer from 1 to 250. In embodiments, z3 is independently an integer from 1 to 300. In embodiments, z3 is independently an integer from 1 to 350. In embodiments, z3 is independently an integer from 1 to 400. In embodiments, z3 is independently an integer from 1 to 450. In embodiments, z3 is independently an integer from 1 to 500. In embodiments, z3 is independently an integer from 1 to 550. In embodiments, z3 is independently an integer from 1 to 600. In embodiments, z3 is independently an integer from 1 to 650. In embodiments, z3 is independently an integer from 1 to 700. In embodiments, z3 is independently an integer from 1 to 750. In embodiments, z3 is independently an integer from 1 to 800. In embodiments, z3 is independently an integer from 1 to 850. In embodiments, z3 is independently an integer from 1 to 900. In embodiments, z3 is independently an integer from 1 to 950. In embodiments, z3 is independently an integer from 1 to 1000. In embodiments, z3 is independently an integer from 1 to 1500. In embodiments, z3 is independently an integer from 1 to 2000. In embodiments, z3 is independently an integer from 1 to 2500. In embodiments, z3 is independently an integer from 1 to 3000. In embodiments, z3 is independently an integer from 1 to 3500. In embodiments, z3 is independently an integer from 1 to 4000. In embodiments, z3 is independently an integer from 1 to 4500. In embodiments, z3 is independently an integer from 1 to 5000.

In embodiments, z4 is independently an integer from 0 to 10. In embodiments, z4 is independently an integer from 0 to 20. In embodiments, z4 is independently an integer from 0 to 30. In embodiments, z4 is independently an integer from 0 to 40. In embodiments, z4 is independently an integer from 0 to 50. In embodiments, z4 is independently an integer from 0 to 60. In embodiments, z4 is independently an integer from 0 to 70. In embodiments, z4 is independently an integer from 0 to 80. In embodiments, z4 is independently an integer from 0 to 90. In embodiments, z4 is independently an integer from 0 to 100. In embodiments, z4 is independently an integer from 0 to 150. In embodiments, z4 is independently an integer from 0 to 200. In embodiments, z4 is independently an integer from 0 to 250. In embodiments, z4 is independently an integer from 0 to 300. In embodiments, z4 is independently an integer from 0 to 350. In embodiments, z4 is independently an integer from 0 to 400. In embodiments, z4 is independently an integer from 0 to 450. In embodiments, z4 is independently an integer from 0 to 500. In embodiments, z4 is independently an integer from 0 to 550. In embodiments, z4 is independently an integer from 0 to 600. In embodiments, z4 is independently an integer from 0 to 650. In embodiments, z4 is independently an integer from 0 to 700. In embodiments, z4 is independently an integer from 0 to 750. In embodiments, z4 is independently an integer from 0 to 800. In embodiments, z4 is independently an integer from 0 to 850. In embodiments, z4 is independently an integer from 0 to 900. In embodiments, z4 is independently an integer from 0 to 950. In embodiments, z4 is independently an integer from 0 to 1000. In embodiments, z4 is independently an integer from 0 to 1500. In embodiments, z4 is independently an integer from 0 to 2000. In embodiments, z4 is independently an integer from 0 to 2500. In embodiments, z4 is independently an integer from 0 to 3000. In embodiments, z4 is independently an integer from 0 to 3500. In embodiments, z4 is independently an integer from 0 to 4000. In embodiments, z4 is independently an integer from 0 to 4500. In embodiments, z4 is independently an integer from 0 to 5000.

In embodiments, z4 is independently an integer from 1 to 10. In embodiments, z4 is independently an integer from 1 to 20. In embodiments, z4 is independently an integer from 1 to 30. In embodiments, z4 is independently an integer from 1 to 40. In embodiments, z4 is independently an integer from 1 to 50. In embodiments, z4 is independently an integer from 1 to 60. In embodiments, z4 is independently an integer from 1 to 70. In embodiments, z4 is independently an integer from 1 to 80. In embodiments, z4 is independently an integer from 1 to 90. In embodiments, z4 is independently an integer from 1 to 100. In embodiments, z4 is independently an integer from 1 to 150. In embodiments, z4 is independently an integer from 1 to 200. In embodiments, z4 is independently an integer from 1 to 250. In embodiments, z4 is independently an integer from 1 to 300. In embodiments, z4 is independently an integer from 1 to 350. In embodiments, z4 is independently an integer from 1 to 400. In embodiments, z4 is independently an integer from 1 to 450. In embodiments, z4 is independently an integer from 1 to 500. In embodiments, z4 is independently an integer from 1 to 550. In embodiments, z4 is independently an integer from 1 to 600. In embodiments, z4 is independently an integer from 1 to 650. In embodiments, z4 is independently an integer from 1 to 700. In embodiments, z4 is independently an integer from 1 to 750. In embodiments, z4 is independently an integer from 1 to 800. In embodiments, z4 is independently an integer from 1 to 850. In embodiments, z4 is independently an integer from 1 to 900. In embodiments, z4 is independently an integer from 1 to 950. In embodiments, z4 is independently an integer from 1 to 1000. In embodiments, z4 is independently an integer from 1 to 1500. In embodiments, z4 is independently an integer from 1 to 2000. In embodiments, z4 is independently an integer from 1 to 2500. In embodiments, z4 is independently an integer from 1 to 3000. In embodiments, z4 is independently an integer from 1 to 3500. In embodiments, z4 is independently an integer from 1 to 4000. In embodiments, z4 is independently an integer from 1 to 4500. In embodiments, z4 is independently an integer from 1 to 5000.

In embodiments, the polymer further includes a subunit having the formula:

(IV)

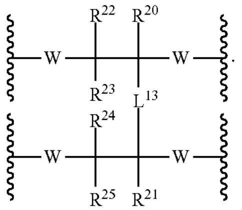

W independently has the formula:

(Va)

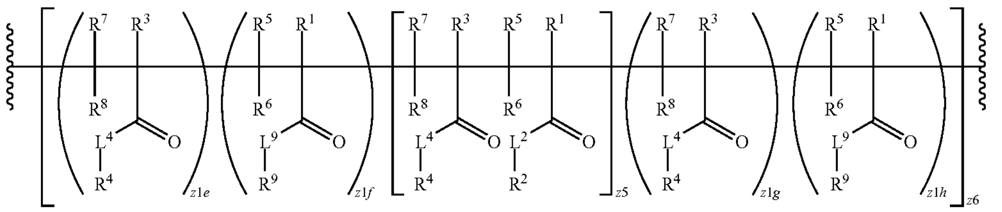

or (Vb)

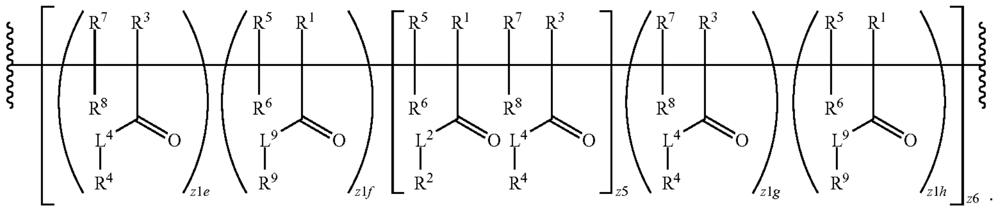

$R^1$, $L^2$, $R^2$, $R^3$, $L^4$, $R^4$, $R^5$, $R^6$, $R^7$, R', $L^9$, $R^9$, z1e, z1f, z1g, z1h, z5, and z6 are as described herein, including in embodiments.

$R^{20}$, $R^{21}$, $R^{22}$, $R^{23}$, $R^{24}$, and $R^{25}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^{13}$ is independently -$L^{13A}$-$L^{13B}$-$L^{13C}$-$L^{13D}$-$L^{13E}$-.

$L^{13A}$ $L^{13B}$ $L^{13C}$, $L^{13D}$, and $L^{13E}$ are independently a bond, —$S(O)_2$—, —S(O)—, —$S(O)_2NH$—, —NH—, —O—, —S—, —C(O)—, —C(O)NH—, —C(O)$CH_2$—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

The symbols z1e, z1f, z1g, and z1h are each independently an integer from 0 to 100.

The symbol z5 is independently an integer from 0 to 1.

The symbol z6 is independently an integer from 0 to 5000.

In embodiments, $L^{13A}$ is independently a bond. In embodiments, $L^{13A}$ is independently —$S(O)_2$—. In embodiments, $L^{13A}$ is independently —S(O)—. In embodiments, $L^{13A}$ is independently —$S(O)_2NH$—. In embodiments, $L^{13A}$ is independently —NH—. In embodiments, $L^{13A}$ is independently —O—. In embodiments, $L^{13A}$ is independently —S—. In embodiments, $L^{13A}$ is independently —C(O)—. In embodiments, $L^{13A}$ is independently —C(O)NH—. In embodiments, $L^{13A}$ is independently —C(O)$CH_2$—. In embodiments, $L^{13A}$ is independently —NHC(O)—. In embodiments, $L^{13A}$ is independently —NHC(O)NH—. In embodiments, $L^{13A}$ is independently —C(O)O—. In embodiments, $L^{13A}$ is independently —OC(O)—. In embodiments, $L^{13A}$ is independently a substituted or unsubstituted $C_1$-$C_4$ alkylene. In embodiments, $L^{13A}$ is independently a substituted or unsubstituted 2 to 4 membered heteroalkylene.

In embodiments, $L^{13B}$ is independently a bond. In embodiments, $L^{13B}$ is independently —$S(O)_2$—. In embodiments, $L^{13B}$ is independently —S(O)—. In embodiments, $L^{13B}$ is independently —$S(O)_2NH$—. In embodiments, $L^{13B}$ is independently —NH—. In embodiments, $L^{13B}$ is independently —O—. In embodiments, $L^{13B}$ is independently —S—. In embodiments, $L^{13B}$ is independently —C(O)—. In embodiments, $L^{13B}$ is independently —C(O)NH—. In embodiments, $L^{13B}$ is independently —C(O)$CH_2$—. In embodiments, $L^{13B}$ is independently —NHC(O)—. In embodiments, $L^{13B}$ is independently —NHC(O)NH—. In embodiments, $L^{13B}$ is independently —C(O)O—. In embodiments, $L^{13B}$ is independently —OC(O)—. In embodiments, $L^{13B}$ is independently a substituted or unsubstituted $C_1$-$C_4$ alkylene. In embodiments, $L^{13B}$ is independently a substituted or unsubstituted 2 to 4 membered heteroalkylene.

In embodiments, $L^{13C}$ is independently a bond. In embodiments, $L^{13C}$ is independently —$S(O)_2$—. In embodiments, $L^{13C}$ is independently —S(O)—. In embodiments, $L^{13C}$ is independently —$S(O)_2NH$—. In embodiments, $L^{13C}$ is independently —NH—. In embodiments, $L^{13C}$ is independently —O—. In embodiments, $L^{13C}$ is independently —S—. In embodiments, $L^{13C}$ is independently —C(O)—. In embodiments, $L^{13C}$ is independently —C(O)NH—. In embodiments, $L^{13C}$ is independently —C(O)$CH_2$—. In embodiments, $L^{13C}$ is independently —NHC(O)—. In embodiments, $L^{13C}$ is independently —NHC(O)NH—. In embodiments, $L^{13C}$ is independently —C(O)O—. In embodiments, $L^{13C}$ is independently —OC(O)—. In embodiments, $L^{13C}$ is independently a substituted or unsubstituted $C_1$-$C_4$ alkylene. In embodiments, $L^{13C}$ is independently a substituted or unsubstituted 2 to 4 membered heteroalkylene.

In embodiments, $L^{13D}$ is independently a bond. In embodiments, $L^{13D}$ is independently —S(O)$_2$—. In embodiments, $L^{13D}$ is independently —S(O)—. In embodiments, $L^{13D}$ is independently —S(O)$_2$NH—. In embodiments, $L^{13D}$ is independently —NH—. In embodiments, $L^{13D}$ is independently —O—. In embodiments, $L^{13D}$ is independently —S—. In embodiments, $L^{13D}$ is independently —C(O)—. In embodiments, $L^{13D}$ is independently —C(O)NH—. In embodiments, $L^{13D}$ is independently —C(O)$CH_2$—. In embodiments, $L^{13D}$ is independently —NHC(O)—. In embodiments, $L^{13D}$ is independently —NHC(O)NH—. In embodiments, $L^{13D}$ is independently —C(O)O—. In embodiments, $L^{13D}$ is independently —OC(O)—. In embodiments, $L^{13D}$ is independently a substituted or unsubstituted $C_1$-$C_4$ alkylene. In embodiments, $L^{13D}$ is independently a substituted or unsubstituted 2 to 4 membered heteroalkylene.

In embodiments, $L^{3E}$ is independently a bond. In embodiments, $L^{13E}$ is independently —S(O)$_2$—. In embodiments, $L^{13E}$ is independently —S(O)—. In embodiments, $L^{13E}$ is independently —S(O)$_2$NH—. In embodiments, $L^{13E}$ is independently —NH—. In embodiments, $L^{13E}$ is independently —O—. In embodiments, $L^{13E}$ is independently —S—. In embodiments, $L^{13E}$ is independently —C(O)—. In embodiments, $L^{13E}$ is independently —C(O)NH—. In embodiments, $L^{13E}$ is independently —C(O)$CH_2$—. In embodiments, $L^{13E}$ is independently —NHC(O)—. In embodiments, $L^{13E}$ is independently —NHC(O)NH—. In embodiments, $L^{13E}$ is independently —C(O)O—. In embodiments, $L^{13E}$ is independently —OC(O)—. In embodiments, $L^{13E}$ is independently a substituted or unsubstituted $C_1$-$C_4$ alkylene. In embodiments, $L^{13E}$ is independently a substituted or unsubstituted 2 to 4 membered heteroalkylene.

In embodiments, $L^{13}$ is independently —NH$CH_2$NH—. In embodiments, $L^{13}$ is independently —C(O)NH$CH_2$NHC(O)—.

In embodiments, each $L^{13}$ is the same.

In embodiments, $R^{21}$ is independently —CN. In embodiments, $R^{20}$ is independently substituted or unsubstituted alkyl. In embodiments, $R^{20}$ is independently substituted or unsubstituted $C_1$-$C_4$ alkyl. In embodiments, $R^{20}$ is independently unsubstituted $C_1$-$C_4$ alkyl. In embodiments, $R^{20}$ is independently unsubstituted methyl. In embodiments, $R^{21}$ is independently unsubstituted ethyl. In embodiments, $R^{20}$ is independently unsubstituted propyl. In embodiments, $R^{20}$ is independently unsubstituted n-propyl. In embodiments, $R^{20}$ is independently unsubstituted isopropyl. In embodiments, $R^{20}$ is independently unsubstituted butyl. In embodiments, $R^{20}$ is independently unsubstituted n-butyl. In embodiments, $R^{20}$ is independently unsubstituted tert-butyl. In embodiments, $R^{20}$ is independently substituted or unsubstituted heteroalkyl. In embodiments, $R^{20}$ is independently substituted or unsubstituted 2 to 6 membered heteroalkyl.

In embodiments, each $R^{20}$ is the same.

In embodiments, $R^{21}$ is independently —CN. In embodiments, $R^{21}$ is independently substituted or unsubstituted alkyl. In embodiments, $R^{21}$ is independently substituted or unsubstituted $C_1$-$C_4$ alkyl. In embodiments, $R^{21}$ is independently unsubstituted $C_1$-$C_4$ alkyl. In embodiments, $R^{21}$ is independently unsubstituted methyl. In embodiments, $R^{21}$ is independently unsubstituted ethyl. In embodiments, $R^{WW}$ is independently unsubstituted propyl. In embodiments, $R^{21}$ is independently unsubstituted n-propyl. In embodiments, $R^{21}$ is independently unsubstituted isopropyl. In embodiments, $R^{21}$ is independently unsubstituted butyl. In embodiments, $R^{21}$ is independently unsubstituted n-butyl. In embodiments, $R^{21}$ is independently unsubstituted tert-butyl. In embodiments, $R^{21}$ is independently substituted or unsubstituted heteroalkyl. In embodiments, $R^{21}$ is independently substituted or unsubstituted 2 to 6 membered heteroalkyl.

In embodiments, each $R^{21}$ is the same.

In embodiments, $R^{22}$ and $R^{23}$ are independently hydrogen.

In embodiments, $R^{22}$ is independently hydrogen. In embodiments, $R^{22}$ is independently substituted or unsubstituted $C_1$-$C_4$ alkyl. In embodiments, $R^{22}$ is independently unsubstituted $C_1$-$C_4$ alkyl. In embodiments, $R^{22}$ is independently unsubstituted methyl. In embodiments, $R^{22}$ is independently unsubstituted ethyl. In embodiments, $R^{22}$ is independently unsubstituted propyl. In embodiments, $R^{22}$ is independently unsubstituted n-propyl. In embodiments, $R^{22}$ is independently unsubstituted isopropyl. In embodiments, $R^{22}$ is independently unsubstituted butyl. In embodiments, $R^{22}$ is independently unsubstituted n-butyl. In embodiments, $R^{22}$ is independently unsubstituted tert-butyl.

In embodiments, each $R^{22}$ is the same.

In embodiments, $R^{23}$ is independently hydrogen. In embodiments, $R^{23}$ is independently substituted or unsubstituted $C_1$-$C_4$ alkyl. In embodiments, $R^{23}$ is independently unsubstituted $C_1$-$C_4$ alkyl. In embodiments, $R^{23}$ is independently unsubstituted methyl. In embodiments, $R^{23}$ is independently unsubstituted ethyl. In embodiments, $R^{23}$ is independently unsubstituted propyl. In embodiments, $R^{23}$ is independently unsubstituted n-propyl. In embodiments, $R^{23}$ is independently unsubstituted isopropyl. In embodiments, $R^{23}$ is independently unsubstituted butyl. In embodiments, $R^{23}$ is independently unsubstituted n-butyl. In embodiments, $R^{23}$ is independently unsubstituted tert-butyl.

In embodiments, each $R^{23}$ is the same.

In embodiments, $R^{24}$ and $R^{21}$ are independently hydrogen.

In embodiments, $R^{24}$ is independently hydrogen. In embodiments, $R^{24}$ is independently substituted or unsubstituted $C_1$-$C_4$ alkyl. In embodiments, $R^{24}$ is independently unsubstituted $C_1$-$C_4$ alkyl. In embodiments, $R^{24}$ is independently unsubstituted methyl. In embodiments, $R^{24}$ is independently unsubstituted ethyl. In embodiments, $R^{24}$ is independently unsubstituted propyl. In embodiments, $R^{24}$ is independently unsubstituted n-propyl. In embodiments, $R^{24}$ is independently unsubstituted isopropyl. In embodiments, $R^{24}$ is independently unsubstituted butyl. In embodiments, $R^{24}$ is independently unsubstituted n-butyl. In embodiments, $R^{24}$ is independently unsubstituted tert-butyl.

In embodiments, each $R^{24}$ is the same.

In embodiments, $R^{21}$ is independently hydrogen. In embodiments, $R^{21}$ is independently substituted or unsubstituted $C_1$-$C_4$ alkyl. In embodiments, $R^{21}$ is independently unsubstituted $C_1$-$C_4$ alkyl. In embodiments, $R^{21}$ is independently unsubstituted methyl. In embodiments, $R^{21}$ is independently unsubstituted ethyl. In embodiments, $R^{21}$ is independently unsubstituted propyl. In embodiments, $R^{21}$ is independently unsubstituted n-propyl. In embodiments, $R^{21}$ is independently unsubstituted isopropyl. In embodiments, $R^{21}$ is independently unsubstituted butyl. In embodiments, $R^{21}$ is independently unsubstituted n-butyl. In embodiments, $R^{21}$ is independently unsubstituted tert-butyl.

In embodiments, each $R^{21}$ is the same.

In embodiments, z1e is independently an integer from 0 to 10. In embodiments, z1e is independently an integer from 0 to 20. In embodiments, z1e is independently an integer from 0 to 30. In embodiments, z1e is independently an integer from 0 to 40. In embodiments, z1e is independently an integer from 0 to 50. In embodiments, z1e is independently an integer from 0 to 60. In embodiments, z1e is independently an integer from 0 to 70. In embodiments, z1e is independently an integer from 0 to 80. In embodiments, z1e is independently an integer from 0 to 90. In embodiments, z1e is independently an integer from 0 to 100. In embodiments, z1e is independently an integer from 0 to 150. In embodiments, z1e is independently an integer from 0 to 200. In embodiments, z1e is independently an integer from 0 to 250. In embodiments, z1e is independently an integer from 0 to 300. In embodiments, z1e is independently an integer from 0 to 350. In embodiments, z1e is independently an integer from 0 to 400. In embodiments, z1e is independently an integer from 0 to 450. In embodiments, z1e is independently an integer from 0 to 500. In embodiments, z1e is independently an integer from 0 to 550. In embodiments, z1e is independently an integer from 0 to 600. In embodiments, z1e is independently an integer from 0 to 650. In embodiments, z1e is independently an integer from 0 to 700. In embodiments, z1e is independently an integer from 0 to 750. In embodiments, z1e is independently an integer from 0 to 800. In embodiments, z1e is independently an integer from 0 to 850. In embodiments, z1e is independently an integer from 0 to 900. In embodiments, z1e is independently an integer from 0 to 950. In embodiments, z1e is independently an integer from 0 to 1000. In embodiments, z1e is independently an integer from 0 to 1500. In embodiments, z1e is independently an integer from 0 to 2000. In embodiments, z1e is independently an integer from 0 to 2500. In embodiments, z1e is independently an integer from 0 to 3000. In embodiments, z1e is independently an integer from 0 to 3500. In embodiments, z1e is independently an integer from 0 to 4000. In embodiments, z1e is independently an integer from 0 to 4500. In embodiments, z1e is independently an integer from 0 to 5000.

In embodiments, z1e is independently an integer from 1 to 10. In embodiments, z1e is independently an integer from 1 to 20. In embodiments, z1e is independently an integer from 1 to 30. In embodiments, z1e is independently an integer from 1 to 40. In embodiments, z1e is independently an integer from 1 to 50. In embodiments, z1e is independently an integer from 1 to 60. In embodiments, z1e is independently an integer from 1 to 70. In embodiments, z1e is independently an integer from 1 to 80. In embodiments, z1e is independently an integer from 1 to 90. In embodiments, z1e is independently an integer from 1 to 100. In embodiments, z1e is independently an integer from 1 to 150. In embodiments, z1e is independently an integer from 1 to 200. In embodiments, z1e is independently an integer from 1 to 250. In embodiments, z1e is independently an integer from 1 to 300. In embodiments, z1e is independently an integer from 1 to 350. In embodiments, z1e is independently an integer from 1 to 400. In embodiments, z1e is independently an integer from 1 to 450. In embodiments, z1e is independently an integer from 1 to 500. In embodiments, z1e is independently an integer from 1 to 550. In embodiments, z1e is independently an integer from 1 to 600. In embodiments, z1e is independently an integer from 1 to 650. In embodiments, z1e is independently an integer from 1 to 700. In embodiments, z1e is independently an integer from 1 to 750. In embodiments, z1e is independently an integer from 1 to 800. In embodiments, z1e is independently an integer from 1 to 850. In embodiments, z1e is independently an integer from 1 to 900. In embodiments, z1e is independently an integer from 1 to 950. In embodiments, z1e is independently an integer from 1 to 1000. In embodiments, z1e is independently an integer from 1 to 1500. In embodiments, z1e is independently an integer from 1 to 2000. In embodiments, z1e is independently an integer from 1 to 2500. In embodiments, z1e is independently an integer from 1 to 3000. In embodiments, z1e is independently an integer from 1 to 3500. In embodiments, z1e is independently an integer from 1 to 4000. In embodiments, z1e is independently an integer from 1 to 4500. In embodiments, z1e is independently an integer from 1 to 5000.

In embodiments, z1f is independently an integer from 0 to 10. In embodiments, z1f is independently an integer from 0 to 20. In embodiments, z1f is independently an integer from 0 to 30. In embodiments, z1f is independently an integer from 0 to 40. In embodiments, z1f is independently an integer from 0 to 50. In embodiments, z1f is independently an integer from 0 to 60. In embodiments, z1f is independently an integer from 0 to 70. In embodiments, z1f is independently an integer from 0 to 80. In embodiments, z1f is independently an integer from 0 to 90. In embodiments, z1f is independently an integer from 0 to 100. In embodiments, z1f is independently an integer from 0 to 150. In embodiments, z1f is independently an integer from 0 to 200. In embodiments, z1f is independently an integer from 0 to 250. In embodiments, z1f is independently an integer from 0 to 300. In embodiments, z1f is independently an integer from 0 to 350. In embodiments, z1f is independently an integer from 0 to 400. In embodiments, z1f is independently an integer from 0 to 450. In embodiments, z1f is independently an integer from 0 to 500. In embodiments, z1f is independently an integer from 0 to 550. In embodiments, z1f is independently an integer from 0 to 600. In embodiments, z1f is independently an integer from 0 to 650. In embodiments, z1f is independently an integer from 0 to 700. In embodiments, z1f is independently an integer from 0 to 750. In embodiments, z1f is independently an integer from 0 to 800. In embodiments, z1f is independently an integer from 0 to 850. In embodiments, z1f is independently an integer from 0 to 900. In embodiments, z1f is independently an integer from 0 to 950. In embodiments, z1f is independently an integer from 0 to 1000. In embodiments, z1f is independently an integer from 0 to 1500. In embodiments, z1f is independently an integer from 0 to 2000. In embodiments, z1f is independently an integer from 0 to 2500. In embodiments, z1f is independently an integer from 0 to 3000. In embodiments, z1f is independently an integer from 0 to 3500. In embodiments, z1f is independently an integer from 0 to 4000. In embodiments, z1f is independently an integer from 0 to 4500. In embodiments, z1f is independently an integer from 0 to 5000.

In embodiments, z1f is independently an integer from 1 to 10. In embodiments, z1f is independently an integer from 1 to 20. In embodiments, z1f is independently an integer from 1 to 30. In embodiments, z1f is independently an integer from 1 to 40. In embodiments, z1f is independently an integer from 1 to 50. In embodiments, z1f is independently an integer from 1 to 60. In embodiments, z1f is independently an integer from 1 to 70. In embodiments, z1f is independently an integer from 1 to 80. In embodiments, z1f is independently an integer from 1 to 90. In embodiments, z1f is independently an integer from 1 to 100. In embodiments, z1f is independently an integer from 1 to 150. In embodiments, z1f is independently an integer from 1 to 200. In embodiments, z1f is independently an integer from 1 to 250. In embodiments, z1f is independently an integer from 1 to 300. In embodiments, z1f is independently an integer from 1 to 350. In embodiments, z1f is independently an integer from 1 to 400. In embodiments, z1f is independently an integer from 1 to 450. In embodiments, z1f is independently an integer from 1 to 500. In embodiments, z1f is independently an integer from 1 to 550. In embodiments, z1f is independently an integer from 1 to 600. In embodiments, z1f is independently an integer from 1 to 650. In embodiments, z1f is independently an integer from 1 to 700. In embodiments, z1f is independently an integer from 1 to 750. In embodiments, z1f is independently an integer from 1 to 800. In embodiments, z1f is independently an integer from 1 to 850. In embodiments, z1f is independently an integer from 1 to 900. In embodiments, z1f is independently an integer from 1 to 950. In embodiments, z1f is independently an integer from 1 to 1000. In embodiments, z1f is independently an integer from 1 to 1500. In embodiments, z1f is independently an integer from 1 to 2000. In embodiments, z1f is independently an integer from 1 to 2500. In embodiments, z1f is independently an integer from 1 to 3000. In embodiments, z1f is independently an integer from 1 to 3500. In embodiments, z1f is independently an integer from 1 to 4000. In embodiments, z1f is independently an integer from 1 to 4500. In embodiments, z1f is independently an integer from 1 to 5000.

In embodiments, z1g is independently an integer from 0 to 10. In embodiments, z1g is independently an integer from 0 to 20. In embodiments, z1g is independently an integer from 0 to 30. In embodiments, z1g is independently an integer from 0 to 40. In embodiments, z1g is independently an integer from 0 to 50. In embodiments, z1g is independently an integer from 0 to 60. In embodiments, z1g is independently an integer from 0 to 70. In embodiments, z1g is independently an integer from 0 to 80. In embodiments, z1g is independently an integer from 0 to 90. In embodiments, z1g is independently an integer from 0 to 100. In embodiments, z1g is independently an integer from 0 to 150. In embodiments, z1g is independently an integer from 0 to 200. In embodiments, z1g is independently an integer from 0 to 250. In embodiments, z1g is independently an integer from 0 to 300. In embodiments, z1g is independently an integer from 0 to 350. In embodiments, z1g is independently an integer from 0 to 400. In embodiments, z1g is independently an integer from 0 to 450. In embodiments, z1g is independently an integer from 0 to 500. In embodiments, z1g is independently an integer from 0 to 550. In embodiments, z1g is independently an integer from 0 to 600. In embodiments, z1g is independently an integer from 0 to 650. In embodiments, z1g is independently an integer from 0 to 700. In embodiments, z1g is independently an integer from 0 to 750. In embodiments, z1g is independently an integer from 0 to 800. In embodiments, z1g is independently an integer from 0 to 850. In embodiments, z1g is independently an integer from 0 to 900. In embodiments, z1g is independently an integer from 0 to 950. In embodiments, z1g is independently an integer from 0 to 1000. In embodiments, z1g is independently an integer from 0 to 1500. In embodiments, z1g is independently an integer from 0 to 2000. In embodiments, z1g is independently an integer from 0 to 2500. In embodiments, z1g is independently an integer from 0 to 3000. In embodiments, z1g is independently an integer from 0 to 3500. In embodiments, z1g is independently an integer from 0 to 4000. In embodiments, z1g is independently an integer from 0 to 4500. In embodiments, zig is independently an integer from 0 to 5000.

In embodiments, z1g is independently an integer from 1 to 10. In embodiments, z1g is independently an integer from 1 to 20. In embodiments, z1g is independently an integer from 1 to 30. In embodiments, z1g is independently an integer from 1 to 40. In embodiments, z1g is independently an integer from 1 to 50. In embodiments, z1g is independently an integer from 1 to 60. In embodiments, z1g is independently an integer from 1 to 70. In embodiments, z1g is independently an integer from 1 to 80. In embodiments, z1g is independently an integer from 1 to 90. In embodiments, z1g is independently an integer from 1 to 100. In embodiments, z1g is independently an integer from 1 to 150. In embodiments, z1g is independently an integer from 1 to 200. In embodiments, z1g is independently an integer from 1 to 250. In embodiments, z1g is independently an integer from 1 to 300. In embodiments, z1g is independently an integer from 1 to 350. In embodiments, z1g is independently an integer from 1 to 400. In embodiments, z1g is independently an integer from 1 to 450. In embodiments, z1g is independently an integer from 1 to 500. In embodiments, z1g is independently an integer from 1 to 550. In embodiments, z1g is independently an integer from 1 to 600. In embodiments, z1g is independently an integer from 1 to 650. In embodiments, z1g is independently an integer from 1 to 700. In embodiments, z1g is independently an integer from 1 to 750. In embodiments, z1g is independently an integer from 1 to 800. In embodiments, z1g is independently an integer from 1 to 850. In embodiments, z1g is independently an integer from 1 to 900. In embodiments, z1g is independently an integer from 1 to 950. In embodiments, z1g is independently an integer from 1 to 1000. In embodiments, z1g is independently an integer from 1 to 1500. In embodiments, z1g is independently an integer from 1 to 2000. In embodiments, z1g is independently an integer from 1 to 2500. In embodiments, z1g is independently an integer from 1 to 3000. In embodiments, z1g is independently an integer from 1 to 3500. In embodiments, z1g is independently an integer from 1 to 4000. In embodiments, z1g is independently an integer from 1 to 4500. In embodiments, zig is independently an integer from 1 to 5000.

In embodiments, z1h is independently an integer from 0 to 10. In embodiments, z1h is independently an integer from 0 to 20. In embodiments, z1h is independently an integer from 0 to 30. In embodiments, z1h is independently an integer from 0 to 40. In embodiments, z1h is independently an integer from 0 to 50. In embodiments, z1h is independently an integer from 0 to 60. In embodiments, z1h is independently an integer from 0 to 70. In embodiments, z1h is independently an integer from 0 to 80. In embodiments, z1h is independently an integer from 0 to 90. In embodiments, z1h is independently an integer from 0 to 100. In embodiments, z1h is independently an integer from 0 to 150. In embodiments, z1h is independently an integer from 0 to 200. In embodiments, z1h is independently an integer from 0 to 250. In embodiments, z1h is independently an integer from 0 to 300. In embodiments, z1h is independently an integer from 0 to 350. In embodiments, z1h is independently an integer from 0 to 400. In embodiments, z1h is independently an integer from 0 to 450. In embodiments, z1h is independently an integer from 0 to 500. In embodiments, z1h is independently an integer from 0 to 550. In embodiments, z1h is independently an integer from 0 to 600. In embodiments, z1h is independently an integer from 0 to 650. In embodiments, z1h is independently an integer from 0 to 700. In embodiments, z1h is independently an integer from 0 to 750. In embodiments, z1h is independently an integer from 0 to 800. In embodiments, z1h is independently an integer from 0 to 850. In embodiments, z1h is independently an integer from 0 to 900. In embodiments, z1h is independently an integer from 0 to 950. In embodiments, z1h is independently an integer from 0 to 1000. In embodiments, z1h is independently an integer from 0 to 1500. In embodiments, z1h is independently an integer from 0 to 2000. In embodiments, z1h is independently an integer from 0 to 2500. In embodiments, z1h is independently an integer from 0 to 3000. In embodiments, z1h is independently an integer from 0 to 3500. In embodiments, z1h is independently an integer from 0 to 4000. In embodiments, z1h is independently an integer from 0 to 4500. In embodiments, z1h is independently an integer from 0 to 5000.

In embodiments, z1h is independently an integer from 1 to 10. In embodiments, z1h is independently an integer from 1 to 20. In embodiments, z1h is independently an integer from 1 to 30. In embodiments, z1h is independently an integer from 1 to 40. In embodiments, z1h is independently an integer from 1 to 50. In embodiments, z1h is independently an integer from 1 to 60. In embodiments, z1h is independently an integer from 1 to 70. In embodiments, z1h is independently an integer from 1 to 80. In embodiments, z1h is independently an integer from 1 to 90. In embodiments, z1h is independently an integer from 1 to 100. In embodiments, z1h is independently an integer from 1 to 150. In embodiments, z1h is independently an integer from 1 to 200. In embodiments, z1h is independently an integer from 1 to 250. In embodiments, z1h is independently an integer from 1 to 300. In embodiments, z1h is independently an integer from 1 to 350. In embodiments, z1h is independently an integer from 1 to 400. In embodiments, z1h is independently an integer from 1 to 450. In embodiments, z1h is independently an integer from 1 to 500. In embodiments, z1h is independently an integer from 1 to 550. In embodiments, z1h is independently an integer from 1 to 600. In embodiments, z1h is independently an integer from 1 to 650. In embodiments, z1h is independently an integer from 1 to 700. In embodiments, z1h is independently an integer from 1 to 750. In embodiments, z1h is independently an integer from 1 to 800. In embodiments, z1h is independently an integer from 1 to 850. In embodiments, z1h is independently an integer from 1 to 900. In embodiments, z1h is independently an integer from 1 to 950. In embodiments, z1h is independently an integer from 1 to 1000. In embodiments, z1h is independently an integer from 1 to 1500. In embodiments, z1h is independently an integer from 1 to 2000. In embodiments, z1h is independently an integer from 1 to 2500. In embodiments, z1h is independently an integer from 1 to 3000. In embodiments, z1h is independently an integer from 1 to 3500. In embodiments, z1h is independently an integer from 1 to 4000. In embodiments, z1h is independently an integer from 1 to 4500. In embodiments, z1h is independently an integer from 1 to 5000.

In embodiments, z5 is independently 0. In embodiments, z5 is independently 1.

In embodiments, z6 is independently an integer from 0 to 10. In embodiments, z6 is independently an integer from 0 to 20. In embodiments, z6 is independently an integer from 0 to 30. In embodiments, z6 is independently an integer from 0 to 40. In embodiments, z6 is independently an integer from 0 to 50. In embodiments, z6 is independently an integer from 0 to 60. In embodiments, z6 is independently an integer from 0 to 70. In embodiments, z6 is independently an integer from 0 to 80. In embodiments, z6 is independently an integer from 0 to 90. In embodiments, z6 is independently an integer from 0 to 100. In embodiments, z6 is independently an integer from 0 to 150. In embodiments, z6 is independently an integer from 0 to 200. In embodiments, z6 is independently an integer from 0 to 250. In embodiments, z6 is independently an integer from 0 to 300. In embodiments, z6 is independently an integer from 0 to 350. In embodiments, z6 is independently an integer from 0 to 400. In embodiments, z6 is independently an integer from 0 to 450. In embodiments, z6 is independently an integer from 0 to 500. In embodiments, z6 is independently an integer from 0 to 550. In embodiments, z6 is independently an integer from 0 to 600. In embodiments, z6 is independently an integer from 0 to 650. In embodiments, z6 is independently an integer from 0 to 700. In embodiments, z6 is independently an integer from 0 to 750. In embodiments, z6 is independently an integer from 0 to 800. In embodiments, z6 is independently an integer from 0 to 850. In embodiments, z6 is independently an integer from 0 to 900. In embodiments, z6 is independently an integer from 0 to 950. In embodiments, z6 is independently an integer from 0 to 1000. In embodiments, z6 is independently an integer from 0 to 1500. In embodiments, z6 is independently an integer from 0 to 2000. In embodiments, z6 is independently an integer from 0 to 2500. In embodiments, z6 is independently an integer from 0 to 3000. In embodiments, z6 is independently an integer from 0 to 3500. In embodiments, z6 is independently an integer from 0 to 4000. In embodiments, z6 is independently an integer from 0 to 4500. In embodiments, z6 is independently an integer from 0 to 5000.

In embodiments, z6 is independently an integer from 1 to 10. In embodiments, z6 is independently an integer from 1 to 20. In embodiments, z6 is independently an integer from 1 to 30. In embodiments, z6 is independently an integer from 1 to 40. In embodiments, z6 is independently an integer from 1 to 50. In embodiments, z6 is independently an integer from 1 to 60. In embodiments, z6 is independently an integer from 1 to 70. In embodiments, z6 is independently an integer from 1 to 80. In embodiments, z6 is independently an integer from 1 to 90. In embodiments, z6 is independently an integer from 1 to 100. In embodiments, z6 is independently an integer from 1 to 150. In embodiments, z6 is independently an integer from 1 to 200. In embodiments, z6 is independently an integer from 1 to 250. In embodiments, z6 is independently an integer from 1 to 300. In embodiments, z6 is independently an integer from 1 to 350. In embodiments, z6 is independently an integer from 1 to 400. In embodiments, z6 is independently an integer from 1 to 450. In embodiments, z6 is independently an integer from 1 to 500. In embodiments, z6 is independently an integer from 1 to 550. In embodiments, z6 is independently an integer from 1 to 600. In embodiments, z6 is independently an integer from 1 to 650. In embodiments, z6 is independently an integer from 1 to 700. In embodiments, z6 is independently an integer from 1 to 750. In embodiments, z6 is independently an integer from 1 to 800. In embodiments, z6 is independently an integer from 1 to 850. In embodiments, z6 is independently an integer from 1 to 900. In embodiments, z6 is independently an integer from 1 to 950. In embodiments, z6 is independently an integer from 1 to 1000. In embodiments, z6 is independently an integer from 1 to 1500. In embodiments, z6 is independently an integer from 1 to 2000. In embodiments, z6 is independently an integer from 1 to 2500. In embodiments, z6 is independently an integer from 1 to 3000. In embodiments, z6 is independently an integer from 1 to 3500. In embodiments, z6 is independently an integer from 1 to 4000. In embodiments, z6 is independently an integer from 1 to 4500. In embodiments, z6 is independently an integer from 1 to 5000.

In embodiments, when $R^1$ is substituted, $R^1$ is substituted with one or more first substituent groups denoted by $R^{1.1}$ as explained in the definitions section above in the description of “first substituent group(s)”. In embodiments, when an $R^{1.1}$ substituent group is substituted, the $R^{1.1}$ substituent group is substituted with one or more second substituent groups denoted by $R^{1.2}$ as explained in the definitions section above in the description of “first substituent group (s)”. In embodiments, when an $R^{1.2}$ substituent group is substituted, the $R^{1.2}$ substituent group is substituted with one or more third substituent groups denoted by $R^{1.3}$ as explained in the definitions section above in the description of “first substituent group(s)”. In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^3$ is substituted, $R^3$ is substituted with one or more first substituent groups denoted by $R^{3.1}$ as explained in the definitions section above in the description of “first substituent group(s)”. In embodiments, when an $R^{3.1}$ substituent group is substituted, the $R^{3.1}$ substituent group is substituted with one or more second substituent groups denoted by $R^{3.2}$ as explained in the definitions section above in the description of “first substituent group (s)”. In embodiments, when an $R^{3.2}$ substituent group is substituted, the $R^{3.2}$ substituent group is substituted with one or more third substituent groups denoted by $R^{3.3}$ as explained in the definitions section above in the description of “first substituent group(s)”. In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when $R^4$ is substituted, $R^4$ is substituted with one or more first substituent groups denoted by $R^{4.1}$ as explained in the definitions section above in the description of “first substituent group(s)”. In embodiments, when an $R^{4.1}$ substituent group is substituted, the $R^{4.1}$ substituent group is substituted with one or more second substituent groups denoted by $R^{4.2}$ as explained in the definitions section above in the description of “first substituent group (s)”. In embodiments, when an $R^{4.2}$ substituent group is substituted, the $R^{4.2}$ substituent group is substituted with one or more third substituent groups denoted by $R^{4.3}$ as explained in the definitions section above in the description of “first substituent group(s)”. In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $R^{4A}$ is substituted, $R^{4A}$ is substituted with one or more first substituent groups denoted by $R^{4A.1}$ as explained in the definitions section above in the description of “first substituent group(s)”. In embodiments, when an $R^{4A}1$ substituent group is substituted, the $R^{4A.1}$ substituent group is substituted with one or more second substituent groups denoted by $R^{4A.2}$ as explained in the definitions section above in the description of “first substituent group(s)”. In embodiments, when an $R^{4A.2}$ substituent group is substituted, the $R^{4A.2}$ substituent group is substituted with one or more third substituent groups denoted by $R^{4A.3}$ as explained in the definitions section above in the description of “first substituent group(s)”. In the above embodiments, $R^{4A}$, $R^{4A.1}$, $R^{4A.2}$, and $R^{4A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{4A}$, $R^{4A.1}$, $R^{4A.2}$, and $R^{4A.3}$, respectively.

In embodiments, when $R^{4B}$ is substituted, $R^{4B}$ is substituted with one or more first substituent groups denoted by $R^{4B.1}$ as explained in the definitions section above in the description of “first substituent group(s)”. In embodiments, when an $R^{4B.1}$ substituent group is substituted, the $R^{4B.1}$ substituent group is substituted with one or more second substituent groups denoted by $R^{4B.2}$ as explained in the definitions section above in the description of “first substituent group(s)”. In embodiments, when an $R^{4B.2}$ substituent group is substituted, the $R^{4B.2}$ substituent group is substituted with one or more third substituent groups denoted by $R^{4B.3}$ as explained in the definitions section above in the description of “first substituent group(s)”. In the above embodiments, $R^{4B}$, $R^{4B.1}$, $R^{4B.2}$, and $R^{4B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{4B}$, $R^{4B.1}$, $R^{4B.2}$, and $R^{4B.3}$, respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4A.1}$ as explained in the definitions section above in the description of “first substituent group(s)”. In embodiments, when an $R^{4A.1}$ substituent group is substituted, the $R^{4A.1}$ substituent group is substituted with one or more second substituent groups denoted by $R^{4A.2}$ as explained in the definitions section above in the description of “first substituent group (s)”. In embodiments, when an $R^{4A.2}$ substituent group is substituted, the $R^{4A.2}$ substituent group is substituted with one or more third substituent groups denoted by $R^{4A.3}$ as explained in the definitions section above in the description of “first substituent group(s)”. In the above embodiments, $R^{4A.1}$, $R^{4A.2}$, and $R^{4A.3}$ have values corresponding to the values of $R^{WW}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{4A.1}$, $R^{4A.2}$, and $R^{4A.3}$ respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4B.1}$ as explained in the definitions section above in the description of “first substituent group(s)”. In embodiments, when an $R^{4B.1}$ substituent group is substituted, the $R^{4B.1}$ substituent group is substituted with one or more second substituent groups denoted by $R^{4B.2}$ as explained in the definitions section above in the description of “first substituent group (s)”. In embodiments, when an $R^{4B.2}$ substituent group is substituted, the $R^{4B.2}$ substituent group is substituted with one or more third substituent groups denoted by $R^{4B.3}$ as explained in the definitions section above in the description of "first substituent group(s)". In the above embodiments, $R^{4B.1}$, $R^{4B.2}$, and $R^{4B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{4B.1}$, $R^{4B.2}$, and $R^{4B.3}$ respectively.

In embodiments, when $R^{4C}$ is substituted, $R^{4C}$ is substituted with one or more first substituent groups denoted by $R^{4C.1}$ as explained in the definitions section above in the description of "first substituent group(s)". In embodiments, when an $R^{4C.1}$ substituent group is substituted, the $R^{4C.1}$ substituent group is substituted with one or more second substituent groups denoted by $R^{4C.2}$ as explained in the definitions section above in the description of "first substituent group(s)". In embodiments, when an $R^{4C.2}$ substituent group is substituted, the $R^{4C.2}$ substituent group is substituted with one or more third substituent groups denoted by $R^{4C.3}$ as explained in the definitions section above in the description of "first substituent group(s)". In the above embodiments, $R^{4C}$, $R^{4C.1}$, $R^{4C.2}$, and $R^{4C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4C}$, $R^{4C.1}$, $R^{4C.2}$, and $R^{4C.3}$, respectively.

In embodiments, when $R^{4D}$ is substituted, $R^{4D}$ is substituted with one or more first substituent groups denoted by $R^{4D.1}$ as explained in the definitions section above in the description of "first substituent group(s)". In embodiments, when an $R^{4D.1}$ substituent group is substituted, the $R^{4D.1}$ substituent group is substituted with one or more second substituent groups denoted by $R^{4D.2}$ as explained in the definitions section above in the description of "first substituent group(s)". In embodiments, when an $R^{4D.2}$ substituent group is substituted, the $R^{4D.2}$ substituent group is substituted with one or more third substituent groups denoted by $R^{4D.3}$ as explained in the definitions section above in the description of "first substituent group(s)". In the above embodiments, $R^{4D}$, $R^{4D.1}$, $R^{4D.2}$, and $R^{4D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4D}$, $R^{4D.1}$, $R^{4D.2}$, and $R^{4D.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group (s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^6$ is substituted, $R^6$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group (s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when $R^7$ is substituted, $R^7$ is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group (s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when $R^8$ is substituted, $R^8$ is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group (s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^8$, $R^{81}$, $R^{82}$, and $R^{83}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^8$, $R^{8.1}$, $R^{8.2}$, and $R^{8.3}$, respectively.

In embodiments, when $R^9$ is substituted, $R^9$ is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group (s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^9$, $R^{9.1}$, $R^{9.2}$, and $R^{9.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9}$, $R^{9.1}$, $R^{9.2}$, and $R^{9.3}$, respectively.

In embodiments, when $R^{9A}$ is substituted, $R^{9A}$ is substituted with one or more first substituent groups denoted by $R^{9A.1}$ as explained in the definitions section above in the description of "first substituent group(s)". In embodiments, when an $R^{9A.1}$ substituent group is substituted, the $R^{9A.1}$ substituent group is substituted with one or more second substituent groups denoted by $R^{9A.2}$ as explained in the definitions section above in the description of "first substituent group(s)". In embodiments, when an $R^{9A.2}$ substituent group is substituted, the $R^{9A.2}$ substituent group is substituted with one or more third substituent groups denoted by $R^{9A.3}$ as explained in the definitions section above in the description of "first substituent group(s)". In the above embodiments, $R^{9A}$, $R^{9A.1}$, $R^{9A.2}$, and $R^{9A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9A}$, $R^{9A.1}$, $R^{9A.2}$, and $R^{9A.3}$, respectively.

In embodiments, when $R^{9B}$ is substituted, $R^{9B}$ is substituted with one or more first substituent groups denoted by $R^{9B.1}$ as explained in the definitions section above in the description of "first substituent group(s)". In embodiments, when an $R^{9B.1}$ substituent group is substituted, the $R^{9B.1}$ substituent group is substituted with one or more second substituent groups denoted by $R^{9B.2}$ as explained in the definitions section above in the description of "first substituent group(s)". In embodiments, when an $R^{9B.2}$ substituent group is substituted, the $R^{9B.2}$ substituent group is substituted with one or more third substituent groups denoted by $R^{9B.3}$ as explained in the definitions section above in the description of "first substituent group(s)". In the above embodiments, $R^{9B}$, $R^{9B.1}$, $R^{9B.2}$, and $R^{9B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9B}$, $R^{9B.1}$, $R^{9B.2}$, and $R^{9B.3}$, respectively.

In embodiments, when $R^{9A}$ and $R^{9B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{9A.1}$ as explained in the definitions section above in the description of "first substituent group(s)". In embodiments, when an $R^{9A.1}$ substituent group is substituted, the $R^{9A.1}$ substituent group is substituted with one or more second substituent groups denoted by $R^{9A.2}$ as explained in the definitions section above in the description of "first substituent group (s)". In embodiments, when an $R^{9A.2}$ substituent group is substituted, the $R^{9A.2}$ substituent group is substituted with one or more third substituent groups denoted by $R^{9A.3}$ as explained in the definitions section above in the description of "first substituent group(s)". In the above embodiments, $R^{9A.1}$, $R^{9A.2}$, and $R^{9A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9A.1}$, $R^{9A.2}$, and $R^{9A.3}$ respectively.

In embodiments, when $R^{9A}$ and $R^{9B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{9B.1}$ as explained in the definitions section above in the description of "first substituent group(s)". In embodiments, when an $R^{9B.1}$ substituent group is substituted, the $R^{9B.1}$ substituent group is substituted with one or more second substituent groups denoted by $R^{9B.2}$ as explained in the definitions section above in the description of "first substituent group (s)". In embodiments, when an $R^{9B.2}$ substituent group is substituted, the $R^{9B.2}$ substituent group is substituted with one or more third substituent groups denoted by $R^{9B.3}$ as explained in the definitions section above in the description of "first substituent group(s)". In the above embodiments, $R^{9B.1}$, $R^{9B.2}$, and $R^{9B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9B.1}$, $R^{9B.2}$, and $R^{9B.3}$, respectively.

In embodiments, when $R^{9C}$ is substituted, $R^{9C}$ is substituted with one or more first substituent groups denoted by $R^{9C.1}$ as explained in the definitions section above in the description of "first substituent group(s)". In embodiments, when an $R^{9C.1}$ substituent group is substituted, the $R^{9C.1}$ substituent group is substituted with one or more second substituent groups denoted by $R^{9C.2}$ as explained in the definitions section above in the description of "first substituent group(s)". In embodiments, when an $R^{9C.2}$ substituent group is substituted, the $R^{9C.2}$ substituent group is substituted with one or more third substituent groups denoted by $R^{9C.3}$ as explained in the definitions section above in the description of "first substituent group(s)". In the above embodiments, $R^{9C}$, $R^{9C.1}$, $R^{9C.2}$, and $R^{9C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9C}$, $R^{9C.1}$, $R^{9C.2}$, and $R^{9C.3}$, respectively.

In embodiments, when $R^{9D}$ is substituted, $R^{9D}$ is substituted with one or more first substituent groups denoted by $R^{9D.1}$ as explained in the definitions section above in the description of "first substituent group(s)". In embodiments, when an $R^{9D.1}$ substituent group is substituted, the $R^{9D.1}$ substituent group is substituted with one or more second substituent groups denoted by $R^{9D.2}$ as explained in the definitions section above in the description of "first substituent group(s)". In embodiments, when an $R^{9D.2}$ substituent group is substituted, the $R^{9D.2}$ substituent group is substituted with one or more third substituent groups denoted by $R^{9D.3}$ as explained in the definitions section above in the description of "first substituent group(s)". In the above embodiments, $R^{9D}$, $R^{9D.1}$, $R^{9D.2}$, and $R^{9D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9D}$, $R^{9D.1}$, $R^{9D.2}$, and $R^{9D.3}$, respectively.

In embodiments, when $R^{10}$ is substituted, $R^{10}$ is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when $R^{12}$ is substituted, $R^{12}$ is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12}$, $R^{12.1}$, $R^{12.2}$, and $R^{12.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12}$, $R^{12.1}$, $R^{12.2}$, and $R^{12.3}$, respectively.

In embodiments, when $R^{13}$ is substituted, $R^{13}$ is substituted with one or more first substituent groups denoted by $R^{13.1}$ as explained in the definitions section above in the description of "first substituent group(s)". In embodiments, when an $R^{13.1}$ substituent group is substituted, the $R^{13.1}$ substituent group is substituted with one or more second substituent groups denoted by $R^{13.2}$ as explained in the definitions section above in the description of "first substituent group(s)". In embodiments, when an $R^{13.2}$ substituent group is substituted, the $R^{13.2}$ substituent group is substituted with one or more third substituent groups denoted by $R^{13.3}$ as explained in the definitions section above in the description of "first substituent group(s)". In the above embodiments, $R^{13}$, $R^{13.1}$, $R^{13.2}$, and $R^{13.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13}$, $R^{131}$, $R^{13.2}$, and $R^{13.3}$, respectively.

In embodiments, when $R^{14}$ is substituted, $R^{14}$ is substituted with one or more first substituent groups denoted by $R^{14.1}$ as explained in the definitions section above in the description of "first substituent group(s)". In embodiments, when an $R^{14.1}$ substituent group is substituted, the $R^{14.1}$ substituent group is substituted with one or more second substituent groups denoted by $R^{14.2}$ as explained in the definitions section above in the description of "first substituent group(s)". In embodiments, when an $R^{14.2}$ substituent group is substituted, the $R^{14.2}$ substituent group is substituted with one or more third substituent groups denoted by $R^{14.3}$ as explained in the definitions section above in the description of "first substituent group(s)". In the above embodiments, $R^{14}$, $R^{14.1}$, $R^{14.2}$, and $R^{14.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14}$, $R^{14.1}$, $R^{14.2}$, and $R^{14.3}$, respectively.

In embodiments, when $R^{15}$ is substituted, $R^{15}$ is substituted with one or more first substituent groups denoted by $R^{15.1}$ as explained in the definitions section above in the description of "first substituent group(s)". In embodiments, when an $R^{15.1}$ substituent group is substituted, the $R^{15.1}$ substituent group is substituted with one or more second substituent groups denoted by $R^{15.2}$ as explained in the definitions section above in the description of "first substituent group(s)". In embodiments, when an $R^{15.2}$ substituent group is substituted, the $R^{15.2}$ substituent group is substituted with one or more third substituent groups denoted by $R^{15.3}$ as explained in the definitions section above in the description of "first substituent group(s)". In the above embodiments, $R^{15}$, $R^{15.1}$, $R^{15.2}$, and $R^{15.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15}$, $R^{15.1}$, $R^{15.2}$, and $R^{15.3}$, respectively.

In embodiments, when $R^{16}$ is substituted, $R^{16}$ is substituted with one or more first substituent groups denoted by $R^{16.1}$ as explained in the definitions section above in the description of "first substituent group(s)". In embodiments, when an $R^{16.1}$ substituent group is substituted, the $R^{16.1}$ substituent group is substituted with one or more second substituent groups denoted by $R^{16.2}$ as explained in the definitions section above in the description of "first substituent group(s)". In embodiments, when an $R^{16.2}$ substituent group is substituted, the $R^{16.2}$ substituent group is substituted with one or more third substituent groups denoted by $R^{16.3}$ as explained in the definitions section above in the description of "first substituent group(s)". In the above embodiments, $R^{16}$, $R^{16.1}$, $R^{16.2}$, and $R^{16.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16}$, $R^{16.1}$, $R^{16.2}$, and $R^{16.3}$, respectively.

In embodiments, when $R^{16A}$ is substituted, $R^{16A}$ is substituted with one or more first substituent groups denoted by $R^{16A.1}$ as explained in the definitions section above in the description of "first substituent group(s)". In embodiments, when an $R^{16A.1}$ substituent group is substituted, the $R^{16A.1}$ substituent group is substituted with one or more second substituent groups denoted by $R^{16A.2}$ as explained in the definitions section above in the description of "first substituent group(s)". In embodiments, when an $R^{16A.2}$ substituent group is substituted, the $R^{16A.2}$ substituent group is substituted with one or more third substituent groups denoted by $R^{16A.3}$ as explained in the definitions section above in the description of "first substituent group(s)". In the above embodiments, $R^{16A}$, $R^{16A.1}$, $R^{16A.2}$, and $R^{16A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16A}$, $R^{16A.1}$, $R^{16A.2}$ and $R^{16A.3}$, respectively.

In embodiments, when $R^{16B}$ is substituted, $R^{16B}$ is substituted with one or more first substituent groups denoted by $R^{16B.1}$ as explained in the definitions section above in the description of "first substituent group(s)". In embodiments, when an $R^{16B.1}$ substituent group is substituted, the $R^{16B.1}$ substituent group is substituted with one or more second substituent groups denoted by $R^{16B.2}$ as explained in the definitions section above in the description of "first substituent group(s)". In embodiments, when an $R^{16B.2}$ substituent group is substituted, the $R^{16B.2}$ substituent group is substituted with one or more third substituent groups denoted by $R^{16B.3}$ as explained in the definitions section above in the description of “first substituent group(s)”. In the above embodiments, $R^{16B}$, $R^{16B.1}$, $R^{16B.2}$, and $R^{16B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{16B}$, $R^{16B.1}$, $R^{16B.2}$, and $R^{16B.3}$, respectively.

In embodiments, when $R^{16A}$ and $R^{16B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{16A.1}$ as explained in the definitions section above in the description of “first substituent group(s)”. In embodiments, when an $R^{16A.1}$ substituent group is substituted, the $R^{16A.1}$ substituent group is substituted with one or more second substituent groups denoted by $R^{16A.2}$ as explained in the definitions section above in the description of “first substituent group(s)”. In embodiments, when an $R^{16A.2}$ substituent group is substituted, the $R^{16A.2}$ substituent group is substituted with one or more third substituent groups denoted by $R^{16A.3}$ as explained in the definitions section above in the description of “first substituent group(s)”. In the above embodiments, $R^{16A.1}$, $R^{16A.2}$, and $R^{16A.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{16A.1}$, $R^{16A.2}$ and $R^{16A.3}$, respectively.

In embodiments, when $R^{16A}$ and $R^{16B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{16B.1}$ as explained in the definitions section above in the description of “first substituent group(s)”. In embodiments, when an $R^{16B.1}$ substituent group is substituted, the $R^{16B.1}$ substituent group is substituted with one or more second substituent groups denoted by $R^{16B.2}$ as explained in the definitions section above in the description of “first substituent group(s)”. In embodiments, when an $R^{16B.2}$ substituent group is substituted, the $R^{16B.2}$ substituent group is substituted with one or more third substituent groups denoted by $R^{16B.3}$ as explained in the definitions section above in the description of “first substituent group(s)”. In the above embodiments, $R^{16B.1}$, $R^{16B.2}$, and $R^{16B.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{16B.1}$, $R^{16B.2}$, and $R^{16B.3}$ respectively.

In embodiments, when $R^{16C}$ is substituted, $R^{16C}$ is substituted with one or more first substituent groups denoted by $R^{16C.1}$ as explained in the definitions section above in the description of “first substituent group(s)”. In embodiments, when an $R^{16C.1}$ substituent group is substituted, the $R^{16C.1}$ substituent group is substituted with one or more second substituent groups denoted by $R^{16C.2}$ as explained in the definitions section above in the description of “first substituent group(s)”. In embodiments, when an $R^{16C.2}$ substituent group is substituted, the $R^{16C.2}$ substituent group is substituted with one or more third substituent groups denoted by $R^{16C.3}$ as explained in the definitions section above in the description of “first substituent group(s)”. In the above embodiments, $R^{16C}$, $R^{16C.1}$, $R^{16C.2}$, and $R^{16C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{16C}$, $R^{16C.1}$, $R^{16C.2}$, and $R^{16C.3}$, respectively.

In embodiments, when $R^{16D}$ is substituted, $R^{16D}$ is substituted with one or more first substituent groups denoted by $R^{16D.1}$ as explained in the definitions section above in the description of “first substituent group(s)”. In embodiments, when an $R^{16D.1}$ substituent group is substituted, the $R^{16D.1}$ substituent group is substituted with one or more second substituent groups denoted by $R^{16D.2}$ as explained in the definitions section above in the description of “first substituent group(s)”. In embodiments, when an $R^{16D.2}$ substituent group is substituted, the $R^{16D.2}$ substituent group is substituted with one or more third substituent groups denoted by $R^{16D.3}$ as explained in the definitions section above in the description of “first substituent group(s)”. In the above embodiments, $R^{16D}$, $R^{16D.1}$, $R^{16D.2}$, and $R^{16D.3}$ have values corresponding to the values of $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{16D}$, $R^{16D.1}$, $R^{16D.2}$ and $R^{16D.3}$ respectively.

In embodiments, when $R^{WW}$ is substituted, $R^{WW}$ is substituted with one or more first substituent groups denoted by $R^{17.1}$ as explained in the definitions section above in the description of “first substituent group(s)”. In embodiments, when an $R^{17.1}$ substituent group is substituted, the $R^{17.1}$ substituent group is substituted with one or more second substituent groups denoted by $R^{17.2}$ as explained in the definitions section above in the description of “first substituent group(s)”. In embodiments, when an $R^{17.2}$ substituent group is substituted, the $R^{17.2}$ substituent group is substituted with one or more third substituent groups denoted by $R^{17.3}$ as explained in the definitions section above in the description of “first substituent group(s)”. In the above embodiments, $R^{17}$, $R^{17.1}$, $R^{17.2}$, and $R^{17.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{17}$, $R^{17.1}$, $R^{17.2}$, and $R^{17.3}$, respectively.

In embodiments, when $R^{18}$ is substituted, $R^{18}$ is substituted with one or more first substituent groups denoted by $R^{18.1}$ as explained in the definitions section above in the description of “first substituent group(s)”. In embodiments, when an $R^{18.1}$ substituent group is substituted, the $R^{18.1}$ substituent group is substituted with one or more second substituent groups denoted by $R^{18.2}$ as explained in the definitions section above in the description of “first substituent group(s)”. In embodiments, when an $R^{18.2}$ substituent group is substituted, the $R^{18.2}$ substituent group is substituted with one or more third substituent groups denoted by $R^{18.3}$ as explained in the definitions section above in the description of “first substituent group(s)”. In the above embodiments, $R^{18}$, $R^{18.1}$, $R^{18.2}$, and $R^{18.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{18}$, $R^{18.1}$, $R^{18.2}$, and $R^{18.3}$, respectively.

In embodiments, when $R^{19}$ is substituted, $R^{19}$ is substituted with one or more first substituent groups denoted by $R^{19.1}$ as explained in the definitions section above in the description of “first substituent group(s)”. In embodiments, when an $R^{19.1}$ substituent group is substituted, the $R^{19.1}$ substituent group is substituted with one or more second substituent groups denoted by $R^{19.2}$ as explained in the definitions section above in the description of “first substituent group(s)". In embodiments, when an $R^{19.2}$ substituent group is substituted, the $R^{19.2}$ substituent group is substituted with one or more third substituent groups denoted by $R^{19}$ as explained in the definitions section above in the description of "first substituent group(s)". In the above embodiments, $R^{19}$, $R^{19.1}$, $R^{19.2}$, and $R^{19.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{19}$, $R^{19.1}$, $R^{19.2}$, and $R^{19.3}$, respectively.

In embodiments, when $R^{20}$ is substituted, $R^{20}$ is substituted with one or more first substituent groups denoted by $R^{20.1}$ as explained in the definitions section above in the description of "first substituent group(s)". In embodiments, when an $R^{20.1}$ substituent group is substituted, the $R^{20.1}$ substituent group is substituted with one or more second substituent groups denoted by $R^{20.2}$ as explained in the definitions section above in the description of "first substituent group(s)". In embodiments, when an $R^{20.2}$ substituent group is substituted, the $R^{20.2}$ substituent group is substituted with one or more third substituent groups denoted by $R^{20.3}$ as explained in the definitions section above in the description of "first substituent group(s)". In the above embodiments, $R^{20}$, $R^{20.1}$, $R^{20.2}$, and $R^{20.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20}$, $R^{20.1}$, $R^{20.2}$, and $R^{20.3}$, respectively.

In embodiments, when $R^{21}$ is substituted, $R^{21}$ is substituted with one or more first substituent groups denoted by $R^{21.1}$ as explained in the definitions section above in the description of "first substituent group(s)". In embodiments, when an $R^{21.1}$ substituent group is substituted, the $R^{21.1}$ substituent group is substituted with one or more second substituent groups denoted by $R^{21.2}$ as explained in the definitions section above in the description of "first substituent group(s)". In embodiments, when an $R^{21.2}$ substituent group is substituted, the $R^{21.2}$ substituent group is substituted with one or more third substituent groups denoted by $R^{21.3}$ as explained in the definitions section above in the description of "first substituent group(s)". In the above embodiments, $R^{21}$, $R^{21.1}$, $R^{21.2}$, and $R^{21.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21}$, $R^{21.1}$, $R^{21.2}$, and $R^{21.3}$, respectively.

In embodiments, when $R^{22}$ is substituted, $R^{22}$ is substituted with one or more first substituent groups denoted by $R^{22.1}$ as explained in the definitions section above in the description of "first substituent group(s)". In embodiments, when an $R^{22.1}$ substituent group is substituted, the $R^{22.1}$ substituent group is substituted with one or more second substituent groups denoted by $R^{22.2}$ as explained in the definitions section above in the description of "first substituent group(s)". In embodiments, when an $R^{22.2}$ substituent group is substituted, the $R^{22.2}$ substituent group is substituted with one or more third substituent groups denoted by $R^{22.3}$ as explained in the definitions section above in the description of "first substituent group(s)". In the above embodiments, $R^{22}$, $R^{22.1}$, $R^{22.2}$, and $R^{22.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22}$, $R^{22.1}$, $R^{22.2}$, and $R^{22.3}$, respectively.

In embodiments, when $R^{23}$ is substituted, $R^{23}$ is substituted with one or more first substituent groups denoted by $R^{23.1}$ as explained in the definitions section above in the description of "first substituent group(s)". In embodiments, when an $R^{23.1}$ substituent group is substituted, the $R^{23.1}$ substituent group is substituted with one or more second substituent groups denoted by $R^{23.2}$ as explained in the definitions section above in the description of "first substituent group(s)". In embodiments, when an $R^{23.2}$ substituent group is substituted, the $R^{23.2}$ substituent group is substituted with one or more third substituent groups denoted by $R^{23.3}$ as explained in the definitions section above in the description of "first substituent group(s)". In the above embodiments, $R^{23}$, $R^{23.1}$, $R^{23.2}$, and $R^{23.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23}$, $R^{23.1}$, $R^{23.2}$, and $R^{23.3}$, respectively.

In embodiments, when $R^{24}$ is substituted, $R^{24}$ is substituted with one or more first substituent groups denoted by $R^{24.1}$ as explained in the definitions section above in the description of "first substituent group(s)". In embodiments, when an $R^{24.1}$ substituent group is substituted, the $R^{24.1}$ substituent group is substituted with one or more second substituent groups denoted by $R^{24.2}$ as explained in the definitions section above in the description of "first substituent group(s)". In embodiments, when an $R^{24.2}$ substituent group is substituted, the $R^{24.2}$ substituent group is substituted with one or more third substituent groups denoted by $R^{24.3}$ as explained in the definitions section above in the description of "first substituent group(s)". In the above embodiments, $R^{24}$, $R^{24.1}$, $R^{24.2}$, and $R^{24.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{24}$, $R^{24.1}$, $R^{24.2}$, and $R^{24.3}$, respectively.

In embodiments, when $R^{25}$ is substituted, $R^{25}$ is substituted with one or more first substituent groups denoted by $R^{25.1}$ as explained in the definitions section above in the description of "first substituent group(s)". In embodiments, when an $R^{25.1}$ substituent group is substituted, the $R^{25.1}$ substituent group is substituted with one or more second substituent groups denoted by $R^{25.2}$ as explained in the definitions section above in the description of "first substituent group(s)". In embodiments, when an $R^{25.2}$ substituent group is substituted, the $R^{25.2}$ substituent group is substituted with one or more third substituent groups denoted by $R^{25.3}$ as explained in the definitions section above in the description of "first substituent group(s)". In the above embodiments, $R^{25}$, $R^{25.1}$, $R^{25.2}$, and $R^{25.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25}$, $R^{25.1}$, $R^{25.2}$, and $R^{25.3}$, respectively.

In embodiments, when $L^{2A}$ is substituted, $L^{2A}$ is substituted with one or more first substituent groups denoted by $R^{L2A.1}$ as explained in the definitions section above in the description of "first substituent group(s)". In embodiments, when an $R^{L2A.1}$ substituent group is substituted, the $R^{L2A.1}$ substituent group is substituted with one or more second substituent groups denoted by $R^{L2A.2}$ as explained in the definitions section above in the description of "first substituent group(s)". In embodiments, when an $R^{L2A.2}$ substituent group is substituted, the $R^{L2A.2}$ substituent group is substituted with one or more third substituent groups denoted by $R^{L2A.3}$ as explained in the definitions section above in the description of "first substituent group(s)". In the above embodiments, $L^{2A}$, $R^{L2A.1}$, $R^{L2A.2}$, and $R^{L2A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{2A}$, $R^{L2A.1}$, $R^{L2A.2}$ and $R^{L2A.3}$ respectively.

In embodiments, when $L^{2B}$ is substituted, $L^{2B}$ is substituted with one or more first substituent groups denoted by $R^{L2B.1}$ as explained in the definitions section above in the description of "first substituent group(s)". In embodiments, when an $R^{L2B.1}$ substituent group is substituted, the $R^{L2B.1}$ substituent group is substituted with one or more second substituent groups denoted by $R^{L2B.2}$ as explained in the definitions section above in the description of "first substituent group(s)". In embodiments, when an $R^{L2B.2}$ substituent group is substituted, the $R^{L2B.2}$ substituent group is substituted with one or more third substituent groups denoted by $R^{L2B.3}$ as explained in the definitions section above in the description of "first substituent group(s)". In the above embodiments, $L^{2B}$, $R^{L2B.1}$, $R^{L2B.2}$, and $R^{L2B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{2B}$, $R^{L2B.1}$, $R^{L2B.2}$, and $R^{L2B.3}$, respectively.

In embodiments, when $L^{2C}$ is substituted, $L^{2C}$ is substituted with one or more first substituent groups denoted by $R^{L2C.1}$ as explained in the definitions section above in the description of "first substituent group(s)". In embodiments, when an $R^{L2C.1}$ substituent group is substituted, the $R^{L2C.1}$ substituent group is substituted with one or more second substituent groups denoted by $R^{L2C.2}$ as explained in the definitions section above in the description of "first substituent group(s)". In embodiments, when an $R^{L2C.2}$ substituent group is substituted, the $R^{L2C.2}$ substituent group is substituted with one or more third substituent groups denoted by $R^{L2C.3}$ as explained in the definitions section above in the description of "first substituent group(s)". In the above embodiments, $L^{2C}$, $R^{L2C.1}$, $R^{L2C.2}$, and $R^{L2C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{2C}$, $R^{L2C.1}$, $R^{L2C.2}$, and $R^{L2C.3}$, respectively.

In embodiments, when $L^{2D}$ is substituted, $L^{2D}$ is substituted with one or more first substituent groups denoted by $R^{L2D.1}$ as explained in the definitions section above in the description of "first substituent group(s)". In embodiments, when an $R^{L2D.1}$ substituent group is substituted, the $R^{L2D.1}$ substituent group is substituted with one or more second substituent groups denoted by $R^{L2D.2}$ as explained in the definitions section above in the description of "first substituent group(s)". In embodiments, when an $R^{L2D.2}$ substituent group is substituted, the $R^{L2D.2}$ substituent group is substituted with one or more third substituent groups denoted by $R^{L2D.3}$ as explained in the definitions section above in the description of "first substituent group(s)". In the above embodiments, $L^{2D}$, $R^{L2D.1}$, $R^{L2D.2}$, and $R^{L2D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{2D}$, $R^{L2D.1}$, $R^{L2D.2}$, and $R^{L2D.3}$, respectively.

In embodiments, when $L^{2E}$ is substituted, $L^{2E}$ is substituted with one or more first substituent groups denoted by $R^{L2E.1}$ as explained in the definitions section above in the description of "first substituent group(s)". In embodiments, when an $R^{L2E.1}$ substituent group is substituted, the $R^{L2E.1}$ substituent group is substituted with one or more second substituent groups denoted by $R^{L2E.2}$ as explained in the definitions section above in the description of "first substituent group(s)". In embodiments, when an $R^{L2E.2}$ substituent group is substituted, the $R^{L2E.2}$ substituent group is substituted with one or more third substituent groups denoted by $R^{L2E.3}$ as explained in the definitions section above in the description of "first substituent group(s)". In the above embodiments, $L^{2E}$, $R^{L2E.1}$, $R^{L2E.2}$, and $R^{L2E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{2E}$, $R^{L2E.1}$, $R^{L2E.2}$, and $R^{L2E.3}$, respectively.

In embodiments, when $L^{4A}$ is substituted, $L^{4A}$ is substituted with one or more first substituent groups denoted by $R^{L4A.1}$ as explained in the definitions section above in the description of "first substituent group(s)". In embodiments, when an $R^{L4A.1}$ substituent group is substituted, the $R^{L4A.1}$ substituent group is substituted with one or more second substituent groups denoted by $R^{L4A.2}$ as explained in the definitions section above in the description of "first substituent group(s)". In embodiments, when an $R^{L4A.2}$ substituent group is substituted, the $R^{L4A.2}$ substituent group is substituted with one or more third substituent groups denoted by $R^{L4A.3}$ as explained in the definitions section above in the description of "first substituent group(s)". In the above embodiments, $L^{4A}$, $R^{L4A.1}$, $R^{L4A.2}$, and $R^{L4A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{4A}$, $R^{L4A.1}$, $R^{L4A.2}$, and $R^{L4A.3}$, respectively.

In embodiments, when $L^{4B}$ is substituted, $L^{4B}$ is substituted with one or more first substituent groups denoted by $R^{4LB.1}$ as explained in the definitions section above in the description of "first substituent group(s)". In embodiments, when an $R^{L4B.1}$ substituent group is substituted, the $R^{L4B.1}$ substituent group is substituted with one or more second substituent groups denoted by $R^{L4B.2}$ as explained in the definitions section above in the description of "first substituent group(s)". In embodiments, when an $R^{L4B.2}$ substituent group is substituted, the $R^{L4B.2}$ substituent group is substituted with one or more third substituent groups denoted by $R^{L4B.3}$ as explained in the definitions section above in the description of "first substituent group(s)". In the above embodiments, $L^{4B}$, $R^{L4B.1}$, $R^{L4B.2}$, and $R^{L4B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{4B}$, $R^{L4B.1}$, $R^{L4B.2}$, and $R^{L4B.3}$, respectively.

In embodiments, when $L^{4C}$ is substituted, $L^{4C}$ is substituted with one or more first substituent groups denoted by $R^{L4C.1}$ as explained in the definitions section above in the description of "first substituent group(s)". In embodiments, when an $R^{L4C.1}$ substituent group is substituted, the $R^{L4C.1}$ substituent group is substituted with one or more second substituent groups denoted by $R^{L4C.2}$ as explained in the definitions section above in the description of "first substituent group(s)". In embodiments, when an $R^{L4C.2}$ substituent group is substituted, the $R^{L4C.2}$ substituent group is substituted with one or more third substituent groups denoted by $R^{L4C.3}$ as explained in the definitions section above in the description of "first substituent group(s)". In the above embodiments, $L^{4C}$, $R^{L4C.1}$, $R^{L4C.2}$, and $R^{L4C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{4C}$, $R^{L4C.1}$, $R^{L4C.2}$, and $R^{L4C.3}$, respectively.

In embodiments, when $L^{4D}$ is substituted, $L^{4D}$ is substituted with one or more first substituent groups denoted by $R^{L4D.1}$ as explained in the definitions section above in the description of "first substituent group(s)". In embodiments, when an $R^{L4D.1}$ substituent group is substituted, the $R^{L4D.1}$ substituent group is substituted with one or more second substituent groups denoted by $R^{L4D.2}$ as explained in the definitions section above in the description of "first substituent group(s)". In embodiments, when an $R^{L4D.2}$ substituent group is substituted, the $R^{L4D.2}$ substituent group is substituted with one or more third substituent groups denoted by $R^{L4D.3}$ as explained in the definitions section above in the description of "first substituent group(s)". In the above embodiments, $L^{4D}$, $R^{L4D.1}$, $R^{L4D.2}$, and $R^{L4D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{4D}$, $R^{L4D.1}$, $R^{L4D.2}$, and $R^{L4D.3}$, respectively.

In embodiments, when $L^{4E}$ is substituted, $L^{4E}$ is substituted with one or more first substituent groups denoted by $R^{L4E.1}$ as explained in the definitions section above in the description of "first substituent group(s)". In embodiments, when an $R^{L4E.1}$ substituent group is substituted, the $R^{L4E.1}$ substituent group is substituted with one or more second substituent groups denoted by $R^{L4E.2}$ as explained in the definitions section above in the description of "first substituent group(s)". In embodiments, when an $R^{L4E.2}$ substituent group is substituted, the $R^{L4E.2}$ substituent group is substituted with one or more third substituent groups denoted by $R^{L4E.3}$ as explained in the definitions section above in the description of "first substituent group(s)". In the above embodiments, $L^{4E}$, $R^{L4E.1}$, $R^{L4E.2}$, and $R^{L4E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{4E}$, $R^{L4E.1}$, $R^{L4E.2}$, and $R^{L4E.3}$, respectively.

In embodiments, when $L^{9A}$ is substituted, $L^{9A}$ is substituted with one or more first substituent groups denoted by $R^{L9A.1}$ as explained in the definitions section above in the description of "first substituent group(s)". In embodiments, when an $R^{L9A.1}$ substituent group is substituted, the $R^{L9A.1}$ substituent group is substituted with one or more second substituent groups denoted by $R^{L9A.2}$ as explained in the definitions section above in the description of "first substituent group(s)". In embodiments, when an $R^{L9A.2}$ substituent group is substituted, the $R^{L9A.2}$ substituent group is substituted with one or more third substituent groups denoted by $R^{L9A.3}$ as explained in the definitions section above in the description of "first substituent group(s)". In the above embodiments, $L^{9A}$, $R^{L9A.1}$, $R^{L9A.2}$, and $R^{L9A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{9A}$, $R^{L9A.1}$, $R^{L9A.2}$ and $R^{L9A.3}$ respectively.

In embodiments, when $L^{9B}$ is substituted, $L^{9B}$ is substituted with one or more first substituent groups denoted by $R^{L9B.1}$ as explained in the definitions section above in the description of "first substituent group(s)". In embodiments, when an $R^{L9B.1}$ substituent group is substituted, the $R^{L9B.1}$ substituent group is substituted with one or more second substituent groups denoted by $R^{L9B.2}$ as explained in the definitions section above in the description of "first substituent group(s)". In embodiments, when an $R^{L9B.2}$ substituent group is substituted, the $R^{L9B.2}$ substituent group is substituted with one or more third substituent groups denoted by $R^{L9B.3}$ as explained in the definitions section above in the description of "first substituent group(s)". In the above embodiments, $L^{9B}$, $R^{L9B.1}$, $R^{L9B.2}$, and $R^{L9B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{9B}$, $R^{L9B.1}$, $R^{L9B.2}$, and $R^{L9B.3}$, respectively.

In embodiments, when $L^9C$ is substituted, $L^9C$ is substituted with one or more first substituent groups denoted by $R^{L9C.1}$ as explained in the definitions section above in the description of "first substituent group(s)". In embodiments, when an $R^{L9C.1}$ substituent group is substituted, the $R^{L9C.1}$ substituent group is substituted with one or more second substituent groups denoted by $R^{L9C.2}$ as explained in the definitions section above in the description of "first substituent group(s)". In embodiments, when an $R^{L9C.2}$ substituent group is substituted, the $R^{L9C.2}$ substituent group is substituted with one or more third substituent groups denoted by $R^{L9C.3}$ as explained in the definitions section above in the description of "first substituent group(s)". In the above embodiments, $L^9C$, $R^{L9C.1}$, $R^{L9C.2}$, and $R^{L9C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{9C}$, $R^{L9C.1}$, $R^{L9C.2}$, and $R^{L9C.3}$, respectively.

In embodiments, when $L^{9D}$ is substituted, $L^{9D}$ is substituted with one or more first substituent groups denoted by $R^{L9D.1}$ as explained in the definitions section above in the description of "first substituent group(s)". In embodiments, when an $R^{L9D.1}$ substituent group is substituted, the $R^{L9D.1}$ substituent group is substituted with one or more second substituent groups denoted by $R^{L9D.2}$ as explained in the definitions section above in the description of "first substituent group(s)". In embodiments, when an $R^{L9D.2}$ substituent group is substituted, the $R^{L9D.2}$ substituent group is substituted with one or more third substituent groups denoted by $R^{L9D.3}$ as explained in the definitions section above in the description of "first substituent group(s)". In the above embodiments, $L^{9D}$, $R^{L9D.1}$, $R^{L9D.2}$, and $R^{L9D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{9D}$, $R^{L9D.1}$, $R^{L9D.2}$, and $R^{L9D.3}$, respectively.

In embodiments, when $L^{9E}$ is substituted, $L^{9E}$ is substituted with one or more first substituent groups denoted by $R^{L9E.1}$ as explained in the definitions section above in the description of "first substituent group(s)". In embodiments, when an $R^{L9E.1}$ substituent group is substituted, the $R^{L9E.1}$ substituent group is substituted with one or more second substituent groups denoted by $R^{L9E.2}$ as explained in the definitions section above in the description of "first substituent group(s)". In embodiments, when an $R^{L9E.2}$ substituent group is substituted, the $R^{L9E.2}$ substituent group is substituted with one or more third substituent groups denoted by $R^{L9E.3}$ as explained in the definitions section above in the description of "first substituent group(s)". In the above embodiments, $L^{9E}$, $R^{L9E.1}$, $R^{L9E.2}$, and $R^{L9E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{9E}$, $R^{L9E.1}$, $R^{L9E.2}$, and $R^{L9E.3}$, respectively.

In embodiments, when $L^{11A}$ is substituted, $L^{11A}$ is substituted with one or more first substituent groups denoted by $R^{L11A.1}$ as explained in the definitions section above in the description of "first substituent group(s)". In embodiments, when an $R^{L11A.1}$ substituent group is substituted, the $R^{L11A.1}$ substituent group is substituted with one or more second substituent groups denoted by $R^{L11A.2}$ as explained in the definitions section above in the description of "first substituent group(s)". In embodiments, when an $R^{L11A.2}$ substituent group is substituted, the $R^{L11A.2}$ substituent group is substituted with one or more third substituent groups denoted by $R^{L11A.3}$ as explained in the definitions section above in the description of "first substituent group(s)". In the above embodiments, $L^{11A}$, $R^{L11A.1}$, $R^{L11A.2}$, and $R^{L11A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{11A}$, $R^{L11A.1}$, $R^{L11A.2}$ and $R^{L11A.3}$ respectively.

In embodiments, when $L^{11B}$ is substituted, $L^{11B}$ is substituted with one or more first substituent groups denoted by $R^{L11B.1}$ as explained in the definitions section above in the description of "first substituent group(s)". In embodiments, when an $R^{L11B.1}$ substituent group is substituted, the $R^{L11B.1}$ substituent group is substituted with one or more second substituent groups denoted by $R^{L11B.2}$ as explained in the definitions section above in the description of "first substituent group(s)". In embodiments, when an $R^{L11B.2}$ substituent group is substituted, the $R^{L11B.2}$ substituent group is substituted with one or more third substituent groups denoted by $R^{L11B.3}$ as explained in the definitions section above in the description of "first substituent group(s)". In the above embodiments, $L^{11B}$, $R^{L11B.1}$, $R^{L11B.2}$, and $R^{L11B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{11B}$, $R^{L11B.1}$, $R^{L11B.2}$, and $R^{L11B.3}$, respectively.

In embodiments, when $L^{11C}$ is substituted, $L^{11C}$ is substituted with one or more first substituent groups denoted by $R^{L11C.1}$ as explained in the definitions section above in the description of "first substituent group(s)". In embodiments, when an $R^{L11C.1}$ substituent group is substituted, the $R^{L11C.1}$ substituent group is substituted with one or more second substituent groups denoted by $R^{L11C.2}$ as explained in the definitions section above in the description of "first substituent group(s)". In embodiments, when an $R^{L11C.2}$ substituent group is substituted, the $R^{L11C.2}$ substituent group is substituted with one or more third substituent groups denoted by $R^{L11C.3}$ as explained in the definitions section above in the description of "first substituent group(s)". In the above embodiments, $L^{11C}$, $R^{L11C.1}$, $R^{L11C.2}$, and $R^{L11C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{L11.1}$, $R^{LWW.2}$, and $R^{LWW.3}$ are $L^{11C}$, $R^{L11C.1}$, $R^{L11C.2}$, and $R^{L11C.3}$, respectively.

In embodiments, when $L^{11D}$ is substituted, $L^{11D}$ is substituted with one or more first substituent groups denoted by $R^{L11D.1}$ as explained in the definitions section above in the description of "first substituent group(s)". In embodiments, when an $R^{L11D.1}$ substituent group is substituted, the $R^{L11D.1}$ substituent group is substituted with one or more second substituent groups denoted by $R^{L11D.2}$ as explained in the definitions section above in the description of "first substituent group(s)". In embodiments, when an $R^{L11D.2}$ substituent group is substituted, the $R^{L11D.2}$ substituent group is substituted with one or more third substituent groups denoted by $R^{L11D.3}$ as explained in the definitions section above in the description of "first substituent group(s)". In the above embodiments, $L^{11D}$, $R^{L11D.1}$, $R^{L11D.2}$, and $R^{L11D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{11D}$, $R^{L11D.1}$, $R^{L11D.2}$, and $R^{L11D.3}$, respectively.

In embodiments, when $L^{11E}$ is substituted, $L^{11E}$ is substituted with one or more first substituent groups denoted by $R^{L11E.1}$ as explained in the definitions section above in the description of "first substituent group(s)". In embodiments, when an $R^{L11E.1}$ substituent group is substituted, the $R^{L11E.1}$ substituent group is substituted with one or more second substituent groups denoted by $R^{L11E.2}$ as explained in the definitions section above in the description of "first substituent group(s)". In embodiments, when an $R^{L11E.2}$ substituent group is substituted, the $R^{L11E.2}$ substituent group is substituted with one or more third substituent groups denoted by $R^{L11E.3}$ as explained in the definitions section above in the description of "first substituent group(s)". In the above embodiments, $L^{11E}$, $R^{L11E.1}$, $R^{L11E.2}$, and $R^{L11E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{11E}$, $R^{L11E.1}$, $R^{L11E.2}$, and $R^{L11E.3}$, respectively.

In embodiments, when $L^{12A}$ is substituted, $L^{12A}$ is substituted with one or more first substituent groups denoted by $R^{L12A.1}$ as explained in the definitions section above in the description of "first substituent group(s)". In embodiments, when an $R^{L12A.1}$ substituent group is substituted, the $R^{L12A.1}$ substituent group is substituted with one or more second substituent groups denoted by $R^{L12A.2}$ as explained in the definitions section above in the description of "first substituent group(s)". In embodiments, when an $R^{L12A.2}$ substituent group is substituted, the $R^{L12A.2}$ substituent group is substituted with one or more third substituent groups denoted by $R^{L12A.3}$ as explained in the definitions section above in the description of "first substituent group(s)". In the above embodiments, $L^{12A}$, $R^{L12A.1}$, $R^{L12A.2}$, and $R^{L12A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{12A}$, $R^{L12A.1}$, $R^{L12A.2}$ and $R^{L12A.3}$ respectively.

In embodiments, when $L^{12B}$ is substituted, $L^{12B}$ is substituted with one or more first substituent groups denoted by $R^{L12B.1}$ as explained in the definitions section above in the description of "first substituent group(s)". In embodiments, when an $R^{L12B.1}$ substituent group is substituted, the $R^{L12B.1}$ substituent group is substituted with one or more second substituent groups denoted by $R^{L12B.2}$ as explained in the definitions section above in the description of "first substituent group(s)". In embodiments, when an $R^{L12B.2}$ substituent group is substituted, the $R^{L12B.2}$ substituent group is substituted with one or more third substituent groups denoted by $R^{L12B.3}$ as explained in the definitions section above in the description of "first substituent group(s)". In the above embodiments, $L^{12B}$, $R^{L12B.1}$, $R^{L12B.2}$, and $R^{L12B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{L11.1}$, $R^{LWW.2}$, and $R^{LWW.3}$ are $L^{12B}$, $R^{L12B.1}$, $R^{L12B.2}$, and $R^{L12B.3}$, respectively.

In embodiments, when $L^{12}C$ is substituted, $L^{12}C$ is substituted with one or more first substituent groups denoted by $R^{L12C.1}$ as explained in the definitions section above in the description of "first substituent group(s)". In embodiments, when an $R^{L12C.1}$ substituent group is substituted, the $R^{L12C.1}$ substituent group is substituted with one or more second substituent groups denoted by $R^{L12C.2}$ as explained in the definitions section above in the description of "first substituent group(s)". In embodiments, when an $R^{L12C.2}$ substituent group is substituted, the $R^{L12C.2}$ substituent group is substituted with one or more third substituent groups denoted by $R^{L12C.3}$ as explained in the definitions section above in the description of "first substituent group(s)". In the above embodiments, $L^{12C}$, $R^{L12C.1}$, $R^{L12C.2}$, and $R^{L12C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{L11.1}$, $R^{LWW.2}$, and $R^{LWW.3}$ are $L^{12C}$, $R^{L12C.1}$, $R^{L12C.2}$, and $R^{L12C.3}$, respectively.

In embodiments, when $L^{12D}$ is substituted, $L^{12D}$ is substituted with one or more first substituent groups denoted by $R^{L12D.1}$ as explained in the definitions section above in the description of "first substituent group(s)". In embodiments, when an $R^{L12D.1}$ substituent group is substituted, the $R^{L12D.1}$ substituent group is substituted with one or more second substituent groups denoted by $R^{L12D.2}$ as explained in the definitions section above in the description of "first substituent group(s)". In embodiments, when an $R^{L12D.2}$ substituent group is substituted, the $R^{L12D.2}$ substituent group is substituted with one or more third substituent groups denoted by $R^{L12D.3}$ as explained in the definitions section above in the description of "first substituent group(s)". In the above embodiments, $L^{12D}$, $R^{L12D.1}$, $R^{L12D.2}$, and $R^{L12D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{12D}$, $R^{L12D.1}$, $R^{L12D.2}$, and $R^{L12D.3}$, respectively.

In embodiments, when $L^{12E}$ is substituted, $L^{12E}$ is substituted with one or more first substituent groups denoted by $R^{L12E.1}$ as explained in the definitions section above in the description of "first substituent group(s)". In embodiments, when an $R^{L12E.1}$ substituent group is substituted, the $R^{L12E.1}$ substituent group is substituted with one or more second substituent groups denoted by $R^{L12E.2}$ as explained in the definitions section above in the description of "first substituent group(s)". In embodiments, when an $R^{L12E.2}$ substituent group is substituted, the $R^{L12E.2}$ substituent group is substituted with one or more third substituent groups denoted by $R^{L12E.3}$ as explained in the definitions section above in the description of "first substituent group(s)". In the above embodiments, $L^{12E}$, $R^{L12E.1}$, $R^{L12E.2}$, and $R^{L12E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{12E}$, $R^{L12E.1}$, $R^{L12E.2}$, and $R^{L12E.3}$, respectively.

In embodiments, when $L^{13A}$ is substituted, $L^{13A}$ is substituted with one or more first substituent groups denoted by $R^{L13A.1}$ as explained in the definitions section above in the description of "first substituent group(s)". In embodiments, when an $R^{L13A.1}$ substituent group is substituted, the $R^{L13A.1}$ substituent group is substituted with one or more second substituent groups denoted by $R^{L13A.2}$ as explained in the definitions section above in the description of "first substituent group(s)". In embodiments, when an $R^{L13A.2}$ substituent group is substituted, the $R^{L13A.2}$ substituent group is substituted with one or more third substituent groups denoted by $R^{L13A.3}$ as explained in the definitions section above in the description of "first substituent group(s)". In the above embodiments, $L^{13A}$, $R^{L13A.1}$, $R^{L13A.2}$, and $R^{L13A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{13A}$, $R^{L13A.1}$, $R^{L13A.2}$, and $R^{L13A.3}$ respectively.

In embodiments, when $L^{13B}$ is substituted, $L^{13B}$ is substituted with one or more first substituent groups denoted by $R^{L13B.1}$ as explained in the definitions section above in the description of "first substituent group(s)". In embodiments, when an $R^{L13B.1}$ substituent group is substituted, the $R^{L13B.1}$ substituent group is substituted with one or more second substituent groups denoted by $R^{L13B.2}$ as explained in the definitions section above in the description of "first substituent group(s)". In embodiments, when an $R^{L13B.2}$ substituent group is substituted, the $R^{L13B.2}$ substituent group is substituted with one or more third substituent groups denoted by $R^{L13B.3}$ as explained in the definitions section above in the description of "first substituent group(s)". In the above embodiments, $L^{13B}$, $R^{L13B.1}$, $R^{L13B.2}$, and $R^{L13B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{13B}$, $R^{L13B.1}$, $R^{L13B.2}$, and $R^{L13B.3}$, respectively.

In embodiments, when $L^{13}C$ is substituted, $L^{13}C$ is substituted with one or more first substituent groups denoted by $R^{L13C.1}$ as explained in the definitions section above in the description of "first substituent group(s)". In embodiments, when an $R^{L13C.1}$ substituent group is substituted, the $R^{L13C.1}$ substituent group is substituted with one or more second substituent groups denoted by $R^{L13C.2}$ as explained in the definitions section above in the description of "first substituent group(s)". In embodiments, when an $R^{L13C.2}$ substituent group is substituted, the $R^{L13C.2}$ substituent group is substituted with one or more third substituent groups denoted by $R^{L13C.3}$ as explained in the definitions section above in the description of "first substituent group(s)". In the above embodiments, $L^{13C}$, $R^{L13C.1}$, $R^{L13C.2}$, and $R^{L13C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{13}C$, $R^{L13C.1}$, $R^{L13C.2}$, and $R^{L13C.3}$, respectively.

In embodiments, when $L^{13D}$ is substituted, $L^{13D}$ is substituted with one or more first substituent groups denoted by $R^{L13D.1}$ as explained in the definitions section above in the description of "first substituent group(s)". In embodiments, when an $R^{L13D.1}$ substituent group is substituted, the $R^{L13D.1}$ substituent group is substituted with one or more second substituent groups denoted by $R^{L13D.2}$ as explained in the definitions section above in the description of "first substituent group(s)". In embodiments, when an $R^{L13D.2}$ substituent group is substituted, the $R^{L13D.2}$ substituent group is substituted with one or more third substituent groups denoted by $R^{L13D.3}$ as explained in the definitions section above in the description of "first substituent group(s)". In the above embodiments, $L^{13D}$, $R^{L13D.1}$, $R^{L13D.2}$, and $R^{L13D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{13D}$, $R^{L13D.1}$, $R^{L13D.2}$, and $R^{L13D.3}$, respectively.

In embodiments, when $L^{13E}$ is substituted, $L^{13E}$ is substituted with one or more first substituent groups denoted by $R^{L13E.1}$ as explained in the definitions section above in the description of "first substituent group(s)". In embodiments, when an $R^{L13E.1}$ substituent group is substituted, the $R^{L13E.1}$ substituent group is substituted with one or more second substituent groups denoted by $R^{L13E.2}$ as explained in the definitions section above in the description of "first substituent group(s)". In embodiments, when an $R^{L13E.2}$ substituent group is substituted, the $R^{L13E.2}$ substituent group is substituted with one or more third substituent groups denoted by $R^{L13E.3}$ as explained in the definitions section above in the description of "first substituent group(s)". In the above embodiments, $L^{13E}$, $R^{L13E.1}$, $R^{L13E.2}$, and $R^{L13E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{13E}$, $R^{L13E.1}$, $R^{L13E.2}$, and $R^{L13E.3}$, respectively.

In embodiments, when $L^{16A}$ is substituted, $L^{16A}$ is substituted with one or more first substituent groups denoted by $R^{L16A.1}$ as explained in the definitions section above in the description of "first substituent group(s)". In embodiments, when an $R^{L16A.1}$ substituent group is substituted, the $R^{L16A.1}$ substituent group is substituted with one or more second substituent groups denoted by $R^{L16A.2}$ as explained in the definitions section above in the description of "first substituent group(s)". In embodiments, when an $R^{L16A.2}$ substituent group is substituted, the $R^{L16A.2}$ substituent group is substituted with one or more third substituent groups denoted by $R^{L16A.3}$ as explained in the definitions section above in the description of "first substituent group(s)". In the above embodiments, $L^{16A}$, $R^{L16A.1}$, $R^{L16A.2}$, and $R^{L16A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$ and $R^{LWW.3}$ are $L^{16A}$, $R^{L16A.1}$, $R^{L16A.2}$ and $R^{L16A.3}$ respectively.

In embodiments, when $L^{6B}$ is substituted, $L^{16B}$ is substituted with one or more first substituent groups denoted by $R^{L16B.1}$ as explained in the definitions section above in the description of "first substituent group(s)". In embodiments, when an $R^{L16B.1}$ substituent group is substituted, the $R^{L16B.1}$ substituent group is substituted with one or more second substituent groups denoted by $R^{L16B.2}$ as explained in the definitions section above in the description of "first substituent group(s)". In embodiments, when an $R^{L16B.2}$ substituent group is substituted, the $R^{L16B.2}$ substituent group is substituted with one or more third substituent groups denoted by $R^{L16B.3}$ as explained in the definitions section above in the description of "first substituent group(s)". In the above embodiments, $L^{16B}$, $R^{L16B.1}$, $R^{L16B.2}$, and $R^{L16B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{L11.1}$, $R^{LWW.2}$, and $R^{LWW.3}$ are $L^{16B}$, $R^{L16B.1}$, $R^{L16B.2}$, and $R^{L16B.3}$, respectively.

In embodiments, when $L^{16C}$ is substituted, $L^{16C}$ is substituted with one or more first substituent groups denoted by $R^{L16C.1}$ as explained in the definitions section above in the description of "first substituent group(s)". In embodiments, when an $R^{L16C.1}$ substituent group is substituted, the $R^{L16C.1}$ substituent group is substituted with one or more second substituent groups denoted by $R^{L16C.2}$ as explained in the definitions section above in the description of "first substituent group(s)". In embodiments, when an $R^{L16C.2}$ substituent group is substituted, the $R^{L16C.2}$ substituent group is substituted with one or more third substituent groups denoted by $R^{L16C.3}$ as explained in the definitions section above in the description of "first substituent group(s)". In the above embodiments, $L^{16C}$, $R^{L16C.1}$, $R^{L16C.2}$, and $R^{L16C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{L11.1}$, $R^{LWW.2}$, and $R^{LWW.3}$ are $L^{16C}$, $R^{L16C.1}$, $R^{L16C.2}$, and $R^{L16C.3}$, respectively.

In embodiments, when $L^{16D}$ is substituted, $L^{16D}$ is substituted with one or more first substituent groups denoted by $R^{L16D.1}$ as explained in the definitions section above in the description of "first substituent group(s)". In embodiments, when an $R^{L16D.1}$ substituent group is substituted, the $R^{L16D.1}$ substituent group is substituted with one or more second substituent groups denoted by $R^{L16D.2}$ as explained in the definitions section above in the description of "first substituent group(s)". In embodiments, when an $R^{L16D.2}$ substituent group is substituted, the $R^{L16D.2}$ substituent group is substituted with one or more third substituent groups denoted by $R^{L16D.3}$ as explained in the definitions section above in the description of "first substituent group(s)". In the above embodiments, $L^{16D}$, $R^{L16D.1}$, $R^{L16D.2}$, and $R^{L16D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{16D}$, $R^{L16D.1}$, $R^{L16D.2}$, and $R^{L16D.3}$, respectively.

In embodiments, when $L^{16E}$ is substituted, $L^{16E}$ is substituted with one or more first substituent groups denoted by $R^{L16E.1}$ as explained in the definitions section above in the description of "first substituent group(s)". In embodiments, when an $R^{L16E.1}$ substituent group is substituted, the $R^{L16E.1}$ substituent group is substituted with one or more second substituent groups denoted by $R^{L16E.2}$ as explained in the definitions section above in the description of "first substituent group(s)". In embodiments, when an $R^{L16E.2}$ substituent group is substituted, the $R^{L16E.2}$ substituent group is substituted with one or more third substituent groups denoted by $R^{L16E.3}$ as explained in the definitions section above in the description of "first substituent group(s)". In the above embodiments, $L^{16E}$, $R^{L16E.1}$, $R^{L16E.2}$, and $R^{L16E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{16E}$, $R^{L16E.1}$, $R^{L16E.2}$, and $R^{L16E.3}$, respectively.

Embodiments

Embodiment 1. A method of sequencing target polynucleotides, the method comprising:

(a) contacting a polymer scaffold with a sample comprising target polynucleotides, wherein the polymer scaffold comprises a polymer covalently attached to polynucleotide primers;

(b) amplifying the target polynucleotides to produce discrete amplicon clusters, wherein (i) amplifying comprises extension of the primers along the target polynucleotides within the polymer scaffold, (ii) each amplicon cluster originates from amplification of a single target polynucleotide, and (iii) the amplicon clusters are arranged in multiple two-dimensional planes; and (c) sequencing the amplicon clusters, wherein sequencing comprises detecting sequences of signals within the polymer scaffold through each of the plurality of two-dimensional planes.

Embodiment 2. The method of embodiment 1, wherein the target polynucleotides are at a concentration in the sample selected to produce amplicon clusters having a desired density.

Embodiment 3. The method of embodiment 1 or 2, wherein the amplicon clusters have a mean or median separation from one another of about 500-5000 nm.

Embodiment 4. The method of any one of embodiments 1-3, wherein the amplicon clusters have a mean or median diameter of about 100-2000 nm, or about 200-1000 nm.

Embodiment 5. The method of any one of embodiments 1-4, wherein the contacting of step (a) is performed under non-hybridizing conditions.

Embodiment 6. The method of any one of embodiments 1-5, wherein the scaffold polymer comprises a plurality of cores surrounded by a shell polymer, wherein:

(a) each core of the plurality of cores is surrounded by the shell polymer;

(b) the core is formed by polymerized units of core monomers forming a core polymer;

(c) a core polynucleotide primer is attached to the core polymer within the core;

(d) a target nucleic acid is hybridized to the core primer;

(e) the shell polymer is formed by polymerized units of shell monomers; and (f) the shell polymer is not attached to a polynucleotide primer.

Embodiment 7. The method of embodiments 1-6, wherein the scaffold polymer comprises water, and optionally wherein the scaffold polymer has a refractive index of about 1.3 when hydrated.

Embodiment 8. The method of any one of embodiments 1-7, wherein the scaffold polymer is a hydrogel.

Embodiment 9. The method of any one of embodiments 1-8, wherein step (b) further comprises contacting the polymer scaffold with one or more reagents for amplifying the target polynucleotides.

Embodiment 10. The method of any one of embodiments 1-9, wherein the sequencing of step (c) comprises (i) extending a sequencing primer to incorporate a detectable label that indicates the identity of a nucleotide in the target polynucleotide, (ii) detecting the detectable label, and (iii) repeating the extending and detecting of steps (i) and (ii).

Embodiment 11. The method of any one of embodiments 1-10, wherein the detecting comprises imaging through each of the multiple two-dimensional planes at a resolution sufficient to distinguish one imaged plane from an adjacent imaged plane.

Embodiment 12. The method of embodiment 11, wherein the imaging comprises confocal microscopy, light sheet fluorescence microscopy (LSFM), or multi-photon microscopy.

Embodiment 13. The method of any one of embodiments 1-12, wherein the polymer scaffold is formed by a process comprising:

(a) forming an emulsion of oil droplets in a hydrophilic continuous phase, wherein the hydrophilic continuous phase comprises a plurality of monomers;

(b) polymerizing the plurality of monomers to form the polymer scaffold; and (c) removing the oil to form a plurality of interconnected pores in the polymer scaffold.

Embodiment 14. The method of any one of embodiments 1-13, wherein the polymer scaffold is formed by a process comprising functionalizing the polymer scaffold with a plurality of first reactive groups, and contacting the functionalized polymer scaffold with polynucleotide primers comprising a second reactive group, wherein the first reactive group and second reactive group react to form a covalent bond.

Embodiment 15. A composition comprising a plurality of cores surrounded by a shell polymer, wherein:

(a) each core of the plurality of cores is surrounded by the shell polymer;

(b) the core is formed by polymerized units of core monomers forming a core polymer;

(c) a core polynucleotide primer is attached to the core polymer within the core;

(d) a target nucleic acid is hybridized to the core primer;

(e) the shell polymer is formed by polymerized units of shell monomers; and (f) the shell polymer is not attached to a polynucleotide primer.

Embodiment 16. The composition of embodiment 15, wherein the plurality of cores are arranged in a two-dimension array.

Embodiment 17. The composition of embodiment 15, wherein the plurality of cores are arranged in multiple two-dimensional planes.

Embodiment 18. The composition of embodiment 17, wherein the plurality of cores are uniformly arranged.

Embodiment 19. The composition of embodiment 18, wherein the plurality of cores surrounded by the shell polymer form a plurality of discrete particles, and the plurality of discrete particles exhibit a filled-space fraction of at least 70%.

Embodiment 20. The composition of embodiment 17, wherein the plurality of cores are not uniformly arranged.

Embodiment 21. The composition of any one of embodiments 17-20, wherein the plurality of cores are contained in a channel of a substrate.

Embodiment 22. The composition of embodiment 21, wherein the channel has a width of about 3-5 mm, a length of about 5-10 cm, and a depth of about 50-200 μm.

Embodiment 23. The composition of embodiment 21 or 22, wherein the composition (i) fills the channel, or (ii) forms a layer within the channel over which a sample fluid can flow.

Embodiment 24. The composition of any one of embodiments 15-23, further comprising a solvent.

Embodiment 25. The composition of embodiment 24, wherein presence of the solvent expands the volume of the composition by up to 90% relative to the absence of the solvent.

Embodiment 26, The composition of any one of embodiments 15-25, wherein the plurality of cores, the shell polymer, or both comprise water.

Embodiment 27. The composition of embodiment 26, wherein the core polymer, the shell polymer, or both have a refractive index of about 1.3 when hydrated.

Embodiment 28. The composition of any one of embodiments 15-27, wherein at least some core monomers are the same as at least some of the shell monomers.

Embodiment 29. The composition of any one of embodiments 15-28, wherein the core polymer, the shell polymer, or both are a hydrogel.

Embodiment 30. The composition of any one of embodiments 15-29, wherein each core has a core diameter, the shell polymer surrounding each core has a thickness defining an outer shell diameter, and the core diameter is (i) about 20% to about 80% of the outer shell diameter, or (ii) about 50% of the shell diameter.

Embodiment 31. The composition of any one of embodiments 15-30, wherein each core has a core diameter, wherein the shell polymer surrounding each core has a thickness defining an outer shell diameter, and further wherein: (i) the core diameter is about 200-1200 nm, and/or (ii) the shell diameter is about 0.25-5 μm.

Embodiment 32. The composition of any one of embodiments 15-31, wherein the core polynucleotide primer is covalently attached to the core polymer.

Embodiment 33. The composition of any one of embodiments 15-32, wherein each core comprises multiple copies of the core polynucleotide primer, and about 5-10% of the core monomers in the core polymer of each core are attached to a copy of the core polynucleotide primer.

Embodiment 34. The composition of any one of embodiments 15-33, wherein the core polymer and shell polymer are permeable to a polymerase for amplifying the target polynucleotide.

Embodiment 35. The composition of embodiment 34, wherein the shell polymer has a higher permeability than the core polymer.

Embodiment 36. The composition of any one of embodiments 15-35, wherein each core contains one or more reagents for amplifying the target polynucleotide.

Embodiment 37. The composition of any one of embodiments 15-36, wherein each core further comprises a detectable label that indicates the identity of a nucleotide in the target polynucleotide.

Embodiment 38. The composition of any one of embodiments 15-37, wherein each core further comprises a silica, magnetic, or paramagnetic bead.

Embodiment 39. A method of amplifying a target polynucleotide, the method comprising:

(a) contacting a composition comprising a plurality of cores with a sample comprising a target polynucleotide, wherein (i) each core of the plurality of cores is surrounded by a shell polymer, (ii) the core is formed by polymerized units of core monomers forming a core polymer, (iii) a core polynucleotide primer is attached to the core polymer within the core, (iv) the shell polymer is formed by polymerized units of shell monomers, and (v) the shell polymer is not attached to a polynucleotide primer;

(b) amplifying the target polynucleotide to produce an amplicon, wherein amplifying comprises extension of the core primer hybridized to the target polynucleotide within the core.

Embodiment 40. The method of embodiment 39, further comprising: (c) sequencing the amplicon, wherein sequencing comprises detecting a sequence of signals within the core.

Embodiment 41. The method of embodiment 39 or 40, wherein the plurality of cores are arranged in a two-dimension array.

Embodiment 42. The method of embodiment 41, wherein the cores are arranged in the two-dimensional array after the amplifying of step (b).

Embodiment 43. The method of embodiment 39 or 40, wherein the plurality of cores are arranged in multiple two-dimensional planes.

Embodiment 44. The method of embodiment 43, wherein the plurality of cores are uniformly arranged.

Embodiment 45. The method of embodiment 44, wherein the plurality of cores surrounded by the shell polymer form a plurality of discrete particles, and the plurality of discrete particles exhibit a filled-space fraction of at least 70%.

Embodiment 46. The method of embodiment 43, wherein the plurality of cores are not uniformly arranged.

Embodiment 47. The method of any one of embodiments 41-46, wherein the cores are arranged after the amplifying of step (b).

Embodiment 48. The method of any one of embodiments 41-47, wherein a plurality of the shells are crosslinked to each other and/or to a surface of a container that contains the plurality of cores.

Embodiment 49. The method of any one of embodiments 43-48, wherein the plurality of cores are contained in a channel of a substrate.

Embodiment 50. The method of embodiment 49, wherein the channel has a width of about 3-5 mm, a length of about 5-10 cm, and a depth of about 50-200 μm.

Embodiment 51. The method of embodiment 49 or 50, wherein the composition comprising the plurality of cores (i) fills the channel, or (ii) forms a layer within the channel over which a sample fluid can flow.

Embodiment 52. The method of any one of embodiments 39-51, wherein the composition comprising the plurality of cores further comprises a solvent.

Embodiment 53. The method of embodiment 52, wherein presence of the solvent expands the volume of the composition by up to 90% relative to the absence of the solvent.

Embodiment 54. The method of any one of embodiments 39-53, wherein the plurality of cores, the shell polymer, or both comprise water.

Embodiment 55. The method of any one of embodiments 39-54, wherein the core polymer, the shell polymer, or both have a refractive index of about 1.3 when hydrated.

Embodiment 56. The method of any one of embodiments 39-55, wherein at least one of the core monomers and at least one of the the shell monomers are the same.

Embodiment 57. The method of any one of embodiments 39-56, wherein the core polymer, the shell polymer, or both are a hydrogel.

Embodiment 58. The method of any one of embodiments 39-57, wherein each core has a core diameter, the shell polymer surrounding each core has a thickness defining a shell diameter, and the core diameter is (i) about 20% to about 80% of the shell diameter, or (ii) about 50% of the shell diameter.

Embodiment 59. The method of any one of embodiments 39-58, wherein each core has a core diameter, wherein the shell polymer surrounding each core has a thickness defining a shell diameter, and further wherein: (i) the core diameter is about 200-1200 nm, and/or (ii) the shell diameter is about 0.25-5 μm.

Embodiment 60. The method of any one of embodiments 39-59, wherein each core comprises multiple copies of the core polynucleotide primer, and about 5-10% of the core monomers in the core polymer of each core are attached to a copy of the core polynucleotide primer.

Embodiment 61. The method of any one of embodiments 39-60, wherein the core polymer and shell polymer are permeable to a polymerase for amplifying the target polynucleotide.

Embodiment 62. The method of any one of embodiments 39-61, wherein the shell polymer has a higher permeability than the core polymer.

Embodiment 63. The method of any one of embodiments 39-62, wherein the contacting of step (a) is performed under non-hybridizing conditions.

Embodiment 64. The method of any one of embodiments 39-63, wherein step (b) further comprises contacting the plurality of cores with one or more reagents for amplifying the target polynucleotide.

Embodiment 65. The method of any one of embodiments 39-64, wherein the sample comprises a plurality of target polynucleotides at a concentration selected such that a majority of the cores in which the amplification occurs comprise amplicons of only one original target polynucleotide.

Embodiment 66. The method of embodiment 65, further comprising the step of separating cores comprising amplicons from cores not comprising amplicons.

Embodiment 67. The method of embodiment 66, further comprising repeating the contacting and amplifying steps using the separated cores not comprising an amplicon.

Embodiment 68. The method of any one of embodiments 40-67, wherein the sequencing of step (c) comprises (i) extending a sequencing primer to incorporate a detectable label that indicates the identity of a nucleotide in the target polynucleotide, (ii) detecting the detectable label, and (iii) repeating the extending and detecting of steps (i) and (ii).

Embodiment 69. The method of any one of embodiments 40 or 43-68, wherein the detecting of step (c) comprises imaging through each of the multiple two-dimensional planes at a resolution sufficient to distinguish one imaged plane from an adjacent imaged plane.

Embodiment 70. The method of embodiment 69, wherein the imaging comprises confocal microscopy, light sheet fluorescence microscopy (LSFM), or multi-photon microscopy.

Embodiment 71. The method of any one of embodiments 40-70, wherein (i) the amplifying of step (b) comprises amplifying a target polynucleotide in two or more cores in the plurality of particles, and (ii) the sequencing of step (c) comprises sequencing an amplicon in two or more cores in the plurality of particles.

Embodiment 72. The method of any one of embodiments 39-71, wherein each of the plurality of cores comprises a silica, magnetic, or paramagnetic bead.

Embodiment 73. A polymer comprising a subunit having the formula:

(Ia)

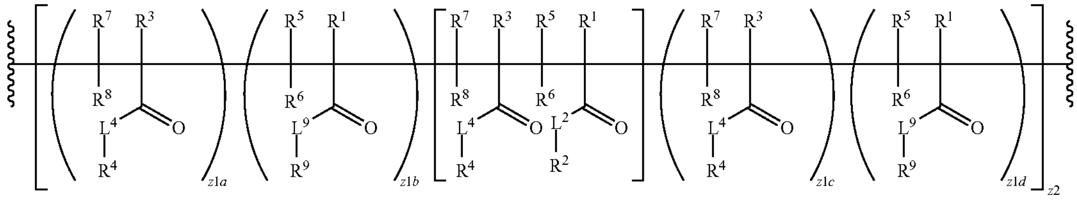

or (Ib)

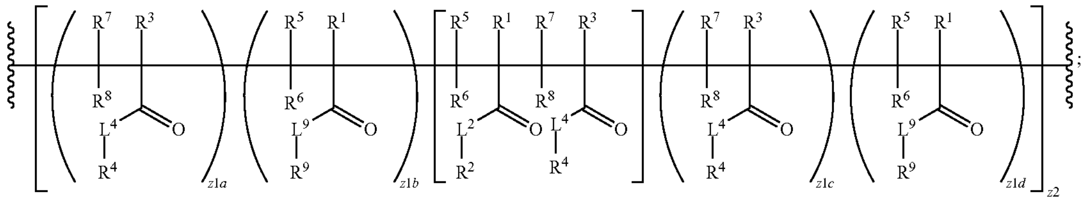

;

wherein, $R^1$, $R^3$, $R^5$, $R^6$, $R^7$, and $R^8$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^2$ is independently $-L^{2A}-L^{2B}-L^{2C}-L^{2D}-L^{2E}-$.

$L^{2A}$, $L^{2B}$, $L^{2C}$, $L^{2D}$, and $L^{2E}$ are independently a bond, $—S(O)_2—$, —S(O)—, $—S(O)_2NH—$, —NH—, —O—, —S—, —SS—, —C(O)—, —C(O)NH—, $—C(O)CH_2—$, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene;

$R^2$ is independently an oligonucleotide moiety;

z1a, z1b, z1c, and z1d are each independently an integer from 0 to 5000;

$L^4$ is independently $-L^{4A}-L^{4B}-L^{4C}-L^{4D}-L^{4E}-$;

$L^{4A}$ $L^{4B}$ $L^{4C}$, $L^{4D}$, and $L^{4E}$ are independently a bond, $—S(O)_2—$, —S(O)—, $—S(O)_2NH—$, —NH—, —O—, —S—, —C(O)—, —C(O)NH—, $—C(O)CH_2—$, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_4NR^{4A}R^{4B}$, $NHC(O)NR^{4A}R^{4B}$, $N(O)_{m4}$, $—NR^{4A}R^{4B}$, $C(O)R^{4C}$, $—C(O)—OR^{4C}$, $—C(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—OC(O)R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein $R^4$ is a first non-reactive moiety;

$R^{4A}$, $R^{4B}$, $R^{4C}$, and $R^{4D}$ are independently hydrogen, $—CX_3$, —CN, —COOH, $—CONH_2$, $—CHX_2$, $—CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protecting group, or a leaving group; $R^{4A}$ and $R^{4B}$ substituents bonded to the same nitrogen atom may optionally be joined to form a substituted or unsubstituted heterocycloalkyl or substituted or unsubstituted heteroaryl;

$L^9$ is independently $-L^{9A}-L^{9B}-L^{9C}-L^{9D}-L^{9E}-$.

$L^{9A}$, $L^{9B}$, $L^{9C}$, $L^{9D}$, and $L^{9E}$ are independently a bond, $—S(O)_2—$, —S(O)—, $—S(O)_2NH—$, —NH—, —O—, —S—, —SS—, —C(O)—, —C(O)NH—, $—C(O)CH_2—$, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^9$ is independently an oligonucleotide or a second non-reactive moiety;

z2 is independently an integer from 1 to 5000;

X and $X^4$ are independently —F, —Cl, —Br, or —I;

n4 is independently an integer from 0 to 4; and m4 and v4 are each independently an integer from 1 to 2.

Embodiment 74. The polymer of embodiment 73, wherein the polymer is covalently bonded to a solid surface through a covalent linker.

Embodiment 75. The polymer of embodiment 73, wherein the polymer is covalently bonded to a solid surface through a covalent linker at more than one position of the solid surface.

Embodiment 76. The polymer of one of embodiments 74 to 75, comprising a subunit having the formula:

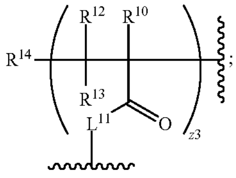

(II)

wherein, $R^{10}$, $R^{1.2}$, $R^{13}$, and $R^{14}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{11}$ is independently $-L^{11A}-L^{11B}$, $-L^{11C}-L^{11D}$, $-L^{11E}-$.

$L^{11A}$ $L^{11B}$, $L^{11C}$ $L^{11D}$, and $L^{11E}$ are independently a bond, $—S(O)_2—$, —S(O)—, $—S(O)_2NH—$, —NH—, —O—, —S—, —SS—, —C(O)—, —C(O)NH—, $—C(O)CH_2—$, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene;

$L^{11}$ is covalently bonded to the solid surface; and z3 is independently an integer from 1 to 5000.

Embodiment 77. The polymer of embodiment 74, wherein the polymer is covalently bonded to the solid surface by a linker $L^{12}$, wherein $L^{12}$ is $-L^{12A}L^{12B}-L^{12C}-L^{12D}-L^{12E}-$;

$L^{12A}$ $L^{12}$B, $L^{12C}$, $L^{12D}$, and $L^{12E}$ are independently a bond, $—S(O)_2—$, —S(O)—, $—S(O)_2NH—$, —NH—, —O—, —S—, —C(O)—, —C(O)NH—, $—C(O)CH_2—$, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene.

Embodiment 78. The polymer of one of embodiments 73 to 77, comprising a subunit having the formula:

(III)

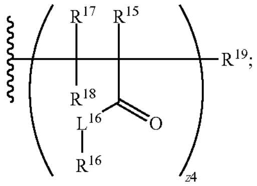

wherein, $R^{15}$, $R^{17}$, $R^{18}$, and $R^{19}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{16}$ is independently $-L^{16A}-L^{16B}-L^{16C}-L^{16D}-L^{16E}-$.

$L^{16A}$ $L^{16B}$ $L^{16C}$ $L^{16D}$, and $L^{16E}$ are independently a bond, $—S(O)_2—$, —S(O)—, $—S(O)_2NH—$, —NH—, —O—, —S—, —C(O)—, —C(O)NH—, —C(O)$CH_2$—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{16}$ is independently hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —$SO_{n16}R^{16D}$, —$SO_{v16}NR^{16A}R^{16B}$, $NHC(O)NR^{16A}R^{16B}$, $N(O)_{m16}$, —$NR^{16A}R^{16B}$, —C(O)$R^{16C}$, —C(O)—$OR^{16C}$, —C(O)$NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, —OC(O)$R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein $R^{16}$ is a third non-reactive moiety;

$R^{16A}$, $R^{16B}$, $R^{16C}$, and $R^{16D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protecting group, or a leaving group; $R^{16A}$ and $R^{16B}$ substituents bonded to the same nitrogen atom may optionally be joined to form a substituted or unsubstituted heterocycloalkyl or substituted or unsubstituted heteroaryl;

z4 is independently an integer from 1 to 5000;

X and $X^{16}$ are independently —F, —Cl, —Br, or —I;

n16 is independently an integer from 0 to 4; and v16 and m16 are each independently 1 to 2.

Embodiment 79. The polymer of one of embodiments 73 to 78, wherein $R^1$ is independently —$CH_3$.

Embodiment 80. The polymer of one of embodiments 73 to 79, wherein $R^5$ and $R^6$ are independently hydrogen.

Embodiment 81. The polymer of one of embodiments 73 to 80, wherein $L^2$ is independently a substituted or unsubstituted heteroalkylene.

Embodiment 82. The polymer of one of embodiments 73 to 80, wherein $L^{2B}$ and $L^{2D}$ are independently substituted or unsubstituted heteroalkylene;

$L^{2C}$ is independently a substituted or unsubstituted heteroarylene; and $L^{2E}$ is independently a bond.

Embodiment 83. The polymer of one of embodiments 73 to 80, wherein $L^{2B}$ and $L^{2E}$ are independently substituted or unsubstituted heteroalkylene;

$L^{2C}$ is independently a substituted or unsubstituted heteroarylene; and $L^{2D}$ is independently a substituted or unsubstituted arylene.

Embodiment 84. The polymer of one of embodiments 82 to 83, wherein $L^{2A}$ is independently a bond.

Embodiment 85. The polymer of one of embodiments 73 to 84, wherein $L^9$ is independently a substituted or unsubstituted heteroalkylene.

Embodiment 86. The polymer of one of embodiments 73 to 84, wherein $L^{9B}$ and $L^{9D}$ are independently substituted or unsubstituted heteroalkylene;

$L^{9C}$ is independently a substituted or unsubstituted heteroarylene; and $L^{9E}$ is independently a bond.

Embodiment 87. The polymer of one of embodiments 73 to 84, wherein $L^{9B}$ and $L^{9E}$ are independently substituted or unsubstituted heteroalkylene;

$L^{9C}$ is independently a substituted or unsubstituted heteroarylene; and $L^{9D}$ is independently a substituted or unsubstituted arylene.

Embodiment 88. The polymer of one of embodiments 86 to 87, wherein $L^{9A}$ is independently a bond.

Embodiment 89. The polymer of one of embodiments 73 to 88, wherein $R^9$ is independently 1) an oligonucleotide moiety; or 2) a second non-reactive moiety selected from hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, $SO_{v9}NR^{9A}R^{9B}$, $NHC(O)NR^{9A}R^{9B}$, $N(O)_{m9}$, —$NR^{9A}R^{9B}$, C(O)$R^{9C}$, —C(O)—$OR^{9C}$, —C(O)$NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —OC(O)$R^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{9A}$, $R^{9B}$, $R^{9C}$, and $R^{9D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protecting group, or a leaving group; $R^{9A}$ and $R^{9B}$ substituents bonded to the same nitrogen atom may optionally be joined to form a substituted or unsubstituted heterocycloalkyl or substituted or unsubstituted heteroaryl;

X and $X^9$ are independently —F, —Cl, —Br, or —I;

n9 is independently an integer from 0 to 4; and m9 and v9 are each independently an integer from 1 to 2.

Embodiment 90. The polymer of one of embodiments 73 to 89, wherein -$L^4$-$R^4$ is independently —$OCH_2CH_2$—$(OCH_2CH_2)_p$—$OCH_3$ or —$N(CH_3)_2$; and p is an integer from 4 to 10.

Embodiment 91. The polymer of one of embodiments 73 to 90, wherein -$L^9$-$R^9$ is independently —$OCH_2CH_2$—$(OCH_2CH_2)_p$—$OCH_3$ or —$N(CH_3)_2$; and p is an integer from 4 to 10.

Embodiment 92. The polymer of one of embodiments 73 to 91, wherein $R^3$ is independently —$CH_3$.

Embodiment 93. The polymer of one of embodiments 73 to 92, wherein $R^7$ and $R^8$ are independently hydrogen.

Embodiment 94. The polymer of one of embodiments 73 to 93, wherein $L^4$ is independently substituted or unsubstituted heteroalkylene.

Embodiment 95. The polymer of one of embodiments 73 to 93, wherein $L^{4B}$ and $L^{4D}$ are independently substituted or unsubstituted heteroalkylene;

$L^{4C}$ is independently a substituted or unsubstituted heteroarylene; and $L^{4E}$ is independently a bond.

Embodiment 96. The polymer of one of embodiments 73 to 93, wherein $L^{4B}$ and $L^{4E}$ are independently substituted or unsubstituted heteroalkylene;

$L^{4C}$ is independently a substituted or unsubstituted heteroarylene; and $L^{4D}$ is independently a substituted or unsubstituted arylene.

Embodiment 97. The polymer of one of embodiments 95 to 96, wherein $L^{4A}$ is independently a bond.

Embodiment 98. The polymer of one of embodiments 73 to 97, wherein $R^4$ is independently hydrogen, $—OCH_2CH_2—(OCH_2CH_2)_p—OCH_3$ or $—N(CH_3)_2$; and p is independently an integer from 0 to 10.

Embodiment 99. The polymer of one of embodiments 76 and 78 to 98, wherein $L^{11}$ is independently a substituted or unsubstituted heteroalkylene.

Embodiment 100. The polymer of one of embodiments 76 and 78 to 98, wherein $L^{11B}$ and $L^{11D}$ are independently substituted or unsubstituted heteroalkylene;

$L^{11C}$ is independently a substituted or unsubstituted heteroarylene; and $L^{11E}$ is independently a bond.

Embodiment 101. The polymer of one of embodiments 76 and 78 to 98, wherein $L^{11B}$ and $L^{11E}$ are independently substituted or unsubstituted heteroalkylene;

$L^{11C}$ is independently a substituted or unsubstituted heteroarylene; and $L^{11D}$ is independently a substituted or unsubstituted arylene.

Embodiment 102. The polymer of one of embodiments 100 to 101, wherein $L^{11A}$ is independently a bond.

Embodiment 103. The polymer of one of embodiments 77 to 98, wherein $L^{12}$ is independently a substituted or unsubstituted heteroalkylene.

Embodiment 104. The polymer of one of embodiments 77 to 98, wherein $L^{12B}$ and $L^{12D}$ are independently substituted or unsubstituted heteroalkylene;

$L^{12C}$ is independently a substituted or unsubstituted heteroarylene; and $L^{12E}$ is independently a bond.

Embodiment 105. The polymer of one of embodiments 77 to 98, wherein $L^{12B}$ and $L^{12E}$ are independently substituted or unsubstituted heteroalkylene;

$L^{12C}$ is independently a substituted or unsubstituted heteroarylene; and $L^{121}$ is independently a substituted or unsubstituted arylene.

Embodiment 106. The polymer of one of embodiments 104 to 105, wherein $L^{12A}$ is independently a bond.

Embodiment 107. The polymer of one of embodiments 73 to 106, wherein $R^9$ is independently $—OCH_2CH_2—(OCH_2CH_2)_p—OCH_3$ or $—N(CH_3)_2$; and p is independently an integer from 0 to 10.

Embodiment 108. The polymer of one of embodiments 73 to 107, further comprising a subunit having the formula:

(IV)

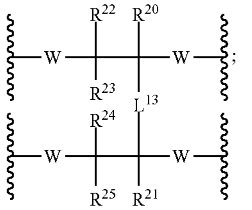

wherein

W independently has the formula:

(Va)

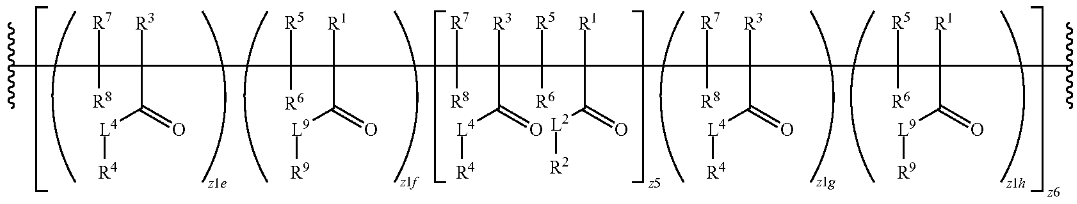

or (Vb)

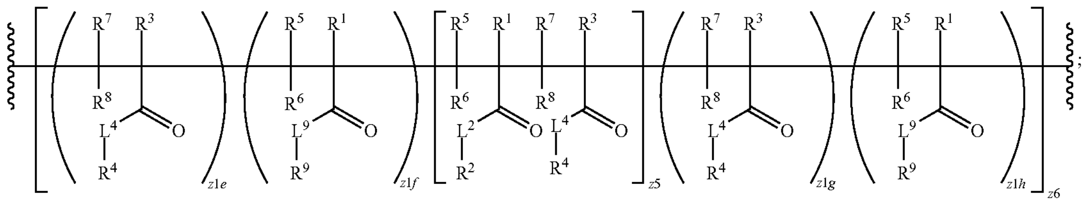

$R^{20}$, $R^{21}$, $R^{22}$, $R^{23}$, $R^{24}$, and $R^{25}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{13}$ is independently -$L^{13A}$-$L^{13B}$-$L^{13C}$-$L^{13D}$-$L^{13E}$-.

$L^{13A}$ $L^{13B}$ $L^{13C}$, $L^{13D}$, and $L^{13E}$ are independently a bond, —$S(O)_2$—, —S(O)—, —$S(O)_2NH$—, —NH—, —O—, —S—, —C(O)—, —C(O)NH—, —C(O)$CH_2$—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

z1e, z1f, z1g, and z1h are each independently an integer from 0 to 100;

z5 is independently an integer from 0 to 1; and z6 is independently an integer from 0 to 5000.

Embodiment 109. The polymer of embodiment 108, wherein $L^{13}$ is independently —$NHCH_2NH$—.

Embodiment 110. The method of any one of embodiments 1-14, wherein the polymer scaffold comprises a polymer of any one of embodiments 73-109.

Embodiment 111. The composition of any one of embodiments 15-38, wherein the core polymer comprises a polymer of any one of embodiments 73-109.

Embodiment 112. The method of any one of embodiments 39-72, wherein the core polymer comprises a polymer of any one of embodiments 73-109.

EXAMPLES

Example 1: Particles and Ordered Structures

This example provides a three-dimensional (3D) structures suitable for DNA sequencing. Adding an extra dimension to typical two-dimensional analyses opens up the possibility of a dramatic increase in the number of sequencing reactions that can be imaged in the same area. For example, at a spacing of 1 μm (on a square grid), a 1 cm×1 cm area would contain $10^8$ features (or clusters). By comparison, if the same spacing was used in a 3D volume of only 0.1 mm depth, a 1 cm×1 cm×0.1 mm volume would contain 100 "layers" or $10^{10}$ features.

The three-dimensional structures are self-assembled by a close packing of individual particles with the desired properties. The particles form a polymeric network, swell in water up to 90%, have a refractive index similar to water when hydrated. The mesh size of the network of particles is tunable and suitable for reagent diffusion to allow amplification and sequencing controlled by amplification kinetics, not by diffusion. One type of particle has a "core and shell" structure, where the core contains between 5-10% functional groups that bind chemically to DNA primers for generating DNA clusters, and the shell acts as a spacer between neighboring particles. The choice of functional group fraction is selected based on parameters of a given cluster amplification reaction and fluorescence intensity to be detected. Having a non-fluorescent shell allows for better resolution and less cross-talk between neighboring particles, or features. The polymeric network of shells has the same or higher permeability with respect to the core, and acts as a non-inhibiting layer for diffusion of reactants in and out of core particles. The clustering reaction may be done before or after the self-assembly of the particles into a 3D arrangement. The functional groups on the surface of the core or core/shell particles react with functional groups of neighboring particles and substrate to form a 3D scaffold attached to the substrate of a flow cell.

The cores have a diameter between 200 to 1200 nm that is 20-80% of the outer diameter of the shell. The diameter of the final core-shell particles is up to 5-6 microns. The choice of the relative size of the core to the shell is based on acceptable parameters for fluorescent intensity (which increases with the size of the core), and acceptable cross-talk between adjacent features (cross-talk is reduced for a larger shell). In some examples, core diameters are about 50% of the outer diameter of the shell. The shell layer may be engineered (e.g., by altering the ratio of starting materials or duration of the reaction) to have a specific thickness. Thickness of a layer, as referred to herein, is defined as the distance from the inner surface of the layer, which contacts (interfaces) with the core, to the outer surface of the layer (the surface that interfaces with a non-core layer and/or the environment), which interfaces with the external environment (e.g., external medium). Layer thickness may be approximately uniform (e.g. no more than 25% variation, 20% variation, 15% variation, 10% variation, 5% variation, 4% variation, 3% variation, 2% variation or 1% variation) over (around) the core. Alternatively, the layer thickness may be non-uniform over the core. In embodiments, the layer thickness is determined by transmission electron microscopy (TEM).

Figure 2A:
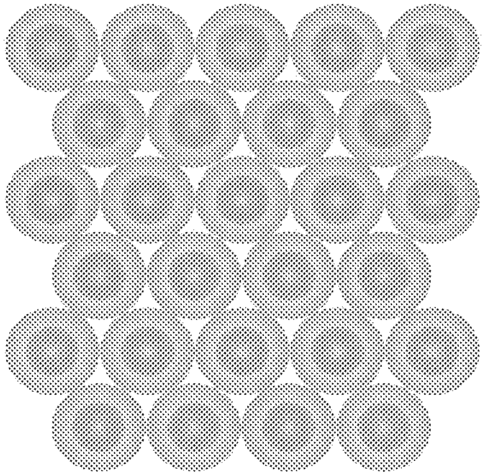
FIGS. 2A-C illustrate particles with a primer-attached core and a primer-less shell, with the shell creating a physical separation between the cores. The physical separation improves the ability to optically resolve signals from each core.
Figure 2B:
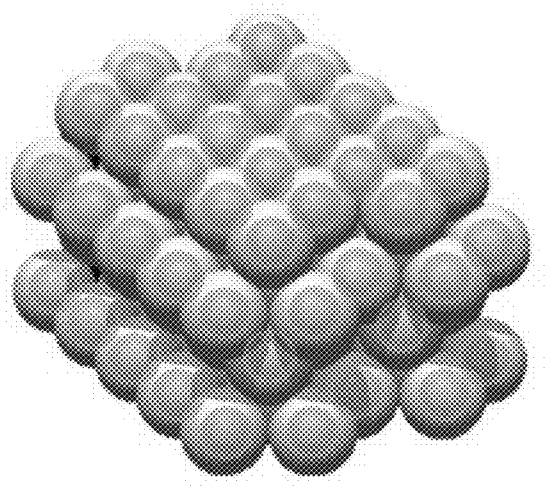
Figure 2C:
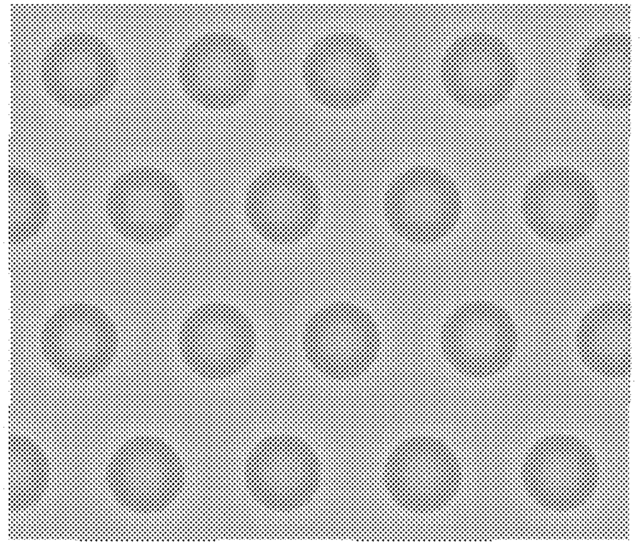

Examples of close-packed 3D structure are hexagonal closest packed (HCP) and cubic closest packed (CCP), both of which have 74% filled space fraction, whether the particles are rigid, porous, spherical, and they touch each other, or if the particles are soft (e.g., swelled particles). However, in both cases, the particles are non-inhibitory for mass transfer of reactants. The two spatial arrangements are illustrated in FIGS. 1A and 1B. Both two-dimensional and three-dimensional arrangements of particles having a core and a shell are illustrated in FIGS. 2A-C. In FIG. 2C, the shell polymer has expanded to fill the gaps between particles shown in FIG. 2A. The self-assembled scaffold structure does not need to be close-packed, nor completely periodic to be useful.

While a 3D arrangement offers a greatly expanded capacity for sequencing, a 2D arrangement is also quite useful, particularly as a low-cost way of self-assembling a periodic array of clusters, rather than requiring the use of top-down patterning techniques such as lithography. In either arrangement, target polynucleotides are amplified to produce a monoclonal DNA cluster contained and compartmentalized in several single core-shell particles.

The use of particles, even without a shell, also offers the possibility for clustering reaction to be carried out "off line," in other words, before they are arranged into the 3D or 2D structures. The clustering reactions may be carried out in a micro-emulsion, digitally formed droplets, or in a bulk solution under conditions that favor localized amplification.

One feature of core-shell particles with a functional core and a non-functional shell is that there is no contact between adjacent cores. This prevents the potential for cross-interaction among particles, and makes it much easier to create conditions under which unique monoclonal clusters are formed inside each particle, even if all the particles are in physical contact or are simply suspended in solution.

For example, the free volume and permeability of the 3D matrix permits carrying out amplification reactions with techniques such as bridge-PCR, RPA, LAMP, RCA with exponential strand displacement amplification, and other isothermal amplification reactions. The primers for these reactions are immobilized in the cores, and the amplification products remain confined to the core and physically separated from other particles. The clustering amplification reactions may be carried out either before or after polymerizing the shell polymer on the core polymer, and assembling the particles.

To facilitate imaging through many layers of particles, the particles themselves have very low scattering. The particles are suspended in an aqueous medium, and have an index of refraction that is close to water (about 1.33). The scaffold material may include hydrogels, and other polymers that hold a high degree of water content. The scaffold material can be functionalized with reactive groups that can be used for coupling polynucleotide primers.

Hydrogels also allow for efficient movement of small molecules, including nucleotides, through the scaffold. Depending on the design of the polymer network (including degree of cross-linking), it can be made permeable to large molecules such as enzymes and DNA.

The core-shell hydrogel particles are prepared by dispersion or precipitation polymerization in two steps: 1) core synthesis and 2) shell growing around the core. The core composition can be a homo- or copolymer of monomers including monomers with active functional end groups. Monomers for preparation of particles can be hydrophilic or a combination of hydrophilic and hydrophobic acrylate or methacrylate monomers but not limited to these types of monomers. The particle size and particle size distribution of the particles can be controlled by solvent composition, and monomer and stabilizer concentrations. For having close packing of particles, the particle size distribution of particles is very important. The permeability of reactants such as the ones mentioned above through the shell can be tuned by the ratio between monomers and cross-linker. The outer layer of particles can be decorated with active functional groups that can be reacted with functional groups of adjacent particles and the surface of the substrate to immobilize them as a 3D scaffold in the flow cell.

Example 2: Non-Structured or Random Clustering

As described above, creating a structured 3D scaffold for clustering offers advantages in terms of defining the volumes where DNA clustering can occur, and ensuring a defined spatial extent of the clusters and a defined separation between clusters. Having an organized, periodic structure also provides advantages for ensuring resolution of individual features by imaging readout. However, such structuring, or patterning, in not required. An alternative approach is to allow clusters to be seeded at random locations in the 3D matrix.

Random 3D clustering is the simplest approach for creating a 3D flow cell for sequencing. The matrix used is permeable to both small and large molecules. Hydrogels, and other polymers that hold a high degree of water, and have a structure with pores large enough for proteins and DNA to move through are example materials. The matrix includes functional groups which allow the chemical attachment of DNA primers that are used in clustering amplification reactions.

One of the techniques for fabricating of this type of 3D scaffold that enables random (or semi-random) 3D cluster amplification is the use of inverse high internal phase emulsions (i-HIPE). In this case, the continuous phase of the inverse emulsion (usually hydrophilic) contains one or more monomeric species, and the dispersed droplets are oil. Polymerization is initialized and crosslinks the monomers in the continuous phase into a polymer or hydrogel layer, followed by removal of the oil droplets. This creates a semi-ordered scaffold with pores defined by the diameter of the dispersed oil droplets in the inverse emulsion. This process can be followed by functionalization of the resulting scaffold with functional groups suitable for tethering DNA primers to the surface, rendering it suitable for 3D cluster amplification and sequencing.

It may be advantageous to first flow in the DNA templates under conditions that are non-hybridizing (e.g. low salt, high temperature, or presence of additives such as formamide), to facilitate a uniform distribution of the templates throughout the 3D volume. A desirable characteristic of the 3D matrix is minimal non-specific binding of DNA template molecules to the matrix, either via electrostatic, van der Waals or hydrophobic interactions. The concentration of the templates is selected to give the desired density of clusters in the 3D volume. Then, clustering reactions start from each of the templates present in the 3D volume. Clustering reactions proceed for a period of time sufficient to reach the desired cluster size—e.g. a diameter of 0.2-1 um.

Figure 3A:
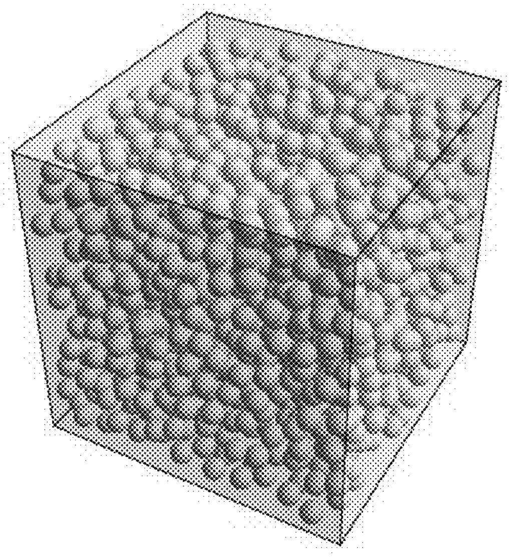
FIGS. 3A-B shows an illustration of a polymer scaffold and amplified DNA.
Figure 3B:
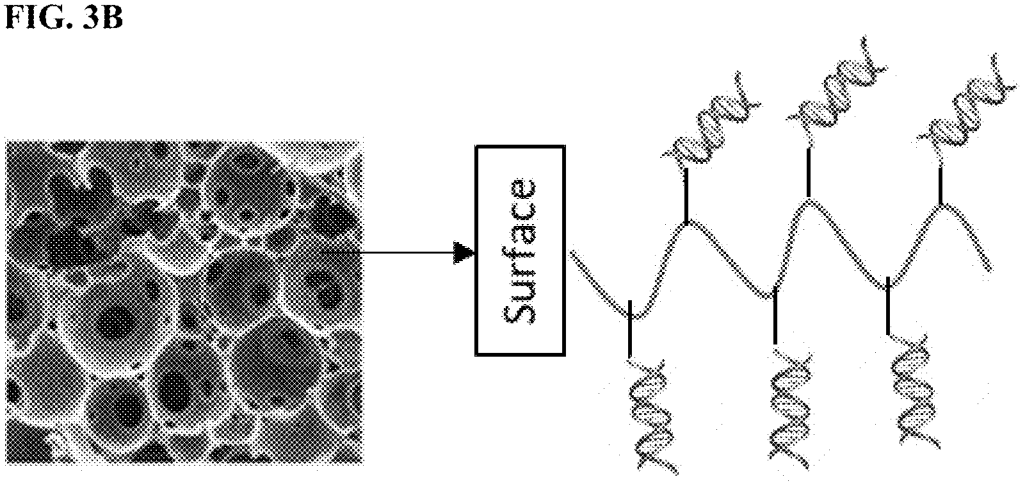
Figure 3C:
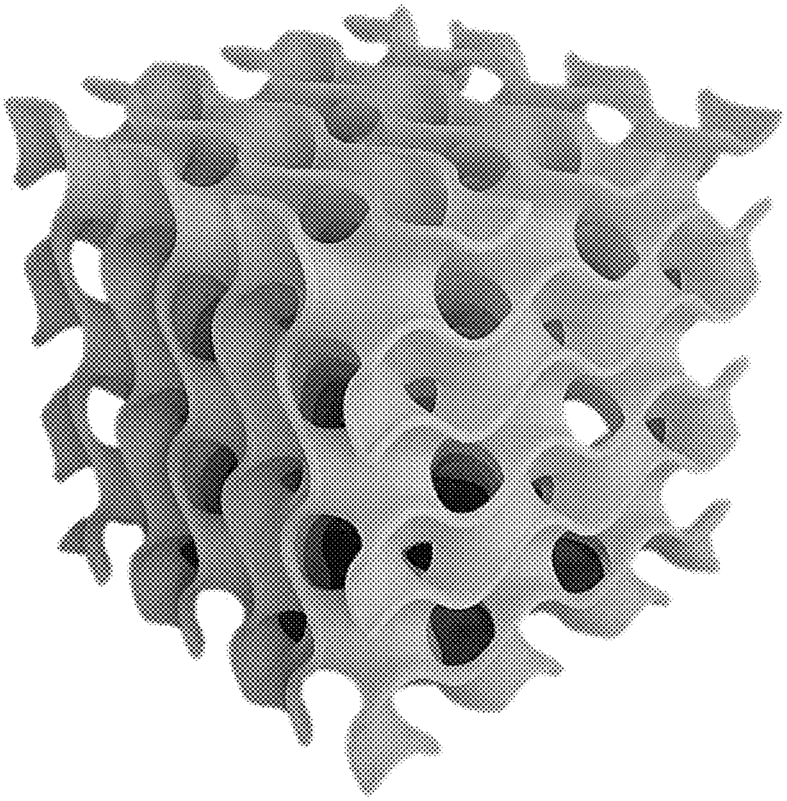
FIG. 3C illustrates an example polymer scaffold having a gyroid structure.

FIG. 3A shows a schematic illustration of clusters in a portion of the 3D volume. The location of the clusters is random, each cluster originating from a single "seed" of a template DNA. The density of the clusters is selected to not exceed the resolving power of the imaging system used in the DNA sequencer. FIG. 3B shows a microscopic image of an example scaffold, and a schematic showing attachments between a surface, a polymer, and polynucleotides.

Example 3: Imaging

During sequencing by synthesis (SBS), reversibly-terminated nucleotides carrying fluorescent dyes are incorporated into a growing strand, complementary to the target strand being sequenced. The nucleotides are labeled with up to four (4) unique fluorescent dyes. The readout is typically accomplished by epifluorescence imaging.

In 3D flow cells, standard epifluorescence as applied in 2D imaging applications would be problematic, as there would be poor resolution along the axial direction. Two approaches can be used to improve the axial resolution: confocal microscopy and multi-photon microscopy.

Figure 4:
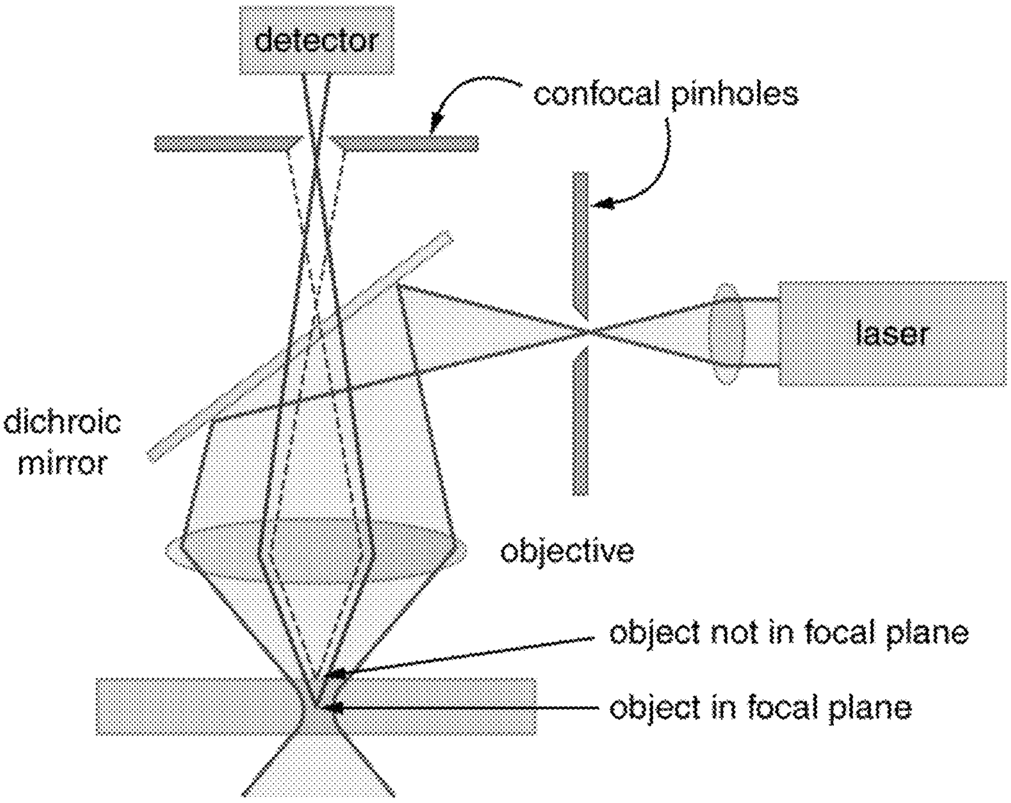
FIG. 4 shows a schematic of a confocal microscope. The green lines represent the laser beam (from the laser at right). The solid red lines represent the fluorescence from the object in the focal plane (at the targeted depth); this emitted light is focused on the pinhole and transmitted to the detector. The dashed red lines represent the fluorescence from an object outside the focal plane, and this emitted light is mostly blocked by the pinhole. (See, e.g., opentextbc.ca/physicstestbook2/chapter/extended-topic-microscopy-enhanced-by-the-wave-characteristics-of-light/)

Confocal fluorescence microscopy involves scanning a focused laser beam across the sample, and imaging the emission from the focal point through an appropriately-sized pinhole. This suppresses the unwanted fluorescence from sections at other depths in the sample. An example of a confocal microscope configuration is show in FIG. 4.

Figure 5:
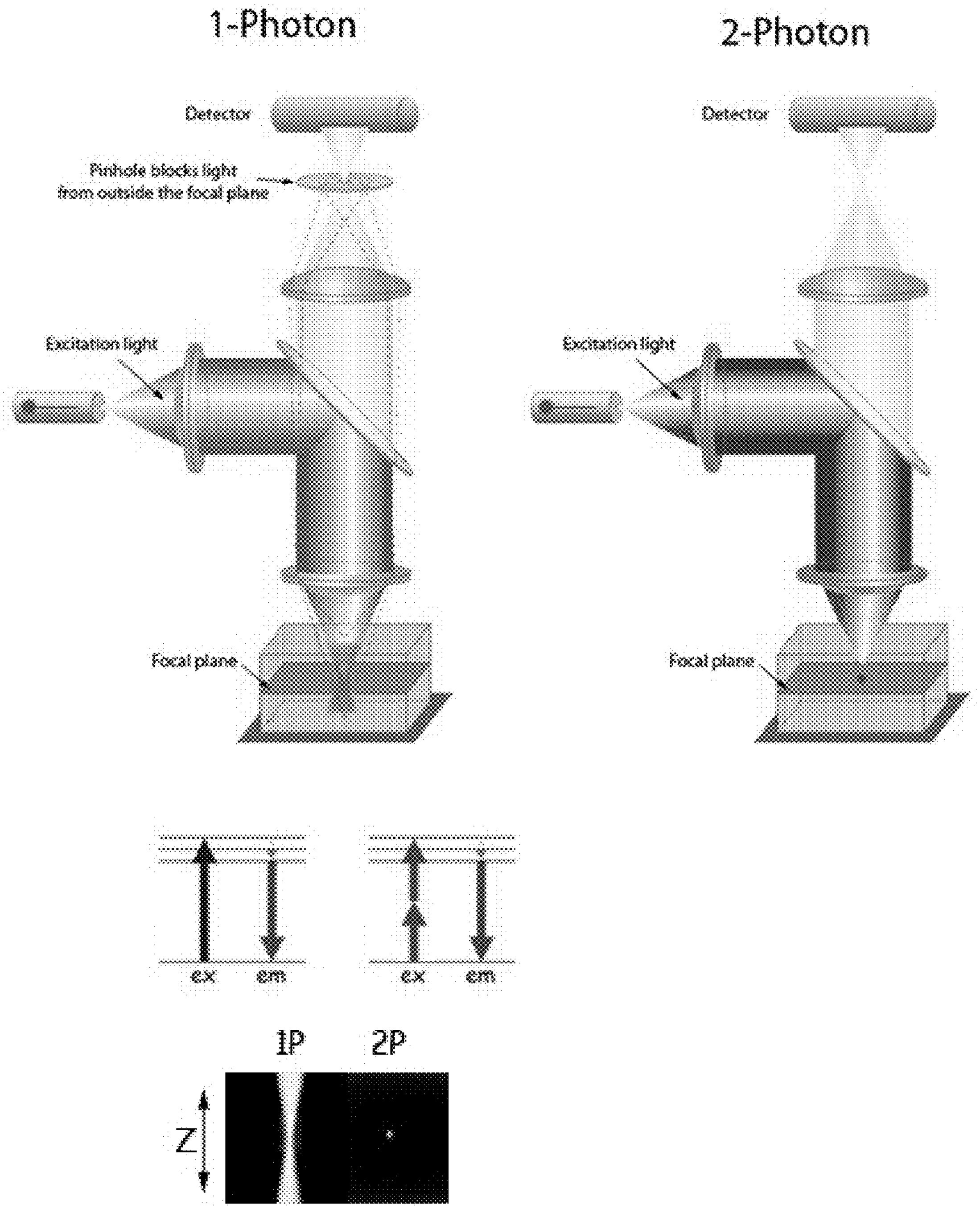
FIG. 5 shows a schematic of a 2-photon microscope compared to a standard 1-photon confocal microscope. Also shown is a vertical cross-section of fluorescence induced by 1-photon vs. 2-photon excitation. With 2-photon excitation, the fluorescence occurs only at the focal depth. (See, e.g., microscopy.duke.edu/introduction-microscopy).
Figure 6:
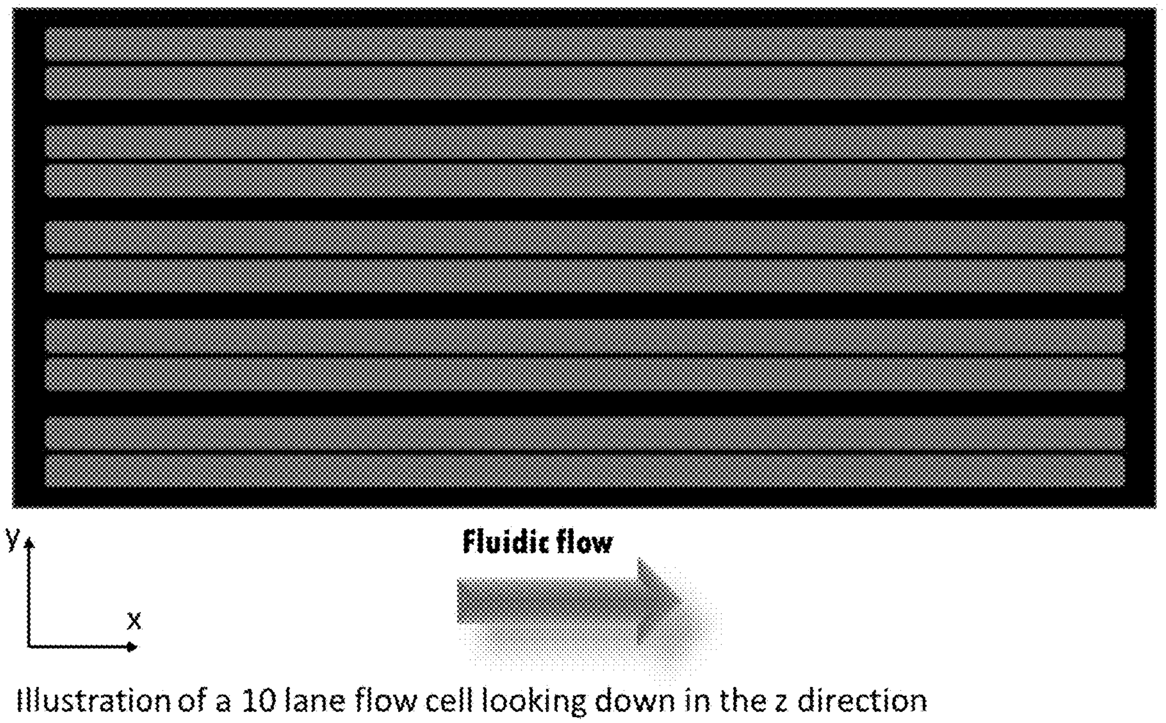
FIG. 6 is an illustration of a 10 lane flow cell looking down in the z direction.
Figure 7:
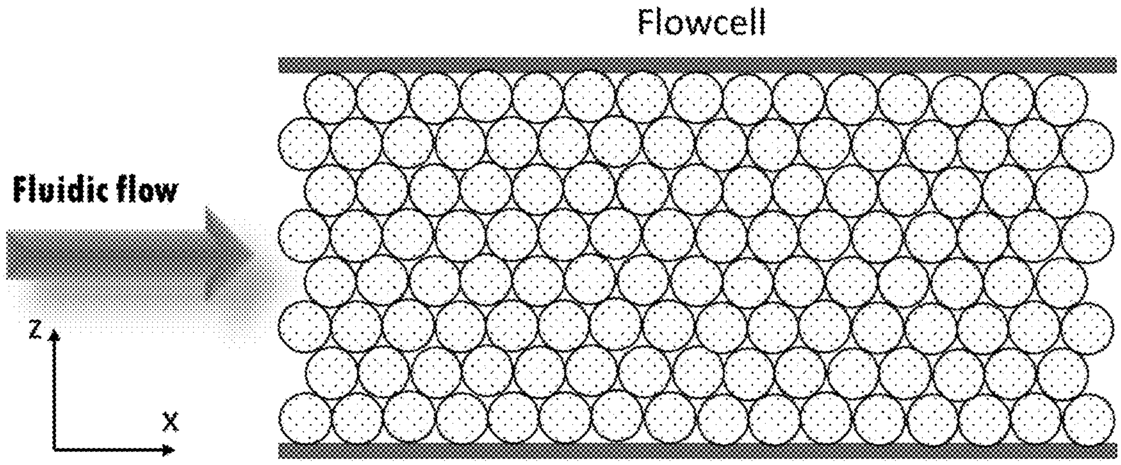
FIG. 7 is an illustration of a 3D flowcell (showing a 2D slice) showing polymer particles homogeneously arranged to occupy the entirety of the flowcell (i.e., particles are packed and in contact with the top and the bottom of the flowcell). Note, the core is not shown as it is contained within the shell, which is shown in the illustration. Detection may occur from the top or bottom (e.g., in the z direction, as illustrated) using the technologies described in the application.
Figure 8:
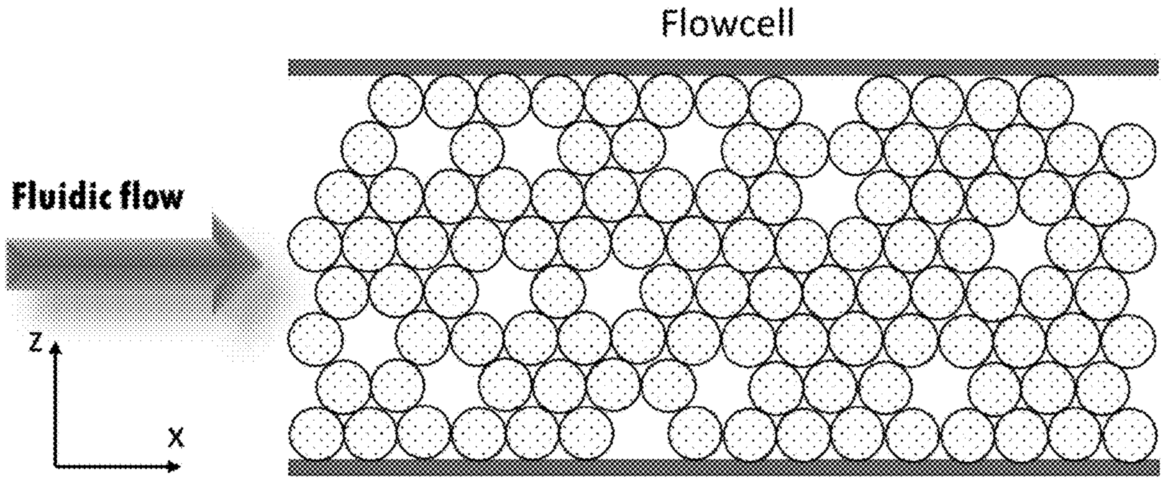
FIG. 8 is an illustration of a 3D flowcell (showing a 2D slice) showing particles arranged to occupy the entirety of the flowcell with vacancies (e.g., gaps or pores). The particles and occasional vacancy are in contact with the top and the bottom of the flowcell.
Figure 9:
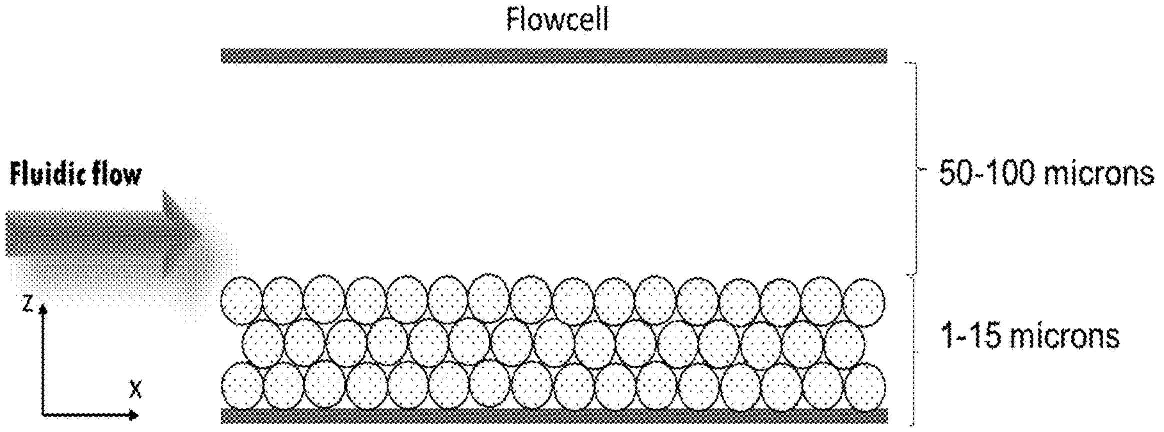
FIG. 9 is an illustration of a 3D flowcell (showing a 2D slice) showing particles homogeneously arranged to occupy a fraction of the flowcell. The particles are in contact with one surface (e.g., the top or the bottom) of the flowcell.
Figure 10:
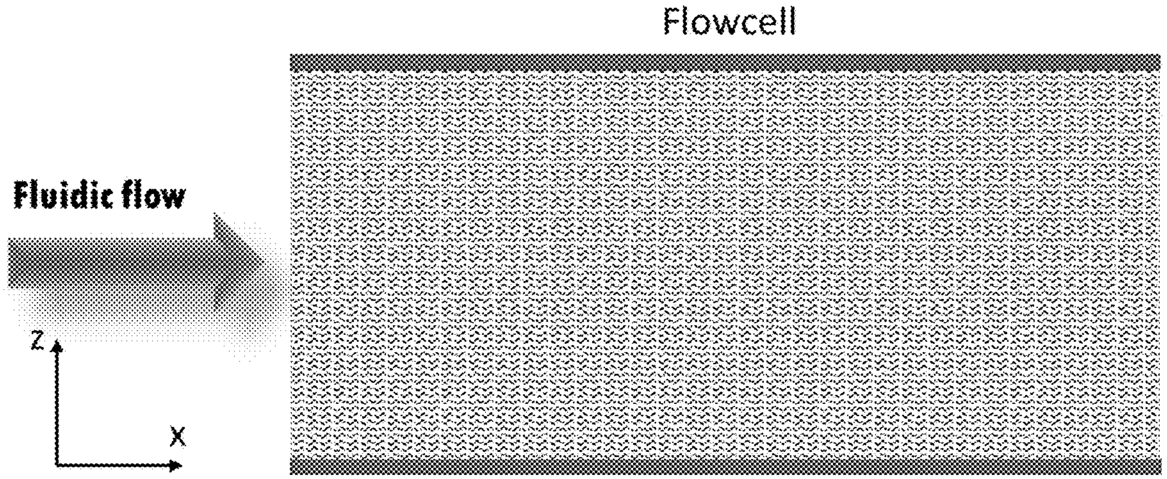
FIG. 10 is an illustration of a 3D flowcell (showing a 2D slice) showing non-particulated polymer (e.g., hydrogel) arranged to occupy the entirety of the flowcell. The non-particle polymer is illustrated as being in contact with the top and the bottom of the flowcell.
Figure 11:
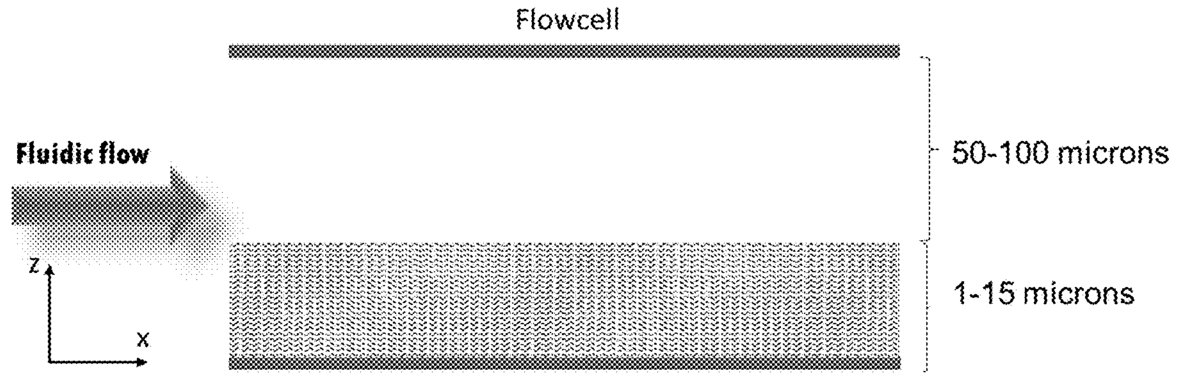
FIG. 11 is an illustration of a 3D flowcell (showing a 2D slice) showing particles homogeneously arranged to occupy a fraction of the flowcell. The particles are in contact with one surface (e.g., the top or the bottom) of the flowcell.
Figure 12A:
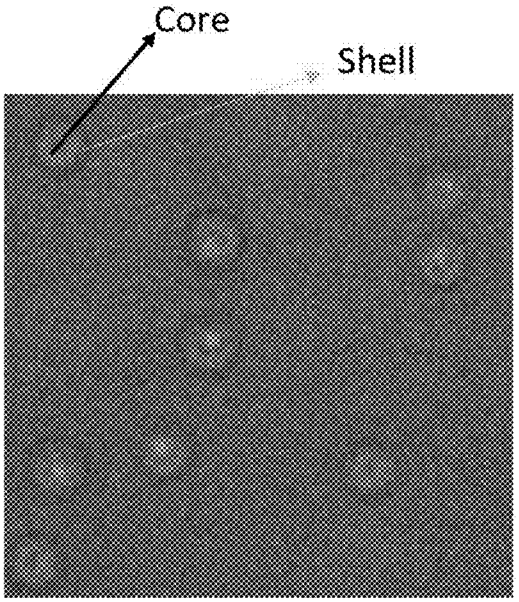
FIGS. 12A-B show images of pure polymer core-shell particles in accordance with an embodiment. The core is comprised of polymerized AAm-GMA azide having an average diameter of 775±80 nm, surrounded by an inactive polymer shell (e.g., DMA) having a diameter of 1290±170 nm.
Figure 12B:
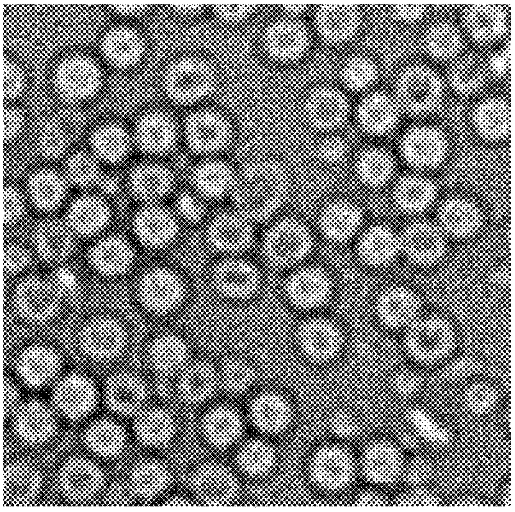
Figure 13A:
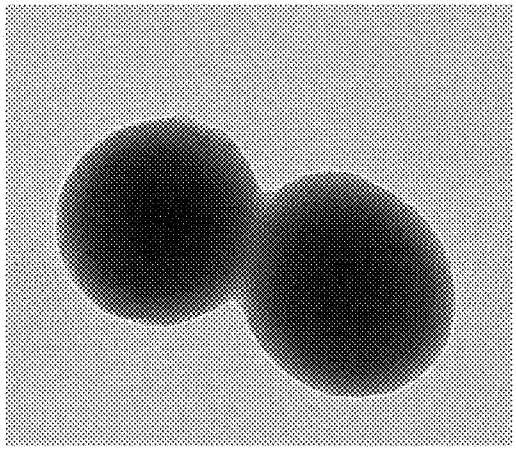
FIGS. 13A-C depict images of particles in accordance with an embodiment.
Figure 13B:
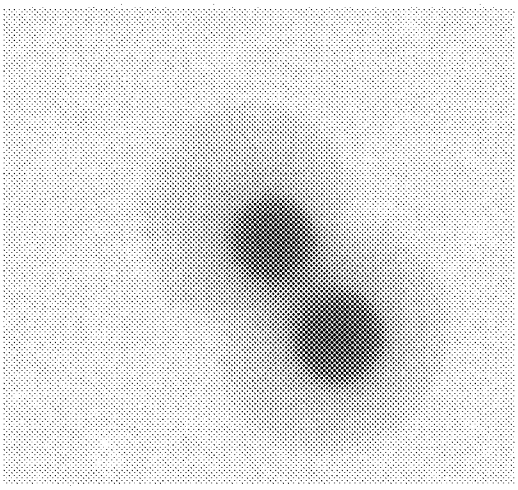
Figure 13C:
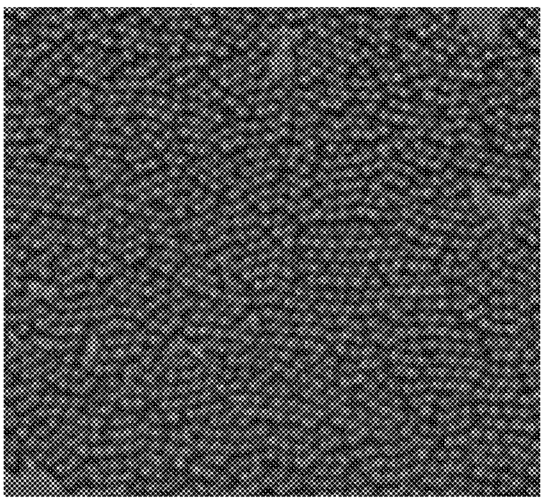

While confocal microscopy provides much better axial resolution than standard epifluorescence, it still encounters the issue of excessive photo-bleaching and photo-damage, as all axial sections are illuminated at all times. One solution to these issues is to use multi-photon excitation, where the optical excitation is limited to the region of high intensity in the focal volume. Multi-photon excitation is illustrated in FIG. 5, next to standard 1-photon confocal microscopy. (The most common form of multi-photon excitation is two-photon.) Multi-photon microscopy solves both of the challenges involved in imaging a 3D flow cell: axial resolution and reduced photo-damage. The excitation only occurs in the focal plane, where the intensity is high enough for 2 photons to be absorbed simultaneously.

Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue.

Example 4: Solution-Based, Emulsion Free Clustering

Monoclonal amplification, or clustering, on beads, is often done by encapsulating individual beads in droplets in an oil/water emulsion (e.g. in Ion Torrent, Roche 454, and Qiagen DNA sequencing systems). PCR amplification products are kept localized within the droplets, resulting in monoclonal clusters on the beads. However, creating and breaking of emulsions can cause complications in carrying out the reactions and challenges in automation. Moreover, solution exchange on beads contained within an emulsion is challenging, limiting the number of steps and reagent exchanges during DNA amplification that can be used in conjunction with these emulsions. It would be preferable be able to carry out monoclonal amplification directly in bulk solution, without the need for creating an emulsion.

Non-Interacting Particles for Clustering

An alternative approach to monoclonal amplification on particles or beads would be to create a physical barrier between the particles such that the amplified products would not interact with other beads. This can be accomplished by a core/shell structure, where the core contains immobilized primers, while the shell is primer-free, and "inert" in the sense that no amplification takes place there.

If desired, the core/shell layers can be formed around a supporting bead. For example, a magnetic bead would offer the advantages of being controlled by magnetic fields, simplifying automation of steps such as washing and purification. In this design, there would be 3 layers: a solid bead support (which itself could include a magnetic core and an encapsulating polymer layer), a functional "core" layer around the bead for primer attachment, followed by an "inert shell" layer.

Amplification Process

A DNA template library is prepared by ligating adapters containing primer binding sites to the ends of the region to be sequenced. The next step is to capture the target DNA with the particles. This is done under conditions that favor approximately one DNA template (or target) per particle on average, or less, to avoid excessive numbers of polyclonal clusters. The DNA template contains a sequence that is complimentary to a set of primers that are immobilized in the core of the particles.

Next, the DNA templates are copied by polymerase extension of the bound primers.

At this point, the original templates can be denatured and washed away. This is helpful to prevent the template from potentially binding to another particle and acting as a template for amplification in further steps.

To generate monoclonal clusters, the particles can then be subjected to solution-based bridge PCR. Other amplification methods, such as various isothermal amplification reactions, can also be used. The core layer of the particles contains 2 sets of primers, allowing both "forward" and "reverse" strands to be replicated. All of the amplified products remain attached to the particles, as the primers are all attached (typically through covalent bonds).

The outer "inert shell" of the particles prevents the amplified products on one bead from interacting with primers on another bead. Thus, the amplification reactions remain confined to individual beads, and produce monoclonal products without requiring the compartmentalization normally afforded by an emulsion.

After a first round of amplification, the vast majority of primers within particles containing a cluster will be extended by the polymerase or sterically inaccessible to bind other template molecules. Therefore, if desired, subsequent rounds of template hybridization and amplification under the same conditions as outlined above can be performed in order to increase the fraction of particles containing monoclonal clusters. Thus, sample-contacting and amplification steps can be repeated without separating empty particles from particles containing amplicons, while still predominantly yielding particles containing amplification products from a single original template.

Option of Selecting Clustered Particles

One limitation of many clustering methods on particles or arrays is that they are subject to the constraints of Poisson statistics of random events. For example, even at an optimal concentration of DNA templates, only about 37% of the particles will have a single template; the other 63% will have 0 or 2 templates (neither of which is desired). It would be preferable to have a greater fraction of monoclonal clusters, so that the space in a sequencing flow cell or another sequencing surface is used more efficiently.

Since DNA carries a negative charge, the particles that contain amplified products will be significantly charged compared to the "blank" particles. The useful clustered particles can be separated from the "blank" particles by an electric field. By choosing a relatively low seeding ratio, e.g. <20%, or <10%, or <5%, the probability of having more than 1 template per particle (multiple seeding) can be greatly reduced. The large fraction of unseeded "blank" particles is then removed by charge-based separation, resulting in nearly pure population of single-seeded particles for monoclonal clustering.

Another method of obtaining a greater fraction of monoclonal clusters is fluorescence based-enrichment of particles containing amplified products. In this method, a fluorescent DNA probe is temporarily hybridized to the clusters and can be removed after particle enrichment. Alternatively, a DNA intercalating dye can be used to attach to the clusters and can removed after particle enrichment. FACS is an example of a technique that can achieve the sorting of clusters that have been hybridized with a fluorescent DNA probe or treated with an intercalating dye.

Example 5: Polymer Synthetic Protocols

The synthesis of hydrogel cores was performed by dispersion polymerization in water/alcohol mixtures in which the monomer(s) are soluble. The general procedure is as follows: AAm and azide functionalized monomers are mixed and added to a reactor along with stabilizer, an FRP initiator, and solvent and are mixed to have a clear solution. The reactor is then sealed and bubbled with inert gas in the ice bath. A crosslinker dissolved in a water/alcohol mixture (note, it can be a different alcohol or different water/alcohol ratios than the one that is used in the reactor) in another reaction vessel and bubbled with an inert gas (e.g., $N_2$), simultaneously. After approximately 30 minutes, the main reactor is immersed in an oil bath (above 60° C.) and mixed with a stirrer bar at a constant rate. After approximately 20 minutes, the crosslinker solution is added in a dropwise manner. Towards the end of the crosslinker addition, decorating agent can be added to the crosslinker solution to add to the main reactor.

In one example, 25 mg Ammonium persulfate (APS), 0.5 g AAm, 130 mg of GMA-N3, 1 g of PVP (average mol wt 40,000), 16 g ethanol and 4 g water were added to reactor (solution 1) along with a magnetic stirrer bar. The reactor was sealed and purged with an inert gas for at least 30 minutes, in an ice bath. To form the crosslinker solution, in another container, 8 g of ethanol, 2 g water and 24 mg N,N'-Methylenebis(acrylamide) was mixed and bubbled with inert gas (solution 2). The reactor is immersed in an oil bath (60° C.) to start the reaction while mixed at a 120 rpm stirring rate. After 20 minutes, solution 2 is added to the reactor with a syringe pump (at the rate of 6 ml/h). At the end of the crosslinker solution addition, 11 ul of glycidyl methacrylate (GMA) added to remaining solution. It was bubbled and then continued to be added to the main reactor to achieve epoxy decorated functionalized particles.

In another example, 25 mg Ammonium persulfate (APS), 0.5 g AAm, 75 mg of HEMA-N3, 0.4 g of PVP (average mol wt 40,000), 17 g ethanol and 3 g water were added to the reactor (solution 1) along with a magnetic stirrer bar. The reactor was sealed and purged with an inert gas for at least 30 minutes, in an ice bath. To form the crosslinker solution, in another container, 8.5 g of ethanol, 1.5 g water and 24 mg N,N'-Methylenebis(acrylamide) was mixed and bubbled with inert gas (solution 2). The reactor is immersed in an oil bath (60° C.) to start the reaction while mixed at a 120 rpm stirring rate. After 20 minutes, solution 2 is added to the reactor with a syringe pump (at a rate of 6 ml/h). At the end of crosslinker solution addition, 11 ul of glycidyl methacrylate (GMA) was added to remaining solution. It was bubbled and then continued to be added to the main reactor to achieve epoxy decorated functionalized particles.

These particles may further be functionalized with an inert shell.

Grafting from. The solution mixture was prepared with mixing anhydrous hexane/dichloromethane (DCM) (50/50 vol/vol) under inert gas flow and bubble it for 10 min. A mixture of ATRP (3-triethoxysilane)propyl 2-bromo-2-methylpropionate (or [11-(2-bromo-2-methyl)propionyloxy]undecyltrichlorosilane)) and spacer silane agents (e.g., Trimethoxy(propyl)silane) are added to the solution mixture (~0.10-0.15% vol/vol) under inert gas; the reaction mixture is allowed to bubble for about 3 more min. The substrate (e.g., glass slide, silica particle, metal particle) is placed into the reaction mixture (or reaction mixture added to the container the substrate). The container is sealed and kept for 18 h. The substrate is then washed with hexane and ethanol/water mixture and dried with nitrogen.

Surface Initiated ATRP Polymerization General Methods. The substrate (e.g., glass slide, silica particle, or metal particle) containing a polymerization initiator is immersed in polymerization reaction mixture. This mixture depends on the type of monomers, and can include (i) solvent(s), monomer(s), initiator, and ligand or (ii) solvent(s), monomer(s) and initiator. Monomer ratios were adjusted to create polymerase brushed with different spacers between neighboring side chains (ng) (i.e., determining the ratio of monomers with functional groups to monomers with non-functional groups).

For system (i), the reaction mixture containing substrates are deoxygenated via bubbling with inert gas (for at least 1 h) and then catalyst added to the system. Afterward, the system is sealed under inert gas and polymerization conducted in the desired temperature. After a set amount of time (or reaching target degree of polymerization), the reaction is stopped by exposing to the air. The substrate (e.g., glass slide) is washed with proper solvents and dried. For system (II), the reaction mixture containing substrates are deoxygenated via bubbling with inert gas (for at least 1 h). In a separate container, a mixture of solvent(s) and ligand are degassed via bubbling and a catalyst is added to this mixture (referred to herein as Cat-mixture). Subsequently, the Cat-mixture is added to the system (II) reaction mixture. Then the system is sealed under inert gas and polymerization is conducted in the desired temperature. After a set amount of time (or reaching target degree of polymerization), the reaction is stopped by exposing to the air. The substrate (e.g., glass slide) is washed with proper solvent(s) and dried. In some cases, post-polymerization modification reaction were conducted on the slide to introduced desired functionality.

The following examples describe polymers growing on planar glass slides. The same procedures may work for growing polymers on glass (e.g., silica) particles as described herein.

20 g poly(ethylene glycol) methyl ether methacrylate (PEGMEMA, Mn~300), 2.35 g GMA, 15 ul 1,1,4,7,10,10-hexamethyltriethylenetetramine (HMTETA) ligand, 7 ul ethyl α-bromoisobutyrate (EBiB) as sacrificial initiator, and 70 ml toluene were added to the Schlenk reactor containing slides with ATRP initiators immobilized thereon. The mixture was deoxygenated via inert gas bubbling for 1 h. Then 8.5 mg CuBr catalyst added to the reactor under the inert gas flow. The reactor was sealed and reaction started by putting the reactor in an oil bath at 70° C. The reaction continued for 3 days and it stopped by exposing to the air. The slides were washed with acetone 3 times, and then dried with air flow.

In another example, 10 g PEGMEMA (Mn~300), 2.0 g GMA-$N_3$, 10 ul HMTETA ligand, 5.8 ul EBiB as sacrificial initiator, and 70 ml toluene were added to the Schlenk reactor containing slides with ATRP initiators immobilized thereon. The mixture was deoxygenated via inert gas bubbling for 1 h. Then, 7.1 mg CuBr catalyst added to the reactor under the inert gas flow. The reactor was sealed and reaction started with putting reactor in an oil bath at 68° C. The reaction continued for 3 days and it stopped by exposing to the air. The slides were washed with acetone 3 times, and then dried with air flow.

In another example, 17.5 g PEGMEMA (Mn~500), 1.66 g GMA, 10.6 ul HMTETA ligand, 5.6 ul EBiB as sacrificial initiator, and 70 ml toluene were added to the Schlenk reactor containing slides with ATRP initiators immobilized thereon. The mixture was deoxygenated via inert gas bubbling for 1 h. Then, 5.7 mg CuBr catalyst added to the reactor under the inert gas flow. The reactor was sealed and reaction started with putting reactor in an oil bath at 68° C. The reaction continued for 3 days and it stopped by exposing to the air. The slides were washed with acetone 3 times, and then dried with air flow.

In another example, 17.5 g PEGMEMA (Mn~500), 2.69 g HEMA-$N_3$, 10.6 ul HMTETA ligand, 5.6 ul EBiB as sacrificial initiator, and 70 ml toluene were added to the Schlenk reactor containing slides with ATRP initiators immobilized thereon. The mixture deoxygenated via inert gas bubbling for 1 h. Then, 5.7 mg CuBr catalyst added to the reactor under the inert gas flow. The reactor was sealed and reaction started with putting reactor in an oil bath at 68° C. The reaction continued for 3 days and it stopped by exposing to the air. The slides were washed with acetone 3 times, and then dried with air flow.

In another example, 17.5 g PEGMEMA (Mn~500), hydroxypropyl methacrylate (HPMA) 1.52 g, 10.6 ul HMTETA ligand, 5.6 ul EBiB as sacrificial initiator, and 70 ml toluene were added to the Schlenk reactor containing slides with ATRP initiators immobilized thereon. The mixture was deoxygenated via inert gas bubbling for 1 h. Then, 5.7 mg CuBr catalyst added to the reactor under the inert gas flow. The reactor was sealed and reaction started with putting reactor in an oil bath at 68° C. The reaction continued for 3 days and it stopped by exposing to the air. The slides were washed with acetone 3 times, and then dried with air flow.

In another example, 8 g N,N-Dimethyl acrylamide (DMAA), 3.83 g GMA, 13 ul EBiB as sacrificial initiator and 70 ml ethanol/water (70/30 vol/vol) were added to the Schlenk reactor containing slides with ATRP initiators immobilized thereon. The mixture was deoxygenated via inert gas bubbling for 1 h. In another Schlenk reactor, 24.5 ul HMTETA ligand added to 5 ml ethanol/water mixture and the reactor was degassed with inert gas bubbling. Then 9 mg CuCl catalyst added to this reactor under the inert gas flow (Cat-mixture). Later, all of the Cat-mixture was injected to the main reactor under inert gas flow and the reactor was sealed. The reaction conducted at room temperature overnight and stopped via being exposed to the air. The slides were washed with ethanol/water (70/30 vol/vol) 3 times and dried with nitrogen flow.

In another example, 5 g Acrylamide (Aam), 2.73 g 2-hydroxyethyl acrylate (HEA), 9 ul 2-Hydroxyethyl 2-bromoisobutyrate as sacrificial initiator, and 70 ml ethanol/water (70/30 vol/vol) were added to the Schlenk reactor containing slides with ATRP initiators immobilized thereon. The mixture was deoxygenated via inert gas bubbling for 1 h. In another Schlenk reactor 16.7 ul tris[2-(dimethylamino) ethyl]amine (Me6TREN) as a ligand was added to 5 ml ethanol/water (30/70 vol/vol) mixture and the reactor was degassed with inert gas bubbling. Then, 6.2 mg CuCl(I) catalyst was added to this reactor under the inert gas flow (Cat-mixture). Later, all of the Cat-mixture was injected to the main reactor under inert gas flow and the reactor was sealed. The reaction was performed at room temperature overnight and stopped via being exposed to the air. The slides were washed with ethanol/water (30/70 vol/vol) 3 times and dried with nitrogen flow.

Azide functionalization with direct NaN3. The slides with polymers containing GMA co-monomers were put in the reactor. 1.5 g sodium azide ($NaN_3$), 0.25 g ammonium chloride and 75 g DMF were added to the reactor and reaction conducted for 5 h in 55° C. under vigorous mixing. This reaction can proceed with an alternate procedure. At first, 1.5 g sodium azide ($NaN_3$), 0.25 g ammonium chloride and 75 g DMF were mixed via vigorous mixing at 55° C. for 1 h. Then, the mixture was filtered and the solution was added to the reaction vessel with slides, and reaction conducted for 5 h in 55° C. under vigorous mixing. The reaction was stopped by pouring out the solution and slides were washed with water and water/ethanol mixture and finally slides were dried with nitrogen.

Grafting to general methods. The solution mixture was prepared with mixing anhydrous hexane/dichloromethane (DCM) (50/50 vol/vol) under inert gas flow and bubbled for 10 min. A mixture of (3-Aminopropyl)triethoxysilane and spacer silane agents (e.g., Trimethoxy(propyl)silane) were added to the solution mixture (~0.10-0.15% vol/vol) under inert gas and the reaction mixture to bubbled for 3 more minutes. The substrate (e.g., glass slide, silica particle, metal particle) was placed into the reaction mixture (or reaction mixture added to the container the substrate). The container is sealed and kept for 18 h. The substrate is then washed with hexane and ethanol/water mixture and dried with nitrogen.

Synthesizing reactive/nonreactive block copolymers general methods. Different block copolymer (C-[A-B]) were synthesized with RAFT and ATRP polymerization techniques (and combination of them). The first block (referred to as Block C) is designed to have functionalities to attach to the surface. For example, this block contains: carboxylic (e.g. acrylic acid), epoxy (e.g. glycidyl methacrylate), and hydroxyl moieties (HEMA, HEA, HPMA) groups. Carboxylic and epoxy group can directly attach to an amine functionalized surfaces (e.g., APTES functionalized silica surface). Hydroxyl containing blocks reacted with isocyanate silanes are then attached to the glass or silica wafer surfaces. The second block (referred to as [A-B]copolymers) B were PEGMEMA-co-GMA-$N_3$, DMA-GMA-$N_3$, AAm-co-HPMA-$N_3$. The block copolymers can be synthesized in either order (e.g., synthesize block C first and react with block [A-B], or synthesize block [A-B]first and react with block C second).

RAFT macroinitiator synthesis (carboxylic acid). RAFT macroinitiators were synthesized with the polymerization of acrylic acid (AAc) with RAFT chain transfer agent (CTA). AAc 1g, 2,2'-Azobis(2-methylpropionitrile) (AIBN) 3 mg, 4-Cyano-4-[(dodecylsulfanylthiocarbonyl)sulfanyl]pentanoic acid (0.284 g), and 7 g ethanol were added to the Schlenk reactor and degassed for 45 min. The reaction started by putting the reactor in an oil batch at 60° C. After reaching the degree of polymerization (DP) to the targeted value, reaction was stopped by being exposed to the air. The sample dried with air flow and kept in refrigerator.

Polymerization with RAFT macroinitiator. PEGMEMA (Mn~500) 5 g, HPMA-N3 0.81 g, 2,2'-Azobis(2-methylpropionitrile) (AIBN) 3 mg, RAFT macroinitiator 9 mg and 7 g ethanol were added to the Schlenk reactor and degassed for 45 min. Reaction started with putting the reactor in the oil batch at 60° C. After reaching DP to the targeted value, the reaction stopped by being exposed to the air. The sample was washed with dissolving and acetone and precipitation in hexane, 3 times. Finally, the sample was dried with air flow and kept in refrigerator.

What is claimed is:

1. A method of detecting polynucleotides in a polymer scaffold, the method comprising:

(a) amplifying polynucleotides to produce discrete amplicon clusters within a three-dimensional polymer scaffold, wherein the amplicons are covalently bound to the polymer scaffold;

(b) contacting the polymer scaffold with a plurality of fluorescently labeled molecules and, within two or more discrete amplicon clusters, binding a fluorescently labeled molecule to a nucleic acid molecule in the amplicon cluster;

(c) detecting the fluorescently labeled molecules to identify the polynucleotide in the polymer scaffold.

2. The method of claim 1, wherein detecting the fluorescently labeled molecules further identifies three-dimensional coordinates of the polynucleotide.

3. The method of claim 2, further comprising forming an image based on the detected labels.

4. The method of claim 1, prior to (a), comprising contacting the polymer scaffold with a plurality of primers and covalently attaching the primers to the polymer scaffold.

5. The method of claim 4, wherein the plurality comprises a first primer comprising a first capture sequence and a second primer comprising a second capture sequence.

6. The method of claim 5, comprising binding a first template polynucleotide to the first capture sequence, wherein the first template polynucleotide comprises a first primer binding sequence.

7. The method of claim 1, comprising cross-linking the amplicons to the polymer scaffold.

8. The method of claim 1, wherein the three-dimensional polymer scaffold is in the channel of a flow cell.

9. The method of claim 1, wherein amplifying comprises isothermal amplification.

10. The method of claim 1, wherein amplifying comprises rolling circle amplification.

11. The method of claim 1, wherein the fluorescently labeled molecules are fluorescently labeled nucleotides.

12. The method of claim 11, wherein each fluorescently labeled nucleotide comprises a fluorophore moiety covalently attached to a nucleotide molecule via a cleavable linker.

13. The method of claim 12, further comprising cleaving the cleavable linker and removing the fluorophore moiety and repeating (b) and (c).

14. The method of claim 13, wherein detecting comprises imaging multiple two-dimensional planes.

15. The method of claim 1, wherein the fluorescently labeled molecules are fluorescently labeled oligonucleotides.

16. The method of claim 15, further comprising removing the fluorescently labeled oligonucleotides and repeating (b) and (c).

17. The method of claim 16, wherein detecting comprises imaging multiple two-dimensional planes.

18. The method of claim 1, wherein the polynucleotides comprise a gene sequence or a portion thereof.

19. The method of claim 1, wherein the polymer scaffold comprises polyacrylamide.

20. The method of claim 1, wherein the polymer scaffold comprises polyacrylate.

* * * * *